US010526328B2

(12) United States Patent
Resnick et al.

(10) Patent No.: US 10,526,328 B2
(45) Date of Patent: Jan. 7, 2020

(54) IMIDAZO[4,5-B]PYRIDIN-2-YL AMIDES AS KV7 CHANNEL ACTIVATORS

(71) Applicant: Knopp Biosciences LLC, Pittsburgh, PA (US)

(72) Inventors: Lynn Resnick, Pittsburgh, PA (US); George T. Topalov, Pittsburgh, PA (US); Charles A. Flentge, Mars, PA (US); James S. Hale, Pittsburgh, PA (US); David A. Mareska, McMurray, PA (US); Justin K. Belardi, Pittsburgh, PA (US); Kai Zhang, Wexford, PA (US); Scott S. Harried, Sun Prairie, WI (US)

(73) Assignee: Knopp Biosciences LLC, Pittsburgh, PA (US)

( * ) Notice: Subject to any disclaimer, the term of this patent is extended or adjusted under 35 U.S.C. 154(b) by 0 days.

(21) Appl. No.: 16/124,853

(22) Filed: Sep. 7, 2018

(65) Prior Publication Data
US 2019/0002464 A1     Jan. 3, 2019

Related U.S. Application Data

(63) Continuation of application No. 15/591,884, filed on May 10, 2017, now Pat. No. 10,106,536, which is a continuation-in-part of application No. 14/776,271, filed as application No. PCT/US2014/030686 on Mar. 17, 2014, now Pat. No. 9,650,376.

(60) Provisional application No. 61/793,892, filed on Mar. 15, 2013.

(51) Int. Cl.
*C07D 471/04*     (2006.01)
*C07D 519/00*     (2006.01)

(52) U.S. Cl.
CPC ......... *C07D 471/04* (2013.01); *C07D 519/00* (2013.01)

(58) Field of Classification Search
CPC ............................ C07D 471/04; C07D 519/00
USPC ......................................................... 546/113
See application file for complete search history.

(56) References Cited

U.S. PATENT DOCUMENTS

| 3,920,669 | A | 11/1975 | Kristinsson et al. |
| 4,002,623 | A | 1/1977 | Kadin |
| 4,247,556 | A | 1/1981 | von Bebenburg et al. |
| 4,391,811 | A | 7/1983 | Lesher et al. |
| 9,481,653 | B2 | 11/2016 | Resnick et al. |
| 9,650,376 | B2 | 5/2017 | Resnick et al. |
| 9,914,708 | B2 * | 3/2018 | Harried ............... C07D 235/30 |
| 10,106,536 | B2 | 10/2018 | Resnick et al. |
| 10,385,025 | B2 * | 8/2019 | Resnick ............... C07D 235/30 |
| 2003/0109549 | A1 | 6/2003 | Ito et al. |
| 2003/0181480 | A1 | 9/2003 | McMahon et al. |
| 2006/0069117 | A1 | 3/2006 | Rault et al. |
| 2008/0039442 | A1 | 2/2008 | Blom et al. |
| 2009/0062290 | A1 | 3/2009 | Christos et al. |
| 2016/0031875 | A1 | 2/2016 | Resnick et al. |
| 2016/0075663 | A1 | 3/2016 | Resnick et al. |
| 2017/0114022 | A1 | 4/2017 | Harried et al. |
| 2017/0240547 | A1 | 8/2017 | Resnick et al. |
| 2018/0148419 | A1 | 5/2018 | Resnick et al. |

FOREIGN PATENT DOCUMENTS

| JP | 2000154189 A | 6/2000 |
| JP | 201199968 A | 7/2001 |
| WO | 199601833 A1 | 1/1996 |
| WO | 2001089499 A2 | 11/2001 |
| WO | 2005021547 A2 | 3/2005 |
| WO | 2007022305 A3 | 4/2007 |
| WO | 2007039297 A1 | 4/2007 |
| WO | 2009085230 A1 | 7/2009 |
| WO | 2010051819 A1 | 5/2010 |
| WO | 2010080503 A1 | 7/2010 |
| WO | 2010094645 A1 | 8/2010 |
| WO | 2011051452 A1 | 5/2011 |
| WO | 2012003576 A1 | 1/2012 |
| WO | 2012004698 A1 | 1/2012 |
| WO | 2014145852 A2 | 9/2014 |
| WO | 2018209074 A1 | 11/2018 |

OTHER PUBLICATIONS

Descours et al. "New Tricyclic Compounds: Pyrido[2', 3':4,5]- and Pyrido[3',2':4,5]-Imidazo[1,2-a]Pyrimidines" 1990, Heterocycles 31(2):259-265.
Hasegawa, M., et al., "Discovery of novel benzimidozales as potent inhibitors of TIE-2 and VEGFR-2 tyrosine kinase receptors", J. Med. Chem, vol. 50(18), pp. 4453-4470, Aug. 4, 2007.
International Search Report and Written Opinion dated Jul. 31, 2018 for International Application No. PCT/US2018/032050 filed on May 10, 2018.
International Search Report and Written Opinion dated Sep. 18, 2014 for International Application No. PCT/US2014/030686 filed on Mar. 17, 2014.
Langguth, et al. "Potassium channels as promising new targets for pharmacologic treatment of tinnitus: Can Internet-based 'crowd sensing'initiated by patients speed up the transition from bench to bedside?." (2016): 251-254.
Munro et al., KV7 (KCNQ) Channel Modulators and Neuropathic Pain, 2007, J. Med. Chem. 50:2576-2582.
Orhan et al., Retigabine/ezogabine, a KCNQ/KvY Channel Opener: Pharmacological and Clinical Data, 2012, Expert Opin. Pharmacother. 13:1807-1816.
Sorensen et al., Synthesis and Structure—Activity Relationahip Studies of 2(N-Substituted)-aminobenzimidazoles as Potent Negative Gating Modulators of Small Conductance CA2+-activated K+ Channels, 2008, J. Med. Chem. 51:7625-7634.

(Continued)

*Primary Examiner* — Daniel R Carcanague
(74) *Attorney, Agent, or Firm* — Pepper Hamilton LLP

(57) ABSTRACT

Compounds represented by formula 1 can be potent and/or partially selective for the Kv7.2/7.3 heteromultimer. They may be useful in treating disorders related to seizures, pain, neurotransmitter release, etc.

1 Claim, No Drawings

(56) References Cited

OTHER PUBLICATIONS

STN Registry database records for Registry Nos. 1145687-44-0, 1145686-94-7, 1145686-93-6, 1145686-91-4, 1145686-90-3, 1145686-79-8, 1145686-41-4,1145686-39-0 and 1145686-29-8, entered on May 12, 2009.
Supplementary European Search Report for European Patent Application No. 15840730.4 dated Jan. 8, 2018.
Supplementary European Search Report dated Aug. 8, 2016 for European Application No. 14765415.6.
Weller et al. "The idiopathic hypereosinophilic syndrome." Blood 83.10 (1994): 2759-2779.
Xiong et al. Activation of KV7 (KCNQ) Voltage-Gated Potassium Channels by Synthetic Compounds, 2008, Trends in Pharmacological Sciences 29:99-107.

* cited by examiner

IMIDAZO[4,5-B]PYRIDIN-2-YL AMIDES AS KV7 CHANNEL ACTIVATORS

CROSS-REFERENCE TO RELATED APPLICATIONS

This application is a continuation of U.S. application Ser. No. 15/591,884, filed May 10, 2017, which is a continuation-in-part of U.S. application Ser. No. 14/776,271, filed Sep. 14, 2015, now U.S. Pat. No. 9,650,376, which is the U.S. national phase of International Application No. PCT/US2014/030686, filed Mar. 17, 2014, which claims the benefit of U.S. Provisional Application No. 61/793,892, filed Mar. 15, 2013. The disclosures of each of these applications are incorporated herein by reference.

GOVERNMENT INTERESTS

This invention was made with United States Government support under Grant No. U44NS093160 awarded by the National Institute Of Neurological Disorders And Stroke of the National Institutes of Health. The United States Government has certain rights in the invention.

BACKGROUND

Potassium (K+) channels, present on the plasma membranes of most cell types, are the most diverse class of all ion channels and are associated with a wide range of physiological functions including the regulation of the electrical properties of excitable cells. The primary pore-forming (a) subunits of these highly selective cation channels are divided into three primary structural classes based on the number of transmembrane (TM)-spanning regions and pore (P) regions: currently there are known to be 6TM/1P, 2TM/1P and 4TM/2P K+ channels. The Kv7 genes (originally termed KCNQ, a name assigned by the HUGO Gene Nomenclature Committee (HGNC)) were assigned to a subfamily of voltage-gated K+ channels by the International Union of Pharmacology (IUPHAR). The Kv7 subfamily consists of five homologous pore-forming a subunits, Kv7.1-7.5, that have a structure typical of voltage-gated K+ channels with 6TM-spanning regions (S1-S6) flanked by intracellular N-terminal and C-terminal domains, a typical voltage-sensor domain located in S4 comprised of alternating positively-charged residues and a single P region between S5 and S6 of each subunit. The channels are formed as tetramers of the primary a subunits, either as homotetramers or heterotetramers. Neurons are known to express Kv7 channels comprised of Kv7.2-7.5 α subunits. Some of these gene products may be exclusively neuronal while others, such as Kv7.4 and Kv7.5, can be found in other tissues such as smooth and skeletal muscle.

Native M-channels, and the corresponding macroscopic M-current, were first characterized in amphibian sympathetic neurons. M-channels were notable because they were slowly activating and non-inactivating, active at membrane potentials at or near the resting membrane potential of neurons and muscarinic cholinergic agonists produced a reduction in the M-current, demonstrating a direct and inhibitory link between G-protein coupled receptors (GPCRs) and a physiological $K^+$ current. It was not until the cloning of this subfamily of genes that the pharmacological and biophysical identity was established between Kv7.2/7.3 (and likely Kv7.5/7.3) heteromultimers and the elusive 'M'-channel, providing significant new evidence for their importance in neuronal regulation.

The distributions of these channels, both regionally and developmentally, as well as their biophysical characteristics, support their role in providing enduring resistance to depolarizing excitatory influences. Under physiological conditions, as was demonstrated with native M-channels, they can be very effective at regulating the sub-threshold excitability of certain neuronal populations with significant roles in regulating the frequency and ultimately the pattern of action potential discharge in many types of neurons. Their importance in neuronal regulation was punctuated by the discovery that neuronal Kv7 mutations lead to benign familial neonatal convulsions (BFNC) indicating that reduction or removal of the influence of Kv7.2 and Kv7.3 channels can dramatically alter neuronal excitability. Mutation analyses demonstrated their involvement in BFNC and suggested their utility as targets for anti-epileptic drugs (AEDs).

Unlike established pharmacological terminology for GPCRs, the mode of action of $K^+$ channel modulators, in particular compounds that activate the channel, is still being refined. The application of voltage-clamp techniques to the study of ion channel pharmacology enabled detailed biophysical studies on either whole-cell currents or single channels, allowing some characterization of the nature of compound-channel interactions but not preventing ongoing confusion around the terminology. The term opener or activator is commonly used throughout the literature but does not adequately describe the mode of action of all these 'positive modulator' compounds. In general, openers or activators are expected to increase the open probability of the channel or increase macroscopic current amplitude, but this nomenclature is really too simplistic. For example, retigabine, the first publicly disclosed Kv7 opener, has a complex and interesting profile in that it has inhibitory activity at higher membrane potentials. Neuronal Kv7 channel openers may work in concert with the activity of a channel over the 'normal' activation-voltage range and enhance currents without significantly affecting the activation threshold while others can significantly alter the activation threshold. In addition, some openers appear to remove the voltage-dependence of activation entirely. Whether these effects represent some continuum is currently unclear since the effects are often concentration-dependent. Clearly, the modes of interaction of compounds that can increase channel current are complex and in most cases not well understood and the implications of these profiles on neuronal responsiveness and systems physiology are also unclear. Retigabine is modestly potent, not highly specific, but it is a very effective opener of Kv7.2, Kv7.5 and heteromultimeric Kv7 channels. Its effects are characterized by a significant increase in channel current over a narrow voltage range. As mentioned above, at more positive voltages the opener is less effective and under some conditions channel current significantly decreases at more positive voltages relative to control currents (this 'crossover' voltage-dependence of opener action is a characteristic of many neuronal Kv7 channel openers). This effect is also concentration-dependent and is more pronounced at higher concentrations.

SUMMARY

Described herein are compounds that can be potent and/or at least partially selective for the Kv7.2/7.3 heteromultimer. These compounds may have reduced untoward side effects as compared to retigabine.

Some embodiments include a compound represented by Formula 1:

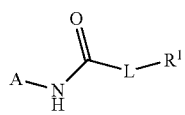

wherein A is optionally substituted 1H-imidazo[4,5-b]pyridin-2-yl or optionally substituted 3H-imidazo[4,5-b]pyridin-2-yl; L is $CH_2$, $CF_2$, $C_2H_4$, $C_3H_6$, O, $CH_2O$, $C_2H_4O$, or $C_3H_6O$; and $R^1$ is $C_{1-12}$ optionally substituted alkyl, $C_{1-12}$ optionally substituted —O-alkyl, optionally substituted $C_6$ to aryl, optionally the compound is active at a Kv7.2 bearing potassium channel, a Kv7.3 bearing potassium channel, a Kv7.4 bearing potassium channel, or a Kv7.5 bearing potassium channel.

In some embodiments, A is optionally substituted 1H-imidazo[4,5-b]pyridin-2-yl or optionally substituted 3H-imidazo[4,5-b]pyridin-2-yl; L is $CH_2$, $CF_2$, $C_2H_4$, $C_3H_6$, O, $CH_2O$, $C_2H_4O$, or $C_3H_6O$; and $R^1$ is $CH_3$, $C_{2-12}$ optionally substituted alkyl, $C_{1-12}$ optionally substituted —O-alkyl, optionally substituted $C_{6-10}$ aryl, optionally substituted $C_{6-10}$ —O-aryl, or optionally substituted $C_{2-9}$ heterocyclyl.

Some embodiments include a composition comprising a compound described herein, wherein the composition is pharmaceutically acceptable.

Some embodiments include a pharmaceutical dosage form comprising a compound described herein.

Some embodiments include a method of treating a disorder associated with a Kv7 potassium channel activator comprising administering an effective amount of a compound described herein.

DETAILED DESCRIPTION

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, Si, F, Cl, Br, or I; provided that the substituent includes one C, N, O, S, Si, F, Cl, Br, or I atom. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by

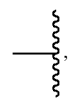

attachment may occur at any position normally occupied by a hydrogen atom.

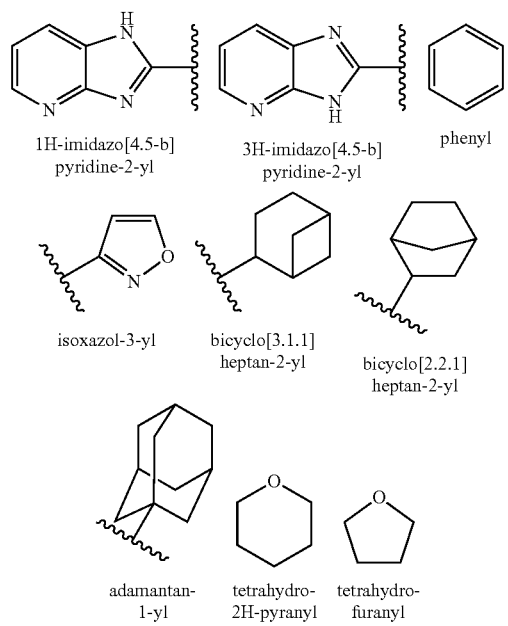

As used herein, the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

With respect to an optionally substituted moiety such as optionally substituted alkyl, a phrase such as "optionally substituted $C_{1-12}$ alkyl" refers to a $C_{1-12}$ alkyl that may be unsubstituted, or may have 1 or more substituents, and does not limit the number of carbon atoms in any substituent. Thus, for example, $CH_2(CH_2)_{11}OCH_3$ is optionally substituted $C_{1-12}$ alkyl because the parent alkyl group has 12 carbon atoms. A phrase such as "$C_{1-12}$ optionally substituted alkyl" refers to unsubstituted $C_{1-12}$ alkyl, or substituted alkyl wherein the alkyl parent and all substituents together have from 1-12 carbon atoms. For example, $CH_2CH_2OCH_3$ is $C_{1-12}$ optionally substituted alkyl because the alkyl group (e.g. ethyl) and the substituent (e.g. methoxy) together contain 3 carbon atoms. Similar conventions may be applied to other optionally substituted moieties such as aryl and heterocyclyl.

Substituents on alkyl may be the same as those described generally above. In some embodiments, substituents on alkyl are independently selected from F, Cl, Br, I, CN, $CO_2H$, —O-alkyl, ester groups, acyl, amine groups, amide groups, phenyl (including fused phenyl resulting optionally substituted alkyl such as indenyl, where the phenyl substituent is fused to the parent alkyl moiety), and may have a molecular weight of about 15 to about 100 or about 500.

As used herein the term "aryl" has the broadest meaning generally understood in the art, and may include an aromatic ring or aromatic ring system such as phenyl, naphthyl, etc.

The term "heterocyclyl" includes any ring or ring system containing a heteroatom such as N, O, S, P, etc. Heterocyclyl includes heteroaryl rings or ring systems (such as those listed below) and non-aromatic rings or ring systems. Examples of non-aromatic heterocyclyl include azetidinyl, oxatanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxalanyl, dithiolanyl, tetrahydropyranyl, piperidinyl, piperazinyl, morpholino, etc.

The term "heteroaryl" also has the meaning understood by a person of ordinary skill in the art, and includes an "aryl" which has one or more heteroatoms in the ring or ring system, such as pyridinyl, furyl, thienyl, oxazolyl, thiazolyl, imidazolyl, triazolyl, oxadiazolyl, isoxazolyl, indolyl, quinolinyl, benzofuranyl, benzothienyl, benzooxazolyl, benzothiazolyl, benzoimidazolyl, etc.

Unless otherwise indicated, any reference to a compound herein by structure, name, or any other means, includes pharmaceutically acceptable salts, such as HCl, HBr, HI, $H_2SO_4$, acetate, citrate, sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described.

If stereochemistry is not indicated, a name or structural representation includes any stereoisomer or any mixture of stereoisomers.

With respect to any relevant formula or structural representation herein, such as Formula 1, A is optionally substituted imidazo[4,5-b]pyridin-2-yl, such as optionally substituted 1H-imidazo[4,5-b]pyridin-2-yl or optionally substituted 3H-imidazo[4,5-b]pyridin-2-yl. If the imidazo[4,5-b]pyridin-2-yl is substituted, it may have 1, 2, 3, or 4 substituents. Any substituent may be included on the imidazo[4,5-b]pyridin-2-yl. In some embodiments, some or all of the substituents on the imidazo[4,5-b]pyridin-2-yl may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy such as $OCH_3$, $OC_2H_5$, $OC_3H_7$, cyclic $OC_3H_5$, $OC_4H_9$, cyclic $OC_4H_7$, $OC_5H_{11}$, cyclic $OC_5H_9$, $OC_6H_{13}$, cyclic $OC_6H_{11}$, etc.; halo, such as F, Cl, Br, I; OH; CN; $NO_2$; $C_{1-6}$ fluoroalkyl, such as $CF_3$, $CF_2H$, $C_2F_5$, etc.; $C_{1-6}$ fluoroalkoxy, such as $OCF_3$, $OCF_2H$, $OC_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc.

In some embodiments, any or all of the substituents of 1H-imidazo[4,5-b]pyridin-2-yl or 3H-imidazo[4,5-b]pyridin-2-yl are independently $CF_3$, Cl, CN, or $OCH_3$. In some embodiments, A has a $CF_3$ substituent. In some embodiments, A has a Cl substituent. In some embodiments, A has a CN substituent. In some embodiments, A has an $OCH_3$ substituent.

In some embodiments, A may be:

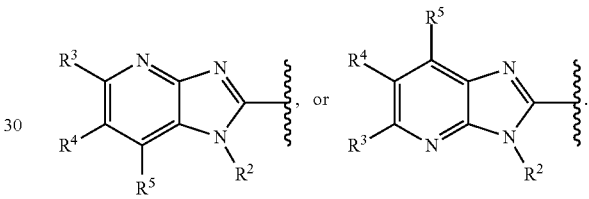

Some embodiments may include a compound represented by one or more of Formulas 2-45.

Formula 2

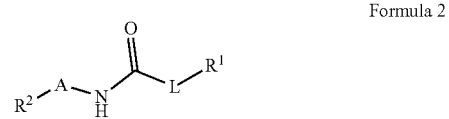

Formula 3

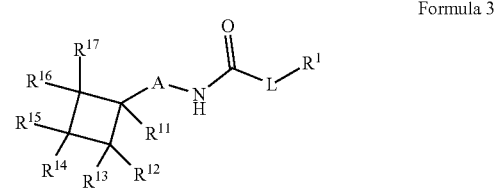

Formula 4

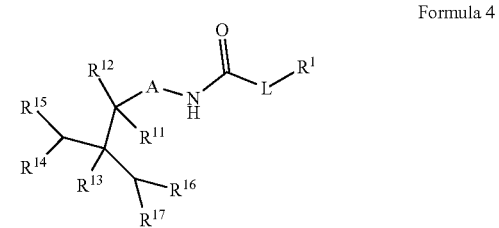

Formula 5

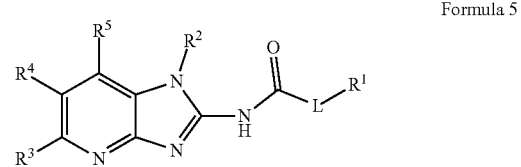

Formula 6
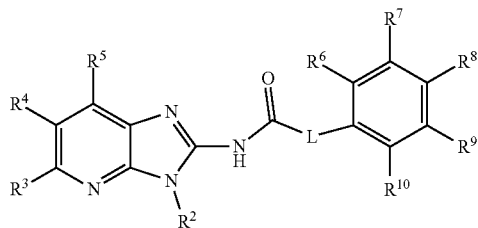
Formula 7
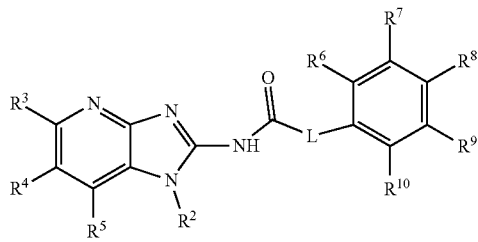
Formula 8
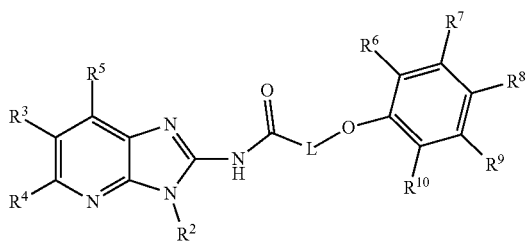
Formula 9
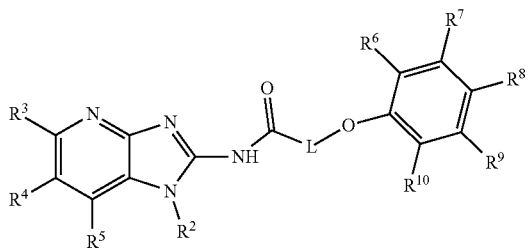
Formula 10
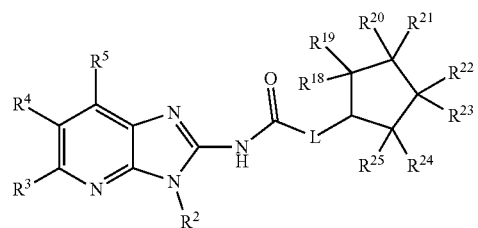
Formula 11
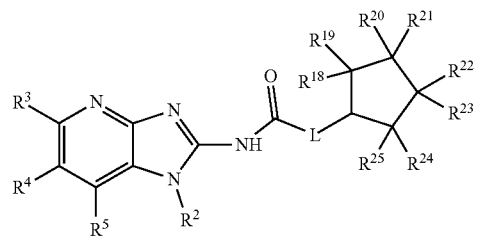
Formula 12
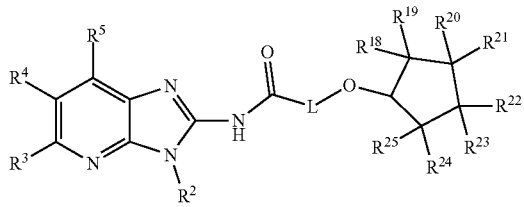
Formula 13
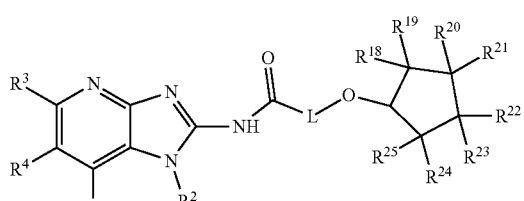
Formula 14
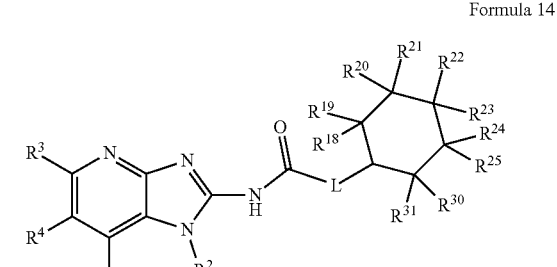
Formula 15
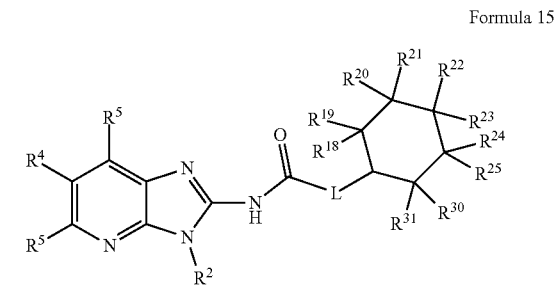
Formula 16
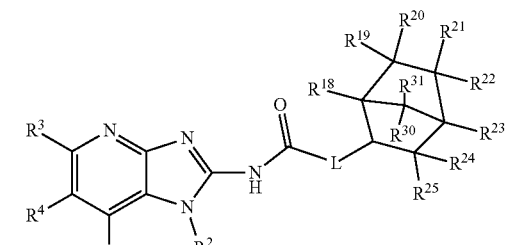
Formula 17
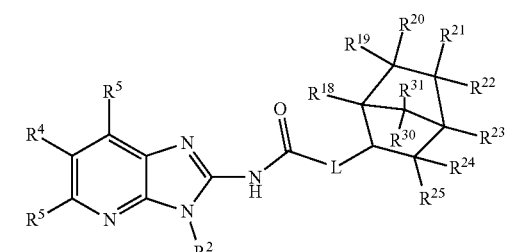

Formula 18
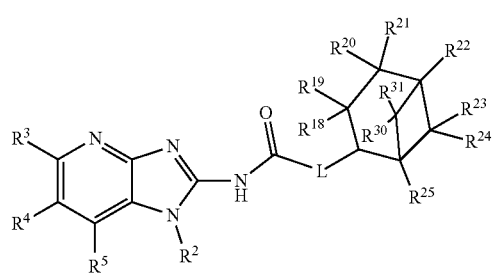
Formula 19
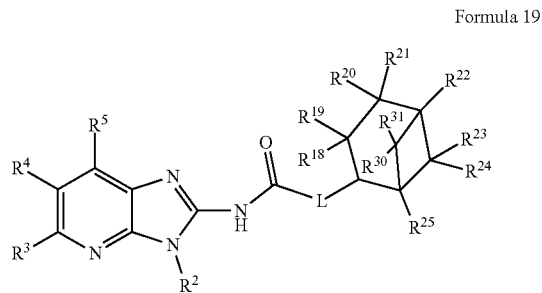
Formula 20
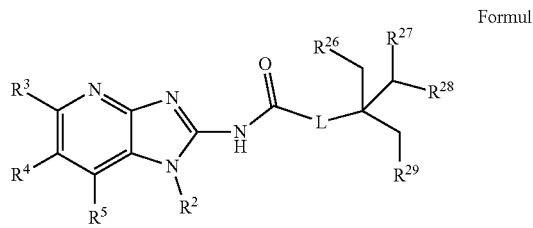
Formula 21
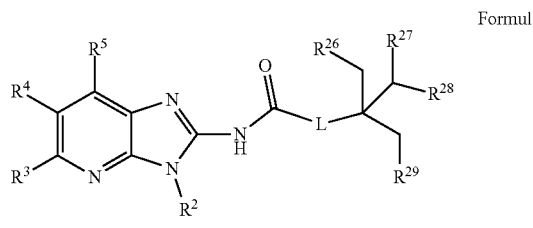
Formula 22
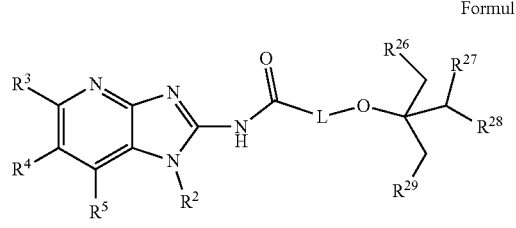
Formula 23
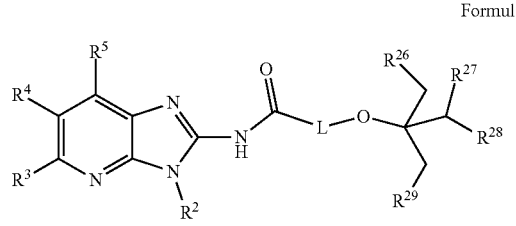
Formula 24
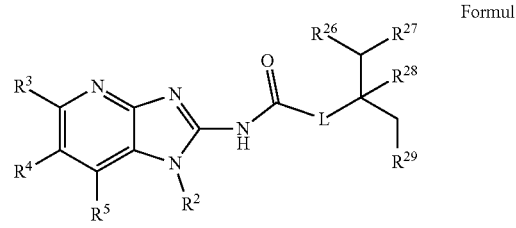
Formula 25
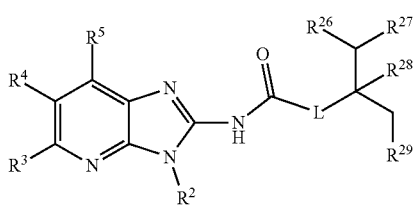
Formula 26
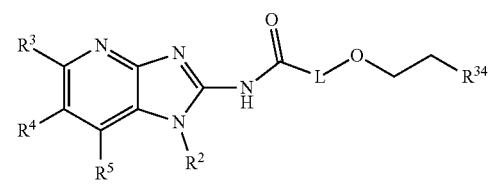
Formula 27
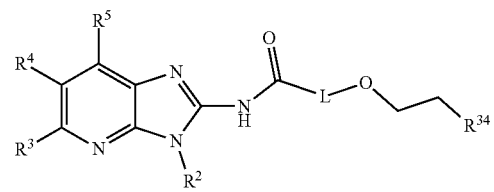
Formula 28
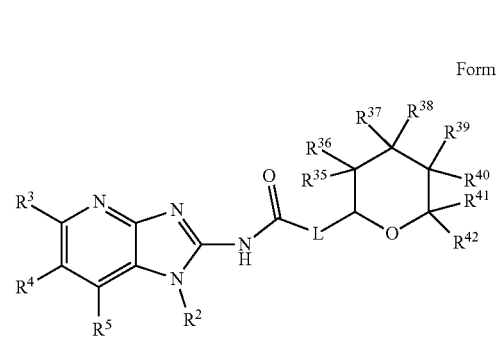
Formula 29
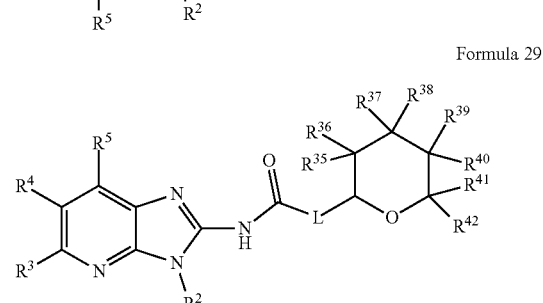
Formula 30
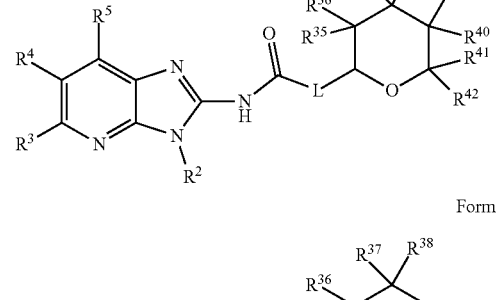

Formula 31
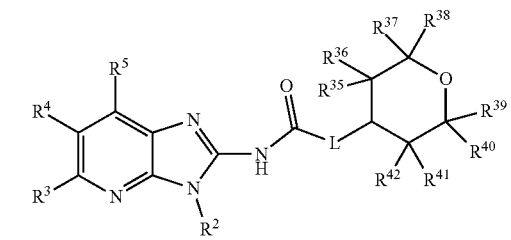

Formula 32
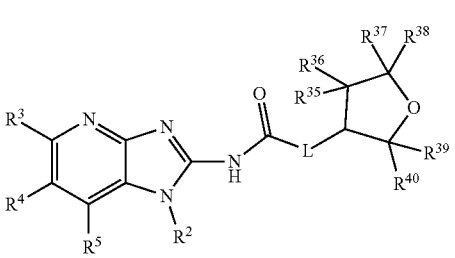

Formula 33
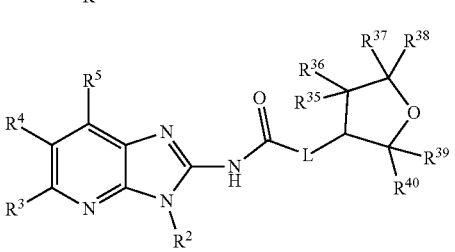

Formula 34
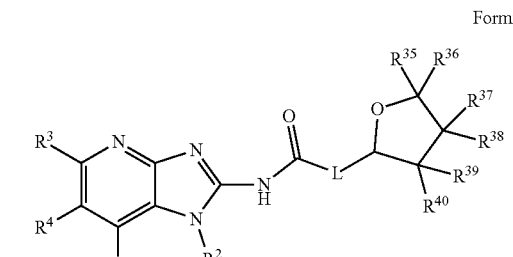

Formula 35
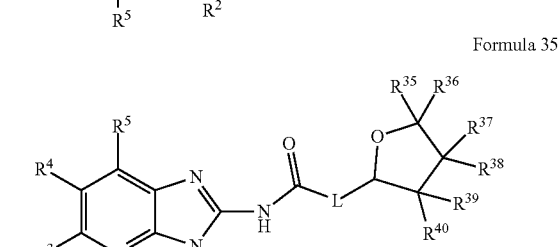

Formula 36
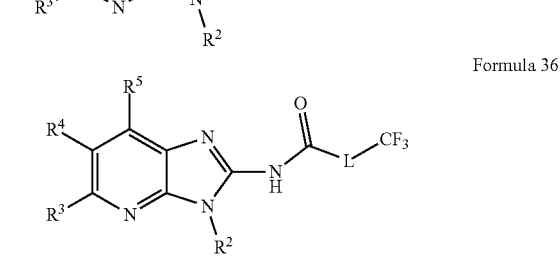

Formula 37
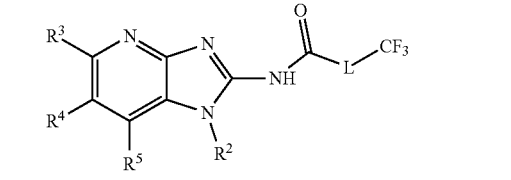

Formula 38
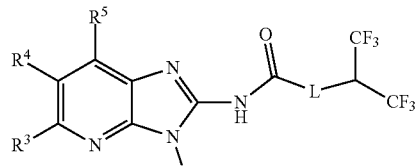

Formula 39
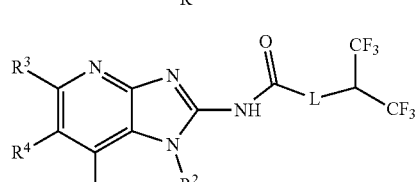

Formula 40
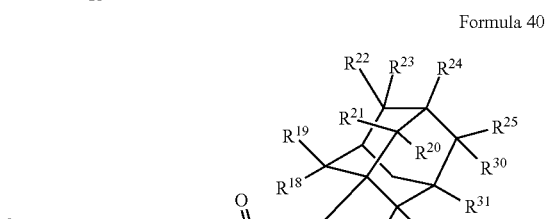

Formula 41
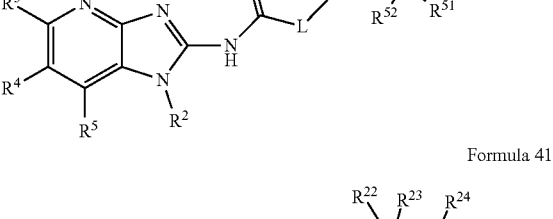

With respect to any relevant formula or structural representation herein, such as Formulas 1-41, L is $CH_2$, $CF_2$, $C_2H_4$ (such as $CH_2CH_2$, $CH(CH_3)$, etc.), $C_3H_6$ (such as $CH_2CH_2CH_2$, $CH_2CH(CH_3)$, $CH(CH_3)CH_2$, $CH(CH_3)_2$, etc.), O, $CH_2O$, $C_2H_4O$ (such as $OCH_2CH_2$ (where the O atom may be on either side of the $CH_2CH_2$), $CH_2OCH_2$, $OCH(CH_3)$, etc.), or $C_3H_6O$.

In some embodiments, L is $CH_2$, $CF_2$, $CH_2CH_2$, $CH(CH_3)_2$, or $C(CH_3)$.

In some embodiments, L is $CH_2$.
In some embodiments, L is $CH_2CH_2$.
In some embodiments, L is $C(CH_3)_2$.
In some embodiments, L is $CH(CH_3)$.
In some embodiments, L is $CH_2CH(CH_3)$.

With respect to any relevant formula or structural representation herein, such as Formulas 1-5, $R^1$ may be $C_{1-12}$ optionally substituted alkyl, such as optionally substituted $CH_3$, optionally substituted $C_2H_5$, optionally substituted $C_3H_7$, optionally substituted cyclic $C_3H_5$, optionally substituted $C_4H_9$, optionally substituted cyclic $C_4H_7$, optionally substituted $C_5H_{11}$, optionally substituted cyclic $C_5H_9$, optionally substituted $C_6H_{13}$, optionally substituted cyclic C₆H₁₁, optionally substituted bicyclo[2.2.1]heptan-2-yl, optionally substituted bicyclo[3.1.1]heptan-2-yl, etc.; $C_{1-12}$ optionally substituted —O-alkyl, such as optionally substituted —O—CH₃, optionally substituted —O—C₂H₅, optionally substituted —O—C₃H₇, optionally substituted cyclic —O—C₃H₅, optionally substituted —O—C₄H₉, optionally substituted cyclic —O—C₄H₇, optionally substituted —O—C₅H₁₁, optionally substituted cyclic —O—C₅H₉, optionally substituted —O—C₆H₁₃, optionally substituted cyclic —O—C₆H₁₁, optionally substituted (2,3-dihydro-1H-inden-1-yl)oxy, etc.; optionally substituted $C_{6-10}$ aryl, such as optionally substituted phenyl; optionally substituted $C_{6-10}$ —O-aryl, such as optionally substituted —O-phenyl; or optionally substituted $C_{2-9}$ heterocyclyl, such as optionally substituted isoxazolyl, optionally substituted tetrahydropyranyl, optionally substituted tetrahydrofuryanyl, etc. In some embodiments, $R^1$ is CH₃, $C_{2-12}$ optionally substituted alkyl, $C_{1-12}$ optionally substituted —O-alkyl, optionally substituted $C_{6-10}$ aryl, optionally substituted $C_{6-10}$ —O-aryl, or optionally substituted $C_{2-9}$ heterocyclyl.

With respect to any relevant formula or structural representation herein, such as Formulas 1-5, in some embodiments, $R^1$ is optionally substituted phenyl. In some embodiments, $R^1$ is $C_{3-4}$ alkyl. In some embodiments, $R^1$ is optionally substituted pyridinyl. In some embodiments, $R^1$ is optionally substituted bicyclo[2.2.1]heptan-2-yl. In some embodiments, $R^1$ is optionally substituted isoxazol-3-yl. In some embodiments, $R^1$ is CF₃. In some embodiments, $R^1$ is optionally substituted cyclopentyl. In some embodiments, $R^1$ is optionally substituted cyclohexyl. In some embodiments, $R^1$ is methyl. In some embodiments, $R^1$ is optionally substituted bicyclo[3.1.1]heptan-2-yl. In some embodiments, $R^1$ is optionally substituted —O-phenyl. In some embodiments, $R^1$ is optionally substituted CH(CF₃)₂. In some embodiments, $R^1$ is $C_{2-4}$ —O-alkyl. In some embodiments, $R^1$ is optionally substituted adamantan-1-yl. In some embodiments, $R^1$ is optionally substituted tetrahydro-2H-pyranyl. In some embodiments, $R^1$ is optionally substituted (2,3-dihydro-1H-inden-1-yl)oxy. In some embodiments, $R^1$ is optionally substituted tetrahydrofuryanyl. In some embodiments, $R^1$ is optionally substituted thiazolyl. In some embodiments, $R^1$ is optionally substituted 2-oxabicyclo[3.2.0]heptanyl With respect to any relevant formula or structural representation herein, such as Formulas 1-5:

In some embodiments, $R^1$ is

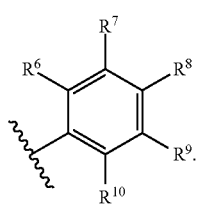

In some embodiments, $R^1$ is

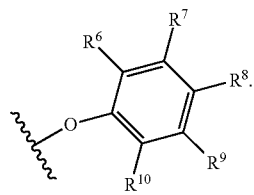

In some embodiments, $R^1$ is

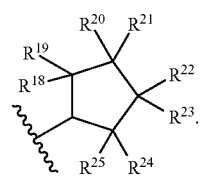

In some embodiments, $R^1$ is

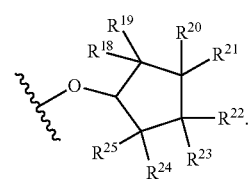

In some embodiments, $R^1$ is

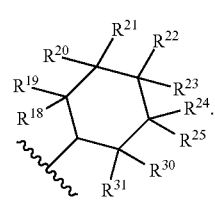

In some embodiments, $R^1$ is

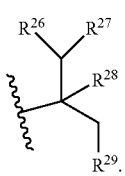

In some embodiments, $R^1$ is

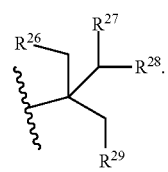

In some embodiments, $R^1$ is

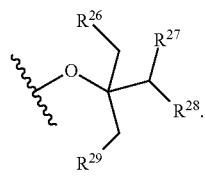

In some embodiments, $R^1$ is

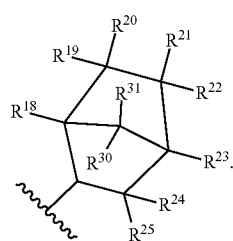

In some embodiments, $R^1$ is

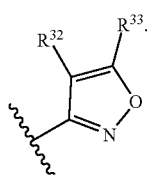

In some embodiments, $R^1$ is $CH_3$. In some embodiments, $R^1$ is $CF_3$.
In some embodiments, $R^1$ is $CH(CF_3)_2$.
In some embodiments, $R^1$ is $CH_2CH_2R^{34}$.
In some embodiments, $R^1$ is $-OCH_2CH_2R^{34}$.
In some embodiments, $R^1$ is $-OCH_2$-cyclopropyl.
In some embodiments, $R^1$ is

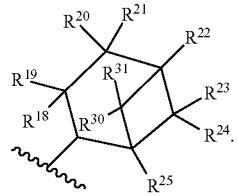

In some embodiments, $R^1$ is

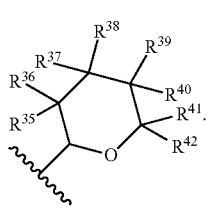

In some embodiments, $R^1$ is

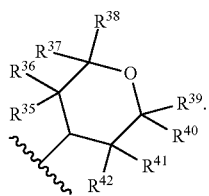

In some embodiments, $R^1$ is

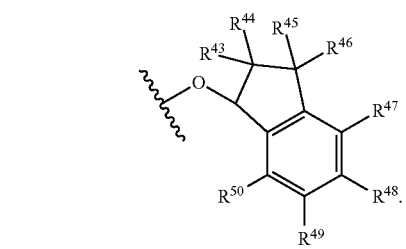

In some embodiments, $R^1$ is

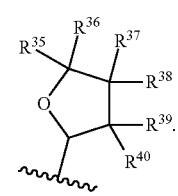

In some embodiments, $R^1$ is

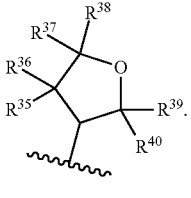

In some embodiments, $R^1$ is

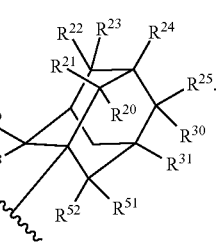

In some embodiments, $R^1$ is

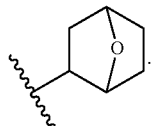 [SMILES: *C1CC2CCC1O2]

In some embodiments, $R^1$ is optionally substituted cyclopropyl.

In some embodiments, $R^1$ is optionally substituted spiro[3.3]heptanyl.

In some embodiments, $R^1$ is $CH_2OCH_3$.

With respect to any relevant formula or structural representation herein, such as Formulas 2 and 5-41, $R^2$ is —$R^a$—Cy. $R^a$ is a bond or $C_{1-12}$ optionally substituted alkyl, such as $CH_2$, $C_2H_4$, $C_3H_6$, $C_4H_8$, $C_5H_{10}$, $C_6H_{12}$, cyclic $C_3H_5$, cyclic $C_4H_7$, cyclic $C_5H_9$, cyclic $C_6H_{11}$, etc. Cy is H; optionally substituted $C_{6-10}$ aryl, such as optionally substituted phenyl; or optionally substituted $C_{2-9}$ heterocyclyl, such as optionally substituted azetidinyl, optionally substituted oxatanyl, optionally substituted thietanyl, optionally substituted isoxazolyl, optionally substituted pyridinyl, optionally substituted furyl, optionally substituted thienyl, etc. In some embodiments, $R^2$ is optionally substituted cyclobutyl (such as difluorocyclobutyl, tetrafluorocyclobutyl, etc.) or optionally substituted 2-methylpropyl.

In some embodiments, $R^2$ is:

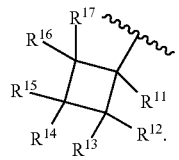

In some embodiments, $R^2$ is:

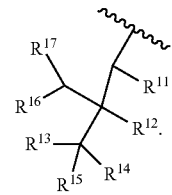

In some embodiments, $R^2$ is:

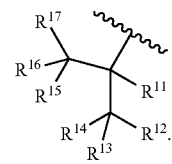

With respect to any relevant formula or structural representation herein, such as Formulas 2 and 5-41, in some embodiments, $R^2$ is cyclobutyl. In some embodiments, $R^2$ is 2-methylpropyl. In some embodiments, $R^2$ is —$CH_2CH$=$CH_2$. In some embodiments, $R^2$ is —$CH_2CF_3$. In some embodiments, $R^2$ is t-butyl. In some embodiments, $R^2$ is n-propyl. In some embodiments, $R^2$ is 4-fluorophenyl. In some embodiments, $R^2$ is optionally substituted isoxazol-3-yl. In some embodiments, $R^2$ is optionally substituted pyridinyl. In some embodiments, $R^2$ is optionally substituted triazolyl. In some embodiments, $R^2$ is optionally substituted oxadiazolyl. In some embodiments, $R^2$ is optionally substituted isoxazolyl.

In some embodiments, $R^2$ is

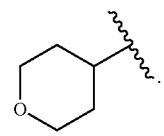

Generally $R^3$-$R^{52}$, may be H or any substituent, such as a substituent having 0 to 12 atoms or 0 to 6 carbon atoms and 0 to 5 heteroatoms, wherein each heteroatom is independently: O, N, S, F, Cl, Br, or I, and/or having a molecular weight of 15 g/mol to 300 g/mol. Any of $R^3$-$R^{52}$ may comprise: a) 1 or more alkyl moieties optionally substituted with, or optionally connected by or to, b) 1 or more functional groups, such as C=C, C—C, CO, $CO_2$, CON, $NCO_2$, OH, SH, O, S, N, N=C, F, Cl, Br, I, CN, $NO_2$, $CO_2H$, $NH_2$, etc.; or may be a substituent having no alkyl portion, such as F, Cl, Br, I, $NO_2$, CN, $NH_2$, OH, COH, $CO_2H$, etc.

With respect to any relevant formula or structural representation herein, some non-limiting examples of $R^3$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^3$ may be H; F; Cl; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^3$ may be H, F, Cl, Br, I, CN, $C_{1-12}$ optionally substituted alkyl, $C_{1-12}$ optionally substituted —O-alkyl, optionally substituted $C_{2-9}$ heterocyclyl, optionally substituted $C_{6-10}$ aryl, optionally substituted $C_{2-9}$ —O-heterocyclyl, optionally substituted $C_{6-10}$ —O-aryl, $C_{1-12}$ optionally substituted acylamino, $C_{1-12}$ optionally substituted aminoacyl, or optionally substituted $C_{1-12}$ aminoalkyl (or alkyl with an amino substituent). In some embodiments, $R^3$ may be H, $CH_3$, OH, $OCH_3$, $NH_2$, $NHCH_3$, $N(CH_3)_2$, COH, $COCH_3$, $CF_3$, Cl, CN, or $OCH_3$. In some embodiments, $R^3$ may be H, $CF_3$, Cl, CN, or $OCH_3$. In some embodiments, $R^3$ is H. In some embodiments, $R^3$ is $CF_3$. In some embodiments, $R^3$ is Cl. In some embodiments, $R^3$ is CN. In some embodiments, $R^3$ is $OCH_3$.

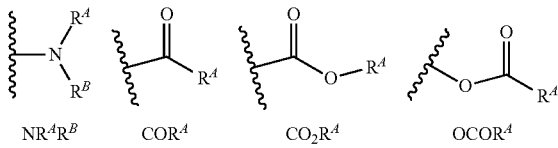

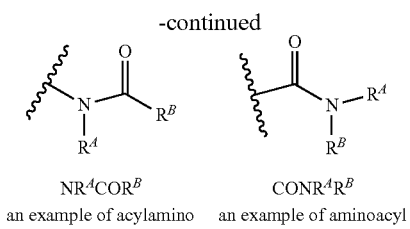

NR$^A$COR$^B$  
an example of acylamino

CONR$^A$R$^B$  
an example of aminoacyl

Each R$^A$ may independently be H, or C$_{1-12}$ alkyl, including: linear or branched alkyl having a formula C$_a$H$_{a+1}$, or cycloalkyl having a formula C$_a$H$_{a+1}$, wherein a is 1, 2, 3, 4, 5, 6, 7, 8, 9, 10, 11, or 12, such as linear or branched alkyl of a formula: CH$_3$, C$_2$H$_5$, C$_3$H$_7$, C$_4$H$_9$, C$_5$H$_{11}$, C$_6$H$_{13}$, C$_7$H$_{15}$, C$_8$H$_{17}$, C$_9$H$_{19}$, C$_{10}$H$_{21}$, etc., or cycloalkyl of a formula: C$_3$H$_5$, C$_4$H$_7$, C$_5$H$_9$, C$_6$H$_{11}$, C$_7$H$_{13}$, C$_8$H$_{15}$, C$_9$H$_{17}$, C$_{10}$H$_{19}$, etc. In some embodiments, R$^A$ may be H or C$_{1-6}$ alkyl. In some embodiments, R$^A$ may be H or C$_{1-3}$ alkyl. In some embodiments, R$^A$ may be H or CH$_3$. In some embodiments, R$^A$ may be H.

Each R$^B$ may independently be H, or C$_{1-12}$ alkyl, including: linear or branched alkyl having a formula C$_a$H$_{a+1}$, or cycloalkyl having a formula C$_a$H$_a$, wherein a is 1, 2, 3, 4, 5, 6, 7, 8, 9, 10, 11, or 12, such as linear or branched alkyl of a formula: CH$_3$, C$_2$H$_5$, C$_3$H$_7$, C$_4$H$_9$, C$_5$H$_{11}$, C$_6$H$_{13}$, C$_8$H$_{17}$, C$_7$H$_{15}$, C$_9$H$_{19}$, C$_{10}$H$_{21}$, etc., or cycloalkyl of a formula: C$_3$H$_5$, C$_4$H$_7$, C$_5$H$_9$, C$_6$H$_{11}$, C$_7$H$_{13}$, C$_8$H$_{15}$, C$_9$H$_{17}$, C$_{10}$H$_{19}$, etc. In some embodiments, R$^B$ may be H or C$_{1-3}$ alkyl. In some embodiments, R$^B$ may be H or CH$_3$. In some embodiments, R$^B$ may be H.

With respect to any relevant formula or structural representation herein, some non-limiting examples of R$^4$ may include R$^A$, F, Cl, CN, OR$^A$, CF$_3$, NO$_2$, NR$^A$R$^B$, COR$^A$, CO$_2$R$^A$, OCOR$^A$, NR$^A$COR$^B$, CONR$^A$R$^B$, etc. In some embodiments, R$^4$ may be H; F; Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—C$_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, R$^4$ may be H, F, Cl, Br, I, CN, C$_{1-12}$ optionally substituted alkyl, C$_{1-12}$ optionally substituted —O-alkyl, optionally substituted C$_{2-9}$ heterocyclyl, optionally substituted C$_{6-10}$ aryl, optionally substituted C$_{2-9}$ —O-heterocyclyl, optionally substituted C$_{6-10}$ —O-aryl, C$_{1-12}$ optionally substituted acylamino, C$_{1-12}$ optionally substituted aminoacyl, or optionally substituted C$_{1-12}$ aminoalkyl. In some embodiments, R$^4$ may be H, CF$_3$, or Cl. In some embodiments, R$^4$ is H. In some embodiments, R$^4$ is CF$_3$. In some embodiments, R$^4$ is Cl. In some embodiments, R$^4$ is CN. In some embodiments, R$^4$ is OCH$_3$.

With respect to any relevant structural representation herein, in some embodiments, R$^3$ is CF$_3$ and R$^4$ is Cl.

With respect to any relevant formula or structural representation herein, some non-limiting examples of R$^5$ may include R$^A$, F, Cl, CN, OR$^A$, CF$_3$, NO$_2$, NR$^A$R$^B$, COR$^A$, CO$_2$R$^A$, OCOR$^A$, NR$^A$COR$^B$, CONR$^A$R$^B$, etc. In some embodiments, R$^5$ may be H; F; Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or C$_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, R$^5$ may be H, F, Cl, Br, I, CN, C$_{1-12}$ optionally substituted alkyl, C$_{1-12}$ optionally substituted —O-alkyl, optionally substituted C$_{2-9}$ heterocyclyl, optionally substituted C$_{6-10}$ aryl, optionally substituted C$_{2-9}$ —O-heterocyclyl, optionally substituted C$_{6-10}$ —O-aryl, C$_{1-12}$ optionally substituted acylamino, C$_{1-12}$ optionally substituted aminoacyl, or optionally substituted C$_{1-12}$ aminoalkyl. In some embodiments, R$^5$ may be H, F, Cl, CN, CF$_3$, OH; NH$_2$, CH$_3$, CH$_2$CH$_3$, CH$_2$CH$_2$CH$_3$, CH(CH$_3$)$_2$, —OCH$_3$, —OCH$_2$CH$_3$, —OCH$_2$CH$_2$CH$_3$, or —OCH(CH$_3$)$_2$. In some embodiments, R$^5$ may be H. In some embodiments, R$^5$ may be CH$_3$.

With respect to any relevant formula or structural representation herein, some non-limiting examples of R$^6$ may include R$^A$, F, Cl, CN, OR$^A$, CF$_3$, NO$_2$, NR$^A$R$^B$, COR$^A$, CO$_2$R$^A$, OCOR$^A$, NR$^A$COR$^B$, CONR$^A$R$^B$, etc. In some embodiments, R$^6$ may be H; F; Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or C$_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, R$^6$ may be H, F, Cl, CN, CF$_3$, OH; NH$_2$, CH$_3$, CH$_2$CH$_3$, CH$_2$CH$_2$CH$_3$, CH(CH$_3$)$_2$, —OCH$_3$, —OCH$_2$CH$_3$, —OCH$_2$CH$_2$CH$_3$, or —OCH(CH$_3$)$_2$. In some embodiments, R$^6$ may be H.

With respect to any relevant formula or structural representation herein, some non-limiting examples of R$^7$ may include R$^A$, F, Cl, CN, OR$^A$, CF$_3$, NO$_2$, NR$^A$R$^B$, COR$^A$, CO$_2$R$^A$, OCOR$^A$, NR$^A$COR$^B$, CONR$^A$R$^B$, etc. In some embodiments, R$^7$ may be H; F; Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or C$_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, R$^7$ may be H, F, Cl, CN, CF$_3$, OH; NH$_2$, CH$_3$, CH$_2$CH$_3$, CH$_2$CH$_2$CH$_3$, CH(CH$_3$)$_2$, —OCH$_3$, —OCH$_2$CH$_3$, —OCH$_2$CH$_2$CH$_3$, or —OCH(CH$_3$)$_2$. In some embodiments, R$^7$ may be H.

With respect to any relevant formula or structural representation herein, some non-limiting examples of R$^8$ may include R$^A$, F, Cl, CN, OR$^A$, CF$_3$, NO$_2$, NR$^A$R$^B$, COR$^A$, CO$_2$R$^A$, OCOR$^A$, NR$^A$COR$^B$, CONR$^A$R$^B$, etc. In some embodiments, R$^8$ may be H; F; Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or C$_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, R$^8$ may be H, F, Cl, CN, CF$_3$, OH; NH$_2$, CH$_3$, CH$_2$CH$_3$, CH$_2$CH$_2$CH$_3$, CH(CH$_3$)$_2$, —OCH$_3$, —OCH$_2$CH$_3$, —OCH$_2$CH$_2$CH$_3$, or —OCH(CH$_3$)$_2$. In some embodiments, R$^8$ is H. In some embodiments, R$^8$ is F.

With respect to any relevant formula or structural representation herein, some non-limiting examples of R$^9$ may include R$^A$, F, Cl, CN, OR$^A$, CF$_3$, NO$_2$, NR$^A$R$^B$, COR$^A$, CO$_2$R$^A$, OCOR$^A$, NR$^A$COR$^B$, CONR$^A$R$^B$, etc. In some embodiments, R$^9$ may be H; F; Cl; CN; CF$_3$; OH; NH$_2$; C$_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^9$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^9$ may be H.

With respect to any relevant formula or structural representation herein, some non-limiting examples of $R^{10}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{10}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{10}$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{10}$ may be H.

With respect to any relevant formula or structural representation herein, some non-limiting examples of $R^{11}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{11}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{11}$ is H, $CH_3$, F, Cl, or $CF_3$. In some embodiments, $R^{11}$ may be H.

With respect to any relevant formula or structural representation herein, some non-limiting examples of $R^{12}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{12}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{12}$ is H, $CH_3$, F, Cl, or $CF_3$. In some embodiments, $R^{12}$ may be H.

With respect to any relevant formula or structural representation herein, some non-limiting examples of $R^{13}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{13}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{13}$ is H, $CH_3$, F, Cl, or $CF_3$. In some embodiments, $R^{13}$ may be H.

With respect to any relevant formula or structural representation herein, some non-limiting examples of $R^{14}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{14}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{14}$ is H, $CH_3$, F, Cl, or $CF_3$. In some embodiments, $R^{14}$ may be H. In some embodiments, $R^{14}$ may be F.

With respect to any relevant formula or structural representation herein, some non-limiting examples of $R^{15}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{15}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{15}$ is H, $CH_3$, F, Cl, or $CF_3$. In some embodiments, $R^{15}$ may be H.

With respect to any relevant formula or structural representation herein, some non-limiting examples of $R^{16}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{16}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{16}$ is H, $CH_3$, F, Cl, or $CF_3$. In some embodiments, $R^{16}$ may be H.

With respect to any relevant formula or structural representation herein, some non-limiting examples of $R^{17}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{17}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{17}$ is H, $CH_3$, F, Cl, or $CF_3$. In some embodiments, $R^{17}$ may be H.

With respect to any relevant formula or structural representation herein, some non-limiting examples of $R^{18}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{18}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{18}$ may be H, F, Cl, OH, CN, $CF_3$, $CH_3$, $CH_2CH_3$, —$OCH_3$, or —$OCH_2CH_3$. In some embodiments, $R^{18}$ may be H.

With respect to any relevant formula or structural representation herein, some non-limiting examples of $R^{19}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{19}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{19}$ may be H, OH, CN, $CF_3$, $CH_3$, $CH_2CH_3$, —$OCH_3$, or —$OCH_2CH_3$. In some embodiments, $R^{19}$ may be H.

With respect to any relevant formula or structural representation herein, some non-limiting examples of $R^{20}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{20}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{20}$ may be H, F, Cl, OH, CN, $CF_3$, $CH_3$, $CH_2CH_3$, —$OCH_3$, or —$OCH_2CH_3$. In some embodiments, $R^{20}$ may be H.

With respect to any relevant formula or structural representation herein, some non-limiting examples of $R^{21}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{21}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{21}$ may be H, OH, CN, $CF_3$, $CH_3$, $CH_2CH_3$, —$OCH_3$, or —$OCH_2CH_3$. In some embodiments, $R^{21}$ may be H.

With respect to any relevant formula or structural representation herein, some non-limiting examples of $R^{22}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{22}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{22}$ may be H, F, Cl, OH, CN, $CF_3$, $CH_3$, $CH_2CH_3$, —$OCH_3$, or —$OCH_2CH_3$. In some embodiments, $R^{22}$ may be H.

With respect to any relevant formula or structural representation herein, some non-limiting examples of $R^{23}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{23}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{23}$ may be H, OH, CN, $CF_3$, $CH_3$, $CH_2CH_3$, —$OCH_3$, or —$OCH_2CH_3$. In some embodiments, $R^{23}$ is H. In some embodiments, $R^{23}$ is $CH_3$.

With respect to any relevant formula or structural representation herein, some non-limiting examples of $R^{24}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{24}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{24}$ may be H, F, Cl, OH, CN, $CF_3$, $CH_3$, $CH_2CH_3$, —$OCH_3$, or —$OCH_2CH_3$. In some embodiments, $R^{24}$ is H. In some embodiments, $R^{24}$ is $CH_3$.

With respect to any relevant formula or structural representation herein, some non-limiting examples of $R^{25}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{25}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{25}$ may be H, OH, CN, $CF_3$, $CH_3$, $CH_2CH_3$, —$OCH_3$, or —$OCH_2CH_3$. In some embodiments, $R^{25}$ may be H.

With respect to any relevant formula or structural representation herein, some non-limiting examples of $R^{26}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{26}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{26}$ may be H, F, Cl, OH, CN, $CF_3$, $CH_3$, or —$OCH_3$. In some embodiments, $R^{26}$ may be H.

With respect to any relevant formula or structural representation herein, some non-limiting examples of $R^{27}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{27}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{27}$ may be H, F, Cl, OH, CN, $CF_3$, $CH_3$, or —$OCH_3$. In some embodiments, $R^{27}$ may be H.

With respect to any relevant formula or structural representation herein, some non-limiting examples of $R^{28}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{28}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{28}$ may be H, F, CN, $CF_3$, or $CH_3$. In some embodiments, $R^{28}$ may be H.

With respect to any relevant formula or structural representation herein, some non-limiting examples of $R^{29}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{29}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{29}$ may be H, F, Cl, OH, CN, $CF_3$, $CH_3$, or —$OCH_3$. In some embodiments, $R^{29}$ may be H.

With respect to any relevant formula or structural representation herein, some non-limiting examples of $R^{30}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{30}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{30}$ may be H, F, Cl, OH, CN, $CF_3$, $CH_3$, $CH_2CH_3$, —$OCH_3$, or —$OCH_2CH_3$. In some embodiments, $R^{30}$ may be H.

With respect to any relevant formula or structural representation herein, some non-limiting examples of $R^{31}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{31}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{31}$ may be H, OH, CN, $CF_3$, $CH_3$, $CH_2CH_3$, —$OCH_3$, or —$OCH_2CH_3$. In some embodiments, $R^{31}$ may be H.

With respect to any relevant formula or structural representation herein, some non-limiting examples of $R^{32}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{32}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{32}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{32}$ may be H.

With respect to any relevant formula or structural representation herein, some non-limiting examples of $R^{33}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{33}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{33}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{33}$ is H. In some embodiments, $R^{33}$ is $CH_3$.

With respect to any relevant formula or structural representation herein, some non-limiting examples of $R^{34}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{34}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{34}$ may be H, F, Cl, OH, CN, $CF_3$, $CH_3$, $NH_2$, $NHCH_3$, $N(CH_3)_2$, or —$OCH_3$. In some embodiments, $R^{34}$ may be H.

With respect to any relevant formula or structural representation herein, some non-limiting examples of $R^{35}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{35}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{35}$ may be H, F, CN, $CF_3$, $CH_3$, $CH_2CH_3$, $CH_2CH_2CH_3$, or $CH(CH_3)_2$. In some embodiments, $R^{35}$ is H. In some embodiments, $R^{35}$ is $CH_3$.

With respect to any relevant formula or structural representation herein, some non-limiting examples of $R^{36}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{36}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{36}$ may be H, F, CN, $CF_3$, $CH_3$, $CH_2CH_3$, $CH_2CH_2CH_3$, or $CH(CH_3)_2$. In some embodiments, $R^{36}$ is H. In some embodiments, $R^{36}$ is $CH_3$.

With respect to any relevant formula or structural representation herein, some non-limiting examples of $R^{37}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{37}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{37}$ may be H, F, CN, $CF_3$, $CH_3$, $CH_2CH_3$, $CH_2CH_2CH_3$, or $CH(CH_3)_2$. In some embodiments, $R^{37}$ is H. In some embodiments, $R^{37}$ is $CH_3$.

With respect to any relevant formula or structural representation herein, some non-limiting examples of $R^{38}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{38}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{38}$ may be H, F, CN, $CF_3$, $CH_3$, $CH_2CH_3$, $CH_2CH_2CH_3$, or $CH(CH_3)_2$. In some embodiments, $R^{38}$ is H. In some embodiments, $R^{38}$ is $CH_3$.

With respect to any relevant formula or structural representation herein, some non-limiting examples of $R^{39}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{39}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{39}$ may be H, F, CN, $CF_3$, $CH_3$, $CH_2CH_3$, $CH_2CH_2CH_3$, or $CH(CH_3)_2$. In some embodiments, $R^{39}$ may be H.

With respect to any relevant formula or structural representation herein, some non-limiting examples of $R^{40}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{40}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{40}$ may be H, F, CN, $CF_3$, $CH_3$, $CH_2CH_3$, $CH_2CH_2CH_3$, or $CH(CH_3)_2$. In some embodiments, $R^{40}$ may be H.

With respect to any relevant formula or structural representation herein, some non-limiting examples of $R^{41}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{41}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{41}$ may be H, F, CN, $CF_3$, $CH_3$, $CH_2CH_3$, $CH_2CH_2CH_3$, or $CH(CH_3)_2$. In some embodiments, $R^{41}$ is H. In some embodiments, $R^{41}$ is $CH_3$.

With respect to any relevant formula or structural representation herein, some non-limiting examples of $R^{42}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{42}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{42}$ may be H, CN, $CF_3$, $CH_3$, $CH_2CH_3$, $CH_2CH_2CH_3$, or $CH(CH_3)_2$. In some embodiments, $R^{42}$ is H. In some embodiments, $R^{42}$ is $CH_3$.

With respect to any relevant formula or structural representation herein, some non-limiting examples of $R^{43}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{43}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{43}$ may be H, F, Cl, CN, $CF_3$, $CH_3$, $CH_2CH_3$, $CH_2CH_2CH_3$, $CH(CH_3)_2$, $—OCH_3$, $—OCH_2CH_3$, $—OCH_2CH_2CH_3$, or $—OCH(CH_3)_2$. In some embodiments, $R^{43}$ may be H.

With respect to any relevant formula or structural representation herein, some non-limiting examples of $R^{44}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{44}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{44}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{44}$ may be H.

With respect to any relevant formula or structural representation herein, some non-limiting examples of $R^{45}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{45}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{45}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{45}$ may be H.

With respect to any relevant formula or structural representation herein, some non-limiting examples of $R^{46}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{46}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{46}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{46}$ may be H.

With respect to any relevant formula or structural representation herein, some non-limiting examples of $R^{47}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{47}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{47}$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{47}$ may be H.

With respect to any relevant formula or structural representation herein, some non-limiting examples of $R^{48}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{48}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{48}$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{48}$ may be H.

With respect to any relevant formula or structural representation herein, some non-limiting examples of $R^{49}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{49}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{49}$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{49}$ may be H.

With respect to any relevant formula or structural representation herein, some non-limiting examples of $R^{50}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{50}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{50}$ may be H, F, Cl, CN, $CF_3$, OH; $NH_2$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{50}$ may be H.

With respect to any relevant formula or structural representation herein, some non-limiting examples of $R^{51}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{51}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{51}$ may be H, F, Cl, CN, $CF_3$, $CH_3$, $CH_2CH_3$, $CH_2CH_2CH_3$, $CH(CH_3)_2$, —$OCH_3$, —$OCH_2CH_3$, —$OCH_2CH_2CH_3$, or —$OCH(CH_3)_2$. In some embodiments, $R^{51}$ may be H.

With respect to any relevant formula or structural representation herein, some non-limiting examples of $R^{52}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{52}$ may be H; F; Cl; CN; $CF_3$; OH; $NH_2$; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{52}$ may be H, F, Cl, CN, $CF_3$, $CH_3$, $CH_2CH_3$, $CH_2CH_2CH_3$, $CH(CH_3)_2$, —OCH$_3$, —OCH$_2$CH$_3$, —OCH$_2$CH$_2$CH$_3$, or —OCH(CH$_3$)$_2$. In some embodiments, R$^{52}$ may be H.
Some embodiments may include one of the compounds below:
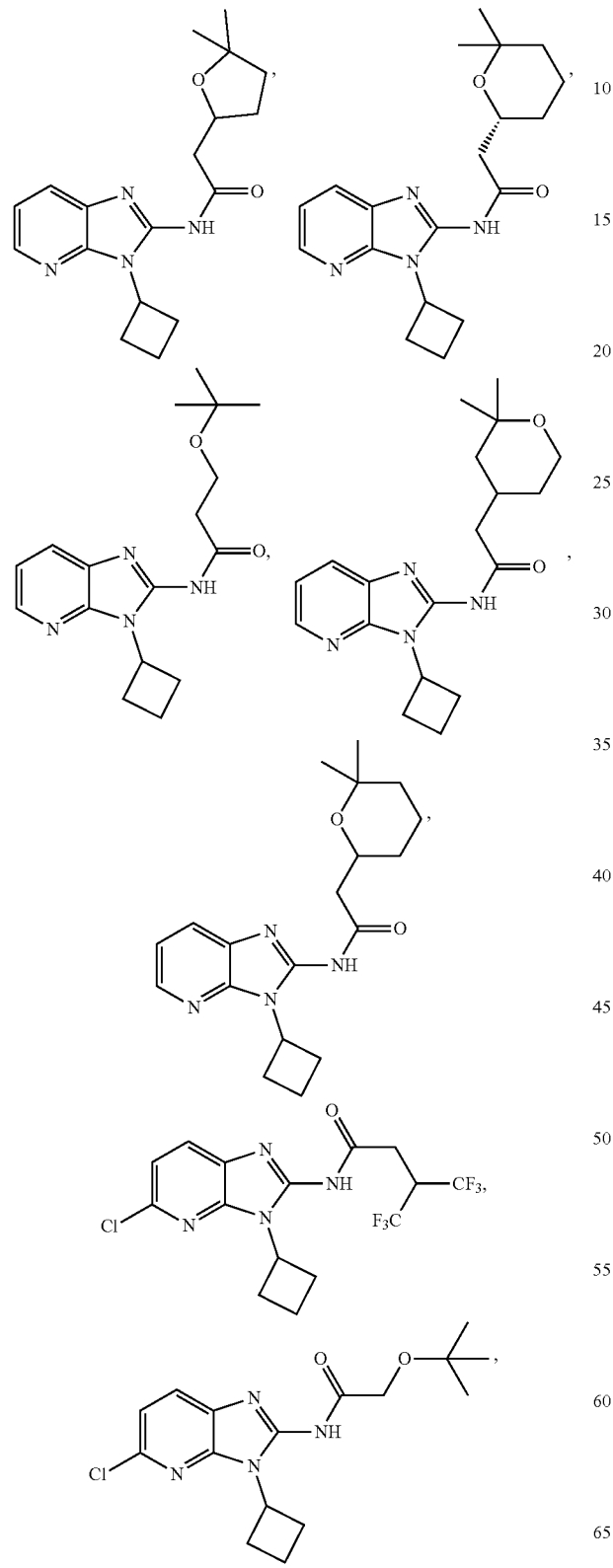
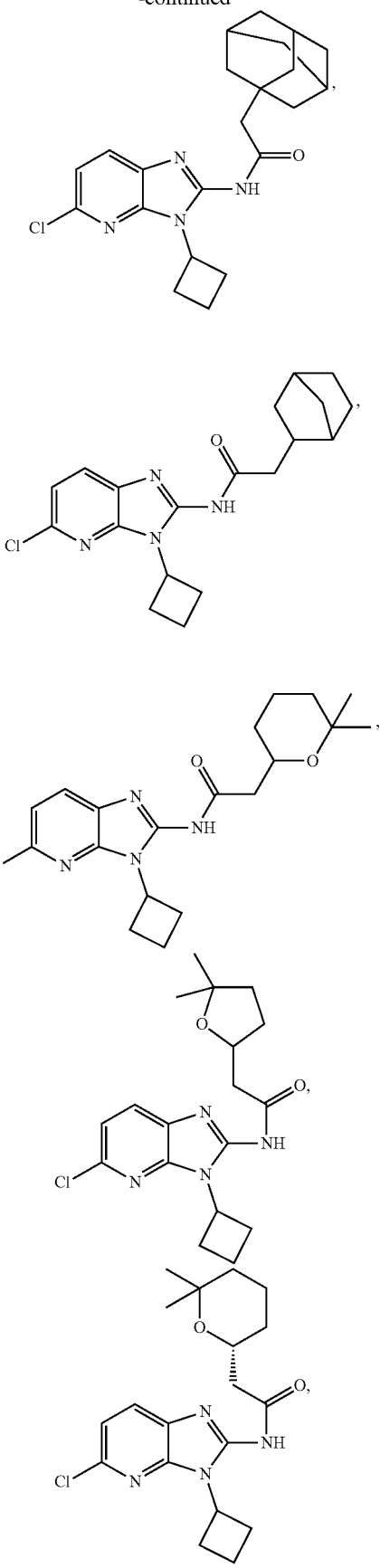

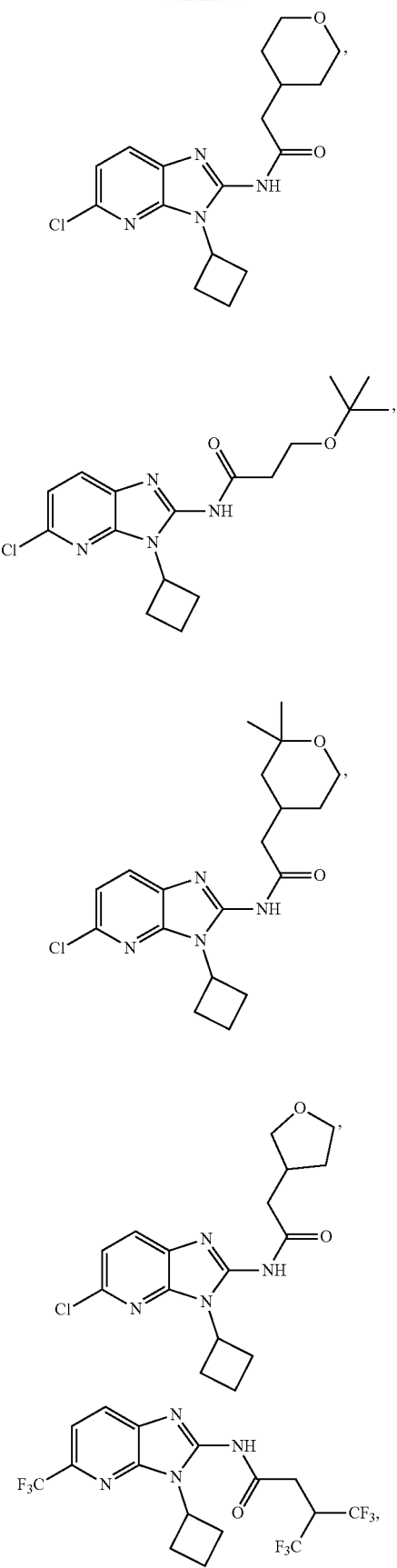
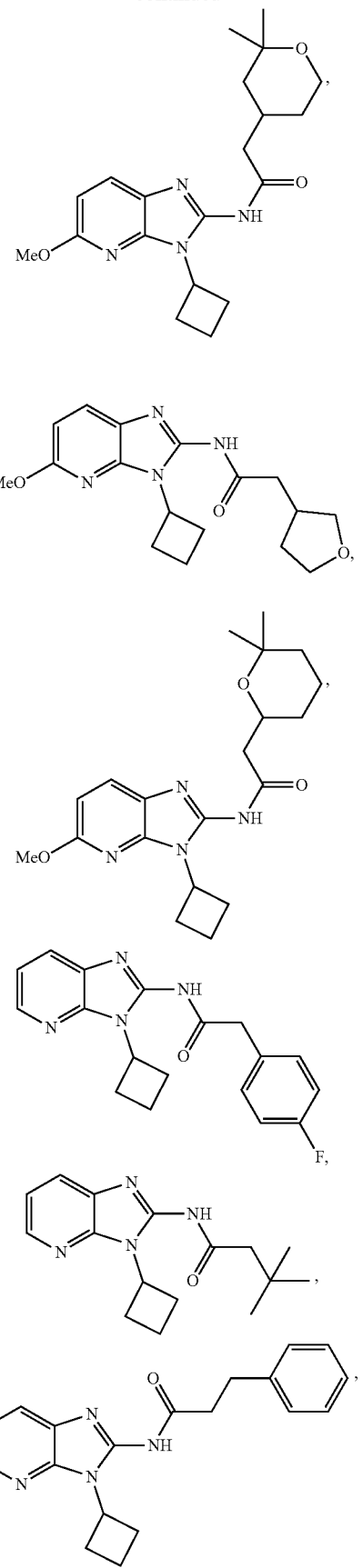

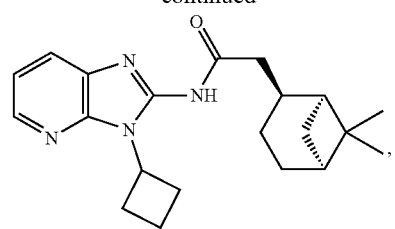
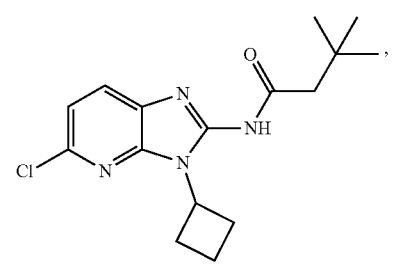
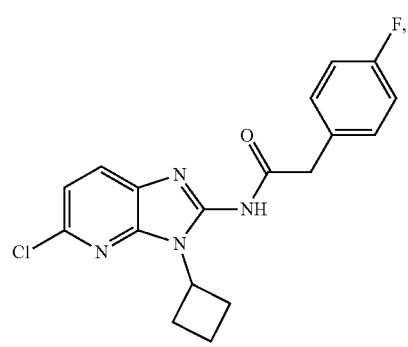
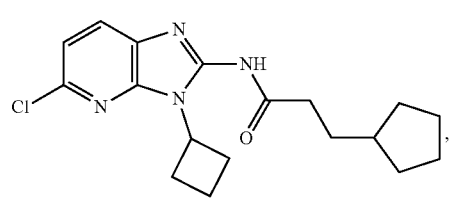
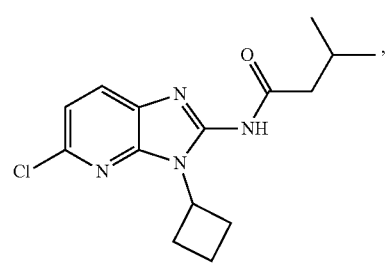
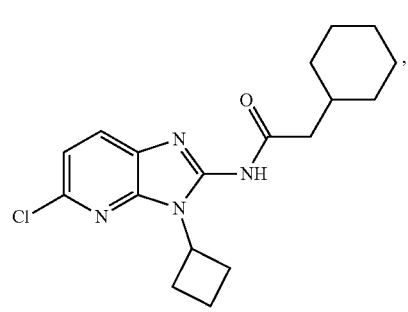
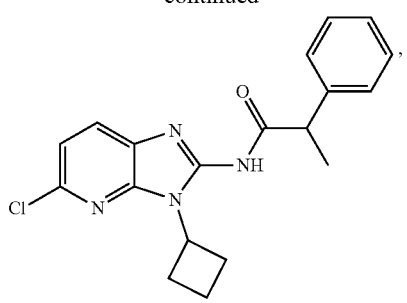
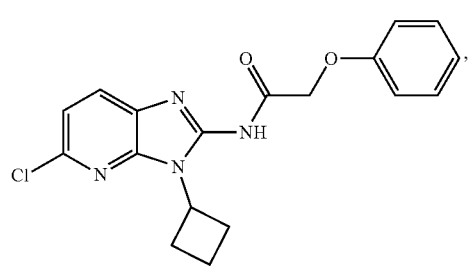
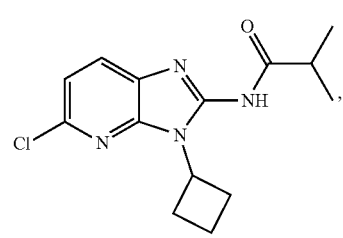
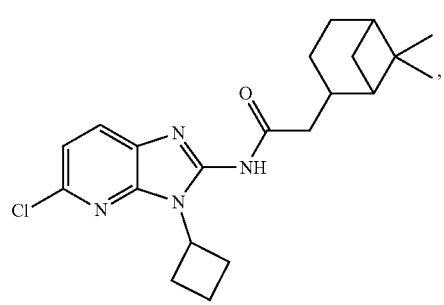
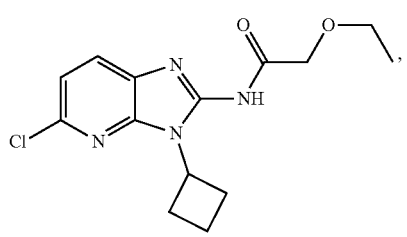
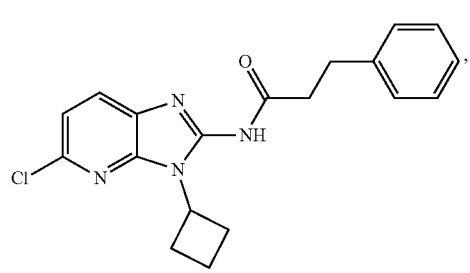

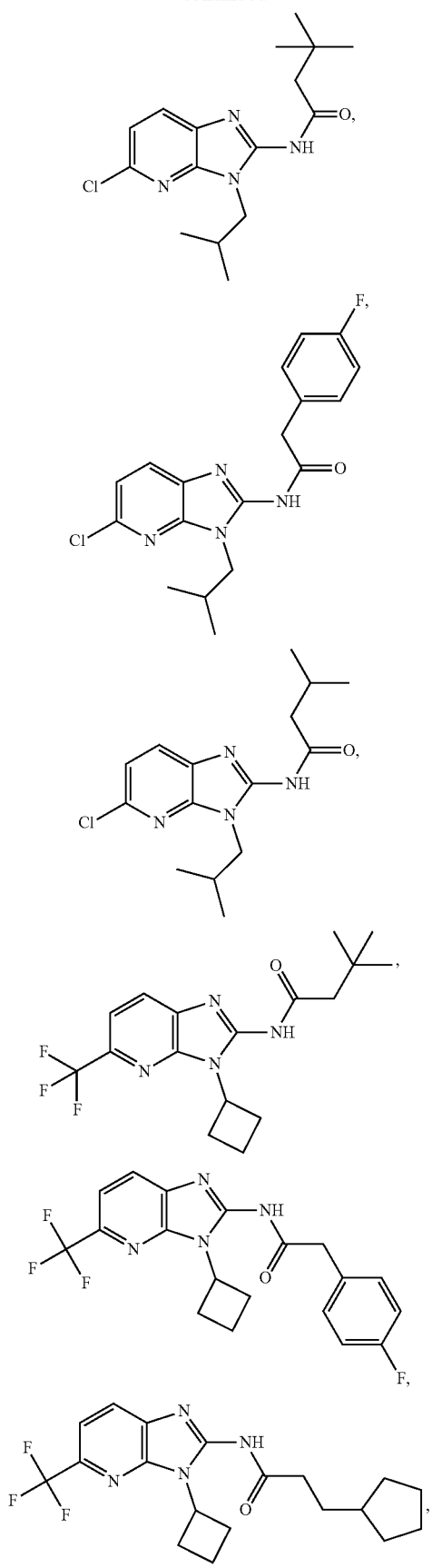
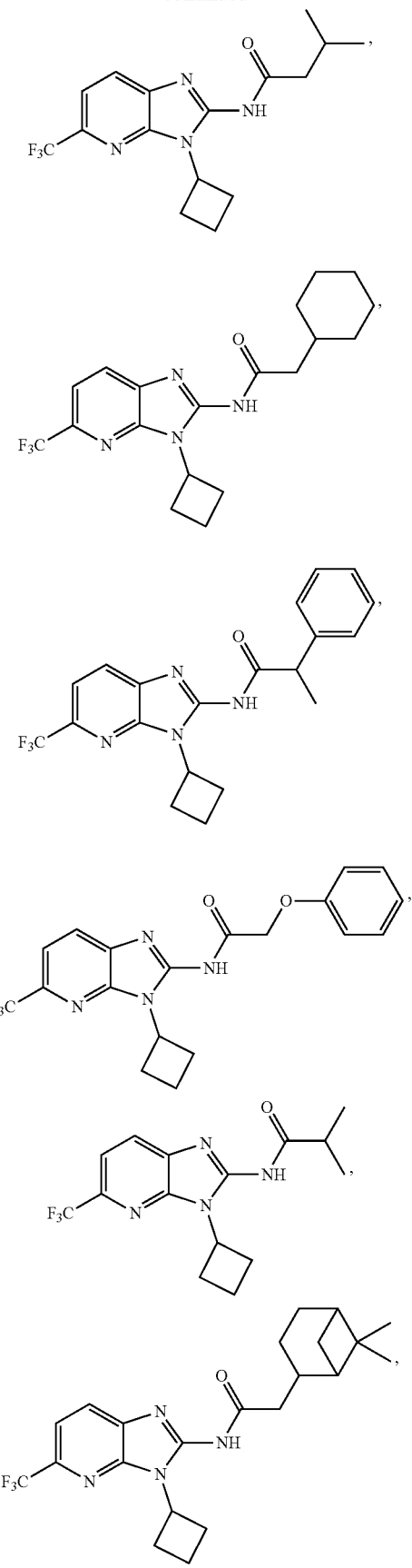

-continued
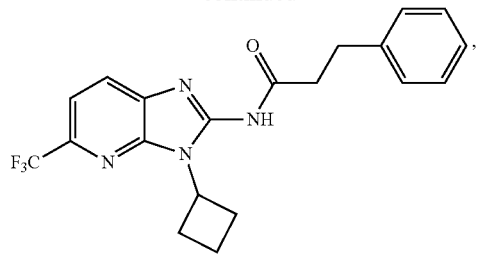
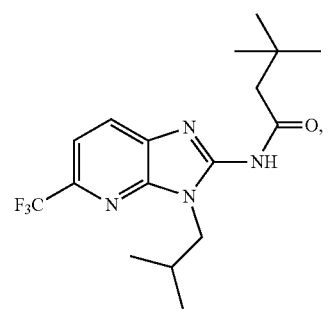
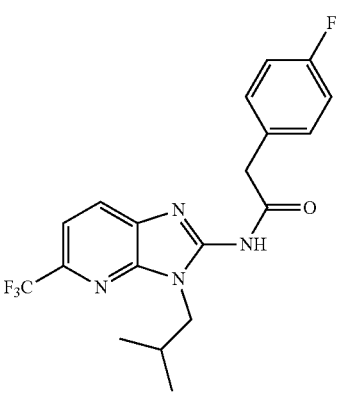
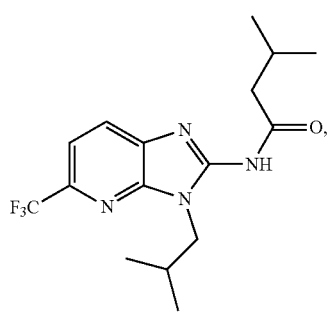
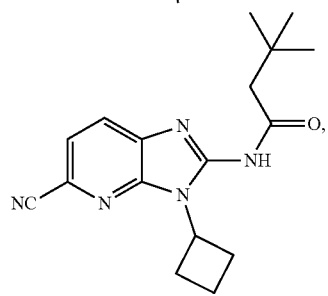
-continued
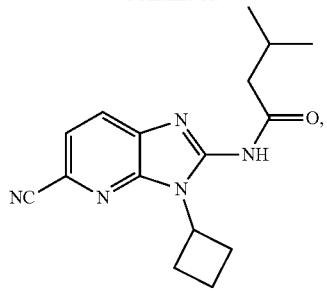
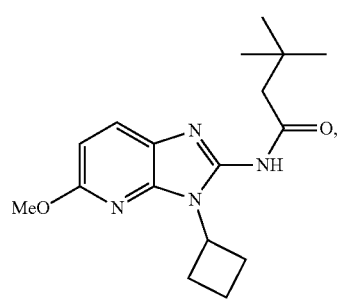
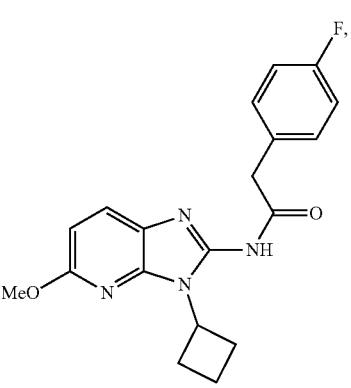
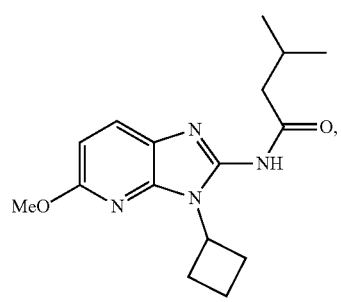
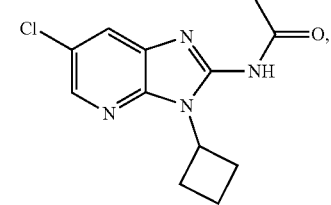

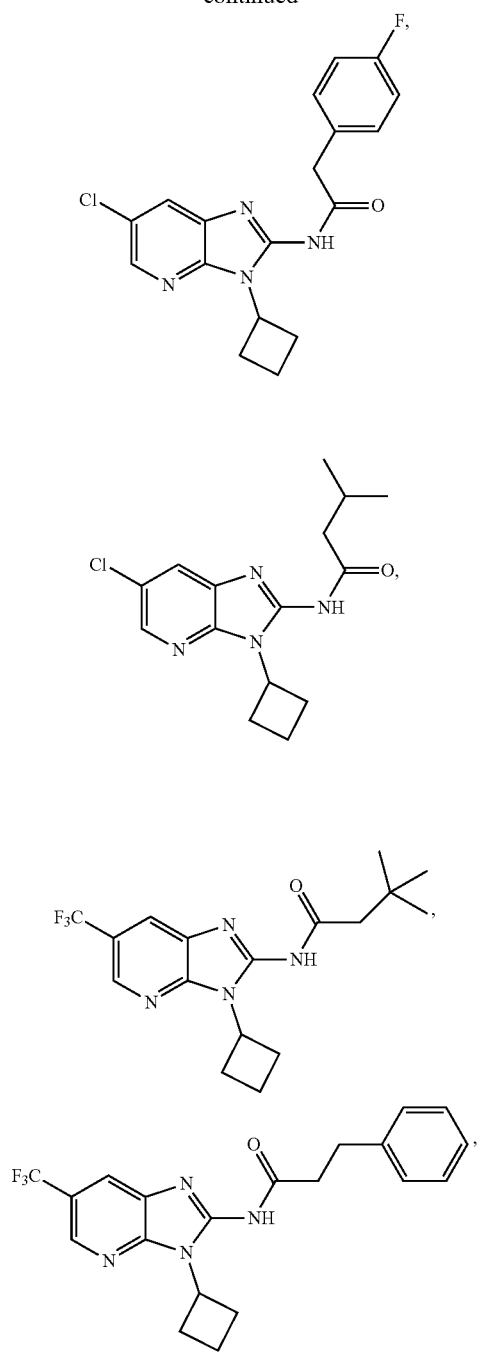
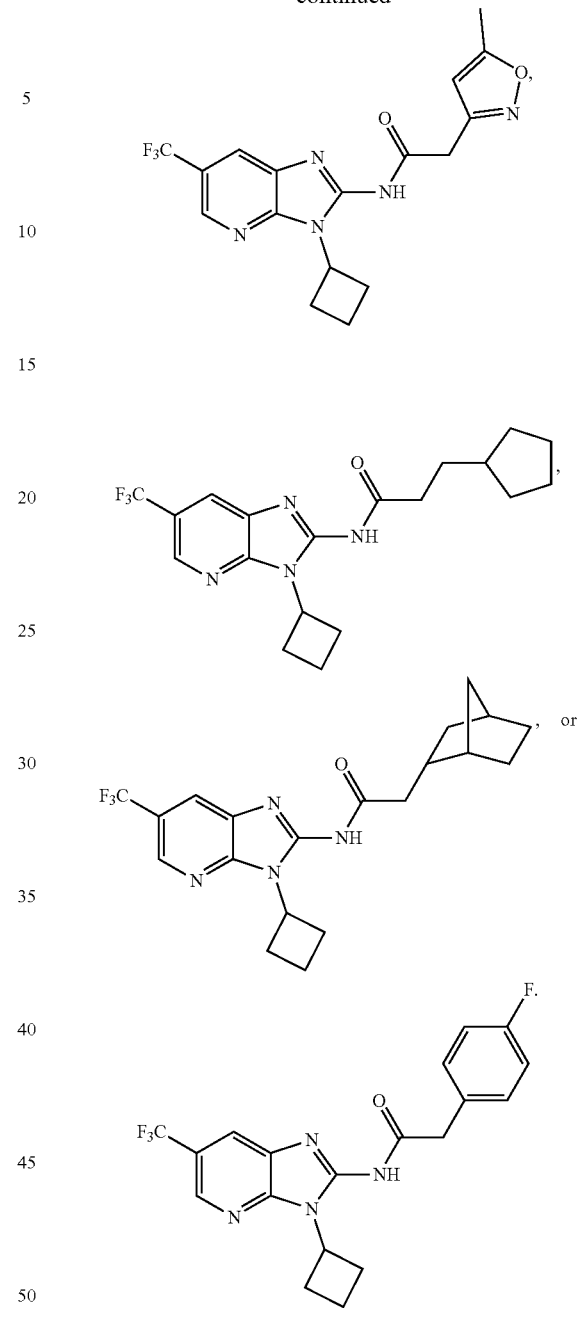
EXPERIMENTAL SECTION
Scheme 1
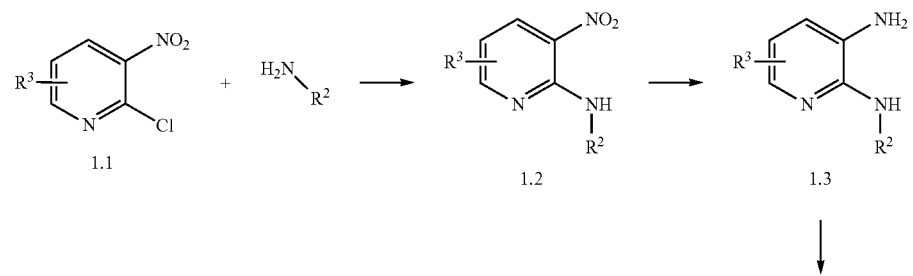

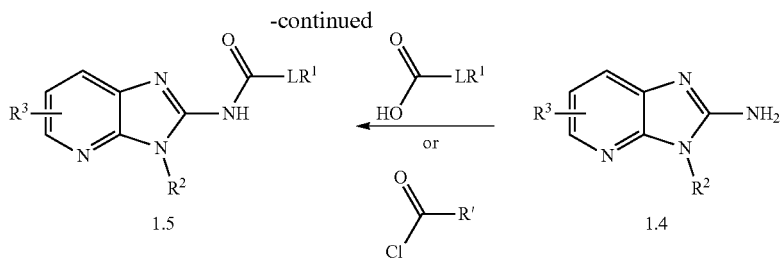

Scheme 1 shows a general methodology for the synthesis of 3H-imidazo[4,5-b]pyridines such as 1.5. An appropriately substituted 2-chloro-3-nitro pyridine 1.1 is reacted with a primary amine to afford 2-amino-3-nitropyridines 1.2. The nitro group may be reduced to the corresponding amine by a variety of well-established methods to provide diaminopyridines 1.3. Reaction of 1.3 with cyanogen bromide affords 3H-imidazo[4,5-b]pyridin-2-amines 1.4. Amide coupling with either an appropriate carboxylic acid or acyl chloride can afford 3H-imidazo[4,5-b]pyridine amides such as 1.5.

Synthetic Methods

Section 1. General Procedures for the Preparation of 3H-imidazo[4,5-b]pyridin-2-amine Intermediates (Scheme 1)

Method 1

Step A.

A mixture of appropriate 2-chloro-3-nitropyridine (1 eq), amine or amine hydrochloride (1.1 eq), and triethylamine (2.5 eq) in THF (~0.2 M) was stirred at ambient temperature until completion of reaction. The mixture was cooled to room temperature and diluted with EtOAc. The precipitated triethylamine hydrochloride was removed by filtration. The filtrate was concentrated and the residue was purified by column chromatography or by recrystallization.

Step B.

To a solution of appropriate 3-nitropyridin-2-amine (3.69 mmol) in EtOH (10 mL) was added iron powder (18 mmol) and a solution of ammonium chloride (18 mmol) in water (4 mL). The mixture was heated in a microwave reactor at 140° C. for 30 min. Alternatively, the mixture was heated to reflux for 2 h. The mixture was diluted with EtOAc, filtered through Celite and concentrated to provide the title compound which was used in the next step without further purification.

Step C.

To a solution of appropriate pyridine-2,3-diamine (3.5 mmol) in EtOH (17 mL) was added a solution of cyanogen bromide (3 M in CH₂Cl₂, 1.7 mL, 5.2 mmol). The mixture was stirred at room temperature for 18 h, then concentrated in-vacuo. The residue was partitioned between EtOAc and saturated aqueous NaHCO₃. The organic layer was dried over sodium sulfate and concentrated. The residue was purified by precipitation with dichloromethane or by column chromatography.

Section 2. Procedures for the Synthesis of Intermediates for Use in Method 1, Step B or Step C for the Preparation of 2-amino-3H-imidazo[4,5-b]pyridines Method 2. 6-(Cyclobutylamino)-5-nitropicolinonitrile for Use in Method 1, Step B for Preparation of 2-amino-3-cyclobutyl-3H-imidazo[4,5-b]pyridine-5-carbonitrile

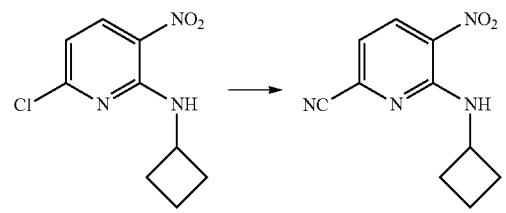 [SMILES: O=[N+]([O-])c1ccc(Cl)nc1NC1CCC1 ; N#Cc1ccc([N+](=O)[O-])c(NC2CCC2)n1]

A mixture of 6-chloro-N-cyclobutyl-3-nitropyridin-2-amine (prepared by procedure described in Method 1, Step A; 100 mg, 0.439 mmol), rac-2-(di-tert-butylphosphino)-1,1'-binaphthyl (15 mg, 0.039 mmol), zinc (0.5 mg, 8.0 μmol), zinc cyanide (29 mg, 0.25 mmol), and palladium(II) trifluoroacetate (6.3 mg, 0.019 mmol) in 1-methyl-2-pyrrolidinone (1 mL) was purged with N₂ (g) by bubbling into the mixture for 5 min. The mixture was heated to 95° C. in a sealed vial for 18 h. The mixture was diluted with EtOAc and washed with water 5 times. The organic layer was dried over sodium sulfate, concentrated and purified by column chromatography (0-50%, EtOAc/hexanes) to give 43 mg (45% yield) of the title compound. MS (ESI) m/z 217.2 (MH⁻).

Method 3. 6-Cyclopropyl-3-nitro-N-(2,2,2-trifluoroethyl)pyridin-2-amine for Use in Method 1, Step B for Preparation of 5-cyclopropyl-3-(2,2,2-trifluoroethyl)-3H-imidazo[4,5-b]pyridin-2-amine

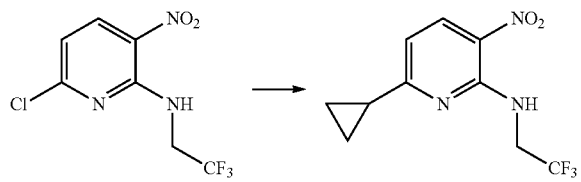 [SMILES: O=[N+]([O-])c1ccc(Cl)nc1NCC(F)(F)F ; O=[N+]([O-])c1ccc(C2CC2)nc1NCC(F)(F)F]

To a degassed mixture of 6-chloro-3-nitro-N-(2,2,2-trifluoroethyl)pyridin-2-amine (prepared by procedure described in Method 1, Step A; 500 mg, 1.96 mmol), cyclopropylboronic acid (336 mg, 3.91 mmol), and potassium phosphate (1.2 g, 5.87 mmol) in a 9:1 mixture of THF/water (10 mL) was added palladium acetate (44 mg, 0.20 mmol) and S-Phos (161 mg, 0.390 mmol). The mixture was stirred at 100° C. for 24 h in a sealed tube, then cooled to ambient temperature and concentrated. The crude mixture was purified by column chromatography (0-20% EtOAc/hexanes) to provide 6-cyclopropyl-3-nitro-N-(2,2,2-trifluoroethyl)pyridin-2-amine (250 mg, 49%). MS (ESI) m/z 262.4 (MH+).

Method 4. 6-Isopropoxy-3-nitro-N-(2,2,2-trifluoroethyl)pyridin-2-amine for Use in Method 1, Step B for Preparation of 5-isopropoxy-3-(2,2,2-trifluoroethyl)-3H-imidazo[4,5-b]pyridin-2-amine

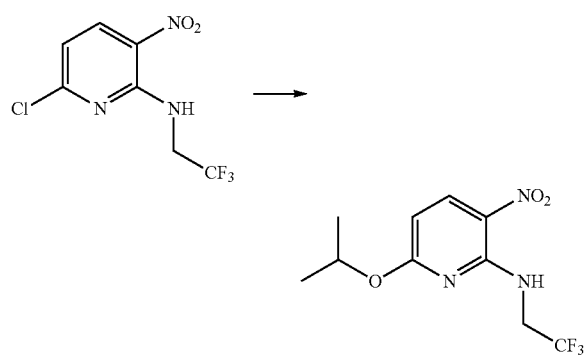

To a solution of 6-chloro-3-nitro-N-(2,2,2-trifluoroethyl)pyridin-2-amine (prepared by procedure described in Method 1, Step A; 500 mg, 1.96 mmol) in isopropanol (10 mL) at room temperature was added 60% sodium hydride (171 mg, 3.91 mmol). The mixture was stirred at room temperature for 4 h before it was partitioned between water (100 mL) and EtOAc (100 mL). The aqueous layer was extracted with EtOAc (3×50 mL), and the combined organic layers were washed with brine (2×50 mL), dried over sodium sulfate, filtered, and concentrated. The crude mixture was purified by column chromatography (0-20%, EtOAc/hexanes) to provide 6-isopropoxy-3-nitro-N-(2,2,2-trifluoroethyl)pyridin-2-amine (220 mg, 40%). MS (ESI) m/z 280.0 (MH+).

The following intermediates were prepared with an analogous procedure and appropriate starting materials:
6-(benzyloxy)-N-cyclobutyl-3-nitropyridin-2-amine
N-cyclobutyl-3-nitro-6-(pyridin-2-ylmethoxy)pyridin-2-amine
N-cyclobutyl-6-((1-methyl-1H-pyrazol-5-yl)methoxy)-3-nitropyridin-2-amine Method 5. 5,6-Dichloro-3-nitro-N-(2,2,2-trifluoroethyl)pyridin-2-amine for Use in Method 1, Step B for Preparation of 5,6-dichloro-3-(2,2,2-trifluoroethyl)-3H-imidazo[4,5-b]pyridin-2-amine

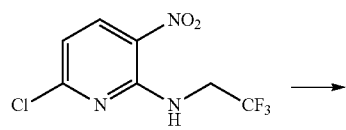

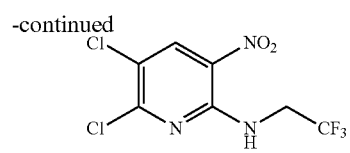

To a solution of 6-chloro-3-nitro-N-(2,2,2-trifluoroethyl)pyridin-2-amine (prepared by procedure described in Method 1, Step A; 600 mg, 2.35 mmol) in acetic acid (12 mL) at room temperature was added N-chlorosuccinimide (345 mg, 2.58 mmol). The mixture was warmed to 80° C. for 2 h before it was cooled to ambient temperature and concentrated. The crude mixture was purified by column chromatography (0-20% EtOAc/hexanes) to provide 5,6-dichloro-3-nitro-N-(2,2,2-trifluoroethyl)pyridin-2-amine (475 mg, 70%). MS (ES, Neg) m/z 288.0 (M−1).

The following intermediates were prepared with an analogous procedure:
5,6-dichloro-N-cyclobutyl-3-nitropyridin-2-amine
5-chloro-N-cyclobutyl-3-nitro-6-(trifluoromethyl)pyridin-2-amine Method 6. 3-Nitro-N-(2,2,2-trifluoroethyl)-6-vinylpyridin-2-amine for Use in Method 1, Step B for Preparation of 3-(2,2,2-trifluoroethyl)-5-vinyl-3H-imidazo[4,5-b]pyridin-2-amine

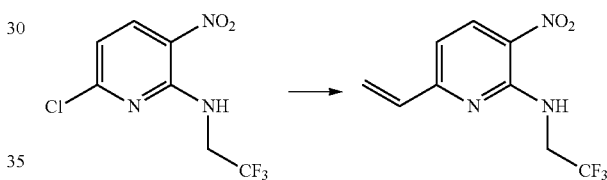

To a degassed mixture of 6-chloro-3-nitro-N-(2,2,2-trifluoroethyl)pyridin-2-amine (prepared by procedure described in Method 1, Step A; 400 mg, 1.8 mmol), potassium vinyltrifluoroborate (353 mg, 2.6 mmol), and cesium carbonate (1.7 g, 5.3 mmol) in a 5:1 mixture of THF/water (9 mL) was added tetrakis(triphenyphosphine) palladium (0) (200 mg, 0.18 mmol). The mixture was stirred at 80° C. for 12 h in a sealed tube, then cooled to ambient temperature and partitioned between saturated aqueous sodium bicarbonate solution (10 mL) and EtOAc (20 mL). The aqueous phase was extracted with EtOAc (3×10 mL), and the combined organic layers were washed with brine (1×10 mL), dried over sodium sulfate, filtered, and concentrated. The crude mixture was purified by column chromatography (0-20% EtOAc/hexanes) to provide 3-nitro-N-(2,2,2-trifluoroethyl)-6-vinylpyridin-2-amine (220 mg, 51%). MS (ESI) m/z 248.4 (MH+).

Method 7. N-Cyclobutyl-6-morpholino-3-nitropyridin-2-amine for Use in Method 1, Step B for Preparation of 3-cyclobutyl-5-morpholino-3H-imidazo[4,5-b]pyridin-2-amine

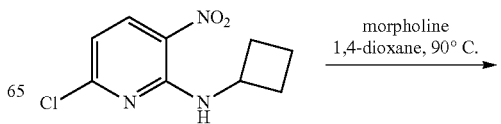

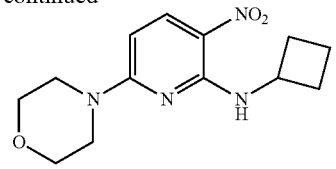

A solution of 6-chloro-N-cyclobutyl-3-nitropyridin-2-amine (prepared by procedure described in Method 1, Step A; 530 mg, 2.3 mmol) and morpholine (0.60 mL, 6.9 mmol) in 1,4-dioxane (10 mL) was heated at 90° C. for 2 h. The reaction was cooled to room temperature, concentrated in vacuo and the residue used directly in the next step.

Method 8. N-Cyclobutyl-5-nitro-[2,3'-bipyridin]-6-amine for Use in Method 1, Step B for Preparation of 3-cyclobutyl-5-(pyridin-3-yl)-3H-imidazo[4,5-b]pyridin-2-amine

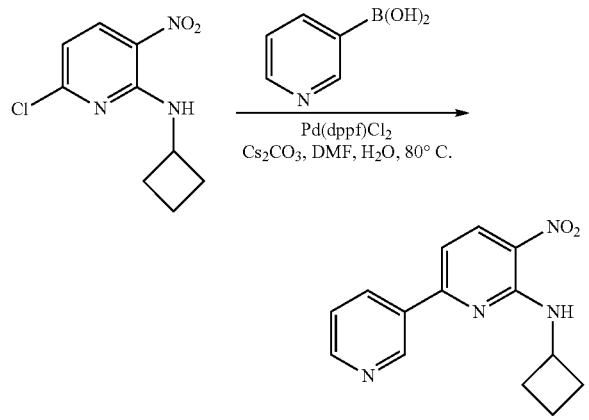

A suspension of 6-chloro-N-cyclobutyl-3-nitropyridin-2-amine (prepared by procedure described in Method 1, Step A; 560 mg, 2.45 mmol), pyridin-3-ylboronic acid (360 mg, 2.9 mmol), Pd(dppf)Cl₂ (204 mg, 0.25 mmol), and cesium carbonate (2.4 g, 7.4 mmol) in DMF (10 mL) and water (5 mL) was heated at 85° C. for 2 h. The reaction was cooled to room temperature and partitioned between water and dichloromethane. The aqueous layer was extracted with CH₂Cl₂. The combined organic layers were dried over sodium sulfate, concentrated in vacuo, and purified by chromatography to provide 0.49 g, (74%) of title compound.

Method 9. N-Cyclobutyl-6-ethynyl-3-nitropyridin-2-amine for Use in Method 1, Step B for Preparation of 3-cyclobutyl-5-ethynyl-3H-imidazo[4,5-b]pyridin-2-amine

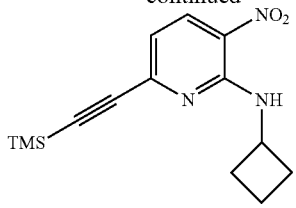

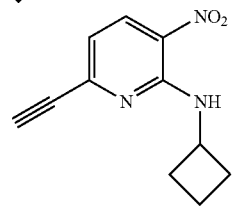

Step A.

A mixture of 6-chloro-N-cyclobutyl-3-nitropyridin-2-amine (prepared by procedure described in Method 1, Step A; 250 mg, 1.10 mmol), trimethylsilylacetylene (140 mg, 1.42 mmol), Pd(PPh₃)₂Cl₂ (39 mg, 0.055 mmol), CuI (11 mg, 0.055 mmol), and triethylamine (460 μL, 3.30 mmol) in toluene (10 mL) was stirred under N₂ (g) at room temperature for 5 h. The mixture was diluted with EtOAc and washed with saturated aqueous ammonium chloride. The organic layer was dried over sodium sulfate and concentrated. Column chromatography (0-50% EtOAc/hexanes) provided 295 mg (90% yield) of N-cyclobutyl-3-nitro-6-((trimethylsilyl)ethynyl)pyridin-2-amine.

Step B.

A mixture of N-cyclobutyl-3-nitro-6-((trimethyl silyl)ethynyl)pyridin-2-amine (280 mg, 0.967 mmol) and potassium carbonate (401 mg, 2.90 mmol) in dichloromethane (5 mL) and methanol (2.5 mL) was heated to 50° C. and stirred overnight. Volatiles were removed in-vacuo. Then the residue was taken up in dichloromethane and solids were removed by filtration. The filtrate was concentrated and the residue was purified by column chromatography (0-50% EtOAc/hexanes) to provide 130 mg (63% yield) of N-cyclobutyl-6-ethynyl-3-nitropyridin-2-amine. MS (ESI) m/z 218 (MH⁺).

Method 10. N,N-Bis-tert-butyl-(6-(cyclobutylamino)-5-nitropyridin-2-yl)carbamate

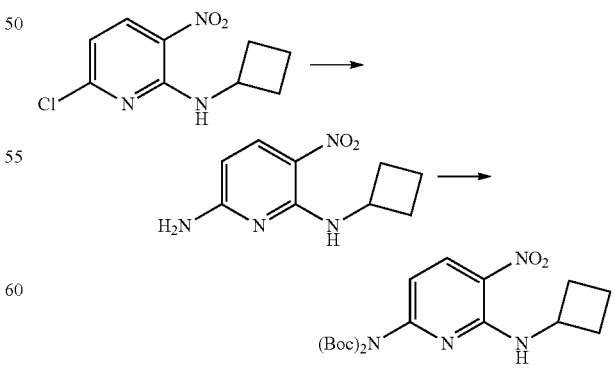

A solution of 6-chloro-N-cyclobutyl-3-nitropyridin-2-amine (540 mg, 2.4 mmol) and concentrated aqueous ammonia (prepared by procedure described in Method 1, Step A;

830 mg, 24 mmol) in EtOH (10 mL) was heated at 50° C. for 3 days in a sealed tube. The reaction was cooled to room temperature and concentrated in vacuo. The residue was partitioned between dichloromethane and water. The organic solution was dried over sodium sulfate and concentrated in vacuo.

The resultant residue was taken up in dichloromethane (~10 mL) and treated with di-tert-butyl dicarbonate (570 mg, 2.6 mmol) and DMAP (15 mg, 0.12 mmol). The reaction was stirred at room temperature overnight and then purified by flash column chromatography (0-100% EtOAc/hexanes) to afford the title compound (0.96 g, 98% for 2 steps).

Method 11. N-Cyclobutyl-6-(ethylthio)-3-nitropyridin-2-amine for Use in Method 1, Step B for Preparation of 3-cyclobutyl-5-(ethylthio)-3H-imidazo[4,5-b]pyridin-2-amine

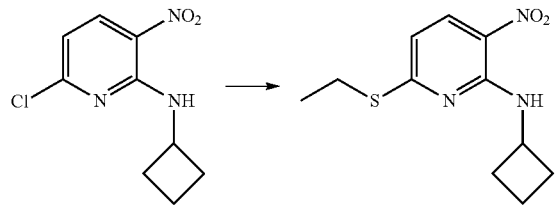 [SMILES: O=[N+]([O-])c1ccc(Cl)nc1NC1CCC1 ; CCSc1ccc([N+](=O)[O-])c(NC2CCC2)n1]

To a solution of 6-chloro-N-cyclobutyl-3-nitropyridin-2-amine (prepared by procedure described in Method 1, Step A; 800 mg, 3.52 mmol, 1 eq) in DMF (5 mL) was added ethanethiol (0.4 mL, 5.20 mmol, 1.5 eq) via syringe. Solid potassium carbonate (1.5 g, 10.5 mml, 3 eq) was added in one portion. The flask was capped and allowed to stir overnight at room temperature. The mixture was diluted with hexanes and EtOAc (approx 1:1, 75 mL) and washed with sodium bicarbonate (2 times, saturated) and brine. It was dried over sodium sulfate, filtered and concentrated to give a crude oil. This material was purified by column chromatography (5-20% EtOAc/hexanes) to give the desired product as a solid (700 mg, 78% yield). Rf=0.75 in 20% EtOAc in hexanes. MS (ESI) m/z 254 (MH+).

Method 12. $N^2$—Cyclobutyl-6-fluoropyridine-2,3-diamine for Use in Method 1, Step C for Preparation of 3-cyclobutyl-5-fluoro-3H-imidazo[4,5-b]pyridin-2-amine

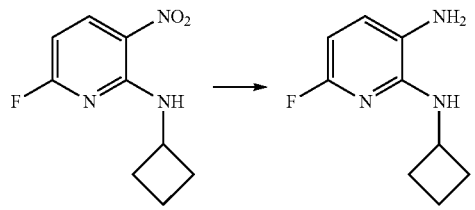 [SMILES: O=[N+]([O-])c1ccc(F)nc1NC1CCC1 ; Nc1ccc(F)nc1NC1CCC1]

To a solution of N-cyclobutyl-6-fluoro-3-nitropyridin-2-amine (prepared from 2,6-difluoro-3-nitropyridine: Shackelford et al. *J. Org. Chem.* 2003, 68, 267, then with Method 1, step A; 350 mg, 1.65 mmol, 1 eq) in MeOH/chloroform (9:1, 10 mL) was added Pd/C (10%, 100 mg) in one portion. After a few minutes, triethylsilane (2 mL, 16.5 mmol, 10 eq) was added dropwise via syringe to produce heat and gas. The reaction was allowed to stir for 30 minutes and then passed though a plug of Celite and concentrated. The crude residue was chromatographed (10-50% EtOAc/hexanes) to give the desired product (45 mg, 15% yield).

Method 13. N-(3-Methylisoxazol-5-yl)-6-(trifluoromethyl)pyridine-2,3-diamine for Use in Method 1, Step C for Preparation of 3-(3-methylisoxazol-5-yl)-5-(trifluoromethyl)-3H-imidazo[4,5-b]pyridin-2-amine

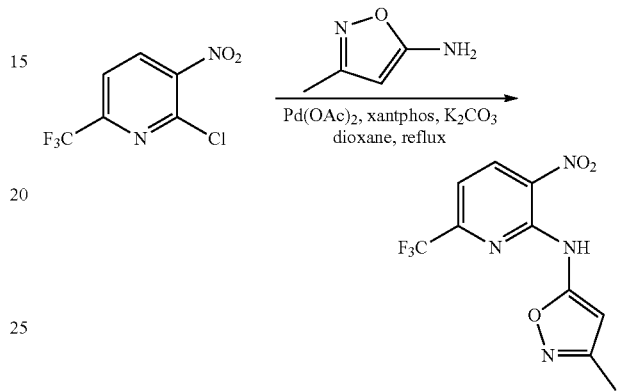

Step A. 3-Methyl-N-(3-nitro-6-(trifluoromethyl)pyridin-2-yl)isoxazol-5-amine

Palladium(II) acetate (0.099 g, 0.441 mmol) was added to xantphos (0.511 g, 0.883 mmol) in degassed dioxane (25 mL) and the suspension was stirred for 15 min under $N_2$. The resulting solution was added to a mixture of 2-chloro-3-nitro-6-(trifluoromethyl)pyridine (1.00 g, 4.41 mmol), 3-methylisoxazol-5-amine (0.520 g, 5.30 mmol) and $K_2CO_3$ (0.915 g, 6.62 mmol) in degassed dioxane (60 mL) and the reaction mixture was refluxed overnight. Conversion was confirmed by TLC (Rf P=0.4; 30% EtOAc/Hexanes) and the solution was filtered through a plug of celite. The volatiles were removed and the crude residue was purified via column chromatography (0-100% EtOAc/hexanes) to give 0.750 g (59%) of the title compound. MS (ESI) m/z 289 (MH+).

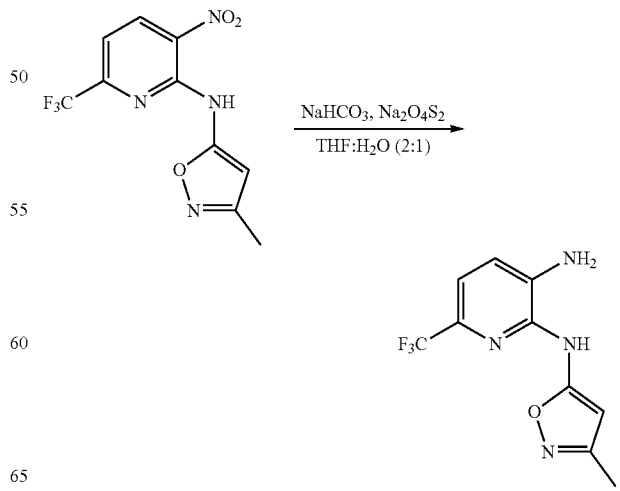

Step B. N-(3-Methylisoxazol-5-yl)-6-(trifluoromethyl)pyridine-2,3-diamine

Sodium bicarbonate (0.437 g, 5.20 mmol), then sodium hydrosulfite (1.36 g, 7.81 mmol) were added to a solution of 3-methyl-N-(3-nitro-6-(trifluoromethyl)pyridin-2-yl)isoxazol-5-amine (0.750 g, 2.60 mmol) in THF/H$_2$O (2:1; 26 mL). The resulting reaction mixture was allowed to stir for 4 h before confirming reaction completion (TLC; Rf p=0.4 10% MeOH/DCM), diluting with H$_2$O and extracting (EtOAc, 2×). The combined organics were dried (MgSO$_4$) and the volatiles were removed to leave a crude residue that was purified via chromatography (0-5% MeOH/DCM) to give 311 mg (46%) of the title compound. MS (ESI) m/z 259 (MH$^+$).

The following compounds were prepared by a procedure analogous to that described for 3-methyl-N-(3-nitro-6-(trifluoromethyl)pyridin-2-yl)isoxazol-5-amine, but with appropriate starting materials:

N-(5-Fluoropyridin-2-yl)-3-nitro-6-(trifluoromethyl)pyridin-2-amine

N-(6-Methylpyridin-3-yl)-3-nitro-6-(trifluoromethyl)pyridin-2-amine

N-(1-Methyl-1H-1,2,3-triazol-4-yl)-3-nitro-6-(trifluoromethyl)pyridin-2-amine

5-Methyl-N-(6-methyl-3-nitropyridin-2-yl)-1,3,4-oxadiazol-2-amine

The Following 3H-Imidazo[4,5-b]Pyridin-2-Amines were Prepared Using the General Procedures Described in Section 1 with Appropriate Starting Materials.

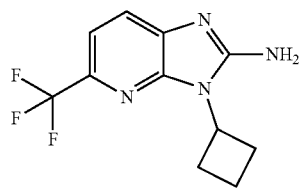

3-Cyclobutyl-5-(trifluoromethyl)-3H-imidazo[4,5-b]pyridin-2-amine

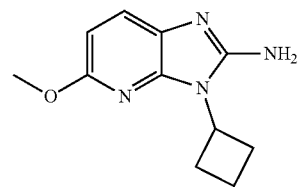

3-Cyclobutyl-5-methoxy-3H-imidazo[4,5-b]pyridin-2-amine

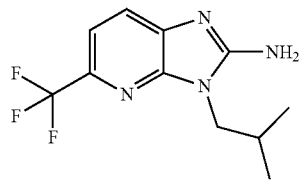

3-isobutyl-5-(trifluoromethyl)-3H-imidazo[4,5-b]pyridin-2-amine

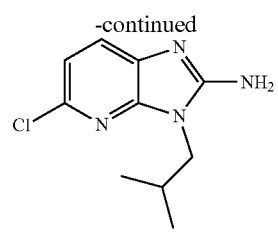

5-chloro-3-isobutyl-3H-imidazo[4,5-b]pyridin-2-amine

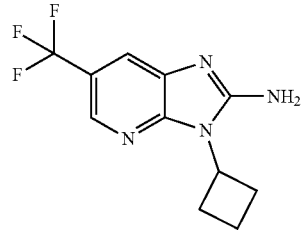

3-Cyclobutyl-6-(trifluoromethyl)-3H-imidazo[4,5-b]pyridin-2-amine

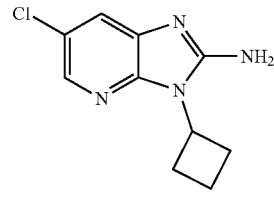

6-chloro-3-cyclobutyl-3H-imidazo[4,5-b]pyridin-2-amine

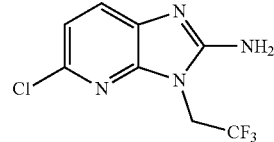

5-chloro-3-(2,2,2-trifluoroethyl)-3H-imidazo[4,5-b]pyridin-2-amine

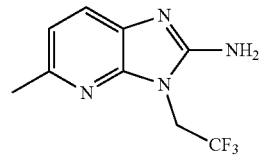

5-methyl-3-(2,2,2-trifluoroethyl)-3H-imidazo[4,5-b]pyridin-2-amine

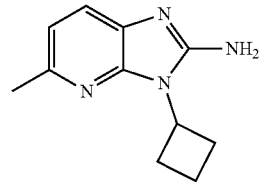

3-cyclobutyl-5-methyl-3H-imidazo[4,5-b]pyridin-2-amine

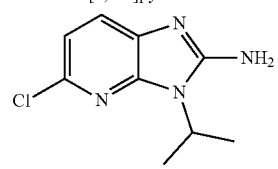

5-chloro-3-isopropyl-3H-imidazo[4,5-b]pyridin-2-amine

-continued

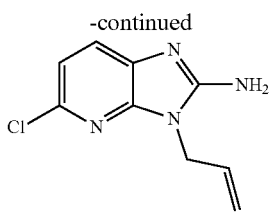

3-allyl-5-chloro-3H-
imidazo[4,5-b]pyridin-2-amine

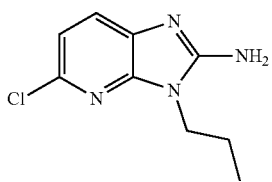

5-chloro-3-propyl-3H-
imidazo[4,5-b]pyridin-2-amine

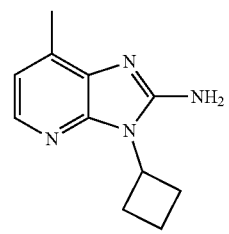

3-cyclobutyl-7-methyl-3H-
imidazo[4,5-b]pyridin-2-amine

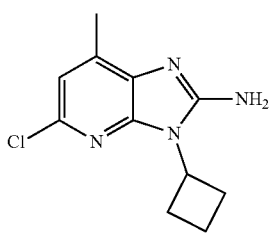

5-chloro-3-cyclobutyl-7-methyl-3H-
imidazo[4,5-b]pyridin-2-amine

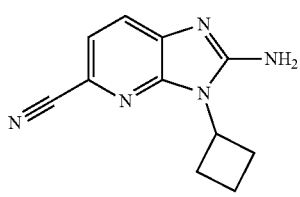

2-Amino-3-cyclobutyl-3H-
imidazo[4,5-b]pyridine-5-carbonitrile

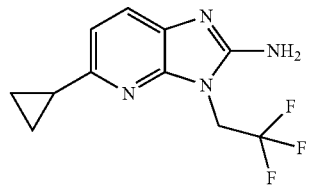

5-cyclopropyl-3-(2,2,2-trifluoroethyl)-3H-
imidazo[4,5-b]pyridin-2-amine

-continued

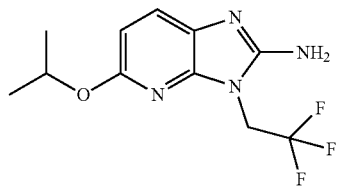

5-isopropoxy-3-(2,2,2-trifluoroethyl)-3H-
imidazo[4,5-b]pyridin-2-amine

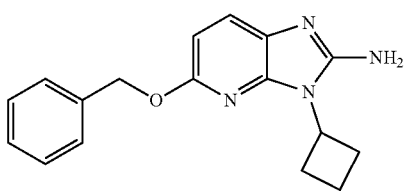

5-(benzyloxy)-3-cyclobutyl-3H-
imidazo[4,5-b]pyridin-2-amine

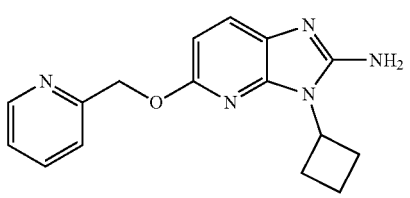

3-cyclobutyl-5-(pyridin-2-ylmethoxy)-3H-
imidazo[4,5-b]pyridin-2-amine

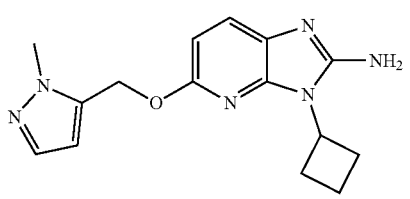

3-cyclobutyl-5-((1-methyl-1H-pyrazol-5-yl)methoxy)-3H-
imidazo[4,5-b]pyridin-2-amine

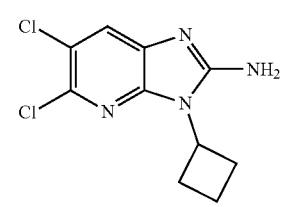

5,6-dichloro-3-cyclobutyl-3H-
imidazo[4,5-b]pyridin-2-amine

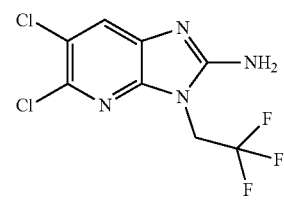

5,6-dichloro-3-(2,2,2-trifluoroethyl)-3H-
imidazo[4,5-b]pyridin-2-amine

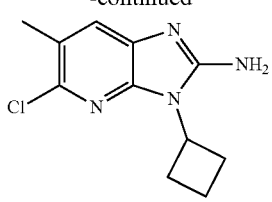

5-chloro-3-cyclobutyl-6-methyl-3H-
imidazo[4,5-b]pyridin-2-amine

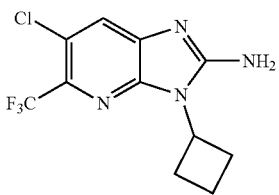

6-chloro-3-cyclobutyl-5-(trifluoromethyl)-3H-
imidazo[4,5-b]pyridin-2-amine

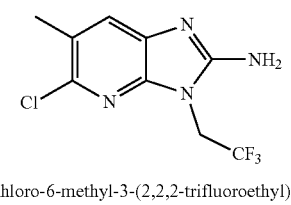

5-chloro-6-methyl-3-(2,2,2-trifluoroethyl)-3H-
imidazo[4,5-b]pyridin-2-amine

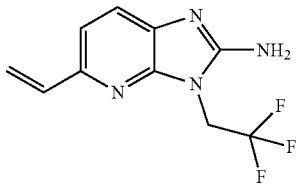

3-(2,2,2-trifluoroethyl)-5-vinyl-3H-
imidazo[4,5-b]pyridin-2-amine

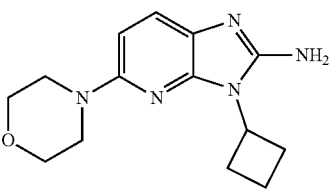

3-cyclobutyl-5-morpholino-3H-
imidazo[4,5-b]pyridin-2-amine

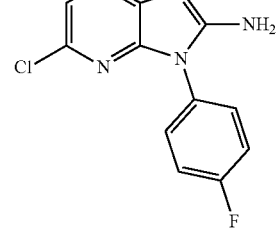

5-chloro-3-(4-fluorophenyl)-3H-
imidazo[4,5-b]pyridin-2-amine

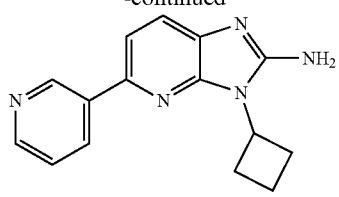

3-cyclobutyl-5-(pyridin-3-yl)-3H-
imidazo[4,5-b]pyridin-2-amine

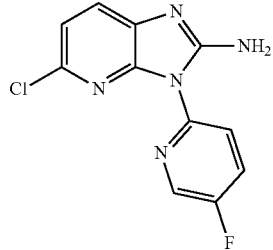

5-Chloro-3-(5-fluoropyridin-2-yl)-3H-
imidazo[4,5-b]pyridin-2-amine

3-Isopropyl-5-(trifluoromethyl)-3H-
imidazo[4,5-b]pyridin-2-amine

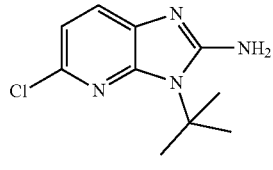

3-(tert-butyl)-5-chloro-3H-
imidazo[4,5-b]pyridin-2-amine

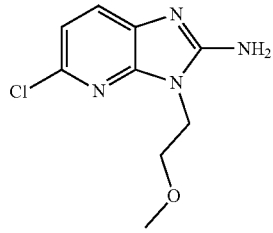

5-chloro-3-(2-methoxyethyl)-3H-
imidazo[4,5-b]pyridin-2-amine

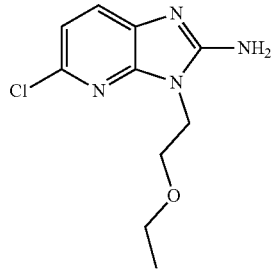

5-chloro-3-(2-ethoxyethyl)-3H-
imidazo[4,5-b]pyridin-2-amine

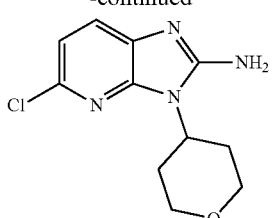

5-chloro-3-(tetrahydro-2H-pyran-4-yl)-3H-
imidazo[4,5-b]pyridin-2-amine

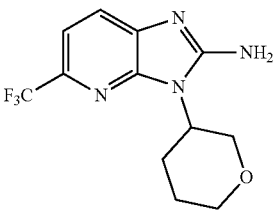

3-(tetrahydro-2H-pyran-3-yl)-5-(trifluoromethyl)-3H-
imidazo[4,5-b]pyridin-2-amine

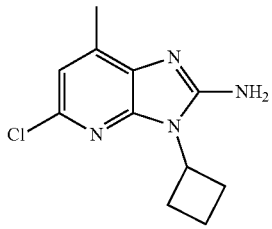

5-chloro-3-cyclobutyl-7-methyl-3H-
imidazo[4,5-b]pyridin-2-amine

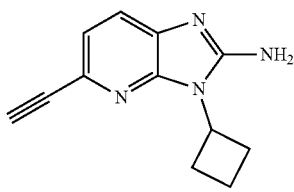

3-cyclobutyl-5-ethynyl-3H-
imidazo[4,5-b]pyridin-2-amine

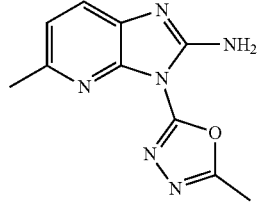

5-methyl-3-(5-methyl-1,3,4-oxadiazol-2-yl)-3H-
imidazo[4,5-b]pyridin-2-amine

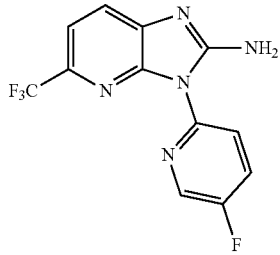

3-(5-fluoropyridin-2-yl)-5-(trifluoromethyl)-3H-
imidazo[4,5-b]pyridin-2-amine

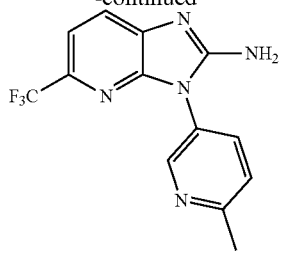

3-(6-methylpyridin-3-yl)-5-(trifluoromethyl)-3H-
imidazo[4,5-b]pyridin-2-amine

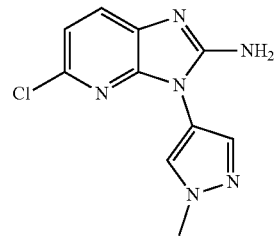

5-chloro-3-(1-methyl-1H-pyrazol-4-yl)-3H-
imidazo[4,5-b]pyridin-2-amine

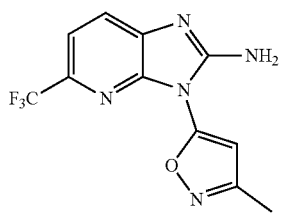

3-(3-methylisoxazol-5-yl)-5-(trifluoromethyl)-3H-
imidazo[4,5-b]pyridin-2-amine

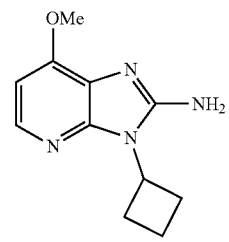

3-cyclobutyl-7-methoxy-3H-
imidazo[4,5-b]pyridin-2-amine

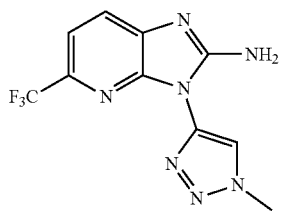

3-(1-methyl-1H-1,2,3-triazol-4-yl)-5-(trifluoromethyl)-3H-
imidazo[4,5-b]pyridin-2-amine Section 3. Alternative Procedures for the Synthesis of 3H-imidazo[4,5-b]pyridin-2-amine Intermediates Method 14. Preparation of 3-cyclobutyl-5-(4-methoxypiperidin-1-yl)-3H-imidazo[4,5-b]pyridin-2-amine Step A. Preparation of N-cyclobutyl-6-(4-methoxypiperidin-1-yl)-3-nitropyridin-2-amine

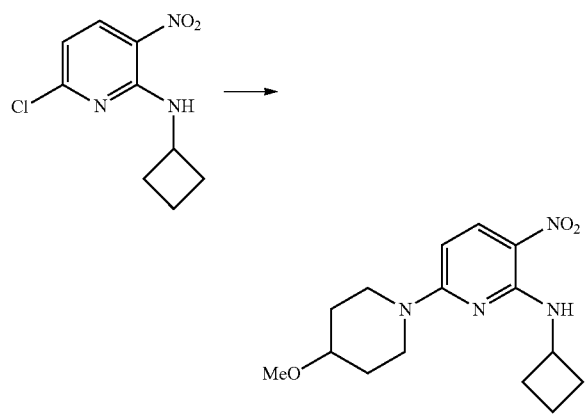

6-Chloro-N-cyclobutyl-3-nitropyridin-2-amine (prepared by procedure described in Method 1, Step A; 500 mg, 2.2 mmol) was dissolved in THF (0.5 mL) and 4-methoxypiperidine (2 equivalents) was added at ambient temperature. The reaction was stirred at ambient temperature overnight and concentrated. Recrystallization from EtOH afforded the title compound as a dark-yellow crystalline solid (0.48 g, 1.6 mmol).

Step B. Preparation of N²-cyclobutyl-6-(4-methoxypiperidin-1-yl)pyridine-2,3-diamine

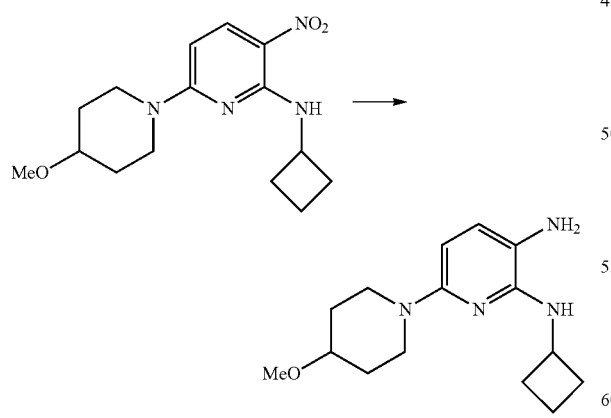

N²-Cyclobutyl-6-(4-methoxypiperidin-1-yl)pyridine-2,3-diamine was prepared from N-cyclobutyl-6-(4-methoxypiperidin-1-yl)-3-nitropyridin-2-amine via an analogous procedure described in Method 1, Step B. The crude product used directly in Step C of the title compound synthesis.

Step C. Preparation of N-(3-cyclobutyl-5-(4-methoxycyclohexyl)-3H-imidazo[4,5-b]pyridin-2-yl)benzamide

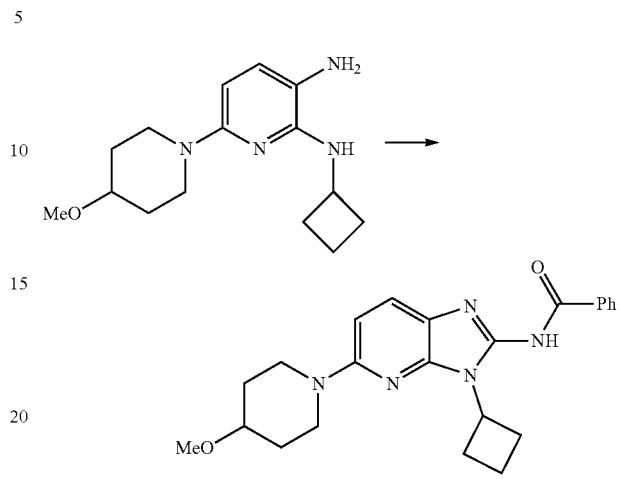

A solution of N²-cyclobutyl-6-(4-methoxypiperidin-1-yl)pyridine-2,3-diamine (405 mg, 1.47 mmol) in anhydrous THF (10 mL) was treated at ambient temperature under a nitrogen atmosphere with benzoylisothiocyanate (0.22 mL, 1.1 equivalents), followed by N,N'-dicyclohexylcarbodiimide (910 mg, 3 equivalents). The reaction mixture was heated at 80° C. for 18 h and allowed to cool to ambient temperature. The mixture was concentrated, treated with water, and the resulting material extracted with dichloromethane and EtOAc. The combined organics were dried over anhydrous sodium sulfate and concentrated. Chromatography on silica with 0-2% MeOH in dichloromethane as eluent afforded a partially purified desired product (229 mg), which was carried directly into Step D.

Step D. Preparation of 3-cyclobutyl-5-(4-methoxypiperidin-1-yl)-3H-imidazo[4,5-b]pyridin-2-amine

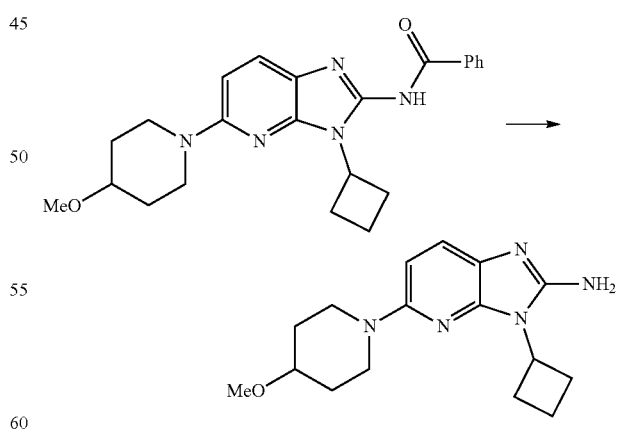

A solution of N-(3-cyclobutyl-5-(4-methoxycyclohexyl)-3H-imidazo[4,5-b]pyridin-2-yl)benzamide (200 mg) in MeOH (5 mL) was treated with hydrazine (0.2 mL) at ambient temperature under nitrogen. The reaction vessel was sealed and heated at 100° C. until the reaction was judged complete by LC/MS analysis. The reaction mixture was cooled, concentrated, and the residue chromatographed on silica (0-10% MeOH/DCM) to afford the title compound (125 mg). MS (ESI) m/z 302 (MH+).

Method 15. Synthesis of 3-cyclobutyl-3H-imidazo[4,5-b]pyridin-2-amine

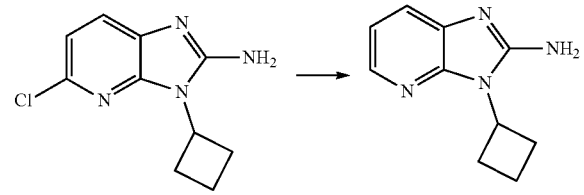 [SMILES: Nc1nc2ccc(Cl)nc2n1C1CCC1 ; Nc1nc2cccnc2n1C1CCC1]

A mixture of 5-chloro-3-cyclobutyl-3H-imidazo[4,5-b]pyridin-2-amine (800 mg, 3.59 mmol), ammonium formate (4.5 g, 72 mmol), and 10% palladium on carbon (100 mg) in EtOH (70 mL) was heated to 50° C. for 18 h. The mixture was filtered through Celite© and concentrated. Column chromatography (0-10% MeOH/DCM) provided 742 mg of title compound with formic acid (as indicated by ¹H NMR). The solid was dissolved in EtOAc and washed with aqueous saturated NaHCO₃. The organic layer was dried over sodium sulfate and concentrated to provide 0.66 g (98%) of title compound. MS (ESI) m/z 189.2 (MH+).

The following compound was prepared according to the method described in Method 15, but with 5-chloro-3-(2,2,2-trifluoroethyl)-3H-imidazo[4,5-b]pyridin-2-amine as the starting material: 3-(2,2,2-trifluoroethyl)-3H-imidazo[4,5-b]pyridin-2-amine.

Section 6. Preparation of Acids

Method 16. Preparation of 2-(2,2-dimethylcyclopropyl)acetic acid

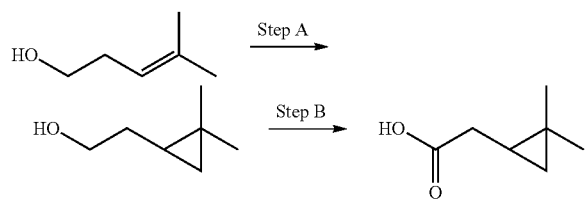

Step A.

To a solution of diiodomethane (0.19 mL, 2.4 mmol) in dichloromethane (6 mL) at 0° C. was added diethylzinc solution (1M in hexane, 2.4 mL, 2.4 mmol). After 10 min, 4-methyl-3-penten-1-ol (0.20 mL, 1.2 mmol) was added. The mixture was allowed to warm to room temperature over 2.5 h. The mixture was quenched with water, then partitioned between EtOAc and aqueous 1 N hydrochloric acid. The aqueous portion was extracted with dichloromethane 2 times. The combined organic extracts were dried over sodium sulfate and concentrated to give 137 mg of 2-(2,2-dimethylcyclopropyl)ethanol, which was used in the next step without further purification.

Step B.

To a solution of 2-(2,2-dimethylcyclopropyl)ethanol (135 mg, 1.20 mmol) in acetone (15 mL) was added Jones reagent (1.8 mL). After 2 h, the mixture was quenched with 1 mL of isopropanol, then partitioned between ether and water. The aqueous layer was extracted again with ether. The organic layer was dried over sodium sulfate and concentrated to provide 100 mg (65% yield) of 2-(2,2-dimethylcyclopropyl)acetic acid. ¹H NMR (CDCl₃): δ 2.37 (dd, J=7.6, 3.2 Hz, 2H), 1.08 (s, 3H), 1.06 (s, 3H), 0.91-0.83 (m, 1H), 0.54 (dd, J=8.6, 4.6 Hz, 1H), 0.054 (t, J=4.8 Hz, 1H).

Method 17. Procedure for Synthesis of [3.2.0]-oxabicyclic acetic acids

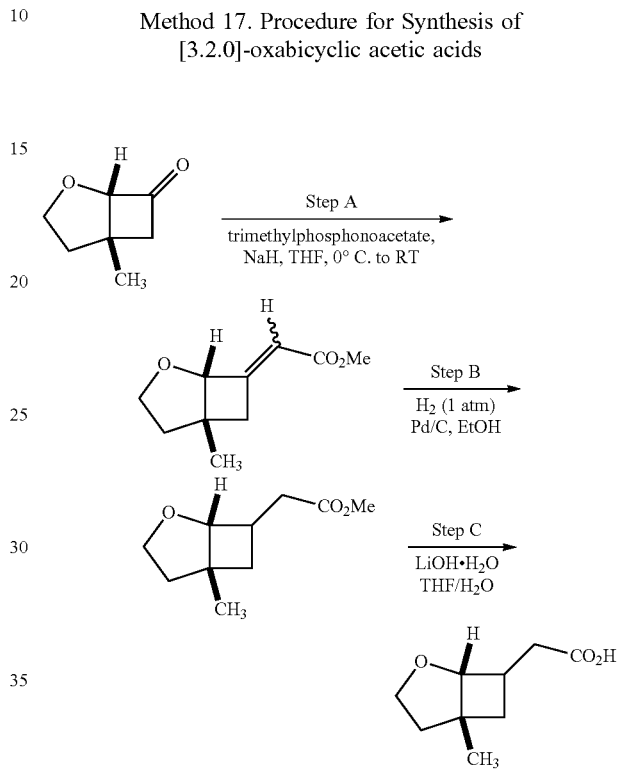

Step A. Synthesis of (Z) and (E)-methyl 2-((1S,5R)-5-methyl-2-oxabicyclo[3.2.0]heptan-7-ylidene)acetate To a suspension of sodium hydride (80 mg, 60% dispersion, 2.0 mmol) in THF (4 mL) at 0° C. under nitrogen, was added trimethylphosphonoacetate (360 mg, 2.0 mmol). The reaction was stirred at 0° C. for 20 min and then (1S,5S)-5-methyl-2-oxabicyclo[3.2.0]heptan-7-one (Snider, B. B. et al. J. Am. Chem. Soc. 1985, 107, 2194; 230 mg, 1.8 mmol) in THF (4 mL) was added. The reaction was warmed to room temperature overnight (20 h) and quenched with saturated aqueous sodium bicarbonate. The mixture was extracted with EtOAc. LC-MS analysis of the crude extracts showed 2 peaks (2:1 ratio by UV), both with m/z=183 (M+H for desired products). The combined organic extracts were dried over sodium sulfate, concentrated in vacuo, and purified by flash column chromatography (0-60% EtOAc/hexanes) to afford the (Z) (130 mg) and (E) (100 mg) isomers as clear colorless oils (combined yield of 69%). Isomer assignments were based on NOESY experiments.

(E) isomer: ¹H NMR (CDCl₃): δ 5.92 (td, J=3.8, 1.2 Hz, 1H), 4.47 (t, J=1.2 Hz, 1H), 4.14-4.10 (m, 1H), 3.90-3.85 (m, 1H), 3.71 (s, 3H), 2.87-2.78 (m, 2H), 1.87 (ddd, J=4.8, 1.7, 0.6 Hz, 1H), 1.69 (d, J=7.9 Hz, 1H), 1.54 (s, 1H), 1.37 (s, 3H).

(Z) isomer: $^1$H NMR (CDCl$_3$): δ 5.78 (q, J=2.3H, 1H), 4.82 (q, J=1.7 Hz, 1H), 4.17 (td, J=7.8, 1.3 Hz, 1H), 3.90-3.85 (m, 1H), 3.73 (s, 3H), 2.58-2.52 (m, 2H), 1.87 (ddd, J=12.2, 5.4, 0.8 Hz, 1H), 1.75-1.69 (m, 1H), 1.35 (s, 3H).

Step B. Synthesis of methyl 2-((1R,5R)-5-methyl-2-oxabicyclo[3.2.0]heptan-7-yl)acetates A solution of (E)-methyl 2-((1S,5R)-5-methyl-2-oxabicyclo[3.2.0]heptan-7-ylidene)acetate (70 mg, 0.38 mmol) in EtOH (5 mL) was purged with nitrogen for 15 min and then palladium on carbon (50 mg, 10% Pd/C, 50% water) was added. The mixture was purged with nitrogen for an additional 2 min and then the reaction was capped with a hydrogen balloon and stirred for 4 h at room temperature. Analysis by LC-MS showed no UV peaks and 2 peaks in the TIC (~1:1 ratio) with m/z=185. The reaction was purged with nitrogen for 15 min and filtered through Celite. The filtrate was concentrated in vacuo and purified by flash column chromatography (0-60% EtOAc/hexanes) to afford a single isomeric product (stereochemistry was not assigned; designated as diastereomer A; 46 mg, 66%) as a clear, colorless oil.

(Z)-methyl 2-((1S,5R)-5-methyl-2-oxabicyclo[3.2.0]heptan-7-ylidene)acetate (110 mg, 0.55 mmol) was subjected to similar conditions to afford diastereomer A (35 mg, 32%) and diastereomer B (70 mg, 64%) as clear, colorless oils. NMR data:

Diastereomer A: $^1$H NMR (CDCl$_3$): δ 4.15 (TD, J=9.1, 1.5 Hz, 1H), 4.07 (dd, J=5.6, 3.9 Hz, 1H), 3.95-3.90 (m, 1H), 3.65 (s, 3H), 2.78-2.74 (m, 1H), 2.48 (dd, J=16.2, 8.0 Hz, 1H), 2.30 (dd, J=17.2, 7.8 Hz, 1H), 1.98 (td, J=9.5, 2.9 Hz, 1H), 1.68 (ddd, J=12.0, 6.6, 1.4 Hz, 1H), 1.61-1.59 (m, 1H), 1.49 (dd, J=12.1, 9.1 Hz, 1H), 1.33 (s, 3H).

Diastereomer B: $^1$H NMR (CDCl$_3$): δ 4.14-4.08 (m, 1H), 4.01-3.96 (m, 1H), 3.82 (dd, J=1.9, 1.0 Hz, 1H), 3.67 (s, 3H), 2.56 (dd, J=15.3, 6.9 Hz, 1H), 2.44 (dd, J=15.2, 9.0 Hz, 1H), 2.38-2.34 (m, 1H), 1.99 (dd, J=12.5, 9.5 Hz, 1H), 1.76 (ddd, J=12.2, 5.8, 2.3 Hz, 1H), 1.62-1.56 (m, 1H), 1.43 (dd, J=12.6, 6.4 Hz, 1H), 1.39 (s, 3H).

Step C. Synthesis of 2-((1R,5R)-5-methyl-2-oxabicyclo[3.2.0]heptan-7-yl)acetic acids To a solution of methyl 2-((1R,5R)-5-methyl-2-oxabicyclo[3.2.0]heptan-7-yl)acetate (diastereomer A, 89 mg, 0.48 mmol) in THF (2.5 mL) and water (0.8 mL) was added LiOH*H$_2$O (31 mg, 0.73 mmol). The reaction was stirred at room temperature for 23 h and then quenched with dilute aqueous HCl. Brine (10 mL) was added and the mixture was extracted with EtOAc. The combined organic extracts were dried over sodium sulfate, filtered, and concentrated in vacuo to afford the titled compound (41 mg, 50%) as a clear, colorless film. $^1$H NMR (CDCl$_3$): δ 4.19 (td, J=7.6, 1.6 Hz, 1H), 4.12 (dd, J=5.7, 2.9 Hz, 1H), 3.98-3.93 (m, 1H), 2.78-2.73 (m, 1H), 2.51 (dd, J=16.1, 8.7 Hz, 1H), 2.35 (dd, J=16.1, 7.3 Hz, 1H), 2.00 (ddd, J=9.6, 2.9, 2.6 Hz, 1H), 1.71 (ddd, J=12.1, 5.7, 1.5 Hz, 1H), 1.64-1.58 (m, 1H), 1.51 (dd, J=12.2, 9.0 Hz, 1H), 1.33 (s, 3H) [note: CO$_2$H was not observed].

Subjection of diastereomer B (80 mg, 0.43 mmol) to similar conditions afforded the corresponding acid (29 mg, 40%). $^1$H NMR (CDCl$_3$): δ 4.11 (tdd, J=9.1, 2.4, 1.6 Hz, 1H), 4.03-3.98 (m, 1H), 3.85 (d, J=2.0 Hz, 1H), 2.59 (dd, J=15.6, 7.4 Hz, 1H), 2.47 (dd, J=15.6, 8.6 Hz, 1H), 3.99-3.60 (m, 1H), 2.02 (dd, J=12.6, 9.5 Hz, 1H), 1.78 (ddd, J=13.2, 5.8, 2.4 Hz, 1H), 1.63-1.57 (m, 1H), 1.44 (dd, J=12.6, 6.5 Hz, 1H), 1.30 (s, 3H) [note: CO$_2$H was not observed].

Method 18. Procedure for Synthesis of [2.2.1]oxabicyclic acetic acids

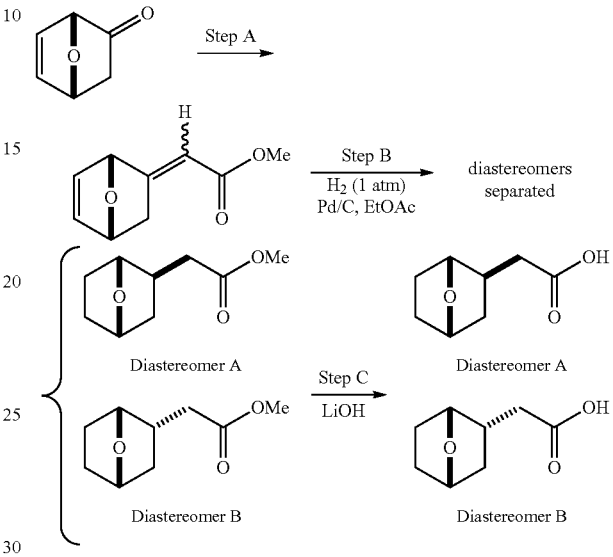

Step A. Synthesis of (Z) and (E)-methyl 2-((1R, 4R)-7-oxabicyclo[2.2.1]hept-5-en-2-ylidene)acetates To a suspension of sodium hydride (840 mg, 60% dispersion, 21 mmol) in THF (73 mL) at 0° C. under nitrogen, was added trimethylphosphonoacetate (3.6 g, 20.0 mmol). The reaction was stirred for 20 min at 0° C. and then (1R,4R)-7-oxabicyclo[2.2.1]hept-5-en-2-one (Black, K. A. et al. *Helv. Chim. Acta*, 1984, 1614; Warm, A . . . *Helv. Chim. Acta*, 1987, 70, 695; 2.0 g, 18.2 mmol) in THF (18 mL) was added over 10 min. The reaction was warmed slowly to room temperature and then stirred for 2 days. The reaction was quenched with saturated aqueous ammonium chloride (100 mL) and extracted with EtOAc. The combined organic extracts were dried over sodium sulfate, filtered, concentrated in vacuo, and purified by flash column chromatography (0-70% EtOAc/hexanes) to afford the titled compounds (1.67 g, 55%) as a 1.0:0.6 mixture (by $^1$H NMR) of alkene isomers (alkene geometry was not assigned).

Step B. Synthesis of methyl 2-((1R,2R,4S)-7-oxabicyclo[2.2.1]heptan-2-yl)acetate and methyl 2-((1R, 2S,4S)-7-oxabicyclo[2.2.1]heptan-2-yl)acetate A solution of (Z) and (E)-methyl 2-((1R,4R)-7-oxabicyclo[2.2.1]hept-5-en-2-ylidene)acetates (1.67 g, 10.1 mmol) in EtOAc (100 mL) was purged with nitrogen for 20 min. Palladium on carbon (300 mg, 10% Pd/C, 50% water) was added and the reaction was purged with nitrogen for 2 min before being capped with a hydrogen balloon and stirred at room temperature for 4 h. The reaction was purged with nitrogen for 20 min and then filtered through Celite. The filtrate was concentrated in vacuo and purified by flash column chromatography (0-70% EtOAc/hexanes) to afford diastereomer A (0.50 g, 29%), diastereomer B (0.38 g, 22%), and mixed fractions (780 mg, 45%, 1:3 mixture of diastereomer A to B). Assignment of the relative stereochemistry was done based on NOESY experiments and ChemDraw3D modeling.

Diastereomer A: $^1$H NMR (CDCl$_3$): δ 4.55 (t, J=5.5 Hz, 1H), 4.27 (d, J=4.8 Hz, 1H), 3.67 (s, 3H), 2.44 (quint, J=7.7 Hz, 1H), 2.25 (d, J=6.9 Hz, 1H), 2.21-2.11 (m, 1H), 1.76-1.62 (m, 3H), 1.53-1.38 (m, 2H), 1.33-1.30 (m, 1H).

Diastereomer B: $^1$H NMR (CDCl$_3$): δ 4.55 (dd, J=5.0, 4.9 Hz, 1H), 4.27 (d, J=4.8 Hz, 1H), 3.67 (s, 3H), 2.43 (q, J=7.7 Hz, 1H), 2.24 (d, J=6.9 Hz, 1H), 2.21-2.11 (m, 1H), 1.76-1.62 (m, 3H), 1.53-1.38 (m, 2H), 1.33-1.31 (m, 1H).

Step C. Synthesis of 2-((1R,2R,4S)-7-oxabicyclo[2.2.1]heptan-2-yl)acetic acid To a solution of methyl 2-((1R,1R,4S)-7-oxabicyclo[2.2.1]heptan-2-yl)acetate (Diastereomer A, 500 mg, 2.9 mmol) in THF (15 mL) and water (5 mL) was added LiOH*H$_2$O (180 mg, 4.4 mmol). The reaction was stirred at rt for 8 h and then quenched with dilute aqueous HCl. The mixture was extracted with EtOAc and the combined extracts were dried with sodium sulfate, filtered, and concentrated in vacuo to afford the title compound (440 mg, 96%) as a thick, yellow oil. $^1$H NMR (CDCl$_3$): δ 4.57 (dd, J=5.0, 4.8 Hz, 1H), 4.31 (d, J=4.8 Hz, 1H), 2.47 (dd, J=16.2, 8.1 Hz, 1H), 2.27 (dd, J=16.2, 6.8 Hz, 1H), 2.21-2.10 (m, 2H), 1.78-1.63 (m, 2H), 1.53-1.39 (m, 2H), 1.36-1.22 (m, 2H)

Synthesis of 2-((1R,2S,4S)-7-oxabicyclo[2.2.1]heptan-2-yl)acetic acid

To a solution of methyl 2-((1R,2S,4S)-7-oxabicyclo[2.2.1]heptan-2-yl)acetate (Diastereomer B, 380 mg, 2.2 mmol) in THF (11 mL) and water (4 mL) was added LiOH*H$_2$O (140 mg, 3.3 mmol). The reaction was stirred at room temperature for 8 h and then quenched with dilute aqueous HCl. The mixture was extracted with EtOAc and the combined extracts were dried over sodium sulfate, filtered, and concentrated in vacuo to afford the title compound (320 mg, 91%) as a clear, colorless oil. $^1$H NMR (CDCl$_3$): δ 4.57-4.53 (m, 2H), 2.53-2.39 (m, 3H), 2.13-2.04 (m, 1H), 1.79-1.62 (m, 3H), 1.44-1.37 (m, 1H), 1.01-0.96 (m, 1H) [note: CO$_2$H not observed].

Method 19. General Procedure for Synthesis of 3-tert-butoxyproprionoic acids

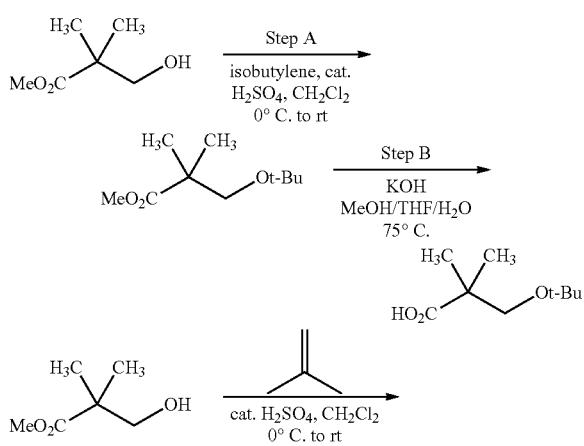

Step A. Synthesis of 3-(tert-butoxy)-2,2-dimethylpropanoic acid

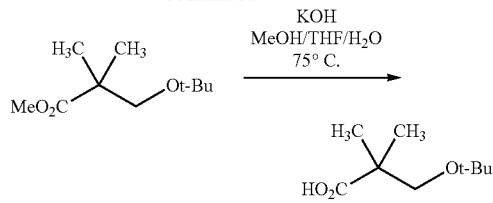

Isobutylene (approx. 8.7 g) was bubbled into a solution of methyl 3-hydroxy-2,2-dimethylpropanoate (1.0 g, 7.6 mmol) in dichloromethane (30 mL) at 0° C. Sulfuric acid (3 drops, 18 M) was added and the reaction vessel was sealed. The reaction was warmed to room temperature overnight then diluted with dichloromethane and washed successively with saturated aqueous sodium bicarbonate and brine. The resultant organic solution was dried with sodium sulfate and concentrated in vacuo to give an oil (1.29 g) which was used directly in the next step.

Step B

To a solution of the above ester (1.29 g, 6.86 mmol) in MeOH/THF/water (14/5/6 mL) was added potassium hydroxide (1.54 g, 27.4 mmol). The reaction was stirred at room temperature for 1 h then heated to 75° C. for 1 h. After cooling to room temperature, brine (50 mL) was added and the pH was adjusted to 4 with 2N aqueous HCl. The mixture was extracted with EtOAc and the combined organic layers were dried with sodium sulfate, concentrated in vacuo, and purified by flash column chromatography (0-20% MeOH/DCM) to afford the title compound (690 mg, 58%) as a pale orange solid.

The following additional intermediates were prepared from an appropriate starting material using Method 19:

(R)-3-(tert-butoxy)-2-methylpropanoic acid (S)-3-(tert-butoxy)-2-methylpropanoic acid

Method 20. General Procedure for Synthesis of 3-Alkoxypropanoic Acids

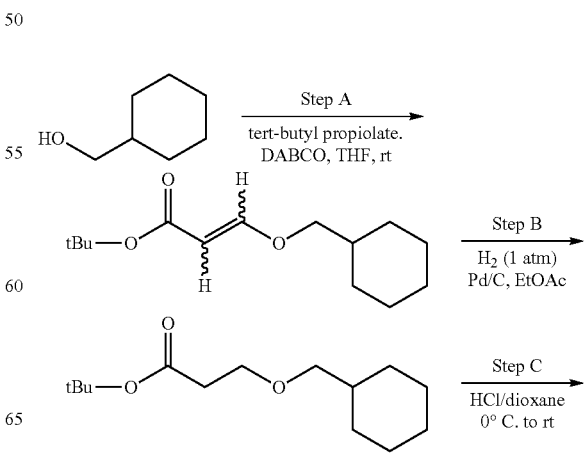

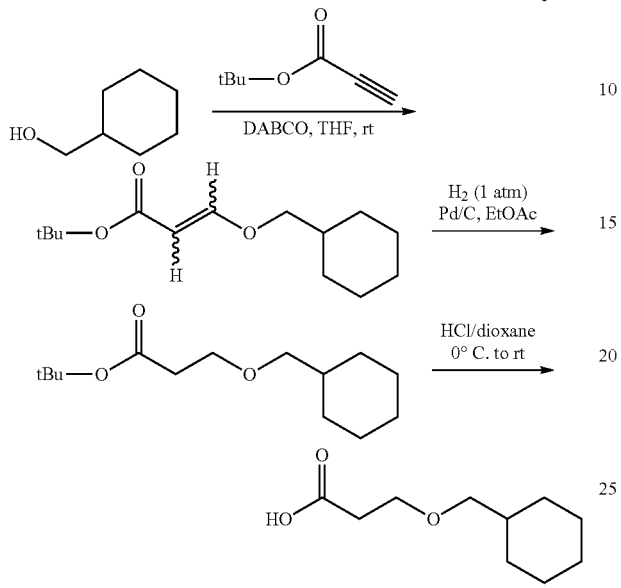

Step A. Preparation of tert-butyl 3-(cyclohexylmethoxy)acrylate

To a solution of cyclohexylmethanol (0.98 g, 8.7 mmol) and DABCO (88 mg, 0.79 mmol) in THF at room temperature under nitrogen was added tert-butyl propiolate (1.0 g, 7.9 mmol). The reaction was stirred for 2 days and then concentrated in vacuo and purified by flash column chromatography (EtOac/hexanes 0-10%) to afford the titled compound (1.4 g, 75%) as a colorless oil. [note: products were generally a mixture of E and Z alkene isomers]

Step B. Preparation of tert-butyl 3-(cyclohexylmethoxy)propanoate

A solution of tert-butyl 3-(cyclohexylmethoxy)acrylate (1.4 g, 5.8 mmol) in EtOAc (50 mL) was purged with nitrogen and then palladium on carbon (300 mg, 10% Pd/C, 50% water) was added. The reaction was stirred under a hydrogen atmosphere for 1 h and then filtered through Celite and concentrated in vacuo to afford the title compound (1.18 g, 84%). $^1$H NMR (CDCl$_3$): δ 3.68 (t, J=6.6 Hz, 2H), 2.47 (t, J=6.5 Hz, 2H), 1.90-1.88 (m, 2H), 1.73-1.71 (m, 2H), 1.45 (s, 9H), 1.28-1.19 (m, 6H).

Step C. Preparation of 3-(cyclohexylmethoxy)propanoic acid

Hydrochloric acid (12 mL, 4N in 1,4-dioxane, 48 mmol) was added to tert-butyl 3-(cyclohexylmethoxy)propanoate (1.18 g, 4.9 mmol) at 0° C. The reaction was kept at 0° C. for 5 min and then stirred at room temperature overnight. The reaction was concentrated in vacuo and co-evaporated with dichloromethane to afford the title compound (800 mg, 89%). $^1$H NMR (CDCl$_3$): δ 3.75 (t, J=6.2 Hz, 2H), 2.63 (d, J=6.2 Hz, 2H), 1.92-1.89 (m, 2H), 1.74-1.71 (m, 2H), 1.33-1.21 (m, 6H).

The following additional intermediates were prepared from an appropriate starting material using Method 20:

3-(cyclopentyloxy)propanoic acid
3-isopropoxypropanoic acid
3-cyclobutoxypropanoic acid
3-(cyclohexyloxy)propanoic acid
3-((4,4-difluorocyclohexyl)oxy)propanoic acid
3-((1R,3r,5S)-bicyclo[3.1.0]hexan-3-yloxy)propanoic acid
3-((1R,3 s,5S)-bicyclo[3.1.0]hexan-3-yloxy)propanoic acid
3-((1R,4S)-7-oxabicyclo[2.2.1]heptan-2-yloxy)propanoic acid

Method 21. Preparation of 2-(4,4-difluoropiperidin-1-yl)acetic acid

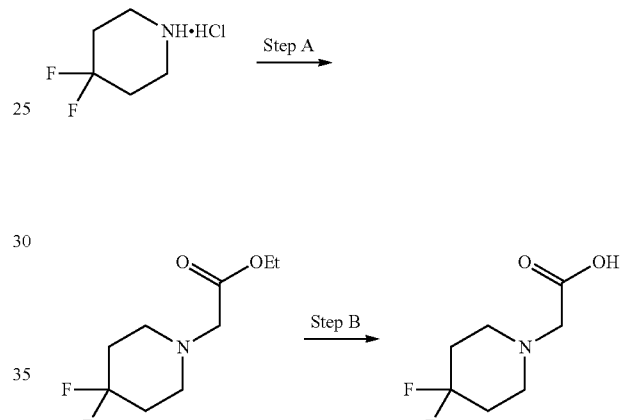

Step A. Preparation of 2-(4,4-difluoropiperidin-1-yl)acetic acid ethyl ester

Prepared from 4,4-difluoropiperidine hydrochloride and ethyl bromoacetate via procedure from WO200911450, p. 76-77.

Step B. Preparation of 2-(4,4-difluoropiperidin-1-yl)acetic acid 2-(4,4-Difluoropiperidin-1-yl)acetic acid ethyl ester (0.61 mmol) was treated at ambient temperature with 1 N aqueous lithium hydroxide (2 equivalents). The reaction was stirred at ambient temperature for 3 h. The mixture was acidified to pH ~1 with concentrated hydrochloric acid and concentrated to afford a white solid. The crude product, as the hydrochloride salt, was used directly in the amide bond forming reaction.

The following amino acids were prepared in a method analogous to the one for 2-(4,4-difluoropiperidin-1-yl)acetic acid from ethyl bromoacetate and the appropriate amine hydrochlorides:

2-(3,3-difluoropiperidin-1-yl)acetic acid
2-(3,3-difluoropyrrolidin-1-yl)acetic acid

Method 22. Preparation of 3-(1-(trifluoromethyl)cyclopropyl)propanoic acid

Step A. Preparation of 5-(hydroxy(1-(trifluoromethyl)cyclopropyl)methylene)-2,2-dimethyl-1,3-dioxane-4,6-dione

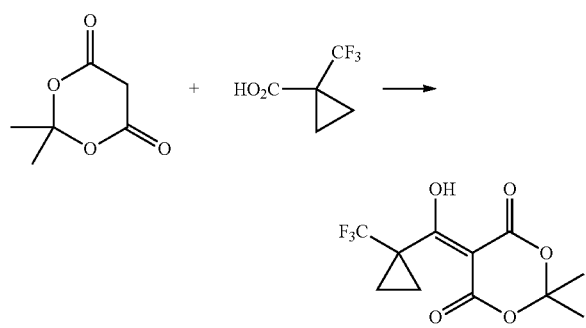

The title compound was prepared from Meldrum's acid and 1-(trifluoromethyl)cyclopropanecarboxylic acid via general procedure outlined in *J. Comb. Chem.* 2002, 4, 470-474.

Step B. Preparation of 2,2-dimethyl-5-((1-(trifluoromethyl)cyclopropyl)methyl)-1,3-dioxane-4,6-dione

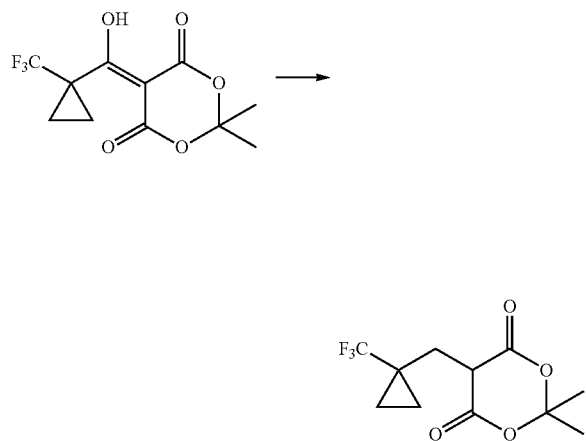

To a cooled (−5° C.) solution of the product from Step A (5 mmol) in dichloromethane (10 mL) was added glacial acetic acid (3.2 mL) and the mixture treated with sodium borohydride (483 mg, added as a solid, in small portions, over 15 min. The reaction was allowed to warm to ambient temperature and stirring continued until the reaction was judged complete by TLC. The mixture was concentrated, diluted with water and extracted with dichloromethane and EtOAc. The combined organic extracts were dried over sodium sulfate and concentrated. Chromatography on silica with ethyl acetate as eluent afforded 0.44 g of the title compound.

Step C. Preparation of 3-(1-(trifluoromethyl)cyclopropyl)propanoic acid

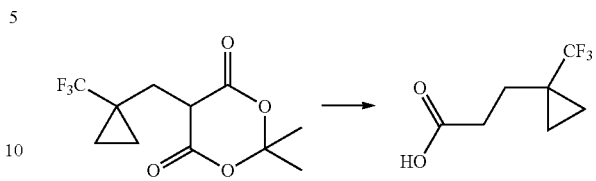

The product from Step B (0.39 g) was refluxed in EtOH (6 mL) for 6 hours. The reaction mixture was concentrated to afford an oil. The oil was dissolved in dioxane (1 mL) and treated with of 2 N aqueous lithium hydroxide (2 equivalents). Stirring was continued overnight, then the mixture was concentrated and acidified with concentrated sulfuric acid. The mixture was extracted with dichloromethane and EtOAc, the organics were dried over sodium sulfate and concentrated. The residue was suspended in a 1:1 dioxane/2 N aqueous lithium hydroxide mixture (4 mL), and heated at 100° C. for 12 h in a microwave reactor. The reaction mixture was concentrated, extracted with dichloromethane and EtOAc, the organics were dried over sodium sulfate and concentrated to afford the desired product as an oil (0.15 g).

In an analogous fashion was prepared (S)-3-(tetrahydrofuran-2-yl)propanoic acid from (S)-tetrahydrofuran-2-carboxylic acid.

Method 23. Preparation of 3-methoxy-3-methylbutanoic acid

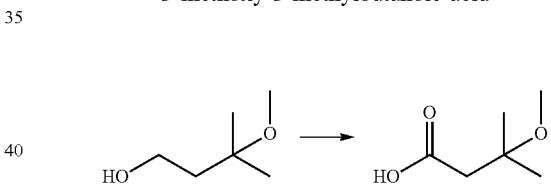

Reference: Schmidt, A.-K. C.; Stark, B. W. *Org Lett.* 2011, 13, 4164-4167.

To a solution of 3-methoxy-3-methylbutan-1-ol (0.6 g, 5 mmol) in acetonitrile (20 mL) was added N-methyl morpholine N-oxide mono hydrate (6.8 g, 50 mmol, 10 eq) and the mixture was allowed to stir at room temperature. After 5 min, TPAP (175 mg, 0.5 mmol, 0.1 eq) was added in one portion and the reaction was allowed to stir for 3 h before the bulk of the solvent was carefully removed on a rotary evaporator (caution, the product is volatile). The residue was purified by column chromatography (50-100% EtOAc/hexanes). The hexanes and EtOAc were removed by both rotary evaporator and a short period of time to high vacuum. The product is volatile and must not be left under vacuum for more than 30 sec. The resulting purified acid was diluted with DMF (7 mL) to make an approximately 0.2 M solution that was used for amide coupling reaction as is. Rf=0.4 to 0.8 streak in 100% EtOAc, not UV active, stains purple to anisaldehyde. MS (ESI) m/z 131 (MH−). $^1$H NMR (CDCl$_3$): δ 12.0-9.0 (bs, 1H), 3.30 (s, 3H), 2.57 (s, 2H), 1.32 (s, 6H).

Method 24. Preparation of 2-(bicyclo[4.2.0]octa-1,3,5-trien-7-yl)acetic acid

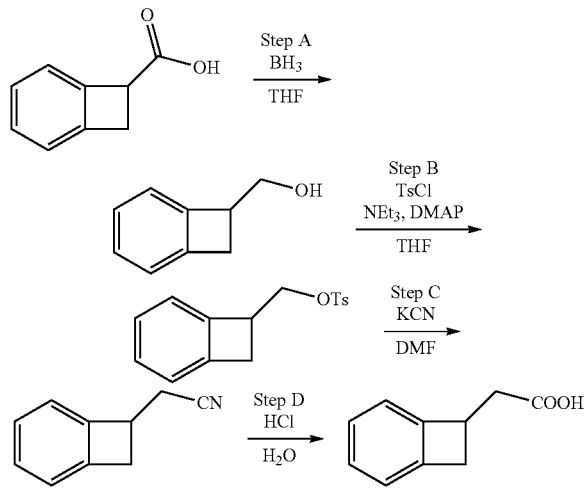

Step A.
Borane in THF solution (1 M, 4 mL, 1.2 eq) was added drop-wise to a solution of bicyclo[4.2.0]octa-1,3,5-triene-7-carboxylic acid (500 mg, 3.38 mmol) in THF (6 mL) at 0° C. The reaction mixture was warmed to room temperature and stirred overnight. The reaction mixture was quenched with water, extracted with EtOAc, and dried over $MgSO_4$. Purification by chromatography (5-20% EtOAc/hexanes) provided bicyclo[4.2.0]octa-1,3,5-trien-7-ylmethanol (388 mg, 86%).

Step B.
p-Toluenesulfonyl chloride (662 mg, 3.47 mmol), triethylamine (0.605 ml), and DMAP (35 mg, 0.29 mmol) were added to a solution of bicyclo[4.2.0]octa-1,3,5-trien-7-ylmethanol (388 mg, 2.89 mmol) in dichloromethane (12 mL) at room temperature and the reaction mixture was stirred overnight. Saturated aqueous $NH_4Cl$ was added to the reaction mixture, and the mixture was extracted with dichloromethane, dried over $MgSO_4$ and purified by chromatography (5-20% EtOAc/hexanes) to provide bicyclo[4.2.0]octa-1,3,5-trien-7-ylmethyl 4-methylbenzenesulfonate (830 mg, 99%).

Step C.
Potassium cyanide (54 mg, 0.83 mmol) was added to a solution of bicyclo[4.2.0]octa-1,3,5-trien-7-ylmethyl 4-methylbenzenesulfonate (200 mg, 0.694 mmol) in DMF (2 mL). The reaction mixture was stirred at 100° C. in a microwave reactor overnight. The reaction was then diluted with water and the mixture was extracted with EtOAc, dried over $MgSO_4$, and purified by chromatography (5-50% EtOAc/hexanes) to provide 2-(bicyclo[4.2.0]octa-1,3,5-trien-7-yl)acetonitrile (74 mg, 75%).

Step D.
To 2-(bicyclo[4.2.0]octa-1,3,5-trien-7-yl)acetonitrile (100 mg, 0.698 mmol) was added 30% aqueous hydrochloric acid (1.25 mL). The reaction mixture was heated to reflux for 18 h. After cooling to room temperature, the reaction mixture was diluted with water, extracted with EtOAc, dried over $MgSO_4$ and purified by chromatography (5-50% EtOAc/hexanes) to provide 2-(bicyclo[4.2.0]octa-1,3,5-trien-7-yl) acetic acid (90 mg, 0.555 mmol, 80%).

Section 4. Reaction of 3H-imidazo[4,5-b]pyridin-2-amine Intermediates to Form Title Compounds in Table 1

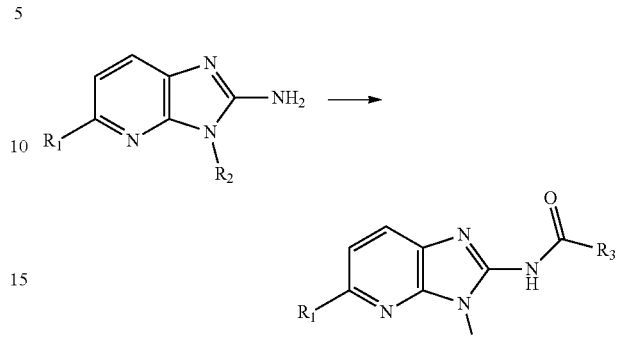

Procedure A. General Procedure for Amide Formation Using Amino Acid Coupling Reaction with HATU (Table 1).
A solution of appropriate 3H-imidazo[4,5-b]pyridin-2-amine intermediate (0.22 mmol), carboxylic acid (0.27 mmol), (dimethylamino)-N,N-dimethyl-(3H-[1,2,3]triazolo[4,5-b]pyridin-3-yloxy)methaniminium hexafluorophosphate (HATU, 0.11 g, 0.29 mmol), and N,N-diisopropylethylamine (78 μL, 0.45 mmol) in DMF or THF (2 mL) was stirred for 18 h at room temperature. The mixture was diluted with EtOAc and washed sequentially with saturated aqueous $NaHCO_3$ and water (4 times). The organic layer was dried over sodium sulfate and concentrated. Purification by column chromatography (0-100% EtOAc/hexanes or 0-10% MeOH/DCM) provided title compounds.

Procedure B. General Procedure for Amide Formation Using Acyl Chlorides (Table 1):
To a solution of appropriate 3H-imidazo[4,5-b]pyridin-2-amine intermediate (0.22 mmol) in THF (1 mL) was added pyridine (27 μL, 0.33 mmol) and acyl chloride (0.26 mmol). The reaction mixture was stirred for 18 h. The mixture was partitioned between EtOAc and water. The organic layer was dried over sodium sulfate and concentrated. The residue was purified by column chromatography (0-100% EtOAc/hexanes) to provide title compounds.

Procedure C. General Procedure for Amide Formation Using Acyl Chlorides (Table 1):
To a mixture of appropriate 3H-imidazo[4,5-b]pyridin-2-amine intermediate (0.14 mmol) and pyridine (0.41 mmol) in dichloromethane (1 mL) was added acyl chloride (0.16 mmol). The mixture was stirred at room temperature for 2 h and then concentrated in vacuum. The residue was dissolved in methanol (1 mL). To the solution, aqueous 1 N NaOH (1 mL) was added and the resulting mixture was stirred at room temperature for 1 h. The mixture was partitioned between water and dichloromethane. The organic layer was dried over sodium sulfate, filtered and concentrated in vacuum. The residue was co-evaporated with heptane in vacuum to remove pyridine and then purified by column chromatography, eluting with solvent A (100%) to solvent B (5%) gradient (where A is methylene chloride, B is methylene chloride/methanol 90:10), to provide the title compounds.

Procedure D. General Procedure for Amide Formation Using Amino Acid Coupling Reaction with EDC (Table 1).
A solution of appropriate imidazo[4,5-b]pyridin-2-amine (0.13 mmol), carboxylic acid (0.16 mmol), EDC (0.19 mmol), HOBt (0.19 mmol) and DIPEA (0.66 mmol) in THF (1 mL) was heated at 50° C. under nitrogen for 2-4 h. The reaction was cooled to room temperature, diluted with EtOAc and washed with water. The organic solution was concentrated in vacuo and purified by column chromatography (silica gel, 0-10% MeOH/DCM) to afford titled compounds.

Procedure E. General Procedure for Amide Formation Using Acylbenzotriazoles.

Reference: Katritzky, *Synlett,* 2005, 11, 1656.

A solution of appropriate 3H-imidazo[4,5-b]pyridin-2-amine intermediate (0.66 mmol) and triethylamine (0.5 mL, 3.3 mmol, 5 eq) in THF (3 mL) was stirred for 5 min at room temperature. To this solution was added a solution of pre-made acylbenzotriazole (0.7 M in DCM, 3.0 mL, 2.0 mmol, 3 eq) and the mixture was placed in a 50° C. sand bath for 12 hours. The mixture was allowed to cool to room temperature, diluted with EtOAc (50 mL) and washed sequentially with saturated aqueous Na₂CO₃ (3 times) and brine. The organic layer was dried over Na₂SO₄ and concentrated. Purification by column chromatography (0-100% EtOAc/hexane or 0-10% MeOH/DCM) provided title compounds.

Section 5. Exemplary Syntheses for Examples in Table 1

Example 65. Preparation of N-(3-cyclobutyl-6-(trifluoromethyl)-3H-imidazo[4,5-b]pyridin-2-yl)-2-(4-fluorophenyl)acetamide Step A. Alternative Preparation of N-cyclobutyl-3-nitro-5-(trifluoromethyl)pyridin-2-amine To a mixture of 2-chloro-3-nitro-5-(trifluoromethyl)pyridine (1.00 g, 4.41 mmol) and NaHCO₃ (1.12 g, 13.2 mmol) in EtOH (10 mL) was added cyclobutylamine (0.94 g, 13.2 mmol) drop-wise over 10 minutes. The mixture was stirred for 30 min, absorbed onto silica and purified on a 40 g ISCO gold silica gel column, eluting with a hexanes (100%) to hexanes (95%)/EtOAc (5%) gradient, to provide the desired compound (1.05 g, 91%) as a bright yellow solid.

Step B. Alternative preparation of N²-cyclobutyl-5-(trifluoromethyl)pyridine-2,3-diamine A mixture of N-cyclobutyl-3-nitro-5-(trifluoromethyl)pyridin-2-amine (500 mg, 1.91 mmol), iron powder (535 mg, 9.57 mmol) and ammonium chloride (153 mg, 2.87 mmol) in EtOH (8 mL)/water (2 mL) was heated to 85° C. for 2 h. The mixture was absorbed onto silica and purified on a 24 g ISCO Gold silica gel column, eluting with a hexanes (100%) to hexanes (50%)/ethyl acetate (50%) gradient, to provide the desired compound (380 mg, 86%) as a green oil.

Step C. Preparation of 3-cyclobutyl-6-(trifluoromethyl)-3H-imidazo[4,5-b]pyridin-2-amine N²-Cyclobutyl-5-(trifluoromethyl)pyridine-2,3-diamine (380 mg, 1.64 mmol) and cyanogen bromide (3 N in CH₂Cl₂, 0.66 mL, 1.97 mmol) were stirred in EtOH (3 mL) for 24 h. The mixture was concentrated and partitioned between EtOAc and NaHCO₃ solution and the organic layer absorbed onto silica and purified on 24 g ISCO Gold silica gel column, eluting with a hexanes (100%) to ethyl acetate (100%) gradient, to provide the desired compound (90 mg, 21%) as a white solid.

Step D. Preparation of N-(3-cyclobutyl-6-(trifluoromethyl)-3H-imidazo[4,5-b]pyridin-2-yl)-2-(4-fluorophenyl)acetamide To a mixture of 3-cyclobutyl-6-(trifluoromethyl)-3H-imidazo[4,5-b]pyridin-2-amine (100 mg, 0.39 mmol) and diisopropylethylamine (140 μL, 0.78 mmol) in dichloromethane (5 mL) was added 2-(4-fluorophenyl)acetyl chloride (70 μL, 0.50 mmol). The mixture was stirred for 24 h, washed with NaHCO₃ solution and the organic layer absorbed onto silica and purified on a 12 g ISCO Gold silica gel column, eluting with solvent A (100%) to solvent B (5%) gradient (where A is methylene chloride, B is methylene chloride/methanol/concentrated ammonium hydroxide 80:18:2), to provide the desired compound (82 mg, 53%) as a white solid. MS (ESI) m/z 393 (MH⁺).

Example 162. Preparation of N-(5-ethyl-3-(2,2,2-trifluoroethyl)-3H-imidazo[4,5-b]pyridin-2-yl)-3,3-dimethylbutanamide

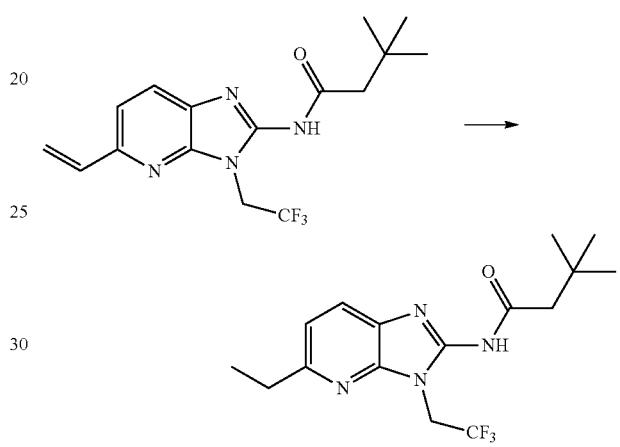

A solution of 3,3-dimethyl-N-(3-(2,2,2-trifluoroethyl)-5-vinyl-3H-imidazo[4,5-b]pyridin-2-yl)butanamide (20 mg, 0.06 mmol) in methanol (1.2 mL) was passed through an H-cube at 10 bar and 25° C. The resulting solution was concentrated to provide N-(5-ethyl-3-(2,2,2-trifluoroethyl)-3H-imidazo[4,5-b]pyridin-2-yl)-3,3-dimethylbutanamide (15 mg, 75%) MS (ESI) m/z 343.2 (MH⁺).

Example 217. Preparation of N-(5-(hydroxymethyl)-3-(2,2,2-trifluoroethyl)-3H-imidazo[4,5-b]pyridin-2-yl)-3,3-dimethylbutanamide

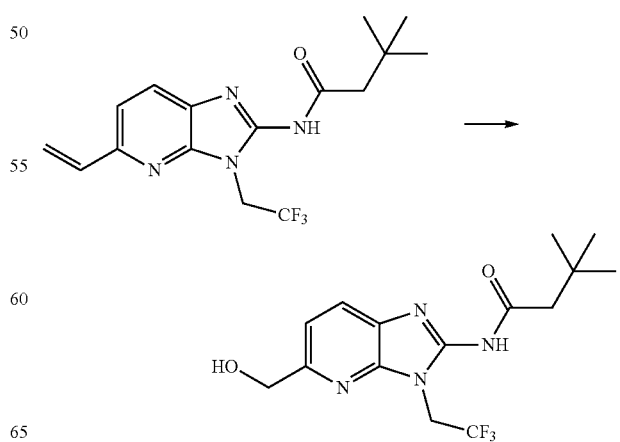

Step A.

A mixture of 3,3-dimethyl-N-(3-(2,2,2-trifluoroethyl)-5-vinyl-3H-imidazo[4,5-b]pyridin-2-yl)butanamide (30 mg, 0.14 mmol), 2.5% osmium tetroxide solution (10 µL, 0.007 mmol), and NMO (32 mg, 0.27 mmol) were stirred at room temperature in dichloromethane (1.4 mL) for 4 h. The crude mixture was purified by column chromatography (0-10% MeOH/DCM) to provide N-(5-(1,2-dihydroxyethyl)-3-(2,2,2-trifluoroethyl)-3H-imidazo[4,5-b]pyridin-2-yl)-3,3-dimethylbutanamide (27 mg, 54%).

Step B.

A mixture of N-(5-(1,2-dihydroxyethyl)-3-(2,2,2-trifluoroethyl)-3H-imidazo[4,5-b]pyridin-2-yl)-3,3-dimethylbutanamide (20 mg, 0.05 mmol) and sodium periodate (17 mg, 0.08 mmol) were stirred in a biphasic 5:1 dichloromethane/water mixture (0.5 mL) at room temperature for 8 h. The mixture was then partitioned between water (3 mL) and dichloromethane (5 mL) and the aqueous was extracted with dichloromethane (1×5 mL). The combined organics were dried over sodium sulfate, filtered, and concentrated to provide crude N-(5-formyl-3-(2,2,2-trifluoroethyl)-3H-imidazo[4,5-b]pyridin-2-yl)-3,3-dimethylbutanamide which was used directly in the following step.

Step C.

To a solution of crude N-(5-formyl-3-(2,2,2-trifluoroethyl)-3H-imidazo[4,5-b]pyridin-2-yl)-3,3-dimethylbutanamide from Step B in MeOH (0.5 mL) was added sodium borohydride (6 mg, 0.2 mmol) at room temperature. The mixture was stirred for 20 min before partitioning between water (5 mL) and EtOAc (10 mL). The aqueous was extracted with EtOAc (3×10 mL), and the combined organic layers were dried over sodium sulfate, filtered, and concentrated. The crude mixture was purified by column chromatography (50-100% EtOAc/hexanes) to provide N-(5-(hydroxymethyl)-3-(2,2,2-trifluoroethyl)-3H-imidazo[4,5-b]pyridin-2-yl)-3,3-dimethylbutanamide (10 mg, 55%, 2 steps). MS (ESI) m/z 345.2 (MH+).

Example 176. Preparation of isobutyl (5-chloro-3-cyclobutyl-3H-imidazo[4,5-b]pyridin-2-yl)carbamate

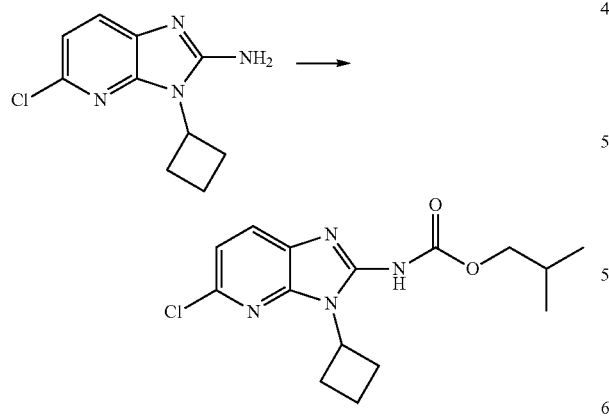

To a solution of 5-chloro-3-cyclobutyl-3H-imidazo[4,5-b]pyridin-2-amine (50 mg, 0.22 mmol) and isobutylchloroformate (44 µL, 0.34 mmol) in dichloromethane (2.2 mL) at room temperature was added N,N-diisopropylethylamine (117 µL, 0.67 mmol). The mixture was stirred at room temperature for 10 min before it was concentrated. The crude mixture was purified by column chromatography (10-100% EtOAc/hexanes) to provide isobutyl (5-chloro-3-cyclobutyl-3H-imidazo[4,5-b]pyridin-2-yl)carbamate (22 mg, 30%). MS (ESI) m/z 323.2 (MH+).

Example 259. Preparation of isobutyl N-(3-cyclobutyl-5-(trifluoromethyl)-3H-imidazo[4,5-b]pyridin-2-yl)-4-hydroxy-3,3-dimethylbutanamide

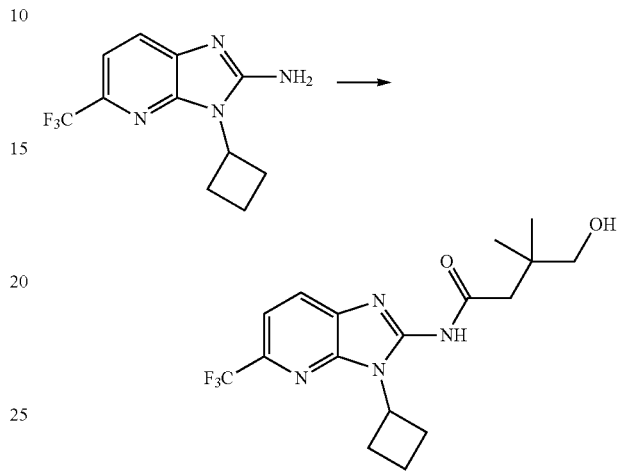

To a solution of 3-cyclobutyl-5-(trifluoromethyl)-3H-imidazo[4,5-b]pyridin-2-amine (18 mg, 0.070 mmol), and 4,4-dimethyldihydrofuran-2(3H)-one (16 mg, 0.14 mmol) in THF (1.5 mL) was added trimethylaluminum (2 M in hexane, 0.21 mL, 0.42 mmol). The mixture was heated to 70° C. After 3 h, the mixture was cooled to room temperature, then quenched slowly with 1M Rochelle's salt. After bubbling ceased, the mixture was poured into saturated aqueous NaHCO₃ and extracted with EtOAc. The organic layer was washed with water 3 times, then dried over sodium sulfate and concentrated. Column chromatography (0-10% MeOH/DCM provided 9.3 mg (36% yield) of N-(3-cyclobutyl-5-(trifluoromethyl)-3H-imidazo[4,5-b]pyridin-2-yl)-4-hydroxy-3,3-dimethylbutanamide.

Example 212. Preparation of 3,3-dimethyl-N-(3-(3-methylisoxazol-5-yl)-5-(trifluoromethyl)-3H-imidazo[4,5-b]pyridin-2-yl)butanamide

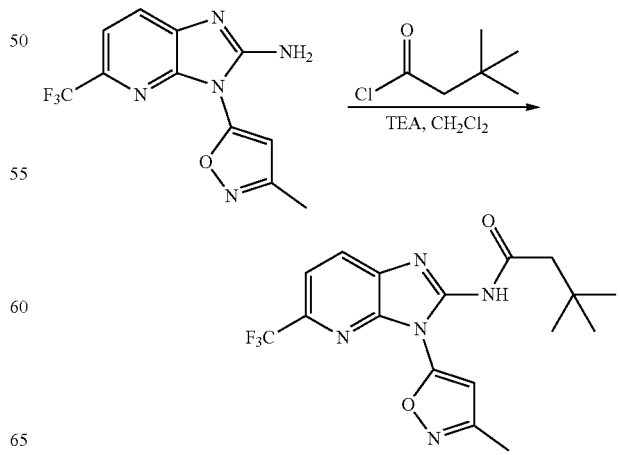

3,3-Dimethylbutanoyl chloride (0.623 mL, 3.47 mmol) was added dropwise to a 0° C. solution of 3-(3-methylisoxazol-5-yl)-5-(trifluoromethyl)-3H-imidazo[4,5-b]pyridin-2-amine (0.100 g, 0.347 mmol) and triethylamine (0.599 mL, 5.20 mmol) in CH$_2$Cl$_2$ (7 mL) and the reaction mixture was allowed to warm to ambient temperature and stir for 30 min. A solution of NH$_3$ (2.0 M in MeOH, 7 mL) was added and the mixture was stirred at 50° C. for 2 h before quenching with saturated aqueous NH$_4$Cl. The aqueous portion was extracted with EtOAc (2×), the combined organics were dried (MgSO$_4$) and the volatiles removed to give a crude residue that was purified via chromatography (0-5% MeOH/DCM) to yield 89 mg (67%) of the title compound. MS (ESI) m/z 382 (MH$^+$).

Example 104. Preparation of N-(5-chloro-3-propyl-3H-imidazo[4,5-b]pyridin-2-yl)-3,3-dimethylbutanamide

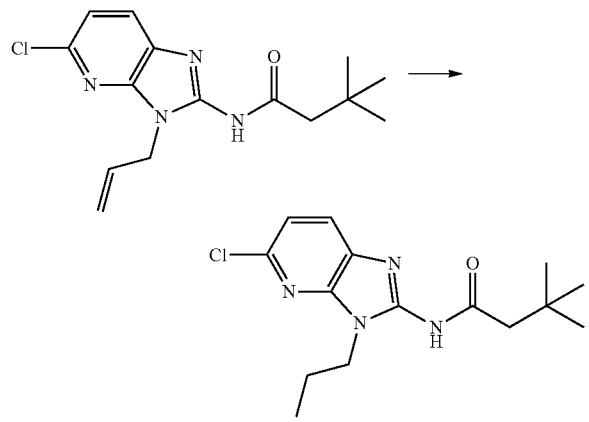

A solution of N-(3-allyl-5-chloro-3H-imidazo[4,5-b]pyridin-2-yl)-3,3-dimethylbutanamide (42 mg, 0.14 mmol, 1 eq) in dry acetonitrile (3 mL) was allowed to chill in a 0° C. bath for 5 min prior to the addition of 2-nitrobenzenesulfonylchloride (91 mg, 0.41 mmol, 3 eq) in one portion. After an additional 5 min, hyrazine hydrate (0.10 mL, 0.82 mmol, 6 eq) was added via syringe. The reaction flask was allowed to slowly warm to room temperature and the reaction was allowed to stir for 18 h prior to the addition of water (10 mL). The mixture was extracted with EtOAc (3 times) and the combined organics were washed with brine. The organic layer was dried with Na$_2$SO$_4$ and concentrated to give 50 mg of a crude material. Purification by column chromatography (50-100% EtOAc/hexane) provided the title compound (24 mg, 57% yield). MS (ESI) m/z 309 (MH$^+$).

Example 118. Preparation of N-(5-chloro-3-propyl-3H-imidazo[4,5-b]pyridin-2-yl)-3-cyclopentylpropanamide The title compound was made in an analogous manner to Example 104, but with N-(3-allyl-5-chloro-3H-imidazo[4,5-b]pyridin-2-yl)-3-cyclopentylpropanamide as the starting material.

Example 192. Preparation of N-(5-chloro-3-((1r,3r)-3-fluorocyclobutyl)-3H-imidazo[4,5-b]pyridin-2-yl)-3,3-dimethylbutanamide

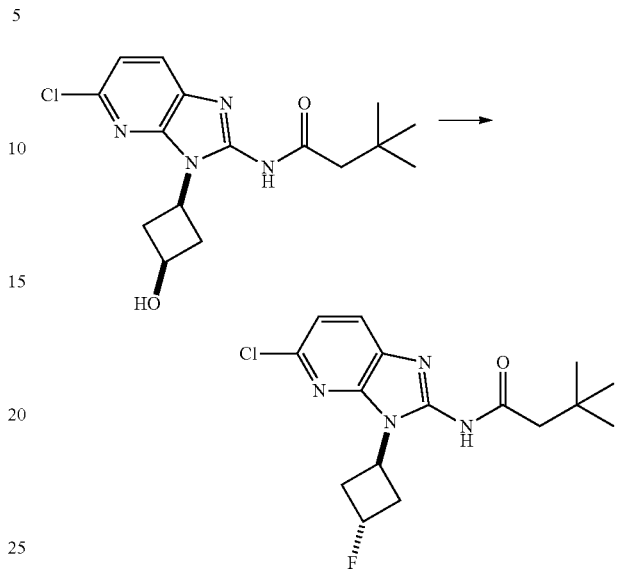

To a solution of triethylamine trihydrofluoride (67 mg, 0.41 mmol, 2 eq) in dichloromethane (2 mL) at −78° C. were successively added triethylamine (0.1 mL), XtalFluor-E (71 mg, 0.31 mmol, 1.5 eq) and a solution of N-(5-chloro-3-((1s,3s)-3-hydroxycyclobutyl)-3H-imidazo[4,5-b]pyridin-2-yl)-3,3-dimethylbutanamide (70 mg, 0.20 mmol, 1 eq) in dry dichloromethane. The reaction was allowed to stir at −78° C. for 5 min and then allowed to warm to room temperature and stirred for 3 h before it was quenched with saturated aqueous sodium bicarbonate and extracted with dichloromethane (3 times). The combined organics were washed with brine, dried over Na$_2$SO$_4$ and concentrated to give 70 mg of a crude material. Purification by column chromatography (50-100% EtOAc/hexane) provided the title compound (5 mg, 7% yield). The material was further purified by reverse phase HPLC (water and acetonitrile, 0.1% TFA buffer, 5 to 100% gradient) to give 2.1 mg of product as a white solid after extraction from sodium carbonate and DCM. M+1=339.2.

General Analytical Methods
HPLC Method A.
Instrument: Agilent 1100 with MSD
Column: Ascentis Express C18, 10 cm×4.6 mm×2.7 mm
Solvent A: 10 mM ammonium acetate in water
Solvent B: 10 mM ammonium acetate in acetonitrile
Flow rate: 1.8 mL/min
Method:
0-6.0 min, gradient from B=5% to B=95%
6.0-8.0 min, hold B=95%
8.0-8.1 min, gradient from B=95% to B=5%
8.1-10.0 min, hold B=5%
HPLC Method B.
Instrument: Agilent 1100 with MSD
Column: Ascentis Express C18, 10 cm×4.6 mm×2.7 mm
Solvent A: 10 mM ammonium acetate in water
Solvent B: 10 mM ammonium acetate in acetonitrile
Flow rate: 1.8 mL/min
Method:
0-2.5 min, gradient from B=5% to B=95%
2.5-3.0 min, hold B=95%

3.0-3.1 min, gradient from B=95% to B=5%
3.1-5.0 min, hold B=5%
  HPLC Method C.
Instrument: Shimadzu LC-8A
Column: Luna C18 (2), 10 cm×4.6 mm, 5 micron
Solvent A: 0.05% TFA in water
Solvent B: 0.05% TFA in acetonitrile
Flow rate: 2 mL/min
Method:
0-10 min, gradient from B=5% to B=95%
10-15 min, hold B=95%
  HPLC Method D.
Instrument: Varian Star #1
Column: Luna C18 (2), 25 cm×4.6 mm, 5 micron
Solvent A: 0.05% TFA in water
Solvent B: 0.05% TFA in acetonitrile
Flow rate: 1.15 mL/min
Method:
0-20 min, gradient from B=10% to B=100%
20-25 min, hold B=100%
  HPLC Method E.
Instrument: Agilent 1100 with MSD
Column: Ascentis Express C18, 10 cm×4.6 mm×2.7 mm
Solvent A: 0.1% formic acid in water
Solvent B: Acetonitrile
Flow rate: 1.4 mL/min
Method:
0-3.0 min gradient from B=10% to B=95%
3.0-4.0 min, hold B=95%
4.0-4.2 min, gradient from B=95% to B=10%
4.2-6.0 min, hold B=10%
  HPLC Method AA.
Instrument: Varian 500
Integration at 230 or 254 nm
Column: YMS ODS-AQ, 150×4.6 mm, 5 micron
Solvent A: H$_2$O w/0.05% TFA
Solvent B: CH$_3$CN w/0.05% TFA
Flow rate: 1.0 mL/min
Method:
0 minutes: 90% A, 10% B
10 minutes: 0% A, 100% B
19 minutes: 0% A, 100% B
  HPLC Method BB.
Instrument: Varian 500
Integration at 230 or 254 nm
Column: Phenonmenex Luna C18(2) column, 250×4.6 mm, 5 micron
Solvent A: H$_2$O w/0.025% TFA
Solvent B: CH$_3$CN w/0.025% TFA
Flow rate: 1.2 mL/min
Method:
0 minutes: 90% A, 10% B
10 minutes: 0% A, 100% B
20 minutes: 0% A, 100% B
  HPLC Method CC.
Instrument: Varian 500
Integration at 230 or 254 nm
Column: Phenonmenex Luna C18(2) column, 250×4.6 mm, 5 micron
Solvent A: H$_2$O w/0.1% TFA
Solvent B: CH$_3$CN w/0.1% TFA
Flow rate: 1.0 mL/min
Gradient:
0 minutes: 90% A, 10% B
10 minutes: 5% A, 95% B
16 minutes: 5% A, 95% B

TABLE 1

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 1 | 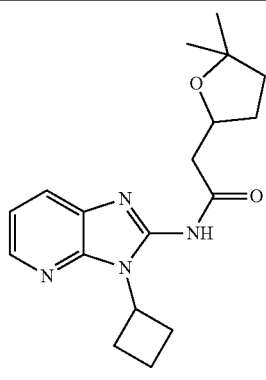 C$_{18}$H$_{24}$N$_4$O$_2$ | N-(3-cyclobutyl-3H-imidazo[4,5-imidazo[4,5-b]pyridin-2-yl)-2-(5,5-dimethyltetrahydro-furan-2-yl)acetamide | Procedure A; Marotta E, et al. *Org Lett*, 2002, 4, 4451 | B | 2.8 | 329 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 2 | 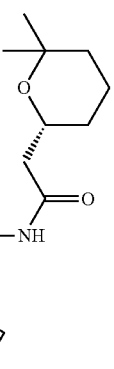<br>C₁₉H₂₆N₄O₂ | (R)-N-(3-cyclobutyl-3H-imidazo[4,5-b]pyridin-2-yl)-2-(6,6-dimethyltetrahydro-2H-pyran-2-yl)acetamide | Procedure A; Marotta E, et al. *Org Lett*, 2002, 4, 4451 | B | 3 | 343 |
| 3 | 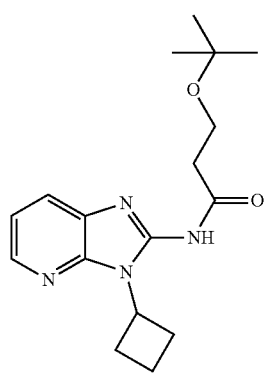<br>C₁₇H₂₄N₄O₂ | 3-(tert-butoxy)-N-(3-cyclobutyl-3H-imidazo[4,5-b]pyridin-2-yl)propanamide | Procedure A; commercial | B | 2.8 | 317 |
| 4 | 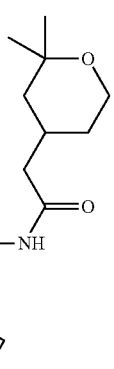<br>C₁₉H₂₆N₄O₂ | N-(3-cyclobutyl-3H-imidazo[4,5-b]pyridin-2-yl)-2-(2,2-dimethyltetrahydro-2H-pyran-4-yl)acetamide | Procedure A; commercial | B | 2.7 | 343 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 5 | 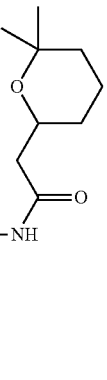<br>C₁₉H₂₆N₄O₂ | N-(3-cyclobutyl-3H-imidazo[4,5-b]pyridin-2-yl)-2-(6,6-dimethyltetrahydro-2H-pyran-2-yl)acetamide | Procedure A; Marotta E, et al. *Org Lett*, 2002, 4, 4451 | B | 3 | 343 |
| 6 | 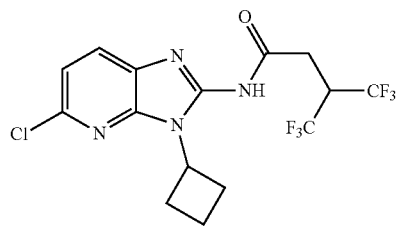<br>C₁₅H₁₃ClF₆N₄O | N-(5-chloro-3-cyclobutyl-3H-imidazo[4,5-b]pyridin-2-yl)-4,4,4-trifluoro-3-(trifluoromethyl)butanamide | Procedure A; commercial | B | 3.8 | 415 |
| 7 | 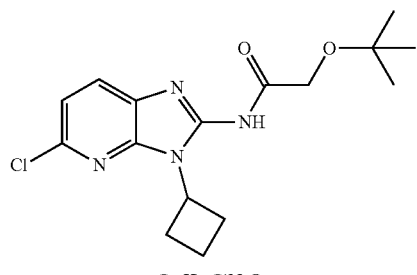<br>C₁₆H₂₁ClN₄O₂ | 2-(tert-butoxy)-N-(5-chloro-3-cyclobutyl-3H-imidazo[4,5-b]pyridin-2-yl)acetamide | Procedure A; commercial | B | 3.2 | 337 |
| 8 | 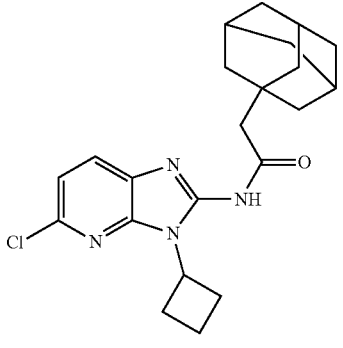<br>C₂₂H₂₇ClN₄O | 2-(adamantan-1-yl)-N-(5-chloro-3-cyclobutyl-3H-imidazo[4,5-b]pyridin-2-yl)acetamide | Procedure A; commercial | B | 4.1 | 399 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 9 | C₁₉H₂₃ClN₄O | 2-(bicyclo[2.2.1]heptan-2-yl)-N-(5-chloro-3-cyclobutyl-3H-imidazo[4,5-b]pyridin-2-yl)acetamide | Procedure A; commercial | B | 3.7 | 359 |
| 10 | C₁₉H₂₅ClN₄O₂ | N-(5-chloro-3-cyclobutyl-3H-imidazo[4,5-b]pyridin-2-yl)-2-(6,6-dimethyltetrahydro-2H-pyran-2-yl)acetamide | Procedure A; Marotta E, et al. *Org Lett*, 2002, 4, 4451 | B | 3.4 | 377 |
| 11 | C₁₈H₂₃ClN₄O₂ | N-(5-chloro-3-cyclobutyl-3H-imidazo[4,5-b]pyridin-2-yl)-2-(5,5-dimethyltetrahydrofuran-2-yl)acetamide | Procedure A; Marotta E, et al. *Org Lett*, 2002, 4, 4451 | B | 3.2 | 363 |
| 12 | C₁₉H₂₅ClN₄O₂ | (R)-N-(5-chloro-3-cyclobutyl-3H-imidazo[4,5-b]pyridin-2-yl)-2-(6,6-dimethyltetrahydro-2H-pyran-2-yl)acetamide | Procedure A; Marotta E, et al. *Org Lett*, 2002, 4, 4451 | B | 3.4 | 377 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 13 | 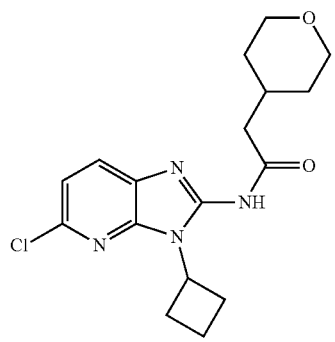<br>C₁₇H₂₁ClN₄O₂ | N-(5-chloro-3-cyclobutyl-3H-imidazo[4,5-b]pyridin-2-yl)-2-(tetrahydro-2H-pyran-4-yl)acetamide | Procedure A; commercial | B | 2.8 | 349 |
| 14 | 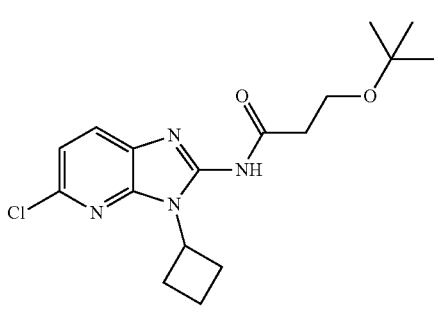<br>C₁₇H₂₃ClN₄O₂ | 3-(tert-butoxy)-N-(5-chloro-3-cyclobutyl-3H-imidazo[4,5-b]pyridin-2-yl)propanamide | Procedure A; commercial | B | 3.2 | 351 |
| 15 | 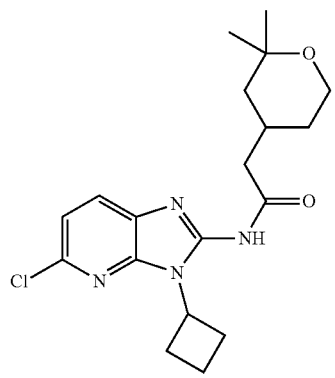<br>C₁₉H₂₅ClN₄O₂ | N-(5-chloro-3-cyclobutyl-3H-imidazo[4,5-b]pyridin-2-yl)-2-(2,2-dimethyltetrahydro-2H-pyran-4-yl)acetamide | Procedure A; commercial | B | 3 | 377 |
| 16 | 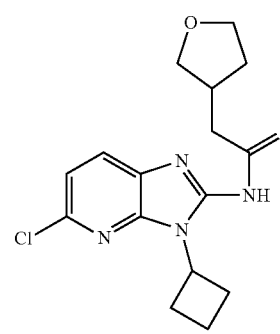<br>C₁₆H₁₉ClN₄O₂ | N-(5-chloro-3-cyclobutyl-3H-imidazo[4,5-b]pyridin-2-yl)-2-(tetrahydrofuran-3-yl)acetamide | Procedure A; commercial | B | 2.7 | 335 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
| --- | --- | --- | --- | --- | --- | --- |
| 17 | $C_{16}H_{13}F_9N_4O$ | N-(3-cyclobutyl-5-(trifluoromethyl)-3H-imidazo[4,5-b]pyridin-2-yl)-4,4,4-trifluoro-3-(trifluoromethyl)butanamide | Procedure A; commercial | B | 3.7 | 449 |
| 18 | $C_{20}H_{28}N_4O_3$ | N-(3-cyclobutyl-5-methoxy-3H-imidazo[4,5-b]pyridin-2-yl)-2-(2,2-dimethyltetrahydro-2H-pyran-4-yl)acetamide | Procedure A; commercial | B | 2.9 | 373 |
| 19 | $C_{17}H_{22}N_4O_3$ | N-(3-cyclobutyl-5-methoxy-3H-imidazo[4,5-b]pyridin-2-yl)-2-(tetrahydrofuran-3-yl)acetamide | Procedure A; commercial | B | 2.6 | 331 |
| 20 | $C_{20}H_{28}N_4O_3$ | N-(3-cyclobutyl-5-methoxy-3H-imidazo[4,5-b]pyridin-2-yl)-2-(6,6-dimethyltetrahydro-2H-pyran-2-yl)acetamide | Procedure A; Marotta E, et al. *Org Lett*, 2002, 4, 4451 | B | 3.3 | 373 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
| --- | --- | --- | --- | --- | --- | --- |
| 21 | $C_{18}H_{17}FN_4O$ | N-(3-cyclobutyl-3H-imidazo[4,5-b]pyridin-2-yl)-2-(4-fluorophenyl)acetamide | Procedure B; commercial | B | 3.1 | 325 |
| 22 | $C_{16}H_{22}N_4O$ | N-(3-cyclobutyl-3H-imidazo[4,5-b]pyridin-2-yl)-3,3-dimethylbutanamide | Procedure B; commercial | B | 3 | 287 |
| 23 | $C_{19}H_{20}N_4O$ | N-(3-cyclobutyl-3H-imidazo[4,5-b]pyridin-2-yl)-3-phenylpropanamide | Procedure B; commercial | B | 3.1 | 321 |
| 24 | $C_{21}H_{28}N_4O$ | N-(3-cyclobutyl-3H-imidazo[4,5-b]pyridin-2-yl)-2-((1S,2S,5S)-6,6-dimethyl-bicyclo[3.1.1]heptan-2-yl)acetamide | Procedure B; U.S. patent application Ser. No. 20120122890 | B | 3.9 | 353 |
| 25 | $C_{16}H_{21}ClN_4O$ | N-(5-chloro-3-cyclobutyl-3H-imidazo[4,5-b]pyridin-2-yl)-3,3-dimethyl-butanamide | Procedure B; commercial | A | 5.5 | 321 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 26 | C₁₈H₁₆ClFN₄O | N-(5-chloro-3-cyclobutyl-3H-imidazo[4,5-b]pyridin-2-yl)-2-(4-fluorophenyl)acetamide | Procedure B; commercial | A | 4.1 | 259 |
| 27 | C₁₈H₂₃ClN₄O | N-(5-chloro-3-cyclobutyl-3H-imidazo[4,5-b]pyridin-2-yl)-3-cyclopentyl-propanamide | Procedure B; commercial | A | 6.2 | 347 |
| 28 | C₁₅H₁₉ClN₄O | N-(5-chloro-3-cyclobutyl-3H-imidazo[4,5-b]pyridin-2-yl)-3-methylbutanamide | Procedure B; commercial | B | 3.2 | 307 |
| 29 | C₁₈H₂₃ClN₄O | N-(5-chloro-3-cyclobutyl-3H-imidazo[4,5-b]pyridin-2-yl)-2-cyclohexylacetamide | Procedure B; commercial | B | 3.6 | 347 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 30 | $C_{19}H_{19}ClN_4O$ | N-(5-chloro-3-cyclobutyl-3H-imidazo[4,5-b]pyridin-2-yl)-2-phenylpropanamide | Procedure B; commercial | B | 3.5 | 355 |
| 31 | $C_{18}H_{17}ClN_4O_2$ | N-(5-chloro-3-cyclobutyl-3H-imidazo[4,5-b]pyridin-2-yl)-2-phenoxyacetamide | Procedure B; commercial | B | 3.5 | 357 |
| 32 | $C_{14}H_{17}ClN_4O$ | N-(5-chloro-3-cyclobutyl-3H-imidazo[4,5-b]pyridin-2-yl)isobutyramide | Procedure B; commercial | B | 3 | 293 |
| 33 | $C_{21}H_{27}ClN_4O$ | N-(5-chloro-3-cyclobutyl-3H-imidazo[4,5-b]pyridin-2-yl)-2-((1S,2S,5S)-6,6-dimethylbicyclo[3.1.1]heptan-2-yl)acetamide | Procedure B; U.S. patent application Ser. No. 20120122890 | B | 4.1 | 385.2 (M − H)− |
| 34 | $C_{14}H_{17}ClN_4O_2$ | N-(5-chloro-3-cyclobutyl-3H-imidazo[4,5-b]pyridin-2-yl)-2-ethoxyacetamide | Procedure B; commercial | B | 3 | 309 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
| --- | --- | --- | --- | --- | --- | --- |
| 35 | $C_{19}H_{19}ClN_4O$ | N-(5-chloro-3-cyclobutyl-3H-imidazo[4,5-b]pyridin-2-yl)-3-phenylpropanamide | Procedure B; commercial | B | 3.3 | 355 |
| 36 | $C_{16}H_{23}ClN_4O$ | N-(5-chloro-3-isobutyl-3H-imidazo[4,5-b]pyridin-2-yl)-3,3-dimethylbutanamide | Procedure B; commercial | B | 3.3 | 323 |
| 37 | $C_{18}H_{18}ClFN_4O$ | N-(5-chloro-3-isobutyl-3H-imidazo[4,5-b]pyridin-2-yl)-2-(4-fluorophenyl)acetamide | Procedure B; commercial | B | 3.3 | 361 |
| 38 | $C_{15}H_{21}ClN_4O$ | N-(5-chloro-3-isobutyl-3H-imidazo[4,5-b]pyridin-2-yl)-3-methylbutanamide | Procedure B; commercial | B | 3.1 | 309 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 39 | $C_{17}H_{21}F_3N_4O$ | N-(3-cyclobutyl-5-(trifluoromethyl)-3H-imidazo[4,5-b]pyridin-2-yl)-3,3-dimethylbutanamide | Procedure B; commercial | A | 6 | 355 |
| 40 | $C_{19}H_{16}F_4N_4O$ | N-(3-cyclobutyl-5-(trifluoromethyl)-3H-imidazo[4,5-b]pyridin-2-yl)-2-(4-fluorophenyl)acetamide | Procedure B; commercial | A | 6 | 393 |
| 41 | $C_{19}H_{23}F_3N_4O$ | N-(3-cyclobutyl-5-(trifluoromethyl)-3H-imidazo[4,5-b]pyridin-2-yl)-3-cyclopentyl-propanamide | Procedure B; commercial | A | 6.6 | 381 |
| 42 | $C_{16}H_{19}F_3N_4O$ | N-(3-cyclobutyl-5-(trifluoromethyl)-3H-imidazo[4,5-b]pyridin-2-yl)-3-methylbutanamide | Procedure B; commercial | A | 5.6 | 341 |
| 43 | $C_{19}H_{23}F_3N_4O$ | N-(3-cyclobutyl-5-(trifluoromethyl)-3H-imidazo[4,5-b]pyridin-2-yl)-2-cyclohexylacetamide | Procedure B; commercial | A | 6.4 | 381 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 44 | 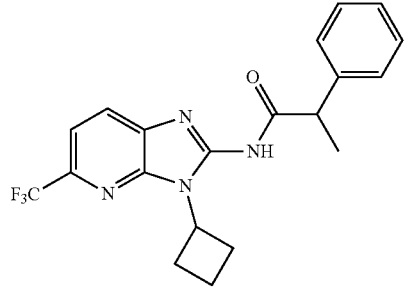 C20H19F3N4O | N-(3-cyclobutyl-5-(trifluoromethyl)-3H-imidazo[4,5-b]pyridin-2-yl)-2-phenylpropanamide | Procedure B; commercial | A | 6.2 | 389 |
| 45 | 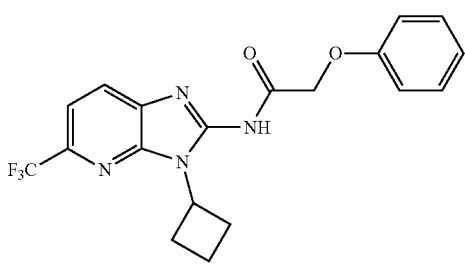 C19H17F3N4O2 | N-(3-cyclobutyl-5-(trifluoromethyl)-3H-imidazo[4,5-b]pyridin-2-yl)-2-phenoxyacetamide | Procedure B; commercial | A | 6.1 | 391 |
| 46 | 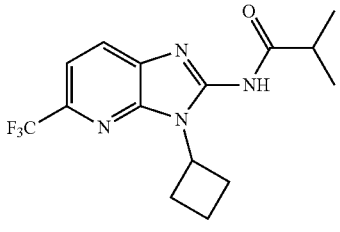 C15H17F3N4O | N-(3-cyclobutyl-5-(trifluoromethyl)-3H-imidazo[4,5-b]pyridin-2-yl)isobutyramide | Procedure B; commercial | A | 5.4 | 327 |
| 47 | 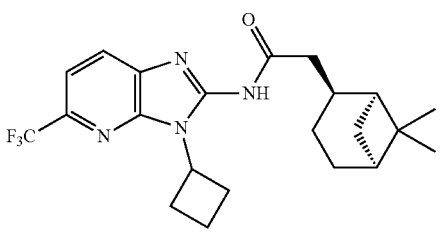 C22H27F3N4O | N-(3-cyclobutyl-5-(trifluoromethyl)-3H-imidazo[4,5-b]pyridin-2-yl)-2-((1S,2S,5S)-6,6-dimethylbicyclo[3.1.1]heptan-2-yl)acetamide | Procedure B; U.S. patent application Ser. No. 20120122890 | A | 7.2 | 422 |
| 48 | 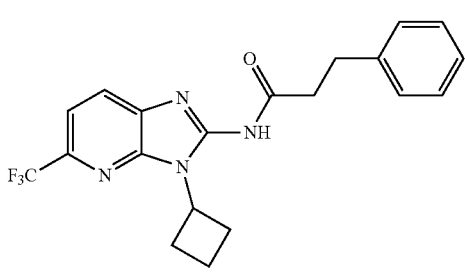 C20H19F3N4O | N-(3-cyclobutyl-5-(trifluoromethyl)-3H-imidazo[4,5-b]pyridin-2-yl)-3-phenylpropanamide | Procedure B; commercial | B | 3.5 | 389 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 49 | 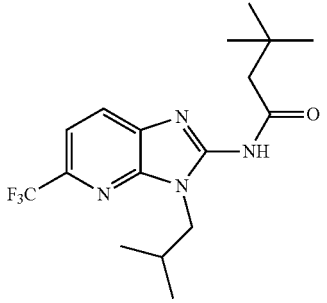 $C_{17}H_{23}F_3N_4O$ | N-(3-isobutyl-5-(trifluoromethyl)-3H-imidazo[4,5-b]pyridin-2-yl)-3,3-dimethylbutanamide | Procedure B; commercial | B | 3.5 | 357 |
| 50 | 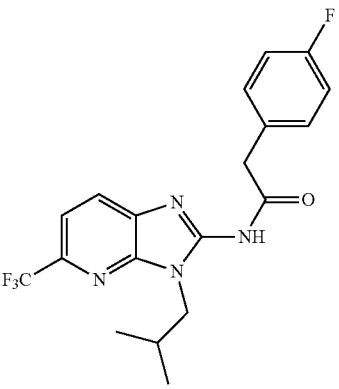 $C_{19}H_{18}F_4N_4O$ | 2-(4-fluorophenyl)-N-(3-isobutyl-5-(trifluoromethyl)-3H-imidazo[4,5-b]pyridin-2-yl)acetamide | Procedure B; commercial | B | 3.5 | 395 |
| 51 | 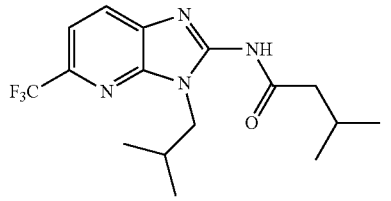 $C_{16}H_{21}F_3N_4O$ | N-(3-isobutyl-5-(trifluoromethyl)-3H-imidazo[4,5-b]pyridin-2-yl)-3-methylbutanamide | Procedure B; commercial | B | 3.4 | 343 |
| 52 | 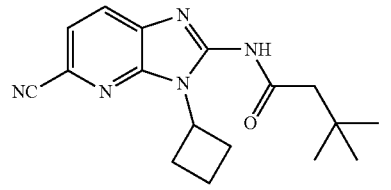 $C_{17}H_{21}N_5O$ | N-(5-cyano-3-cyclobutyl-3H-imidazo[4,5-b]pyridin-2-yl)-3,3-dimethylbutanamide | Procedure B; commercial | B | 3.1 | 312 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 53 | $C_{16}H_{19}N_5O$ | N-(5-cyano-3-cyclobutyl-3H-imidazo[4,5-b]pyridin-2-yl)-3-methylbutanamide | Procedure B; commercial | E | 3.5 | 298 |
| 54 | $C_{17}H_{24}N_4O_2$ | N-(3-cyclobutyl-5-methoxy-3H-imidazo[4,5-b]pyridin-2-yl)-3,3-dimethylbutanamide | Procedure B; commercial | B | 3.2 | 317 |
| 55 | $C_{19}H_{19}FN_4O_2$ | N-(3-cyclobutyl-5-methoxy-3H-imidazo[4,5-b]pyridin-2-yl)-2-(4-fluorophenyl)acetamide | Procedure B; commercial | B | 3.2 | 355 |
| 56 | $C_{16}H_{22}N_4O_2$ | N-(3-cyclobutyl-5-methoxy-3H-imidazo[4,5-b]pyridin-2-yl)-3-methylbutanamide | Procedure B; commercial | B | 3.1 | 303 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 57 | $C_{16}H_{21}ClN_4O$ | N-(6-chloro-3-cyclobutyl-3H-imidazo[4,5-b]pyridin-2-yl)-3,3-dimethylbutanamide | Procedure B; commercial | B | 3.4 | 321 |
| 58 | $C_{18}H_{16}ClFN_4O$ | N-(6-chloro-3-cyclobutyl-3H-imidazo[4,5-b]pyridin-2-yl)-2-(4-fluorophenyl)acetamide | Procedure B; commercial | B | 3.4 | 359 |
| 59 | $C_{15}H_{19}ClN_4O$ | N-(6-chloro-3-cyclobutyl-3H-imidazo[4,5-b]pyridin-2-yl)-3-methylbutanamide | Procedure B; commercial | B | 3.2 | 307 |
| 60 | $C_{17}H_{21}F_3N_4O$ | N-(3-cyclobutyl-6-(trifluoromethyl)-3H-imidazo[4,5-b]pyridin-2-yl)-3,3-dimethylbutanamide | Procedure C; commercial | D | 17.5 | 355 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 61 | $C_{20}H_{19}F_3N_4O$ | N-(3-cyclobutyl-6-(trifluoromethyl)-3H-imidazo[4,5-b]pyridin-2-yl)-3-phenylpropanamide | Procedure C; commercial | D | 17.1 | 380 |
| 62 | $C_{17}H_{16}F_3N_5O_2$ | N-(3-cyclobutyl-6-(trifluoromethyl)-3H-imidazo[4,5-b]pyridin-2-yl)-2-(5-methylisoxazol-3-yl)acetamide | Procedure C; commercial | D | 9.2 | 381 |
| 63 | $C_{19}H_{23}F_3N_4O$ | N-(3-cyclobutyl-6-(trifluoromethyl)-3H-imidazo[4,5-b]pyridin-2-yl)-3-cyclopentyl-propanamide | Procedure C; commercial | C | 18.1 | 389 |
| 64 | $C_{20}H_{23}F_3N_4O$ | 2-((1S,4R)-bicyclo[2.2.1]heptan-2-yl)-N-(3-cyclobutyl-6-(trifluoromethyl)-3H-imidazo[4,5-b]pyridin-2-yl)acetamide | Procedure D; commercial | D | 19.1 | 393 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 65 | $C_{19}H_{16}F_4N_4O$ | N-(3-cyclobutyl-6-(trifluoromethyl)-3H-imidazo[4,5-b]pyridin-2-yl)-2-(4-fluorophenyl)acetamide | Example 65; commercial | C | 8.5 | 393 |
| 66 | $C_{15}H_{16}ClF_3N_4O$ | N-(5-chloro-3-cyclobutyl-3H-imidazo[4,5-b]pyridin-2-yl)-3,3,3-trifluoro-2,2-dimethyl-propanamide | Procedure A; commercial | E | 4.7 | 361 |
| 67 | $C_{17}H_{24}N_4O$ | N-(3-cyclobutyl-7-methyl-3H-imidazo[4,5-b]pyridin-2-yl)-3,3-dimethylbutanamide | Procedure B; commercial | E | 3.4 | 301 |
| 68 | $C_{18}H_{26}N_4O_2$ | 3-(tert-butoxy)-N-(3-cyclobutyl-7-methyl-3H-imidazo[4,5-b]pyridin-2-yl)propanamide | Procedure A; commercial | E | 3.3 | 331 |
| 69 | $C_{14}H_{16}ClF_3N_4O$ | N-(5-chloro-3-(2,2,2-trifluoroethyl)-3H-imidazo[4,5-b]pyridin-2-yl)-3,3-dimethylbutanamide | Procedure D; commercial | E | 3.8 | 349 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 70 | C$_{16}$H$_{23}$ClN$_4$O$_2$ | 3-(tert-butoxy)-N-(5-chloro-3-isopropyl-3H-imidazo[4,5-b]pyridin-2-yl)propanamide | Procedure A; commercial | E | 3.6 | 339 |
| 71 | C$_{18}$H$_{25}$ClN$_4$O$_2$ | (S)-N-(5-chloro-3-isopropyl-3H-imidazo[4,5-b]pyridin-2-yl)-2-(6,6-dimethyltetrahydro-2H-pyran-2-yl)acetamide | Procedure A; Larcheveque M, et al. *Tetrahedron*, 1990, 46(12), Marotta E, et al. *Org Lett*, 2002, 4, 4451 | E | 3.9 | 365 |
| 72 | C$_{15}$H$_{18}$ClF$_3$N$_4$O$_2$ | 3-(tert-butoxy)-N-(5-chloro-3-(2,2,2-trifluoroethyl)-3H-imidazo[4,5-b]pyridin-2-yl)propanamide | Procedure A; commercial | E | 3.6 | 379 |
| 73 | C$_{17}$H$_{20}$ClF$_3$N$_4$O$_2$ | (S)-N-(5-chloro-3-(2,2,2-trifluoroethyl)-3H-imidazo[4,5-b]pyridin-2-yl)-2-(6,6-dimethyltetrahydro-2H-pyran-2-yl)acetamide | Procedure A; Larcheveque M, et al. *Tetrahedron*, 1990, 46(12), Marotta E, et al. *Org Lett*, 2002, 4, 4451 | E | 3.9 | 405 |
| 74 | C$_{15}$H$_{21}$ClN$_4$O | N-(5-chloro-3-isopropyl-3H-imidazo[4,5-b]pyridin-2-yl)-3,3-dimethylbutanamide | Procedure D; commercial | E | 3.8 | 309 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 75 | $C_{17}H_{21}ClN_4O$ | N-(3-allyl-5-chloro-3H-imidazo[4,5-b]pyridin-2-yl)-3-cyclopentyl-propanamide | Procedure E; commercial | E | 3.9 | 333 |
| 76 | $C_{15}H_{19}ClN_4O$ | N-(3-allyl-5-chloro-3H-imidazo[4,5-b]pyridin-2-yl)-3,3-dimethylbutanamide | Procedure E; commercial | E | 3.5 | 307 |
| 77 | $C_{16}H_{23}ClN_4O$ | N-(3-(tert-butyl)-5-chloro-3H-imidazo[4,5-b]pyridin-2-yl)-3,3-dimethylbutanamide | Procedure D; commercial | E | 4 | 323 |
| 78 | $C_{17}H_{23}ClN_4O_2$ | N-(5-chloro-3-(tetrahydro-2H-pyran-4-yl)-3H-imidazo[4,5-b]pyridin-2-yl)-3,3-dimethylbutanamide | Procedure D; commercial | E | 3.4 | 351 |
| 79 | $C_{18}H_{25}ClN_4O_2$ | (R)-3-(tert-butoxy)-N-(5-chloro-3-cyclobutyl-3H-imidazo[4,5-b]pyridin-2-yl)butanamide | Procedure A; Balibar CJ, et al. *Chem & Biol*, 2005, 12(11), 1189. | E | 4.0 | 365 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 80 | C$_{18}$H$_{25}$ClN$_4$O$_2$ | (S)-3-(tert-butoxy)-N-(5-chloro-3-cyclobutyl-3H-imidazo[4,5-b]pyridin-2-yl)butanamide | Procedure A; Balibar CJ, et al. Chem & Biol, 2005, 12(11), 1189. | E | 4.0 | 365 |
| 81 | C$_{17}$H$_{21}$ClN$_4$O$_2$ | N-(5-chloro-3-cyclobutyl-3H-imidazo[4,5-b]pyridin-2-yl)-3-(cyclopropyl-methoxy)propanamide | Procedure A; commercial | E | 3.7 | 349 |
| 82 | C$_{18}$H$_{26}$N$_4$O$_2$ | (S)-3-(tert-butoxy)-N-(3-cyclobutyl-3H-imidazo[4,5-b]pyridin-2-yl)butanamide | Procedure A; Balibar CJ, et al. Chem & Biol, 2005, 12(11), 1189. | E | 3.3 | 331 |
| 83 | C$_{18}$H$_{21}$ClN$_4$O$_2$ | 2-((1R,2R,4S)-7-oxabicyclo[2.2.1]heptan-2-yl)-N-(5-chloro-3-cyclobutyl-3H-imidazo[4,5-b]pyridin-2-yl)acetamide | Procedure A; Method 18 | E | 3.4 | 361 |
| 84 | C$_{18}$H$_{21}$ClN$_4$O$_2$ | 2-((1R,2S,4S)-7-oxabicyclo[2.2.1]heptan-2-yl)-N-(5-chloro-3-cyclobutyl-3H-imidazo[4,5-b]pyridin-2-yl)acetamide | Procedure A; Method 18 | E | 3.4 | 361 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 85 | C₁₈H₂₃ClN₄O₂ | N-(5-chloro-3-cyclobutyl-3H-imidazo[4,5-b]pyridin-2-yl)-2-(1-hydroxycyclohexyl)acetamide | Procedure A; commercial | E | 3.8 | 363 |
| 86 | C₁₈H₂₅ClN₄O₂ | N-(5-chloro-3-cyclobutyl-3H-imidazo[4,5-b]pyridin-2-yl)-3-(cyclopentyloxy)propanamide | Procedure A; commercial | E | 4.0 | 363 |
| 87 | C₁₈H₂₅F₃N₄O₂ | 3-(tert-butoxy)-N-(3-cyclobutyl-5-(trifluoromethyl)-3H-imidazo[4,5-b]pyridin-2-yl)propanamide | Procedure A; commercial | E | 4 | 385 |
| 88 | C₂₀H₂₅F₃N₄O₂ | (R)-N-(3-cyclobutyl-5-(trifluoromethyl)-3H-imidazo[4,5-b]pyridin-2-yl)-2-(6,6-dimethyltetrahydro-2H-pyran-2-yl)acetamide | Procedure A; Marotta E, et al. *Org Lett*, 2002, 4, 4451 | E | 4.3 | 411 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 89 | C₁₇H₂₁F₃N₄O | N-(3-cyclobutyl-5-(trifluoromethyl)-3H-imidazo[4,5-b]pyridin-2-yl)-3-methylpentanamide | Procedure A; commercial | E | 4.3 | 355 |
| 90 | C₁₉H₂₃F₃N₄O₂ | N-(3-cyclobutyl-5-(trifluoromethyl)-3H-imidazo[4,5-b]pyridin-2-yl)-2-(1-hydroxycyclohexyl)acetamide | Procedure A; commercial | E | 4 | 397 |
| 91 | C₁₉H₂₃F₃N₄O₂ | N-(3-cyclobutyl-5-(trifluoromethyl)-3H-imidazo[4,5-b]pyridin-2-yl)-3-(cyclopentyloxy)propanamide | Procedure A; Method 20 | E | 4.2 | 397 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 92 | $C_{19}H_{25}F_3N_4O_2$ | (S)-3-(tert-butoxy)-N-(3-cyclobutyl-5-(trifluoromethyl)-3H-imidazo[4,5-b]pyridin-2-yl)butanamide | Procedure A; Balibar CJ, et al. Chem & Biol, 2005, 12(11), 1189. | E | 4.2 | 399 |
| 93 | $C_{19}H_{25}F_3N_4O_2$ | (R)-3-(tert-butoxy)-N-(3-cyclobutyl-5-(trifluoromethyl)-3H-imidazo[4,5-b]pyridin-2-yl)butanamide | Procedure A; Balibar CJ, et al. Chem & Biol, 2005, 12(11), 1189. | E | 4.2 | 399 |
| 94 | $C_{16}H_{16}F_6N_4O_2$ | N-(3-cyclobutyl-5-(trifluoromethyl)-3H-imidazo[4,5-b]pyridin-2-yl)-3-(2,2,2-trifluoroethoxy)propanamide | Procedure A; commercial | E | 3.9 | 411 |
| 95 | $C_{17}H_{21}F_3N_4O_2$ | N-(3-cyclobutyl-5-(trifluoromethyl)-3H-imidazo[4,5-b]pyridin-2-yl)-3-isopropoxy-propanamide | Procedure A; Method 20 | E | 3.9 | 371 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 96 | $C_{19}H_{23}F_3N_4O_2$ | N-(3-cyclobutyl-5-(trifluoromethyl)-3H-imidazo[4,5-b]pyridin-2-yl)-2-(5,5-dimethyltetrahydrofuran-2-yl)acetamide | Procedure A; Marotta E, et al. *Org Lett*, 2002, 4, 4451 | E | 4 | 397 |
| 97 | $C_{17}H_{25}ClN_4O_2$ | 3-(tert-butoxy)-N-(3-(tert-butyl)-5-chloro-3H-imidazo[4,5-b]pyridin-2-yl)propanamide | Procedure A; commercial | E | 3.8 | 353 |
| 98 | $C_{19}H_{27}ClN_4O_2$ | (R)-N-(3-(tert-butyl)-5-chloro-3H-imidazo[4,5-b]pyridin-2-yl)-2-(6,6-dimethyltetrahydro-2H-pyran-2-yl)acetamide | Procedure A; Marotta E, et al. *Org Lett*, 2002, 4, 4451 | E | 4 | 379 |
| 99 | $C_{18}H_{25}ClN_4O_3$ | 3-(tert-butoxy)-N-(5-chloro-3-(tetrahydro-2H-pyran-4-yl)-3H-imidazo[4,5-b]pyridin-2-yl)propanamide | Procedure A; commercial | E | 3.3 | 381 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 100 | $C_{16}H_{21}ClN_4O_2$ | N-(3-allyl-5-chloro-3H-imidazo[4,5-b]pyridin-2-yl)-3-(tert-butoxy)propanamide | Procedure A; commercial | E | 3.3 | 337 |
| 101 | $C_{22}H_{33}ClN_4O_5$ | 2-(2-(3-(tert-butoxy)propanamido)-5-chloro-3H-imidazo[4,5-b]pyridin-3-yl)ethyl 3-(tert-butoxy)propanoate | Procedure A; commercial | E | 3.7 | 469 |
| 102 | $C_{18}H_{23}ClN_4O_2$ | (R)-N-(5-chloro-3-cyclobutyl-3H-imidazo[4,5-b]pyridin-2-yl)-2-(5,5-dimethyltetrahydrofuran-2-yl)acetamide | Procedure A; Hirama M, J Chem Soc, Chem Commun 1983, 599; Marotta E, et al. Org Lett, 2002, 4, 4451 | E | 3.8 | 363 |
| 103 | $C_{15}H_{16}ClF_3N_4O_2$ | N-(5-chloro-3-cyclobutyl-3H-imidazo[4,5-b]pyridin-2-yl)-3-(2,2,2-trifluoroethoxy)propanamide | Procedure A; commercial | E | 3.8 | 377 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 104 | $C_{15}H_{21}ClN_4O$ | N-(5-chloro-3-propyl-3H-imidazo[4,5-b]pyridin-2-yl)-3,3-dimethylbutanamide | Example 104; commercial | E | 3.6 | 309 |
| 105 | $C_{18}H_{18}ClFN_4O$ | N-(5-chloro-3-(4-fluorophenyl)-3H-imidazo[4,5-b]pyridin-2-yl)-3,3-dimethylbutanamide | Procedure D; commercial | E | 3.6 | 361 |
| 106 | $C_{21}H_{22}ClFN_4O_2$ | (R)-N-(5-chloro-3-(4-fluorophenyl)-3H-imidazo[4,5-b]pyridin-2-yl)-2-(6,6-dimethyltetrahydro-2H-pyran-2-yl)acetamide | Procedure A; Marotta E, et al. *Org Lett*, 2002, 4, 4451 | E | 3.7 | 417 |
| 107 | $C_{17}H_{21}F_3N_4O$ | N-(5-cyclopropyl-3-(2,2,2-trifluoroethyl)-3H-imidazo[4,5-b]pyridin-2-yl)-3,3-dimethylbutanamide | Procedure D; commercial | E | 4.1 | 355 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 108 | C$_{18}$H$_{23}$F$_3$N$_4$O$_2$ | 3-(tert-butoxy)-N-(5-cyclopropyl-3-(2,2,2-trifluoroethyl)-3H-imidazo[4,5-b]pyridin-2-yl)propanamide | Procedure D; commercial | E | 3.9 | 385 |
| 109 | C$_{19}$H$_{25}$ClN$_4$O$_2$ | (S)-N-(5-chloro-3-cyclobutyl-3H-imidazo[4,5-b]pyridin-2-yl)-2-(6,6-dimethyltetrahydro-2H-pyran-2-yl)acetamide | Procedure A; Larcheveque M, et al. *Tetrahedron*, 1990, 46(12), Marotta E, et al. *Org Lett*, 2002, 4, 4451 | E | 4.0 | 377 |
| 110 | C$_{16}$H$_{23}$ClN$_4$O$_2$ | 3-(tert-butoxy)-N-(5-chloro-3-propyl-3H-imidazo[4,5-b]pyridin-2-yl)propanamide | Procedure A; commercial | E | 3.4 | 339 |
| 111 | C$_{17}$H$_{23}$ClN$_4$O$_2$ | N-(5-chloro-3-propyl-3H-imidazo[4,5-b]pyridin-2-yl)-2-(5,5-dimethyltetrahydrofuran-2-yl)acetamide | Procedure A; Marotta E, et al. *Org Lett*, 2002, 4, 4451 | E | 3.4 | 351 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 112 | $C_{20}H_{25}F_3N_4O_2$ | (S)-N-(3-cyclobutyl-5-(trifluoromethyl)-3H-imidazo[4,5-b]pyridin-2-yl)-2-(6,6-dimethyltetrahydro-2H-pyran-2-yl)acetamide | Procedure A; Larcheveque M, et al. *Tetrahedron*, 1990, 46(12), Marotta E, et al. *Org Lett*, 2002, 4, 4451 | E | 4.3 | 411 |
| 113 | $C_{19}H_{23}F_3N_4O_2$ | (R)-N-(3-cyclobutyl-5-(trifluoromethyl)-3H-imidazo[4,5-b]pyridin-2-yl)-2-(5,5-dimethyltetrahydrofuran-2-yl)acetamide | Procedure A; Hirama M, J *Chem Soc, Chem Commun* 1983, 599; Marotta E, et al. *Org Lett*, 2002, 4, 4451 | E | 4 | 397 |
| 114 | $C_{20}H_{23}F_3N_4O_3$ | 3-((1R,2R,4S)-7-oxabicyclo[2.2.1]heptan-2-yloxy)-N-(3-cyclobutyl-5-(trifluoromethyl)-3H-imidazo[4,5-b]pyridin-2-yl)propanamide | Procedure A; Method 20 | E | 3.7 | 425 |
| 115 | $C_{16}H_{16}F_6N_4O_2$ | N-(3-cyclobutyl-5-(trifluoromethyl)-3H-imidazo[4,5-b]pyridin-2-yl)-4,4,4-trifluoro-3-hydroxy-3-methylbutanamide | Procedure A; commercial | E | 4.1 | 411 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 116 | C$_{19}$H$_{20}$ClFN$_4$O$_2$ | 3-(tert-butoxy)-N-(5-chloro-3-(4-fluorophenyl)-3H-imidazo[4,5-b]pyridin-2-yl)propanamide | Procedure A; commercial | E | 3.5 | 391 |
| 117 | C$_{16}$H$_{23}$ClN$_4$O$_3$ | methyl 3-(5-chloro-2-(3,3-dimethyl-butanamido)-3H-imidazo[4,5-b]pyridin-3-yl)propanoate | Procedure E; commercial | E | 3.3 | 353 |
| 118 | C$_{17}$H$_{23}$ClN$_4$O | N-(5-chloro-3-propyl-3H-imidazo[4,5-b]pyridin-2-yl)-3-cyclopentyl-propanamide | Example 118; commercial | E | 4 | 335 |
| 119 | C$_{15}$H$_{22}$Cl$_2$N$_4$O$_2$ | N-(5-chloro-3-(2-methoxyethyl)-3H-imidazo[4,5-b]pyridin-2-yl)-3,3-dimethylbutanamide hydrochloride | Procedure E; commercial | E | 3.3 | 325 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 120 | $C_{18}H_{25}F_3N_4O_3$ | 3-(tert-butoxy)-N-(5-isopropoxy-3-(2,2,2-trifluoroethyl)-3H-imidazo[4,5-b]pyridin-2-yl)propanamide | Procedure A; commercial | E | 4.0 | 403 |
| 121 | $C_{17}H_{21}ClN_4O_2$ | N-(5-chloro-3-cyclobutyl-3H-imidazo[4,5-b]pyridin-2-yl)-3-(tetrahydrofuran-2-yl)propanamide | Procedure A; commercial | E | 3.4 | 349 |
| 122 | $C_{17}H_{21}ClN_4O_2$ | N-(5-chloro-3-cyclobutyl-3H-imidazo[4,5-b]pyridin-2-yl)-3-(tetrahydrofuran-3-yl)propanamide | Procedure A; commercial | E | 3.3 | 349 |
| 123 | $C_{18}H_{23}ClN_4O_2$ | (S)-N-(5-chloro-3-cyclobutyl-3H-imidazo[4,5-b]pyridin-2-yl)-2-(5,5-dimethyltetrahydro-furan-2-yl)acetamide | Procedure A; Larcheveque M, et al. *Tetrahedron*, 1990, 46(12), Marotta E, et al. *Org Lett*, 2002, 4, 4451 | E | 3.8 | 363 |
| 124 | $C_{18}H_{21}F_3N_4O_2$ | N-(3-cyclobutyl-5-(trifluoromethyl)-3H-imidazo[4,5-b]pyridin-2-yl)-3-(tetrahydrofuran-3-yl)propanamide | Procedure A; commercial | E | 3.7 | 383 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 125 | $C_{18}H_{21}F_3N_4O_2$ | N-(3-cyclobutyl-5-(trifluoromethyl)-3H-imidazo[4,5-b]pyridin-2-yl)-3-(tetrahydrofuran-2-yl)propanamide | Procedure A; commercial | E | 3.6 | 383 |
| 126 | $C_{19}H_{23}F_3N_4O_2$ | (S)-N-(3-cyclobutyl-5-(trifluoromethyl)-3H-imidazo[4,5-b]pyridin-2-yl)-2-(5,5-dimethyltetrahydrofuran-2-yl)acetamide | Procedure A; Larcheveque M, et al. Tetrahedron, 1990, 46(12), Marotta E, et al. Org Lett, 2002, 4, 4451 | E | 4.02 | 397 |
| 127 | $C_{18}H_{25}ClN_4O_2$ | 3-(tert-butoxy)-N-(5-chloro-3-cyclobutyl-7-methyl-3H-imidazo[4,5-b]pyridin-2-yl)propanamide | Procedure A; commercial | E | 3.9 | 365 |
| 128 | $C_{17}H_{23}ClN_4O$ | N-(5-chloro-3-cyclobutyl-7-methyl-3H-imidazo[4,5-b]pyridin-2-yl)-3,3-dimethylbutanamide | Procedure B; commercial | E | 4 | 335 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 129 | C₁₈H₁₇Cl₃N₄O | N-(5-chloro-3-cyclobutyl-3H-imidazo[4,5-b]pyridin-2-yl)-2-(3-chlorophenyl)acetamide hydrochloride | Procedure A; commercial | E | 4.4 | 375 |
| 130 | C₁₇H₂₄Cl₂N₄O₂ | N-(5-chloro-3-(2-methoxyethyl)-3H-imidazo[4,5-b]pyridin-2-yl)-3-cyclopentyl-propanamide hydrochloride | Procedure E; commercial | E | 3.7 | 351 |
| 131 | C₁₅H₁₉F₃N₄O | 3,3-dimethyl-N-(5-methyl-3-(2,2,2-trifluoroethyl)-3H-imidazo[4,5-b]pyridin-2-yl)butanamide | Procedure A; commercial | E | 3.6 | 329 |
| 132 | C₁₆H₂₁F₃N₄O₂ | 3-(tert-butoxy)-N-(5-methyl-3-(2,2,2-trifluoroethyl)-3H-imidazo[4,5-b]pyridin-2-yl)propanamide | Procedure A; commercial | E | 3.4 | 359 |
| 133 | C₁₇H₂₄N₄O | N-(3-cyclobutyl-5-methyl-3H-imidazo[4,5-b]pyridin-2-yl)-3,3-dimethylbutanamide | Procedure D; commercial | E | 3.5 | 301 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 134 | C₁₈H₂₆N₄O₂ | 3-(tert-butoxy)-N-(3-cyclobutyl-5-methyl-3H-imidazo[4,5-b]pyridin-2-yl)propanamide | Procedure D; commercial | E | 3.4 | 331 |
| 135 | C₁₅H₁₉F₃N₄O₂ | 3-(tert-butoxy)-N-(3-(2,2,2-trifluoroethyl)-3H-imidazo[4,5-b]pyridin-2-yl)propanamide | Procedure A; commercial | E | 3.2 | 345 |
| 136 | C₁₇H₁₆ClN₅O | N-(5-chloro-3-cyclobutyl-3H-imidazo[4,5-b]pyridin-2-yl)-2-(pyridin-2-yl)acetamide | Procedure A; commercial | E | 2.6 | 342 |
| 137 | C₁₈H₂₀Cl₂N₄O | N-(5-chloro-3-propyl-3H-imidazo[4,5-b]pyridin-2-yl)-3-phenylpropanamide hydrochloride | Procedure C; commercial | E | 3.7 | 343 |
| 138 | C₂₀H₂₉N₅O₂ | N-(3-cyclobutyl-5-morpholino-3H-imidazo[4,5-b]pyridin-2-yl)-3,3-dimethylbutanamide | Procedure C; commercial | CC | 9.76 | 372 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 139 | 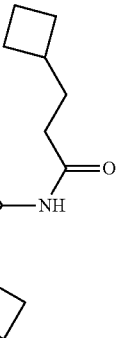 C₁₈H₂₁F₃N₄O | 3-cyclobutyl-N-(3-cyclobutyl-5-(trifluoromethyl)-3H-imidazo[4,5-b]pyridin-2-yl)propanamide | Procedure A; commercial | E | 4.4 | 367 |
| 140 | 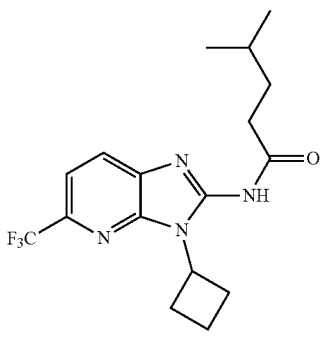 C₁₇H₂₁F₃N₄O | N-(3-cyclobutyl-5-(trifluoromethyl)-3H-imidazo[4,5-b]pyridin-2-yl)-4-methylpentanamide | Procedure A; commercial | E | 4.3 | 355 |
| 141 | 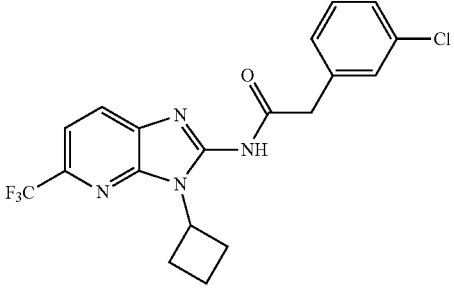 C₁₉H₁₆ClF₃N₄O | 2-(3-chlorophenyl)-N-(3-cyclobutyl-5-(trifluoromethyl)-3H-imidazo[4,5-b]pyridin-2-yl)acetamide | Procedure A; commercial | E | 4.5 | 409 |
| 142 | 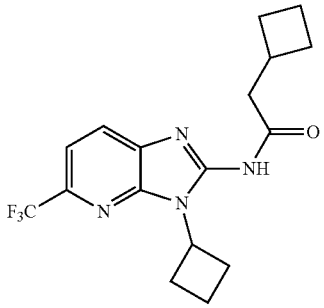 C₁₇H₁₉F₃N₄O | 2-cyclobutyl-N-(3-cyclobutyl-5-(trifluoromethyl)-3H-imidazo[4,5-b]pyridin-2-yl)acetamide | Procedure A; commercial | E | 4.1 | 353 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 143 | $C_{18}H_{23}F_3N_4O_2$ | 3,3-dimethyl-N-(3-(tetrahydro-2H-pyran-3-yl)-5-(trifluoromethyl)-3H-imidazo[4,5-b]pyridin-2-yl)butanamide | Procedure B; commercial | E | 3.8 | 385 |
| 144 | $C_{19}H_{25}F_3N_4O_3$ | 3-(tert-butoxy)-N-(3-(tetrahydro-2H-pyran-3-yl)-5-(trifluoromethyl)-3H-imidazo[4,5-b]pyridin-2-yl)propanamide | Procedure A; commercial | E | 3.7 | 415 |
| 145 | $C_{19}H_{23}ClN_4O_3$ | 3-((1R,2R,4S)-7-oxabicyclo[2.2.1]heptan-2-yloxy)-N-(5-chloro-3-cyclobutyl-3H-imidazo[4,5-b]pyridin-2-yl)propanamide | Procedure D; Method 18 | E | 3.4 | 391 |
| 146 | $C_{21}H_{31}N_5O_3$ | 3-(tert-butoxy)-N-(3-cyclobutyl-5-morpholino-3H-imidazo[4,5-b]pyridin-2-yl)propanamide | Procedure D; commercial | CC | 9.48 | 402 |
| 147 | $C_{16}H_{24}ClN_5O$ | N-(5-amino-3-cyclobutyl-3H-imidazo[4,5-b]pyridin-2-yl)-3,3-dimethylbutanamide hydrochloride | Example 147; commercial | E | 2.5 | 302 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 148 | C$_{18}$H$_{18}$ClN$_5$O | N-(5-chloro-3-cyclobutyl-3H-imidazo[4,5-b]pyridin-2-yl)-2-(6-methylpyridin-2-yl)acetamide | Procedure A; commercial | E | 2.5 | 356 |
| 149 | C$_{17}$H$_{23}$ClN$_4$O | N-(5-chloro-3-cyclobutyl-6-methyl-3H-imidazo[4,5-b]pyridin-2-yl)-3,3-dimethylbutanamide | Procedure D; commercial | E | 4.1 | 335 |
| 150 | C$_{18}$H$_{22}$N$_4$O | N-(3-cyclobutyl-5-ethynyl-3H-imidazo[4,5-b]pyridin-2-yl)-3,3-dimethylbutanamide | Procedure B; commercial | E | 3.7 | 311 |
| 151 | C$_{21}$H$_{26}$ClN$_5$O | N-(3-cyclobutyl-5-(pyridin-3-yl)-3H-imidazo[4,5-b]pyridin-2-yl)-3,3-dimethylbutanamide hydrochloride | Example 151; commercial | E | 2.8 | 364 |
| 152 | C$_{21}$H$_{31}$N$_5$O$_3$ | tert-butyl (3-cyclobutyl-2-(3,3-dimethyl-butanamido)-3H-imidazo[4,5-b]pyridin-5-yl)carbamate | Procedure C; commercial | CC | 10.85 | 402 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 153 | C₁₅H₁₈ClF₃N₄O | N-(5-chloro-6-methyl-3-(2,2,2-trifluoroethyl)-3H-imidazo[4,5-b]pyridin-2-yl)-3,3-dimethylbutanamide | Procedure D; commercial | E | 4.0 | 363 |
| 154 | C₁₉H₂₇ClN₄O₂ | 3-(tert-butoxy)-N-(5-chloro-3-cyclobutyl-3H-imidazo[4,5-b]pyridin-2-yl)-2,2-dimethylpropanamide | Procedure A; Method 19 | E | 4.7 | 379 |
| 155 | C₁₈H₂₃F₃N₄O | N-(3-cyclobutyl-5-(trifluoromethyl)-3H-imidazo[4,5-b]pyridin-2-yl)-3-ethylpentanamide | Procedure A; Mayer SC, et al. *J Med Chem* 2008, 51, 7348. | E | 4.5 | 369 |
| 156 | C₁₇H₁₈F₃N₅O₂ | 3,3-dimethyl-N-(3-(5-methylisoxazol-3-yl)-5-(trifluoromethyl)-3H-imidazo[4,5-b]pyridin-2-yl)butanamide | Example 156; commercial | E | 4 | 382 |
| 157 | C₂₂H₂₇N₅O₂ | 3-(tert-butoxy)-N-(3-cyclobutyl-5-(pyridin-3-yl)-3H-imidazo[4,5-b]pyridin-2-yl)propanamide | Procedure D; commercial | CC | 8.05 | 394 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 158 | C₁₅H₂₁ClN₄O₂ | N-(5-chloro-3-propyl-3H-imidazo[4,5-b]pyridin-2-yl)-3-methoxy-3-methylbutanamide | Procedure A; Method 23 | E | 3.1 | 325 |
| 159 | C₁₆H₂₁ClN₄O₂ | N-(5-chloro-3-cyclobutyl-3H-imidazo[4,5-b]pyridin-2-yl)-3-methoxy-3-methylbutanamide | Procedure A; Method 23 | E | 3.5 | 337 |
| 160 | C₁₆H₂₁F₃N₄O | N-(3-isopropyl-5-(trifluoromethyl)-3H-imidazo[4,5-b]pyridin-2-yl)-3,3-dimethylbutanamide | Procedure D; commercial | E | 4.1 | 343 |
| 161 | C₁₆H₁₉F₃N₄O | 3,3-dimethyl-N-(3-(2,2,2-trifluoroethyl)-5-vinyl-3H-imidazo[4,5-b]pyridin-2-yl)butanamide | Procedure D; commercial | E | 4.0 | 341 |
| 162 | C₁₆H₂₁F₃N₄O | N-(5-ethyl-3-(2,2,2-trifluoroethyl)-3H-imidazo[4,5-b]pyridin-2-yl)-3,3-dimethylbutanamide | Example 162; commercial | E | 3.9 | 343 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 163 | C₁₆H₁₉F₃N₄O₂ | N-(3-cyclobutyl-5-(trifluoromethyl)-3H-imidazo[4,5-b]pyridin-2-yl)-3-hydroxy-3-methylbutanamide | Procedure A; commercial | E | 3.4 | 357 |
| 164 | C₁₈H₂₃F₃N₄O | N-(3-cyclobutyl-5-(trifluoromethyl)-3H-imidazo[4,5-b]pyridin-2-yl)-4,4-dimethylpentanamide | Procedure A; commercial | E | 4.4 | 369 |
| 165 | C₂₀H₂₇F₃N₄O₂ | 3-(tert-butoxy)-N-(3-cyclobutyl-5-(trifluoromethyl)-3H-imidazo[4,5-b]pyridin-2-yl)-2,2-dimethylpropanamide | Procedure A; Method 19 | E | 4.9 | 413 |
| 166 | C₁₈H₂₃F₃N₄O₂ | N-(3-cyclobutyl-5-(trifluoromethyl)-3H-imidazo[4,5-b]pyridin-2-yl)-4-methoxy-4-methylpentanamide | Procedure A; King, SA, J Org Chem, 1994, 59, 2253; base hydrolysis | E | 3.8 | 385 |
| 167 | C₁₇H₁₈F₆N₄O | N-(3-cyclobutyl-5-(trifluoromethyl)-3H-imidazo[4,5-b]pyridin-2-yl)-4,4,4-trifluoro-3,3-dimethylbutanamide | Procedure A; Pat. Appl. WO 2011102964 | E | 4.5 | 409 |
| 168 | C₁₉H₂₅F₃N₄O₂ | (R)-3-(tert-butoxy)-N-(3-cyclobutyl-5-(trifluoromethyl)-3H-imidazo[4,5-b]pyridin-2-yl)-2-methylpropanamide | Procedure A; Method 19 | E | 4.3 | 399 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 169 | C₁₉H₂₅F₃N₄O₂ | (S)-3-(tert-butoxy)-N-(3-cyclobutyl-5-(trifluoromethyl)-3H-imidazo[4,5-b]pyridin-2-yl)-2-methylpropanamide | Procedure A; Method 19 | E | 4.3 | 399 |
| 170 | C₁₈H₂₁F₃N₄O | N-(3-cyclobutyl-5-(trifluoromethyl)-3H-imidazo[4,5-b]pyridin-2-yl)-2-cyclopentylacetamide | Procedure A; commercial | E | 4.3 | 367 |
| 171 | C₁₇H₂₁F₃N₄O₂ | N-(3-cyclobutyl-5-(trifluoromethyl)-3H-imidazo[4,5-b]pyridin-2-yl)-3-methoxy-3-methylbutanamide | Procedure A; Method 23 | E | 3.8 | 371 |
| 172 | C₁₉H₂₀F₃N₅O | 3,3-dimethyl-N-(3-(6-methylpyridin-3-yl)-5-(trifluoromethyl)-3H-imidazo[4,5-b]pyridin-2-yl)butanamide | Example 172; commercial | E | 3.3 | 392 |
| 173 | C₁₇H₂₃ClN₄O | N-(5-chloro-3-cyclobutyl-3H-imidazo[4,5-b]pyridin-2-yl)-3-ethylpentanamide | Procedure A; Mayer SC, et al. *J Med Chem* 2008, 51, 7348. | E | 4.2 | 335 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 174 | C₁₆H₁₈ClF₃N₄O | N-(5-chloro-3-cyclobutyl-3H-imidazo[4,5-b]pyridin-2-yl)-4,4,4-trifluoro-3,3-dimethylbutanamide | Procedure A; Pat. Appl. WO 2011102964 | E | 4.4 | 375 |
| 175 | C₁₇H₂₃ClN₄O | N-(5-chloro-3-cyclobutyl-3H-imidazo[4,5-b]pyridin-2-yl)-4,4-dimethylpentanamide | Procedure A; commercial | E | 4.2 | 335 |
| 176 | C₁₅H₁₉ClN₄O₂ | isobutyl (5-chloro-3-cyclobutyl-3H-imidazo[4,5-b]pyridin-2-yl)carbamate | Example 176; commercial | E | 2.7 | 323 |
| 177 | C₁₇H₁₇ClFN₅O | N-(5-chloro-3-(5-fluoropyridin-2-yl)-3H-imidazo[4,5-b]pyridin-2-yl)-3,3-dimethylbutanamide | Procedure D; commercial | E | 3.8 | 362 |
| 178 | C₁₇H₂₁ClN₄O₂ | N-(6-chloro-3-cyclobutyl-3H-imidazo[4,5-b]pyridin-2-yl)-3-(tetrahydrofuran-2-yl)propanamide | Procedure A; commercial | E | 3.4 | 349 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 179 | C<sub>19</sub>H<sub>27</sub>ClN<sub>4</sub>O<sub>2</sub> | 3-(tert-butoxy)-N-(6-chloro-3-cyclobutyl-3H-imidazo[4,5-b]pyridin-2-yl)-2,2-dimethylpropanamide | Procedure A; Method 19 | E | 4.8 | 379 |
| 180 | $C_{18}H_{21}F_3N_4O_2$ | N-(3-cyclobutyl-6-(trifluoromethyl)-3H-imidazo[4,5-b]pyridin-2-yl)-3-(tetrahydrofuran-2-yl)propanamide | Procedure A; commercial | E | 3.6 | 383 |
| 181 | $C_{20}H_{27}F_3N_4O_2$ | 3-(tert-butoxy)-N-(3-cyclobutyl-6-(trifluoromethyl)-3H-imidazo[4,5-b]pyridin-2-yl)-2,2-dimethylpropanamide | Procedure A; Method 19 | EE | 4.9 | 413 |
| 182 | $C_{21}H_{21}F_3N_4O$ | (R)-N-(3-cyclobutyl-5-(trifluoromethyl)-3H-imidazo[4,5-b]pyridin-2-yl)-3-phenylbutanamide | Procedure A; commercial | E | 4.4 | 403 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 183 | $C_{21}H_{21}F_3N_4O$ | (S)-N-(3-cyclobutyl-5-(trifluoromethyl)-3H-imidazo[4,5-b]pyridin-2-yl)-3-phenylbutanamide | Procedure A; commercial | E | 4.4 | 403 |
| 184 | $C_{17}H_{15}F_7N_4O$ | N-(3-cyclobutyl-5-(trifluoromethyl)-3H-imidazo[4,5-b]pyridin-2-yl)-2-(2,2,3,3-tetrafluorocyclobutyl)acetamide | Procedure A; commercial | E | 4.3 | 425 |
| 185 | $C_{18}H_{17}F_3N_4O_2$ | N-(3-cyclobutyl-5-(trifluoromethyl)-3H-imidazo[4,5-b]pyridin-2-yl)-3-(furan-2-yl)propanamide | Procedure A; commercial | E | 4.1 | 379 |
| 186 | $C_{18}H_{17}F_3N_4OS$ | N-(3-cyclobutyl-5-(trifluoromethyl)-3H-imidazo[4,5-b]pyridin-2-yl)-3-(thiophen-2-yl)propanamide | Procedure A; commercial | E | 4.2 | 395 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 187 | C₁₇H₁₇F₅N₄O | N-(3-cyclobutyl-5-(trifluoromethyl)-3H-imidazo[4,5-b]pyridin-2-yl)-2-(3,3-difluorocyclobutyl)acetamide | Procedure A; commercial | E | 4.1 | 389 |
| 188 | C₁₇H₂₁F₃N₄O₂ | N-(3-cyclobutyl-5-(trifluoromethyl)-3H-imidazo[4,5-b]pyridin-2-yl)-4-methoxypentanamide | Procedure A; King, SA, J Org Chem, 1994, 59, 2253; base hydrolysis | E | 3.7 | 371 |
| 189 | C₁₈H₁₉ClFN₅O₂ | 3-(tert-butoxy)-N-(5-chloro-3-(5-fluoropyridin-2-yl)-3H-imidazo[4,5-b]pyridin-2-yl)propanamide | Procedure D; commercial | E | 3.6 | 392 |
| 190 | C₂₀H₁₅ClFN₅O | N-(5-chloro-3-(5-fluoropyridin-2-yl)-3H-imidazo[4,5-b]pyridin-2-yl)-3-phenylpropanamide | Procedure B; commercial | E | 3.9 | 396 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 191 | C₁₇H₂₁F₃N₄O | (S)-N-(3-cyclobutyl-5-(trifluoromethyl)-3H-imidazo[4,5-b]pyridin-2-yl)-3-methylpentanamide | Procedure A; commercial | E | 4.2 | 355 |
| 192 | C₁₆H₂₀ClFN₄O | N-(5-chloro-3-((1s,3s)-3-fluorocyclobutyl)-3H-imidazo[4,5-b]pyridin-2-yl)-3,3-dimethylbutanamide | Example 192; commercial | E | 3.8 | 339 |
| 193 | C₁₆H₂₃ClN₄O₂ | N-(5-chloro-3-(2-ethoxyethyl)-3H-imidazo[4,5-b]pyridin-2-yl)-3,3-dimethylbutanamide | Procedure A; commercial | E | 3.5 | 339 |
| 194 | C₁₇H₂₃ClN₄O₂ | N-(5-chloro-3-cyclobutyl-3H-imidazo[4,5-b]pyridin-2-yl)-4-methoxy-4-methylpentanamide | Procedure A; U.S. patent application Ser. No. 20080019978 | E | 3.6 | 351 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 195 | $C_{16}H_{17}ClF_2N_4O$ | N-(5-chloro-3-cyclobutyl-3H-imidazo[4,5-b]pyridin-2-yl)-2-(3,3-difluorocyclobutyl)acetamide | Procedure A; commercial | E | 3.9 | 355 |
| 196 | $C_{19}H_{26}N_4O_2$ | (S)-N-(3-cyclobutyl-3H-imidazo[4,5-b]pyridin-2-yl)-2-(6,6-dimethyltetrahydro-2H-pyran-2-yl)acetamide | Procedure A; Larcheveque M, et al. *Tetrahedron*, 1990, 46(12), Marotta E, et al. *Org Lett*, 2002, 4, 4451 | E | 3.4 | 343 |
| 197 | $C_{18}H_{23}N_5O_2$ | N-(5-cyano-3-cyclobutyl-3H-imidazo[4,5-b]pyridin-2-yl)-4-methoxy-4-methylpentanamide | Procedure A; U.S. patent application Ser. No. 20080019978 | E | 3.3 | 342 |
| 198 | $C_{16}H_{20}Cl_2N_4O$ | N-(5,6-dichloro-3-cyclobutyl-3H-imidazo[4,5-b]pyridin-2-yl)-3,3-dimethylbutanamide | Procedure D; commercial | E | 4.4 | 355 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 199 | C₁₆H₁₉F₃N₄O | N-(3-cyclobutyl-3H-imidazo[4,5-b]pyridin-2-yl)-4,4,4-trifluoro-3,3-dimethylbutanamide | Procedure A; commercial | E | 4 | 341 |
| 200 | C₁₇H₁₈F₃N₅O | N-(5-cyano-3-cyclobutyl-3H-imidazo[4,5-b]pyridin-2-yl)-4,4,4-trifluoro-3,3-dimethylbutanamide | Procedure A; commercial | E | 4 | 366 |
| 201 | C₁₇H₁₈F₆N₄O | N-(3-cyclobutyl-6-(trifluoromethyl)-3H-imidazo[4,5-b]pyridin-2-yl)-4,4,4-trifluoro-3,3-dimethylbutanamide | Procedure A; commercial | E | 4.5 | 409 |
| 202 | C₁₆H₁₈ClF₃N₄O | N-(6-chloro-3-cyclobutyl-3H-imidazo[4,5-b]pyridin-2-yl)-4,4,4-trifluoro-3,3-dimethylbutanamide | Procedure A; commercial | E | 4.5 | 375 |
| 203 | C₁₉H₂₅ClN₄O₂ | N-(5-chloro-3-cyclobutyl-3H-imidazo[4,5-b]pyridin-2-yl)-3-(cyclohexyloxy)propanamide | Procedure A; Method 20 | BB | 13.72 | 377 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 204 | $C_{16}H_{21}ClN_4O_2$ | N-(5-chloro-3-cyclobutyl-3H-imidazo[4,5-b]pyridin-2-yl)-3-methoxy-2,2-dimethylpropanamide | Procedure A; commercial | BB | 16.94 | 337 |
| 205 | $C_{17}H_{21}ClN_4O_2$ | N-(5-chloro-3-cyclobutyl-3H-imidazo[4,5-b]pyridin-2-yl)-3-cyclobutoxy-propanamide | Procedure A; Method 20 | AA | 9.41 | 349 |
| 206 | $C_{19}H_{23}ClF_2N_4O_2$ | N-(5-chloro-3-cyclobutyl-3H-imidazo[4,5-b]pyridin-2-yl)-3-((4,4-difluorocyclohexyl)oxy)propanamide | Procedure A; Method 20 | AA | 9.63 | 413 |
| 207 | $C_{19}H_{23}ClN_4O_2$ | 3-((1R,3r,5S)-bicyclo[3.1.0]hexan-3-yloxy)-N-(5-chloro-3-cyclobutyl-3H-imidazo[4,5-b]pyridin-2-yl)propanamide | Procedure A; Method 20 | AA | 9.84 | 375 |
| 208 | $C_{14}H_{15}Cl_2F_3N_4O$ | N-(5,6-dichloro-3-(2,2,2-trifluoroethyl)-3H-imidazo[4,5-b]pyridin-2-yl)-3,3-dimethylbutanamide | Procedure D; commercial | E | 4.1 | 383 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 209 | C₂₁H₂₁F₃N₄O | (R)-N-(3-cyclobutyl-6-(trifluoromethyl)-3H-imidazo[4,5-b]pyridin-2-yl)-3-phenylbutanamide | Procedure A; commercial | E | 4.3 | 403 |
| 210 | C₂₁H₂₁F₃N₄O | (S)-N-(3-cyclobutyl-6-(trifluoromethyl)-3H-imidazo[4,5-b]pyridin-2-yl)-3-phenylbutanamide | Procedure A; commercial | E | 4.3 | 403 |
| 211 | C₁₉H₁₅Cl₂F₃N₄O | N-(3-cyclobutyl-6-(trifluoromethyl)-3H-imidazo[4,5-b]pyridin-2-yl)-2-(2,5-dichlorophenyl)acetamide | Procedure A; commercial | E | 4.8 | 444 |
| 212 | C₁₇H₁₈F₃N₅O₂ | 3,3-dimethyl-N-(3-(3-methylisoxazol-5-yl)-5-(trifluoromethyl)-3H-imidazo[4,5-b]pyridin-2-yl)butanamide | Example 212; commercial | E | 3.6 | 382 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 213 | C₁₆H₁₈ClF₃N₄O | N-(5-chloro-3-cyclobutyl-3H-imidazo[4,5-b]pyridin-2-yl)-5,5,5-trifluoro-3-methylpentanamide | Procedure A; Pat. Appl. WO 2008024433 | AA | 10.05 | 375 |
| 214 | C₁₈H₂₁ClF₂N₄O | N-(5-chloro-3-cyclobutyl-3H-imidazo[4,5-b]pyridin-2-yl)-2-(4,4-difluorocyclohexyl)acetamide | Procedure A; commercial | AA | 9.79 | 383 |
| 215 | C₁₇H₁₆F₃N₅OS | N-(3-cyclobutyl-5-(trifluoromethyl)-3H-imidazo[4,5-b]pyridin-2-yl)-3-(thiazol-2-yl)propanamide | Procedure A; commercial | E | 3.7 | 396 |
| 216 | C₁₇H₂₁F₃N₄O | N-(3-cyclobutyl-5-methyl-3H-imidazo[4,5-b]pyridin-2-yl)-4,4,4-trifluoro-3,3-dimethylbutanamide | Procedure A; commercial | E | 4.4 | 355 |
| 217 | C₁₅H₁₉F₃N₄O₂ | N-(5-(hydroxymethyl)-3-(2,2,2-trifluoroethyl)-3H-imidazo[4,5-b]pyridin-2-yl)-3,3-dimethylbutanamide | Example 217; commercial | E | 3.0 | 345 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 218 | $C_{19}H_{17}ClN_6O$ | N-(5-chloro-3-(1-methyl-1H-pyrazol-4-yl)-3H-imidazo[4,5-b]pyridin-2-yl)-3-phenylpropanamide | Example 218; commercial | E | 3.1 | 381 |
| 219 | $C_{18}H_{18}F_6N_4O$ | N-(3-cyclobutyl-5-(trifluoromethyl)-3H-imidazo[4,5-b]pyridin-2-yl)-3-(1-(trifluoromethyl)cyclopropyl)propanamide | Procedure A; Method 22 | E | 4.3 | 421 |
| 220 | $C_{18}H_{21}F_3N_4O_2$ | (S)-N-(3-cyclobutyl-5-(trifluoromethyl)-3H-imidazo[4,5-b]pyridin-2-yl)-3-(tetrahydrofuran-2-yl)propanamide | Procedure A; Method 22 | E | 3.7 | 383 |
| 221 | $C_{20}H_{23}F_3N_4O_2$ | N-(3-cyclobutyl-5-(trifluoromethyl)-3H-imidazo[4,5-b]pyridin-2-yl)-2-((1R,5R)-5-methyl-2-oxabicyclo[3.2.0]heptan-7-yl)acetamide | Procedure A; Method 17 | E | 4 | 409 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 222 | C$_{20}$H$_{23}$F$_3$N$_4$O$_2$ | N-(3-cyclobutyl-5-(trifluoromethyl)-3H-imidazo[4,5-b]pyridin-2-yl)-2-((1R,5S)-5-methyl-2-oxabicyclo[3.2.0]heptan-7-yl)acetamide | Procedure A; Method 17 | E | 4 | 409 |
| 223 | C$_{17}$H$_{18}$ClF$_3$N$_4$O | N-(5-chloro-3-cyclobutyl-3H-imidazo[4,5-b]pyridin-2-yl)-3-(1-(trifluoromethyl)cyclopropyl)propanamide | Procedure A; Method 22 | E | 4.1 | 387 |
| 224 | C$_{17}$H$_{20}$ClF$_3$N$_4$O | N-(6-chloro-3-cyclobutyl-5-(trifluoromethyl)-3H-imidazo[4,5-b]pyridin-2-yl)-3,3-dimethylbutanamide | Procedure D; commercial | E | 4.5 | 389 |
| 225 | C$_{18}$H$_{21}$F$_3$N$_4$O | N-(3-cyclobutyl-5-(trifluoromethyl)-3H-imidazo[4,5-b]pyridin-2-yl)-2-(2,2-dimethylcyclopropyl)acetamide | Procedure A; Method 16 | E | 4.3 | 367 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 226 | $C_{21}H_{19}F_3N_4O$ | 2-(bicyclo[4.2.0]octa-1(6),2,4-trien-7-yl)-N-(3-cyclobutyl-5-(trifluoromethyl)-3H-imidazo[4,5-b]pyridin-2-yl)acetamide | Procedure A; Method 24 | E | 4.4 | 401 |
| 227 | $C_{23}H_{28}N_4O_2$ | N-(5-(benzyloxy)-3-cyclobutyl-3H-imidazo[4,5-b]pyridin-2-yl)-3,3-dimethylbutanamide | Procedure D; commercial | E | 4.1 | 393 |
| 228 | $C_{18}H_{20}F_5N_5O$ | N-(3-cyclobutyl-5-(trifluoromethyl)-3H-imidazo[4,5-b]pyridin-2-yl)-2-(4,4-difluoropiperidin-1-yl)acetamide | Procedure A; Method 21 | E | 2.6 | 418 |
| 229 | $C_{18}H_{23}F_3N_5O$ | N-(3-cyclobutyl-5-methyl-3H-imidazo[4,5-b]pyridin-2-yl)-2-(4,4-difluoropiperidin-1-yl)acetamide | Procedure A; Method 21 | E | 2.4 | 364 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 230 | $C_{20}H_{25}F_3N_4O_2$ | N-(3-cyclobutyl-5-(trifluoromethyl)-3H-imidazo[4,5-b]pyridin-2-yl)-2-(2,5,5-trimethyltetrahydrofuran-2-yl)acetamide | Procedure A; Marotta E, et al. *Org Lett*, 2002, 4, 4451 | E | 4.2 | 411 |
| 231 | $C_{19}H_{25}ClN_4O_2$ | N-(5-chloro-3-cyclobutyl-3H-imidazo[4,5-b]pyridin-2-yl)-2-(2,5,5-trimethyltetrahydrofuran-2-yl)acetamide | Procedure A; Marotta E, et al. *Org Lett*, 2002, 4, 4451 | E | 3.9 | 377 |
| 232 | $C_{20}H_{25}N_5O_2$ | N-(5-cyano-3-cyclobutyl-3H-imidazo[4,5-b]pyridin-2-yl)-2-(2,5,5-trimethyltetrahydrofuran-2-yl)acetamide | Procedure A; Marotta E, et al. *Org Lett*, 2002, 4, 4451 | E | 3.7 | 368 |
| 233 | $C_{19}H_{26}N_4O_2$ | N-(3-cyclobutyl-3H-imidazo[4,5-b]pyridin-2-yl)-2-(2,5,5-trimethyltetrahydrofuran-2-yl)acetamide | Procedure A; Marotta E, et al. *Org Lett*, 2002, 4, 4451 | E | 3.2 | 343 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 234 | C₁₇H₂₀ClF₂N₅O | N-(5-chloro-3-cyclobutyl-3H-imidazo[4,5-b]pyridin-2-yl)-2-(3,3-difluoropiperidin-1-yl)acetamide | Procedure A; Method 21 | E | 2.7 | 384 |
| 235 | C₁₈H₂₀F₅N₅O | N-(3-cyclobutyl-5-(trifluoromethyl)-3H-imidazo[4,5-b]pyridin-2-yl)-2-(3,3-difluoropiperidin-1-yl)acetamide | Procedure A; Method 21 | E | 2.9 | 418 |
| 236 | C₁₇H₁₂D₉F₃N₄O | | Procedure B; Oonishi Y, *Angew Chemie, IEE* 2012, 51(29), 7305 | E | 4.2 | 364 |
| 237 | 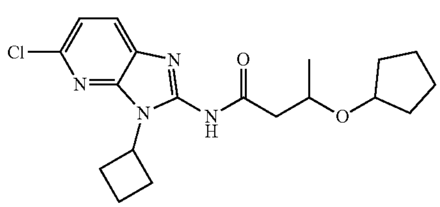 [SMILES: CC(CC(=O)Nc1nc2ccc(Cl)nc2n1C1CCC1)OC1CCCC1] | N-(5-chloro-3-cyclobutyl-3H-imidazo[4,5-b]pyridin-2-yl)-3-(cyclopentyloxy)butanamide | Procedure A; Harschneck T, et al., *J Org Chem* 2001, 76, 2145; Method 20 | AA | 10.51 | 377 |
| 238 | C₁₉H₂₃ClN₄O₂ | 3-((1R,3s,5S)-bicyclo[3.1.0]hexan-3-yloxy)-N-(5-chloro-3-cyclobutyl-3H-imidazo[4,5-b]pyridin-2-yl)propanamide | Procedure A; Method 20 | AA | 10.61 | 375 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 239 | $C_{16}H_{20}N_6O_2$ | 3,3-dimethyl-N-(5-methyl-3-(5-methyl-1,3,4-oxadiazol-2-yl)-3H-imidazo[4,5-b]pyridin-2-yl)butanamide | Procedure B; commercial | E | 2.9 | 329 |
| 240 | $C_{22}H_{27}N_5O_2$ | N-(3-cyclobutyl-5-(pyridin-2-ylmethoxy)-3H-imidazo[4,5-b]pyridin-2-yl)-3,3-dimethylbutanamide | Procedure D; commercial | E | 2.9 | 394 |
| 241 | $C_{17}H_{14}F_5N_5O_2$ | 2-(3,3-difluorocyclobutyl)-N-(3-(3-methylisoxazol-5-yl)-5-(trifluoromethyl)-3H-imidazo[4,5-b]pyridin-2-yl)acetamide | Example 241; commercial | E | 3.5 | 416 |
| 242 | $C_{21}H_{28}N_6O_2$ | N-(3-cyclobutyl-5-((1-methyl-1H-pyrazol-5-yl)meoxy)-3H-imidazo[4,5-b]pyridin-2-yl)-3,3-dimethylbutanamide | Procedure B; commercial | E | 3.2 | 397 |
| 243 | $C_{17}H_{20}F_2N_4O_2$ | N-(3-cyclobutyl-7-methoxy-3H-imidazo[4,5-b]pyridin-2-yl)-2-(3,3-difluorocyclobutyl)acetamide | Procedure A; commercial | E | 3.1 | 351 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 244 | C₁₈H₂₂F₂N₄OS | N-(3-cyclobutyl-5-(ethylthio)-3H-imidazo[4,5-b]pyridin-2-yl)-2-(3,3-difluorocyclobutyl)acetamide | Procedure A; commercial | E | 4 | 381 |
| 245 | C₁₇H₁₈F₅N₅O | N-(3-cyclobutyl-5-(trifluoromethyl)-3H-imidazo[4,5-b]pyridin-2-yl)-2-(3,3-difluoropyrrolidin-1-yl)acetamide | Procedure A; Method 21 | E | 2.8 | 404 |
| 246 | C₁₈H₁₅ClF₄N₅O | N-(5-chloro-3-(4-fluorophenyl)-3H-imidazo[4,5-b]pyridin-2-yl)-4,4,4-trifluoro-3,3-dimethylbutanamide | Procedure A; commercial | E | 3.8 | 415 |
| 247 | C₁₉H₂₁F₂N₅O | N-(5-cyano-3-cyclobutyl-3H-imidazo[4,5-b]pyridin-2-yl)-2-(4,4-difluorocyclohexyl)acetamide | Procedure A; commercial | E | 3.7 | 374 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 248 | C$_{18}$H$_{21}$N$_5$O$_2$ | N-(5-cyano-3-cyclobutyl-3H-imidazo[4,5-b]pyridin-2-yl)-3-cyclobutoxy-propanamide | Procedure A; Method 20 | E | 3.5 | 340 |
| 249 | C$_{18}$H$_{24}$N$_4$O$_2$ | 3-cyclobutoxy-N-(3-cyclobutyl-5-methyl-3H-imidazo[4,5-b]pyridin-2-yl)propanamide | Procedure A; Method 20 | E | 3.5 | 329 |
| 250 | C$_{17}$H$_{17}$F$_2$N$_5$O | N-(5-cyano-3-cyclobutyl-3H-imidazo[4,5-b]pyridin-2-yl)-2-(3,3-difluorocyclobutyl)acetamide | Procedure A; commercial | E | 3.6 | 346 |
| 251 | C$_{17}$H$_{20}$F$_2$N$_4$O | N-(3-cyclobutyl-5-methyl-3H-imidazo[4,5-b]pyridin-2-yl)-2-(3,3-difluorocyclobutyl)acetamide | Procedure A; commercial | E | 3.7 | 335 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 252 | 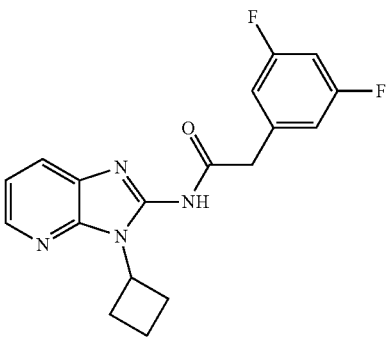<br>C₁₈H₁₆F₂N₄O | N-(3-cyclobutyl-3H-imidazo[4,5-b]pyridin-2-yl)-2-(3,5-difluorophenyl)acetamide | Procedure A; commercial | E | 3.9 | 343 |
| 253 | 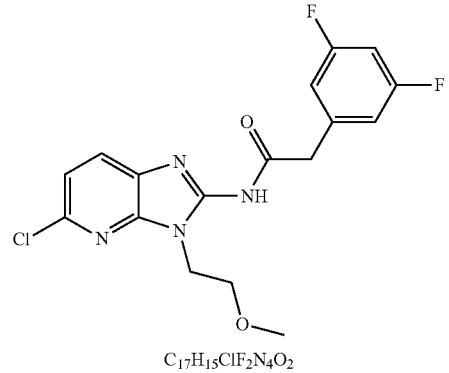 [SMILES: COCCn1c(NC(=O)Cc2cc(F)cc(F)c2)nc2ccc(Cl)nc21 ; "C17H15ClF2N4O2"]<br>C₁₇H₁₅ClF₂N₄O₂ | N-(5-chloro-3-(2-methoxyethyl)-3H-imidazo[4,5-b]pyridin-2-yl)-2-(3,5-difluorophenyl)acetamide | Procedure A; commercial | E | 3.6 | 381 |
| 254 | 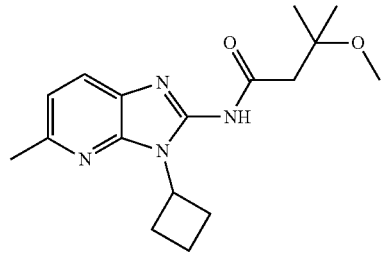<br>C₁₇H₂₄N₄O₂ | N-(3-cyclobutyl-5-methyl-3H-imidazo[4,5-b]pyridin-2-yl)-3-methoxy-3-methylbutanamide | Procedure A; Method 23 | E | 3 | 317 |
| 255 | 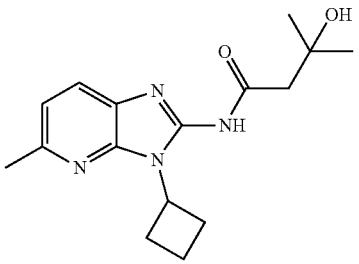<br>C₁₆H₂₂N₄O₂ | N-(3-cyclobutyl-5-methyl-3H-imidazo[4,5-b]pyridin-2-yl)-3-hydroxy-3-methylbutanamide | Procedure A; commercial | E | 2.9 | 314 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 256 | C₁₅H₁₄F₆N₄O | N-(3-cyclobutyl-3H-imidazo[4,5-b]pyridin-2-yl)-4,4,4-trifluoro-3-(trifluoromethyl)butanamide | Procedure A; commercial | E | 4.3 | 381 |
| 257 | C₁₆H₂₁FN₄O₂ | N-(3-cyclobutyl-5-fluoro-3H-imidazo[4,5-b]pyridin-2-yl)-3-methoxy-3-methylbutanamide | Procedure A; Method 23 | E | 3.2 | 321 |
| 258 | C₁₆H₂₁ClN₄O | (S)-N-(5-chloro-3-cyclobutyl-3H-imidazo[4,5-b]pyridin-2-yl)-2,3-dimethylbutanamide | Procedure A; Tanasova M, et al., *Eur J Org Chem* 2012, 3261. | E | 4 | 321 |
| 259 | C₁₇H₂₁F₃N₄O₂ | N-(3-cyclobutyl-5-(trifluoromethyl)-3H-imidazo[4,5-b]pyridin-2-yl)-4-hydroxy-3,3-dimethylbutanamide | Example 259 | E | 3.5 | 369 |
| 260 | C₁₆H₂₂N₄O | (S)-N-(3-cyclobutyl-3H-imidazo[4,5-b]pyridin-2-yl)-2,3-dimethylbutanamide | Procedure A; Tanasova M, et al., *Eur J Org Chem* 2012, 3261. | E | 3.5 | 287 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 261 | C$_{17}$H$_{24}$N$_4$O | (S)-N-(3-cyclobutyl-5-methyl-3H-imidazo[4,5-b]pyridin-2-yl)-2,3-dimethylbutanamide | Procedure A; Tanasova M, et al., *Eur J Org Chem* 2012, 3261. | E | 3.7 | 301 |
| 262 | C$_{17}$H$_{21}$F$_3$N$_4$O | (S)-N-(3-cyclobutyl-5-(trifluoromethyl)-3H-imidazo[4,5-b]pyridin-2-yl)-2,3-dimethylbutanamide | Procedure A; Tanasova M, et al., *Eur J Org Chem* 2012, 3261. | E | 4.3 | 355 |
| 263 | C$_{14}$H$_{16}$ClF$_3$N$_4$O | (S)-N-(5-chloro-3-(2,2,2-trifluoroethyl)-3H-imidazo[4,5-b]pyridin-2-yl)-2,3-dimethylbutanamide | Procedure A; Tanasova M, et al., *Eur J Org Chem* 2012, 3261. | E | 3.8 | 349 |
| 264 | C$_{18}$H$_{17}$F$_4$N$_5$O | N-(3-(5-fluoropyridin-2-yl)-5-(trifluoromethyl)-3H-imidazo[4,5-b]pyridin-2-yl)-3,3-dimethylbutanamide | Procedure A; commercial | E | 4 | 396 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
|---|---|---|---|---|---|---|
| 265 | C₁₇H₁₅F₄N₅O₂ | N-(3-(5-fluoropyridin-2-yl)-5-(trifluoromethyl)-3H-imidazo[4,5-b]pyridin-2-yl)-3-hydroxy-3-methylbutanamide | Procedure A; commercial | E | 3.2 | 398 |
| 266 | C₁₈H₁₇F₄N₅O | (S)-N-(3-(5-fluoropyridin-2-yl)-5-(trifluoromethyl)-3H-imidazo[4,5-b]pyridin-2-yl)-2,3-dimethylbutanamide | Procedure A; Tanasova M, et al., *Eur J Org Chem* 2012, 3261. | E | 4 | 396 |
| 267 | C₁₈H₁₃F₆N₅O | 2-(3,3-difluorocyclobutyl)-N-(3-(5-fluoropyridin-2-yl)-5-(trifluoromethyl)-3H-imidazo[4,5-b]pyridin-2-yl)acetamide | Procedure A; commercial | E | 3.8 | 430 |
| 268 | C₁₇H₂₁N₅O | (S)-N-(5-cyano-3-cyclobutyl-3H-imidazo[4,5-b]pyridin-2-yl)-2,3-dimethylbutanamide | Procedure A; Tanasova M, et al., *Eur J Org Chem* 2012, 3261. | E | 3.8 | 312 |

TABLE 1-continued

LIST OF EXAMPLES, SYNTHETIC ROUTES AND ANALYTICAL DATA

| Ex. No. | Structure | Name | Method of Synthesis; Coupling partner | HPLC Method | LC/MS Retention time (min) | m/Z (MH+) |
| --- | --- | --- | --- | --- | --- | --- |
| 269 | $C_{17}H_{15}F_6N_5O_2$ | 4,4,4-trifluoro-3,3-dimethyl-N-(3-(3-methylisoxazol-5-yl)-5-(trifluoromethyl)-3H-imidazo[4,5-b]pyridin-2-yl)butanamide | Example 269; commercial | E | 3.7 | 436 |
| 270 | $C_{16}H_{18}F_3N_7O$ | 3,3-dimethyl-N-(3-(1-methyl-1H-1,2,3-triazol-4-yl)-5-(trifluoromethyl)-3H-imidazo[4,5-b]pyridin-2-yl)butanamide | Procedure A; commercial | E | 3.4 | 382 |
| 271 | $C_{22}H_{33}N_5O_2$ | N-(3-cyclobutyl-5-(4-methoxypiperidin-1-yl)-3H-imidazo[4,5-b]pyridin-2-yl)-3,3-dimethylbutanamide | Procedure A; commercial | E | 3 | 400 |

The following is a listing of embodiments that are specifically contemplated herein.

Embodiment 1

A compound represented by a formula:

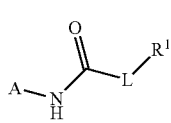

wherein A is optionally substituted 1H-imidazo[4,5-b]pyridin-2-yl or optionally substituted 3H-imidazo[4,5-b]pyridin-2-yl;

L is $CH_2$, $CF_2$, $C_2H_4$, $C_3H_6$, O, $CH_2O$, $C_2H_4O$, or $C_3H_6O$;

$R^1$ is $C_{1-12}$ optionally substituted alkyl, $C_{1-12}$ optionally substituted —O-alkyl, optionally substituted $C_{6-10}$ aryl, optionally substituted $C_{6-10}$ —O-aryl, or optionally substituted $C_{2-9}$ heterocyclyl;

wherein the compound is active at a Kv7.2 bearing potassium channel, a Kv7.3 bearing potassium channel, a Kv7.4 bearing potassium channel, or a Kv7.5 bearing potassium channel.

Embodiment 2

A compound represented by a formula:

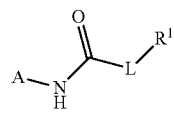

wherein A is optionally substituted 1H-imidazo[4,5-b]pyridin-2-yl or optionally substituted 3H-imidazo[4,5-b]pyridin-2-yl;

L is $CH_2$, $CF_2$, $C_2H_4$, $C_3H_6$, O, $CH_2O$, $C_2H_4O$, or $C_3H_6O$; and $R^1$ is $CH_3$, $C_{2-12}$ optionally substituted alkyl, $C_{1-12}$ optionally substituted —O-alkyl, optionally substituted $C_{6-10}$ aryl, optionally substituted $C_{6-10}$ —O-aryl, or optionally substituted $C_{2-9}$ heterocyclyl.

Embodiment 3

The compound of embodiment 1 or 2, wherein the compound is active at a homotetrameric Kv7.2 bearing potassium channel, a Kv7.3 homotetrameric bearing potassium channel, a heterotetrameric Kv7.2/7.3 bearing channel, a heterotetrameric Kv7.3/7.5 bearing channel, a homotetrameric Kv7.4 bearing potassium channel, or a homotetrameric Kv7.5 bearing potassium channel at a concentration below about 10 μM.

Embodiment 4

The compound of any preceding embodiment, further represented by a formula:

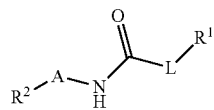

wherein $R^2$ is —$R^a$—Cy, wherein $R^a$ is a bond or $C_{1-12}$ optionally substituted alkyl, and Cy is H, optionally substituted $C_{6-10}$ aryl, or optionally substituted $C_{2-9}$ heterocyclyl.

Embodiment 5

The compound of any preceding embodiment, wherein the compound has a molecular weight of less than 1500 g/mol.

Embodiment 6

The compound of any preceding embodiment, wherein any substituent present in the compound independently has a molecular weight of 15 g/mol to 200 g/mol.

Embodiment 7

The compound of any of embodiments 4-6, wherein all substituents of $R^2$ are independently $C_{1-6}$ alkyl, $C_{1-6}$ —O-alkyl, OH, F, Cl, Br, I, $C_{1-6}$ amino, $C_{1-6}$ aminoalkyl, $C_{1-6}$ aminoacyl, $C_{1-6}$ acylamino, $C_{1-6}$ alkythio, or $C_{1-6}$ alkylsulfonyl.

Embodiment 8

The compound of any preceding embodiment, further represented by a formula:

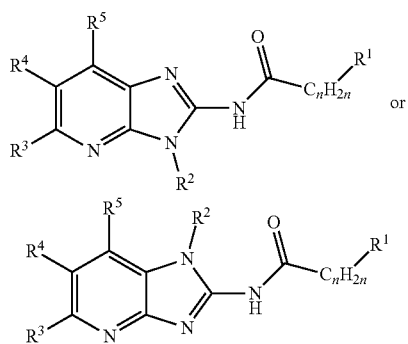

Wherein n is 1, 2, or 3, $R^3$, $R^4$, and $R^5$ are independently H, F, Cl, Br, I, CN, $C_{1-12}$ optionally substituted alkyl, $C_{1-12}$ optionally substituted —O-alkyl, optionally substituted $C_{2-9}$ heterocyclyl, optionally substituted $C_{6-10}$ aryl, optionally substituted $C_{2-9}$ —O-heterocyclyl, optionally substituted $C_{6-10}$ —O-aryl, $C_{1-12}$ optionally substituted acylamino, $C_{1-12}$ optionally substituted aminoacyl, or optionally substituted $C_{1-12}$ aminoalkyl.

Embodiment 9

The compound of embodiment 7, wherein all substituents of $R^3$, $R^4$, and $R^5$ are independently F, Cl, Br, I, CN, $C_{1-6}$ alkyl, $C_{1-6}$ —O-alkyl, $C_{1-6}$ amino, $C_{1-6}$ aminoalkyl, $C_{1-6}$ aminoacyl, $C_{1-6}$ acylamino, $C_{1-6}$ alkylthio, or $C_{1-6}$ alkylsulfonyl.

Embodiment 10

The compound of any of embodiments 4-9, wherein $R^2$ is cyclobutyl.

Embodiment 11

The compound of any of embodiments 4-9, wherein $R^2$ is —$CH_2CH(CH_3)_2$.

Embodiment 11a

The compound of any of embodiments 4-9, wherein $R^2$ triazolyl.

Embodiment 11 b

The compound of any of embodiments 4-9, wherein $R^2$ oxadiazolyl.

Embodiment 11c

The compound of any of embodiments 4-9, wherein $R^2$ isoxazolyl.

Embodiment 12

The compound of any of embodiments 2-11c, wherein $R^1$ is optionally substituted phenyl.

Embodiment 13

The compound of any of embodiments 2-11c, wherein $R^1$ is $C_{3-4}$ alkyl.

Embodiment 14

The compound of any of embodiments 2-11c, wherein $R^1$ is optionally substituted bicyclo[2.2.1]heptan-2-yl.

Embodiment 15

The compound of any of embodiments 2-11c, wherein $R^1$ is optionally substituted isoxazol-3-yl.

Embodiment 16

The compound of any of embodiments 2-11c, wherein $R^1$ is $CF_3$.

Embodiment 17

The compound of any of embodiments 2-11c, wherein $R^1$ is optionally substituted cyclopentyl.

Embodiment 18

The compound of any of embodiments 2-11c, wherein $R^1$ is optionally substituted cyclohexyl.

Embodiment 19

The compound of any of embodiments 2-11c, wherein $R^1$ is methyl.

Embodiment 20

The compound of any of embodiments 2-11c, wherein $R^1$ is optionally substituted bicyclo[3.1.1]heptan-2-yl.

Embodiment 21

The compound of any of embodiments 2-11c, wherein $R^1$ is optionally substituted —O-phenyl.

Embodiment 22

The compound of any of embodiments 2-11c, wherein $R^1$ is optionally substituted $CH(CF_3)_2$.

Embodiment 23

The compound of any of embodiments 2-11c, wherein $R^1$ is $C_{2-4}$—O-alkyl.

Embodiment 24

The compound of any of embodiments 2-11c, wherein $R^1$ is optionally substituted adamantan-1-yl.

Embodiment 25

The compound of any of embodiments 2-11c, wherein $R^1$ is optionally substituted tetrahydro-2H-pyranyl.

Embodiment 26

The compound of any of embodiments 2-11c, wherein $R^1$ is optionally substituted tetrahydrofuranyl.

Embodiment 27

The compound of any of embodiments 8-26, wherein $R^3$ is $CF_3$.

Embodiment 28

The compound of any of embodiments 8-26, wherein $R^3$ is Cl.

Embodiment 29

The compound of any of embodiments 8-26, wherein $R^3$ is CN.

Embodiment 30

The compound of any of embodiments 8-26, wherein $R^3$ is $OCH_3$.

Embodiment 31

The compound of any of embodiments 8-26, wherein $R^3$ is H.

Embodiment 32

The compound of any of embodiments 8-31, wherein $R^4$ is $CF_3$.

Embodiment 33

The compound of any of embodiments 8-31, wherein $R^4$ is Cl.

Embodiment 34

The compound of any of embodiments 8-31, wherein $R^4$ is H.

Embodiment 35

The compound of embodiment 4, wherein Cy is H and $R^a$ is substituted with a $CF_3$ substituent.

Embodiment 36

The compound of embodiments 1-9, and 12-35, wherein $R^2$ is —$CH_2CH=CH_2$

Embodiment 37

The compound of embodiments 1-9, and 12-35, wherein $R^2$ is —$CH_2CF_3$

Embodiment 38

The compound of embodiments 1-9, and 12-35, wherein $R^2$ is —$C(CH_3)_3$

Embodiment 39

The compound of embodiment 1, further represented by a formula:

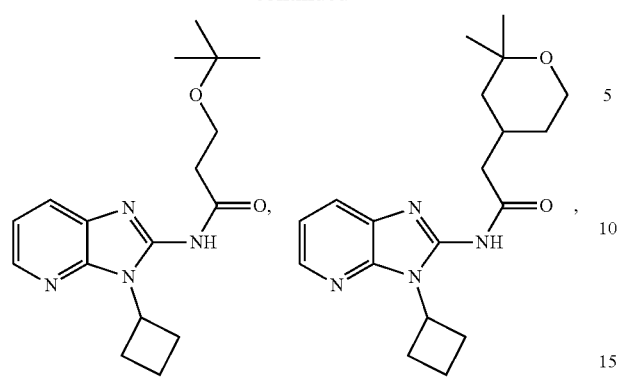
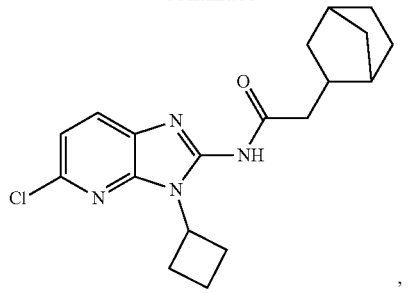
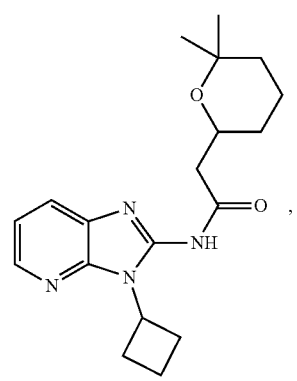
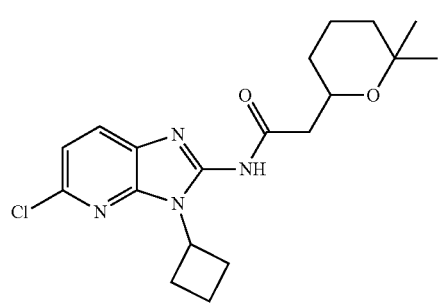
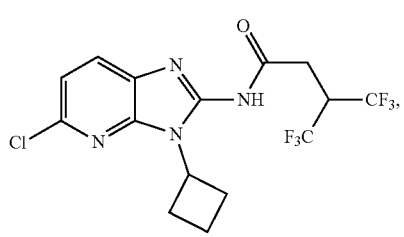
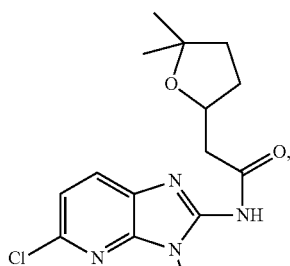
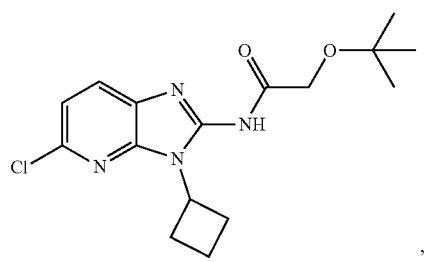
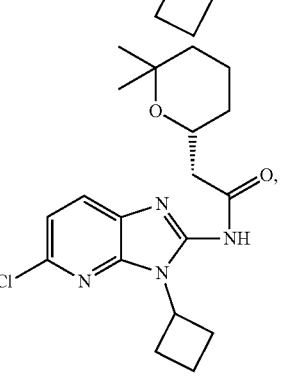
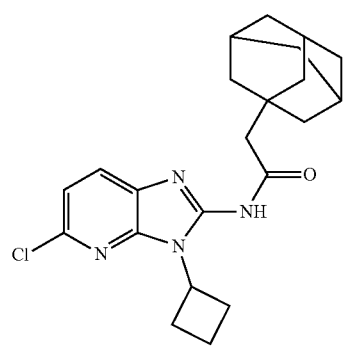
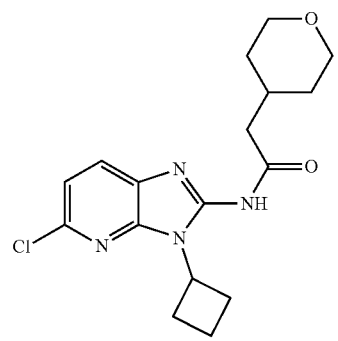

211
-continued
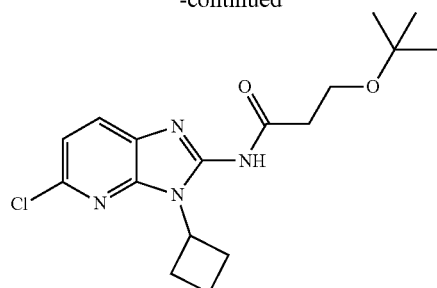
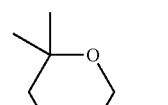
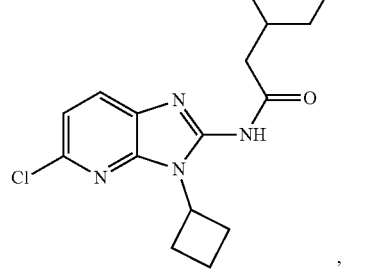
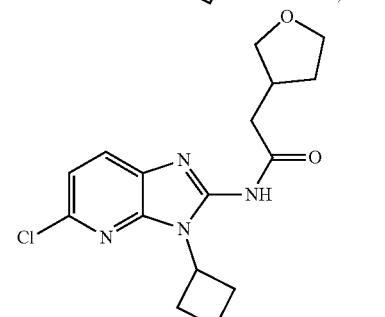
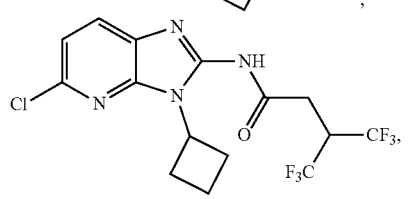
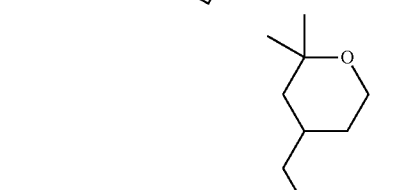
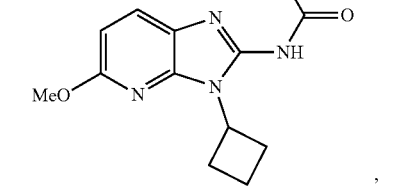
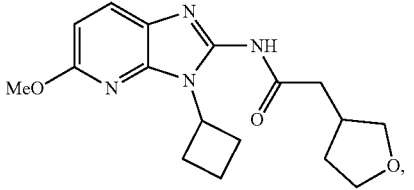
212
-continued
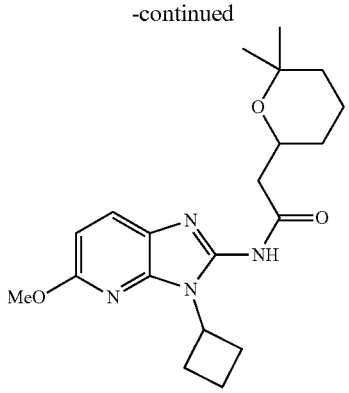
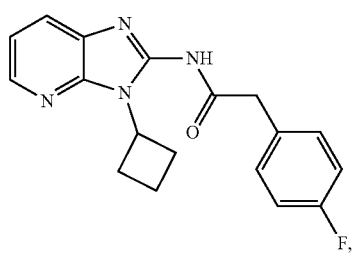
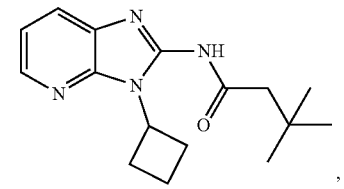
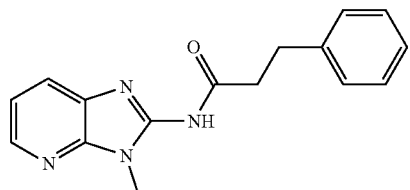
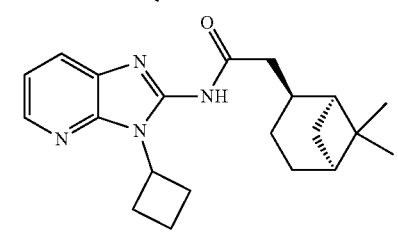
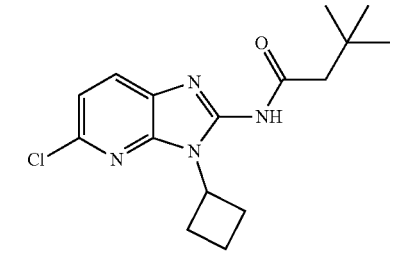

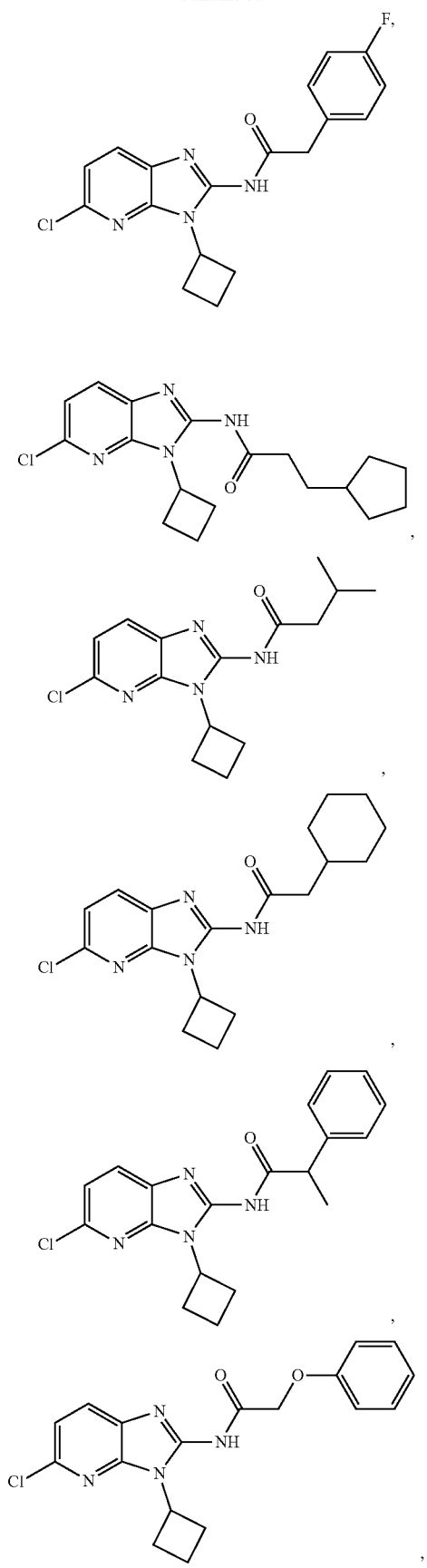
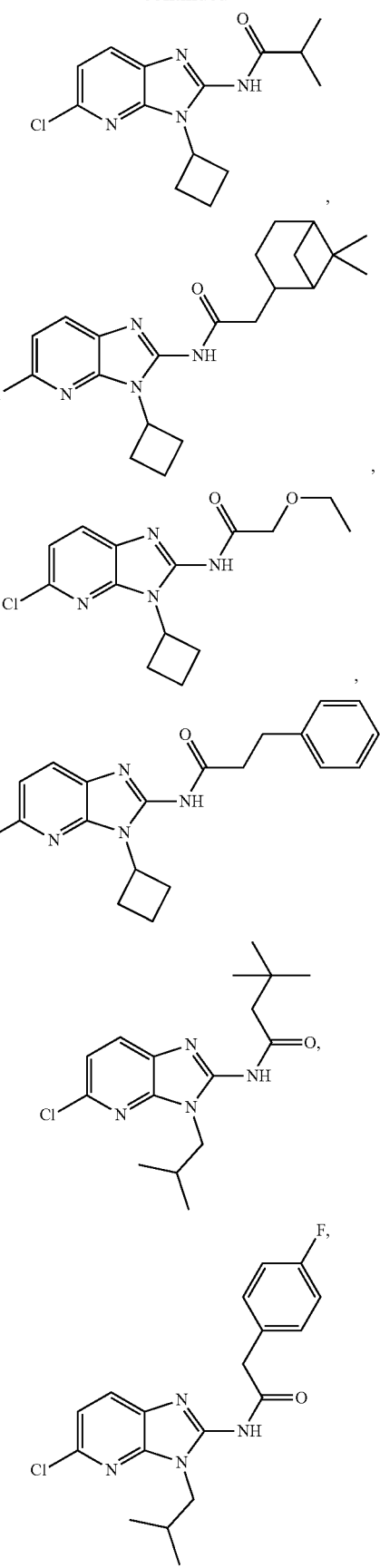

215
-continued
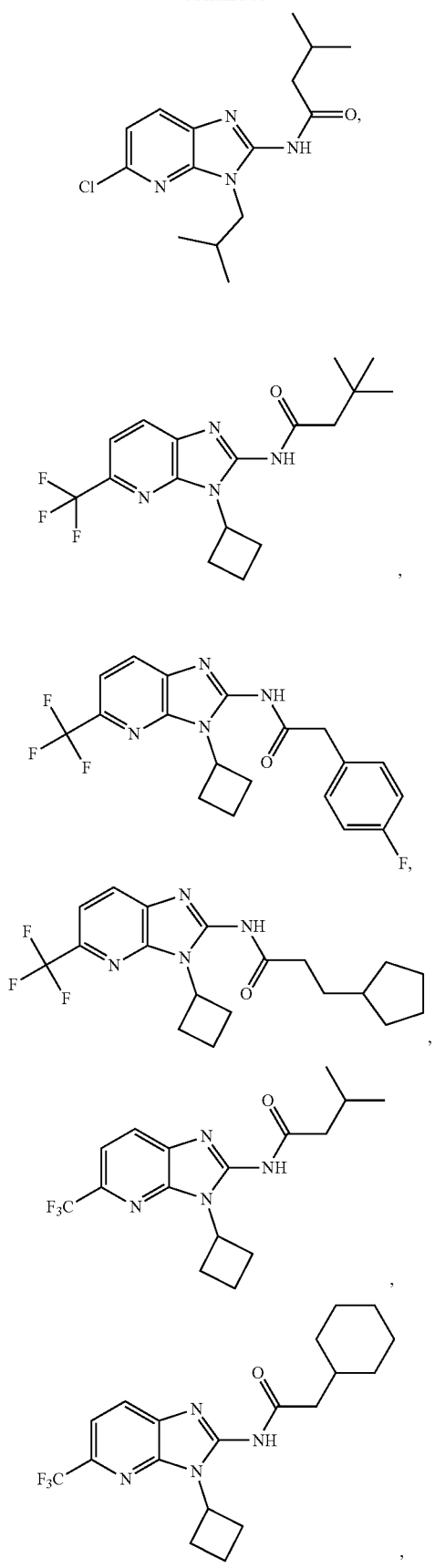
216
-continued
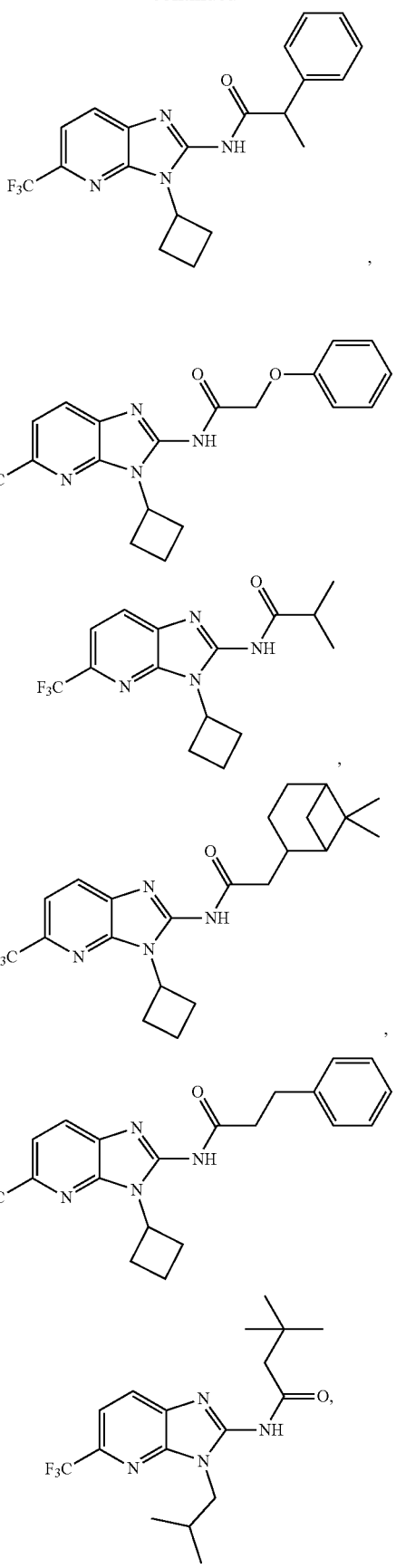

217
-continued
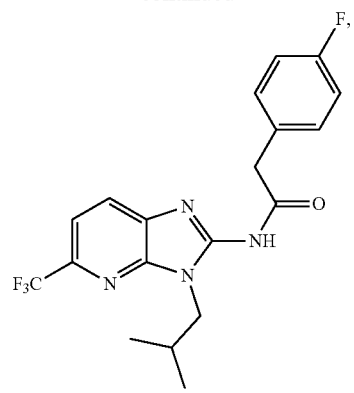
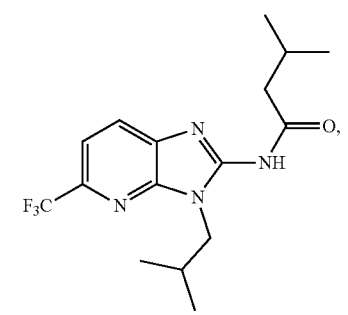
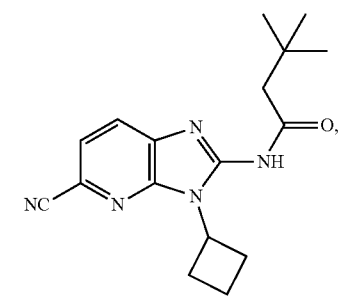
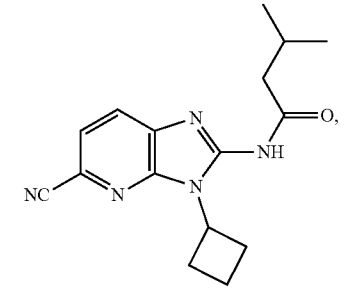
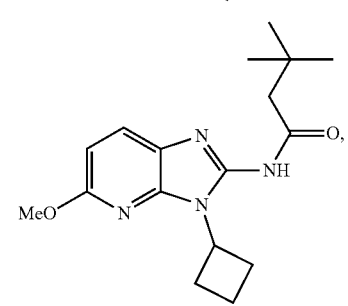
218
-continued
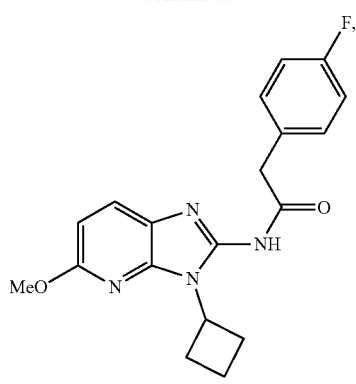
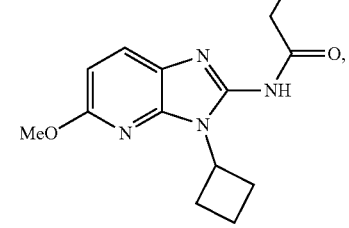
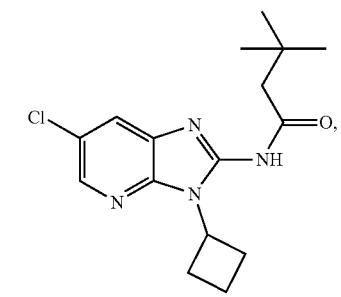
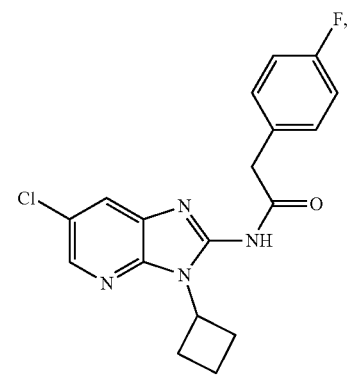
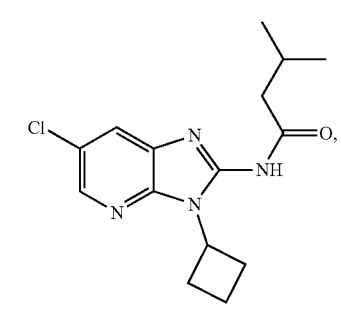

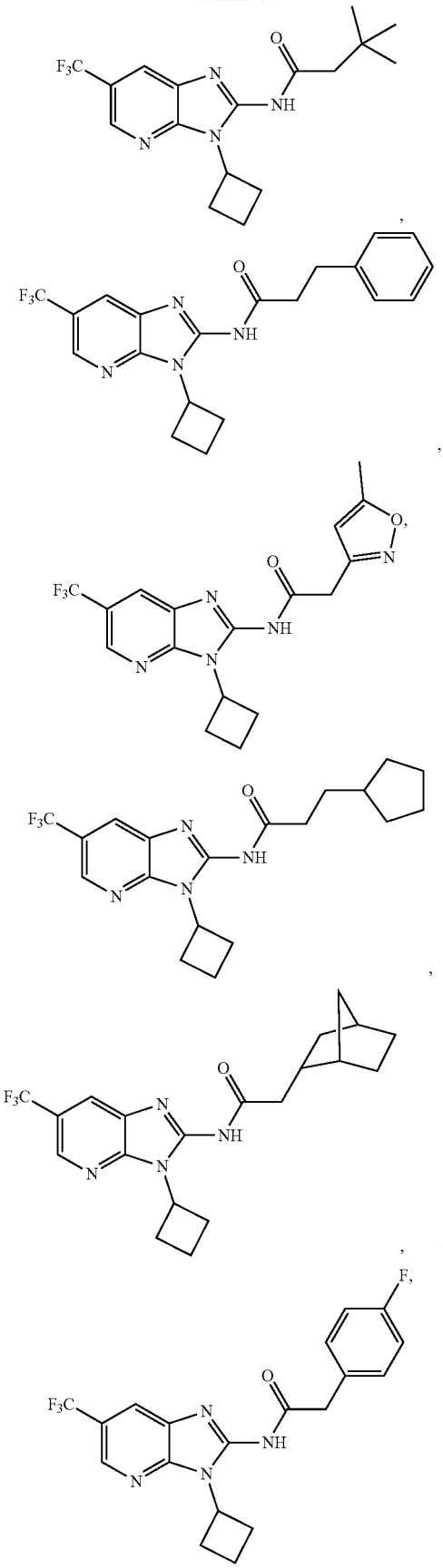
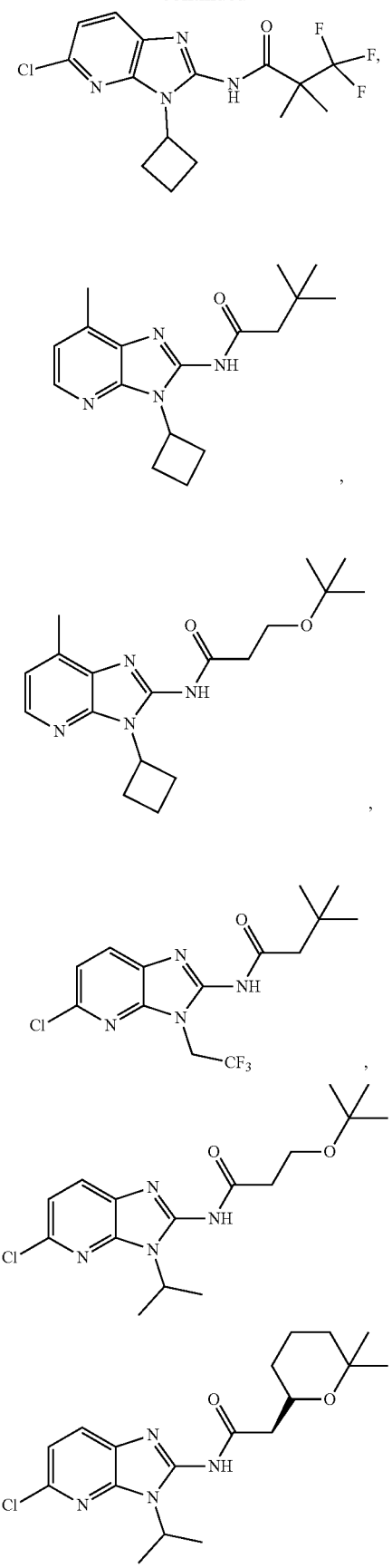

221
-continued
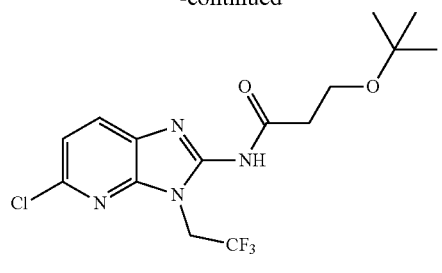
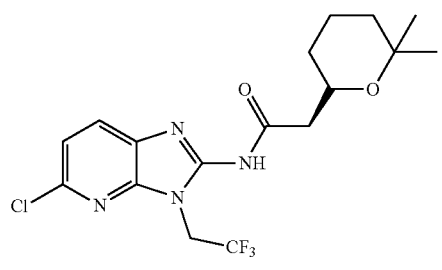
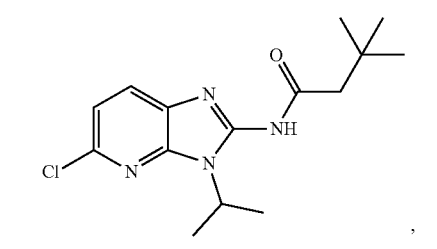
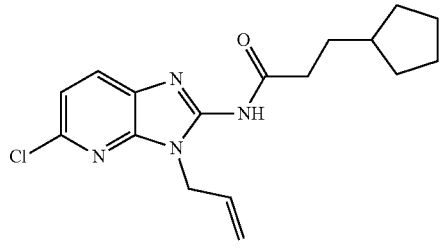
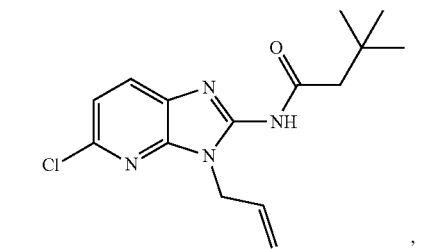
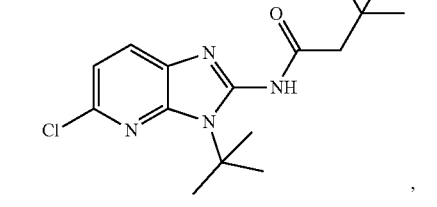
222
-continued
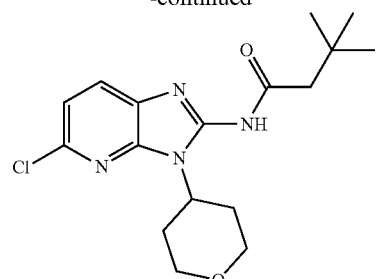
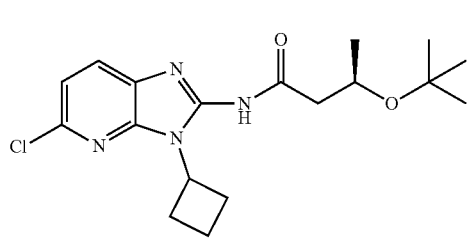
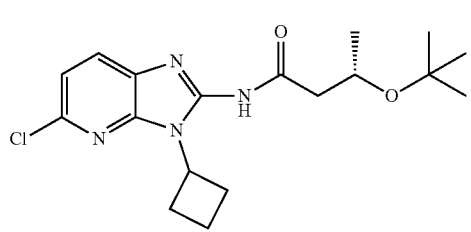
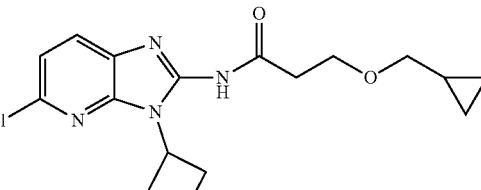
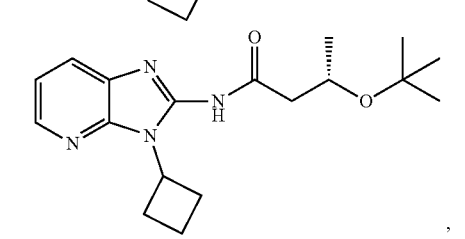
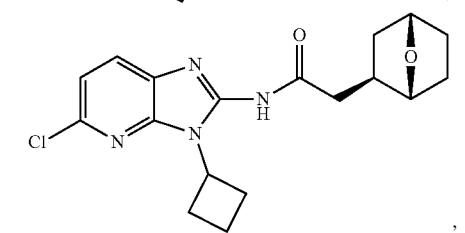
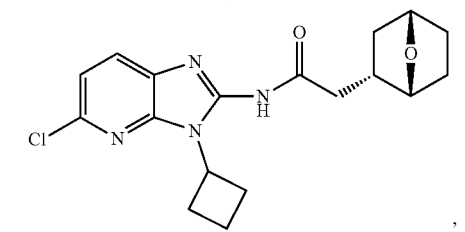

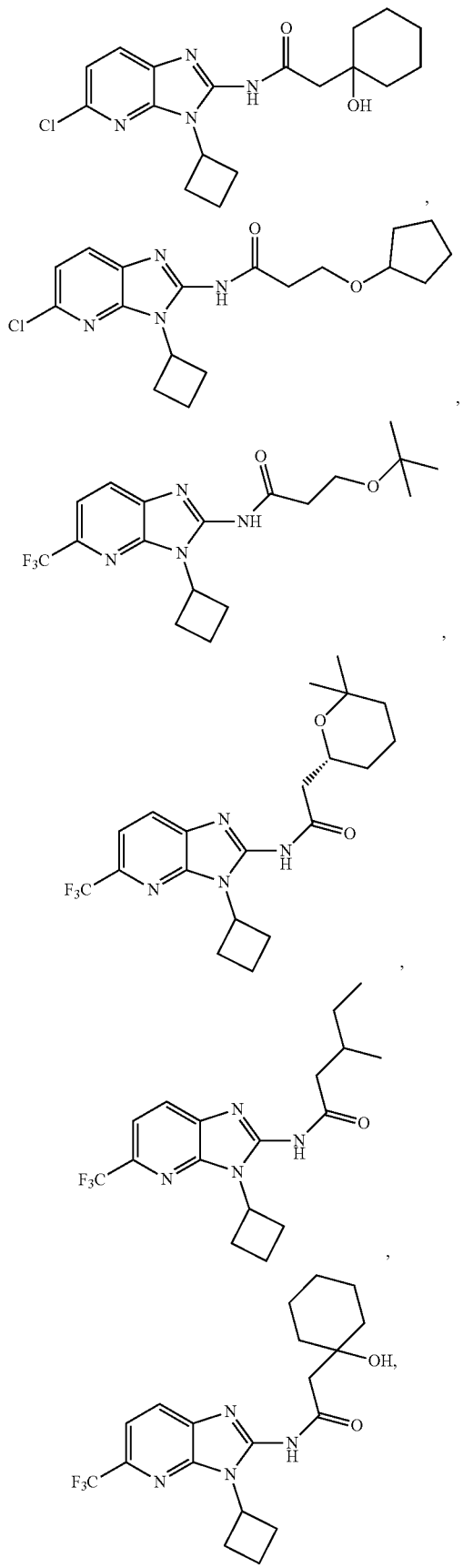
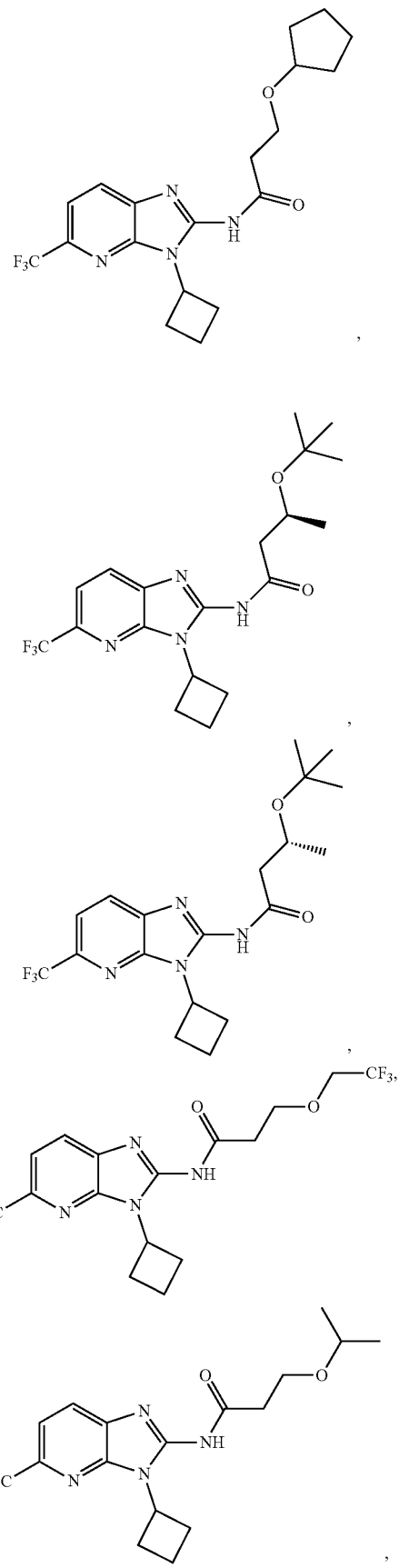

225
-continued
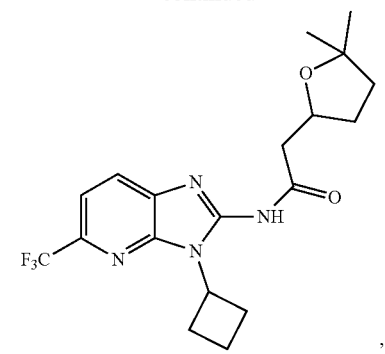
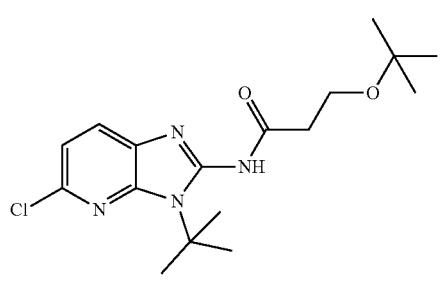
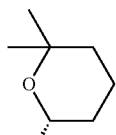
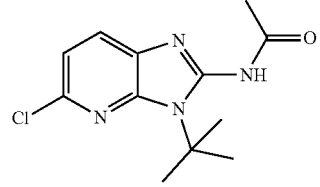
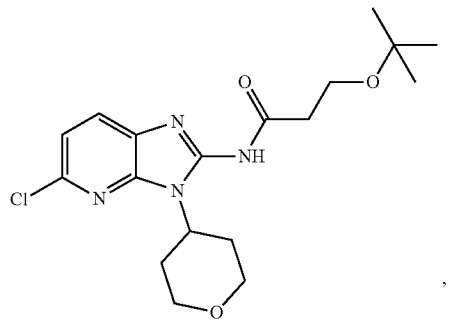
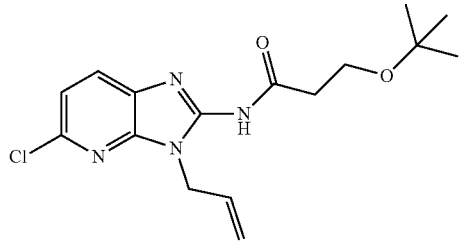
226
-continued
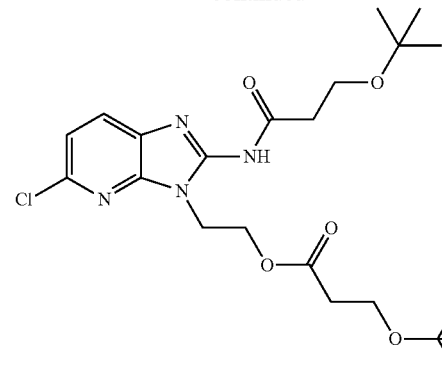
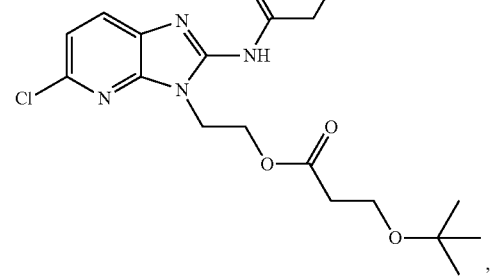
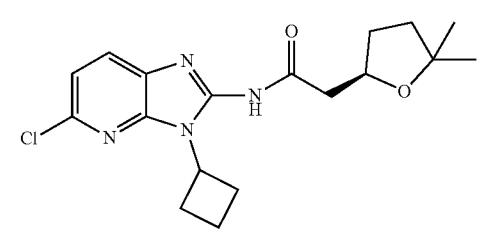
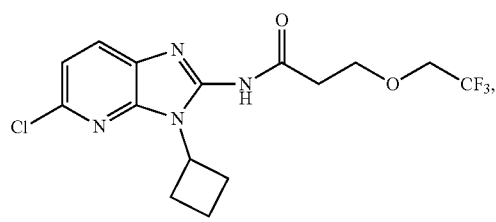
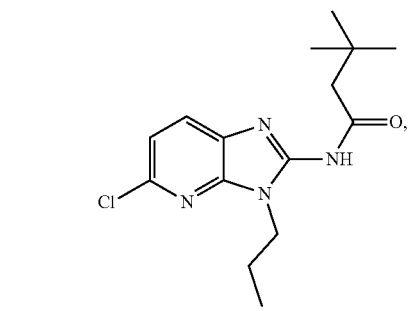
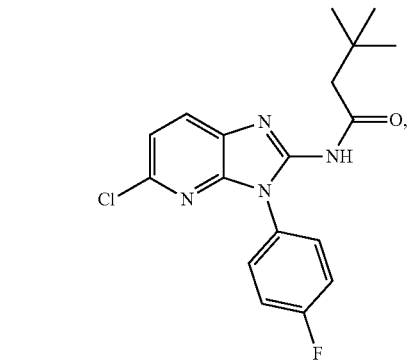

227
-continued
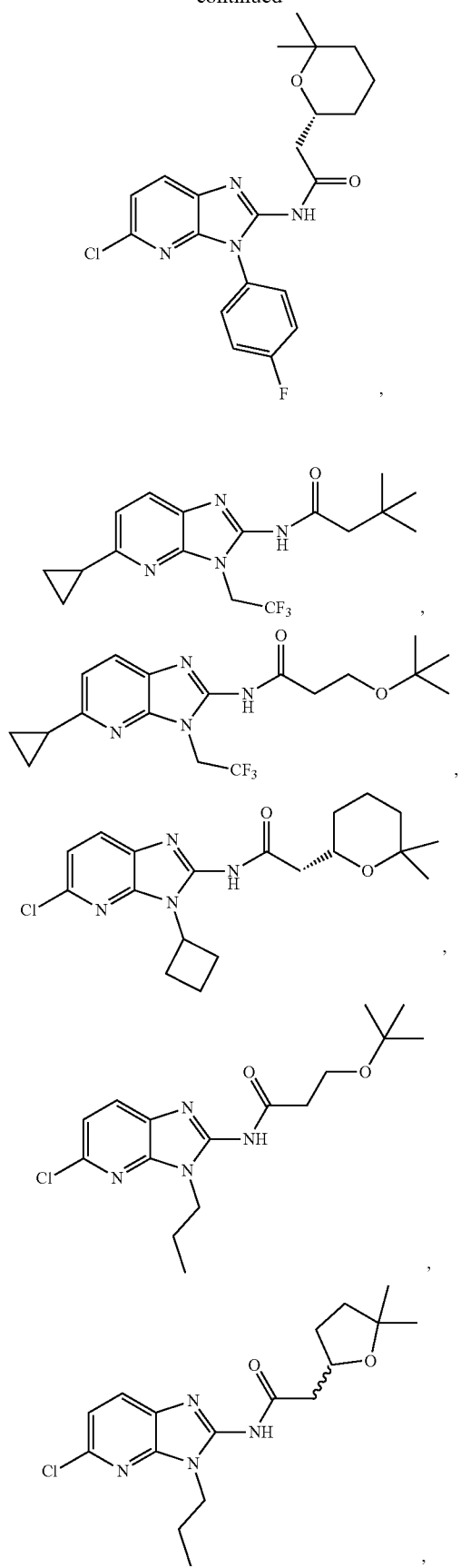
228
-continued
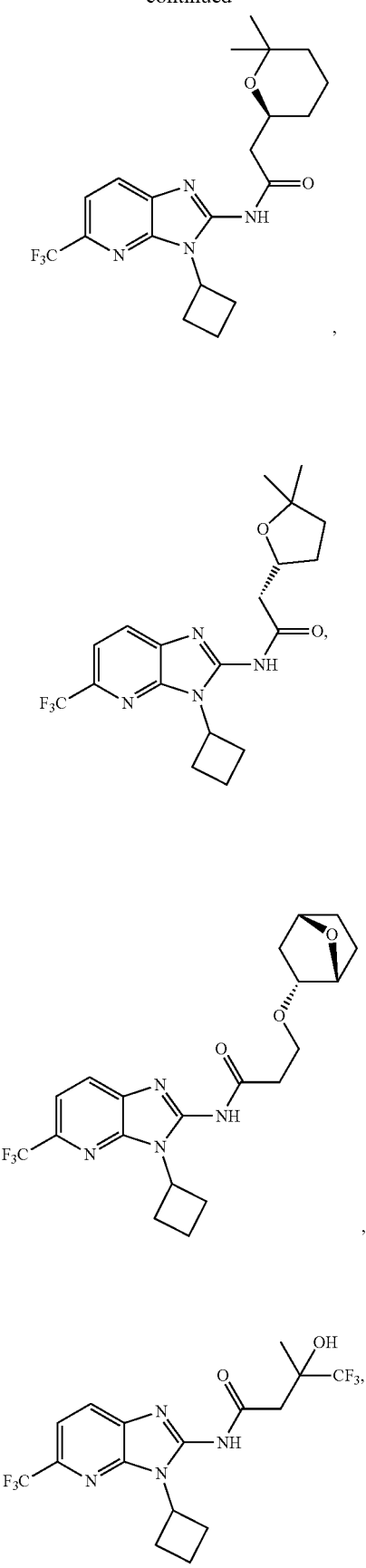

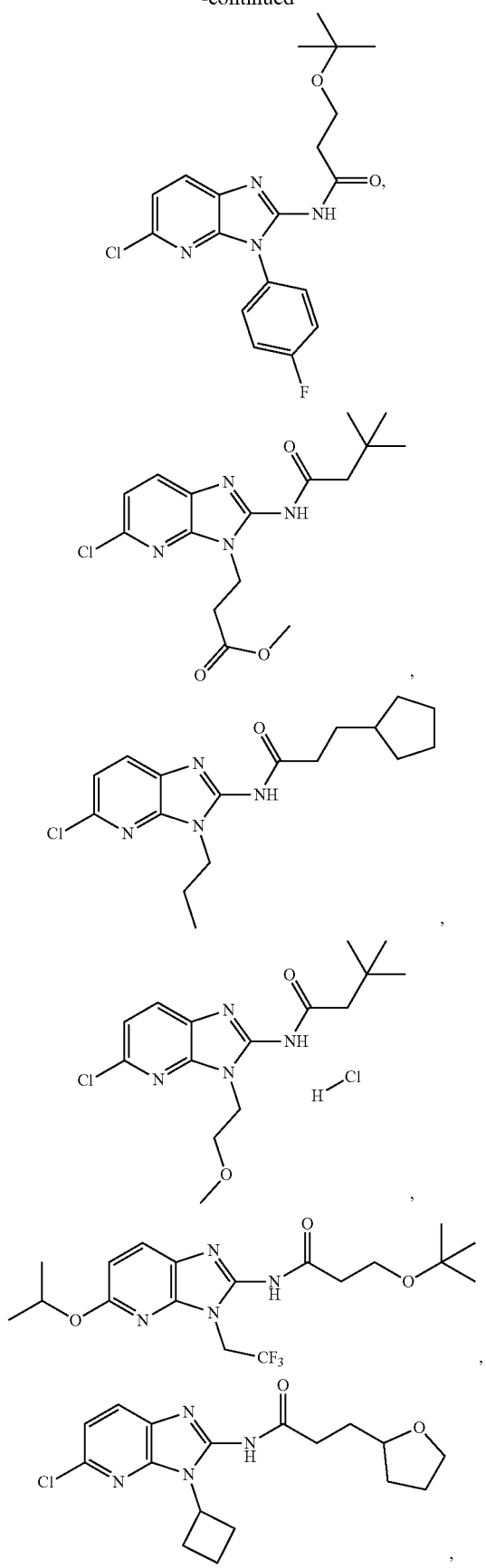

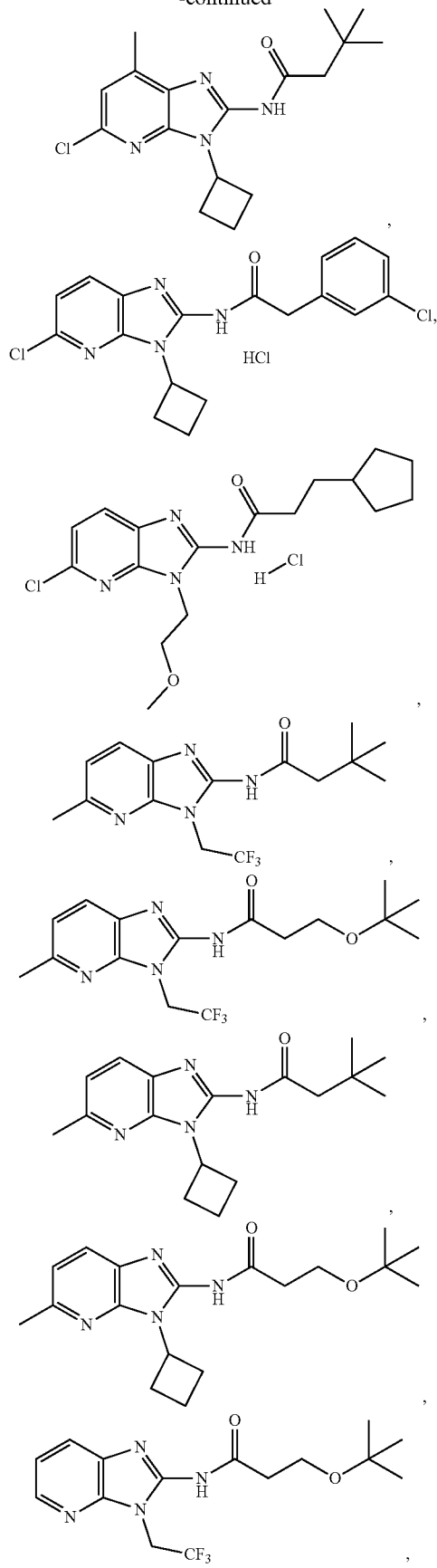
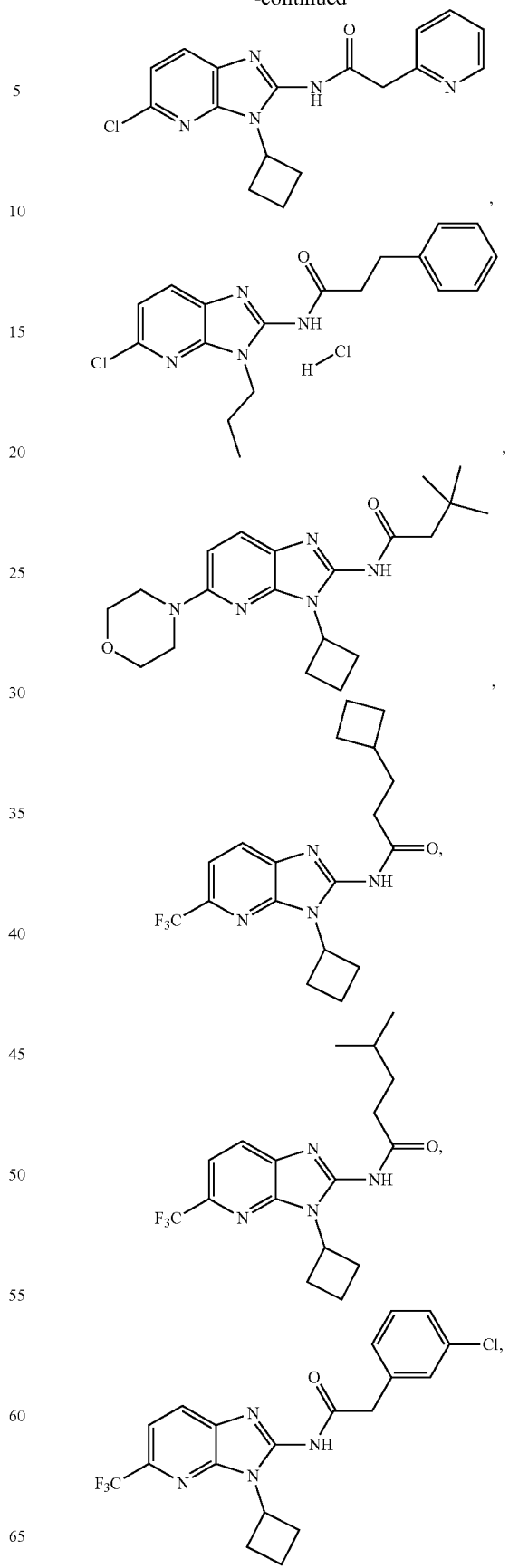

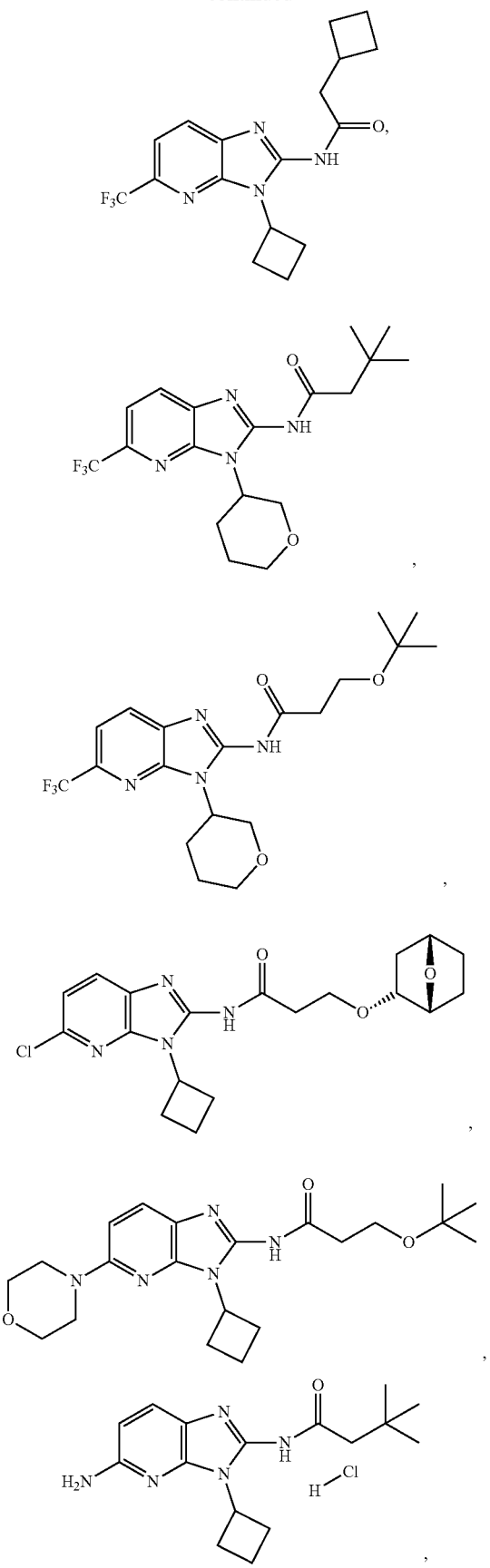
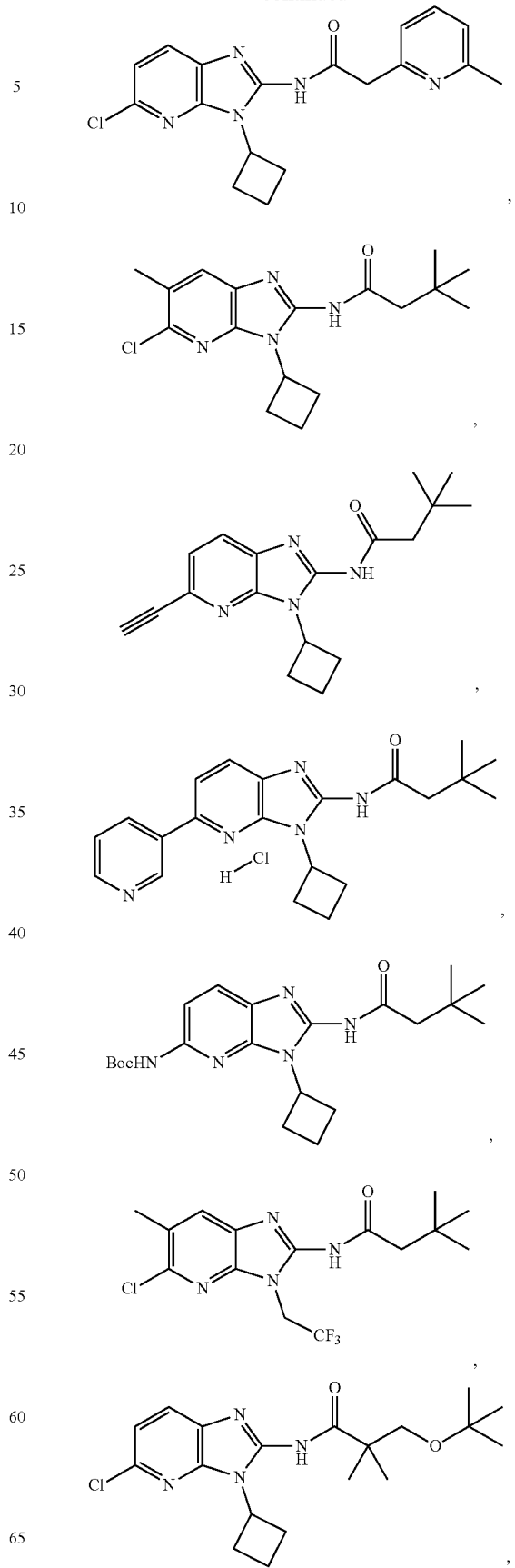

235
-continued
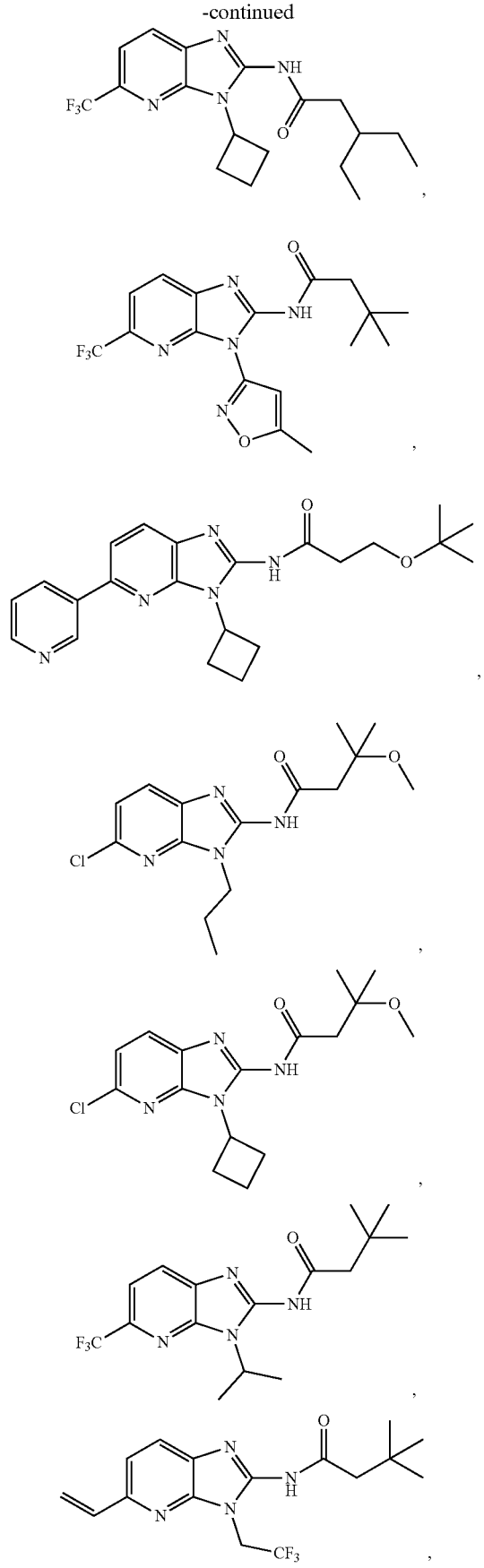
236
-continued
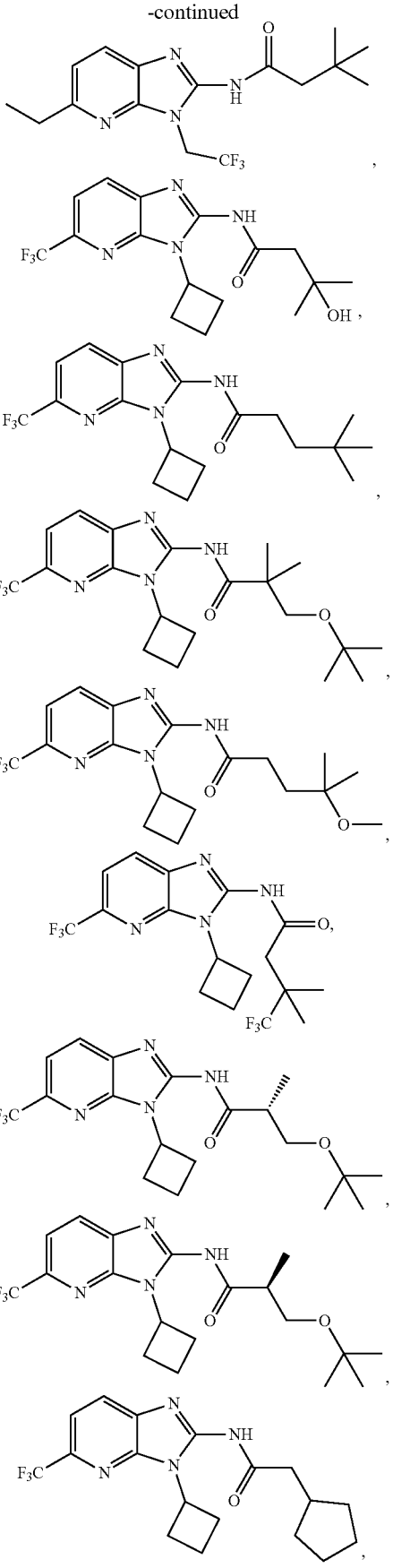

237
-continued
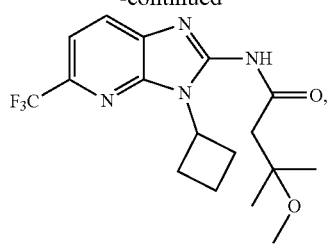
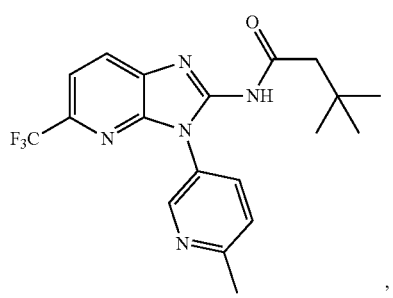
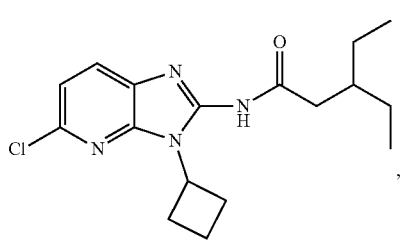
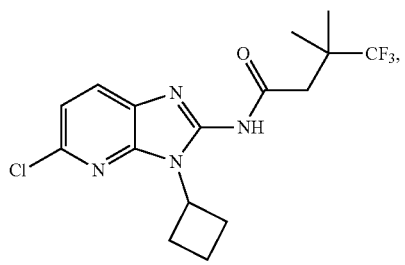
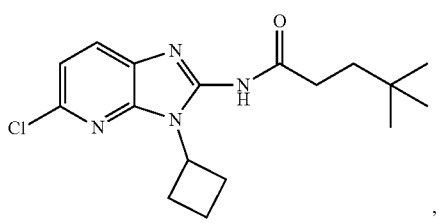
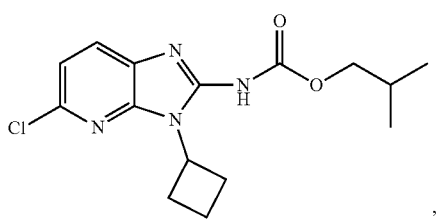
238
-continued
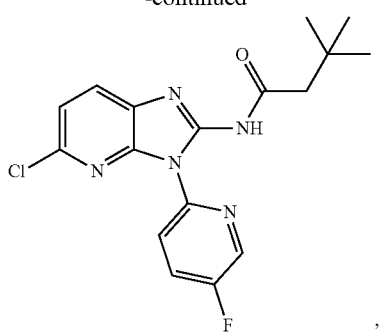
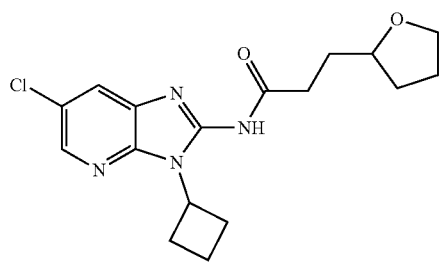
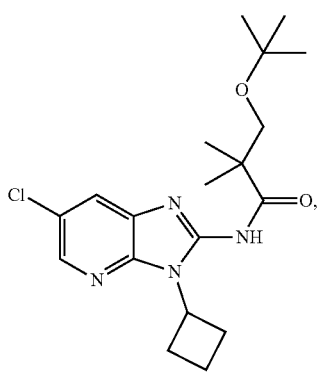
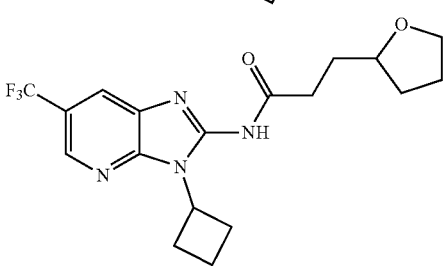
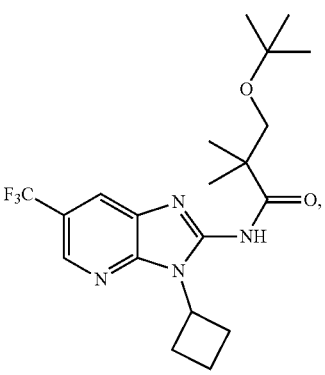

239
-continued
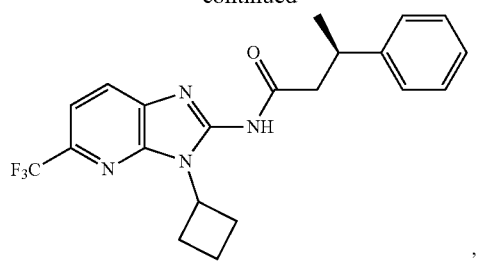
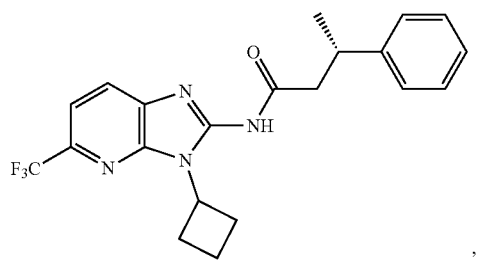
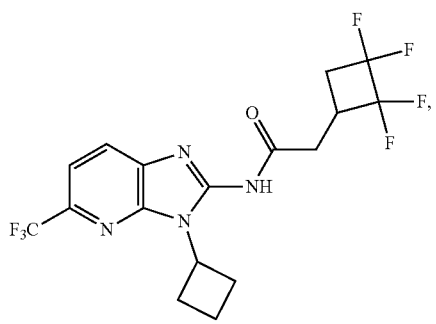
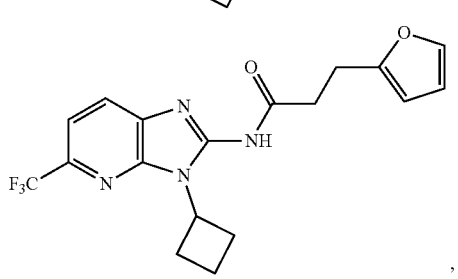
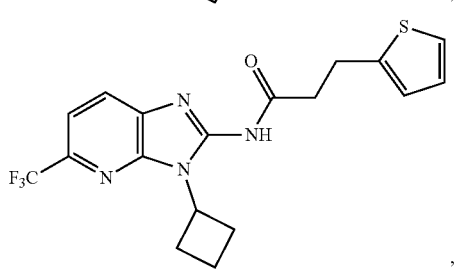
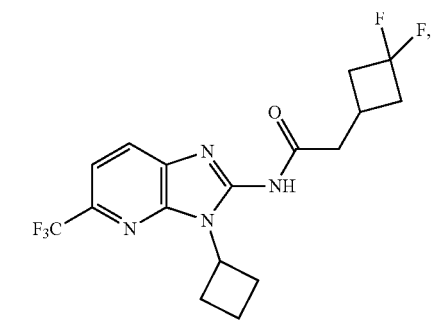
240
-continued
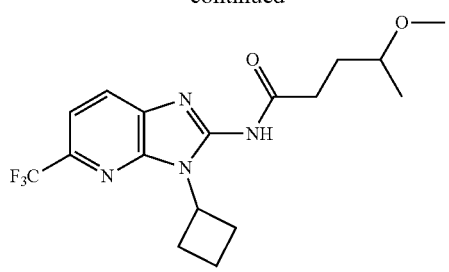
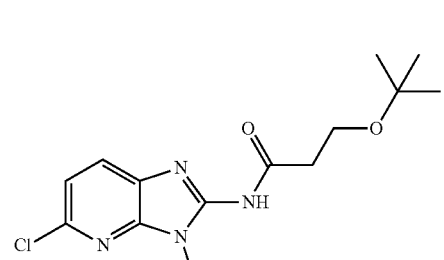
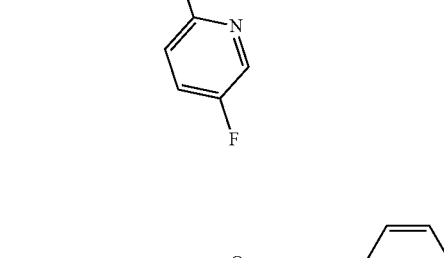
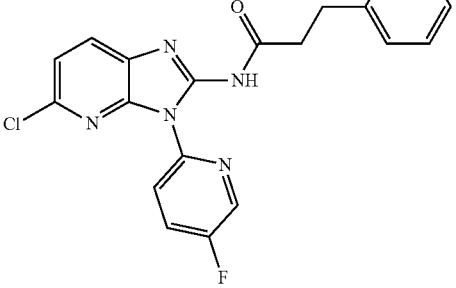
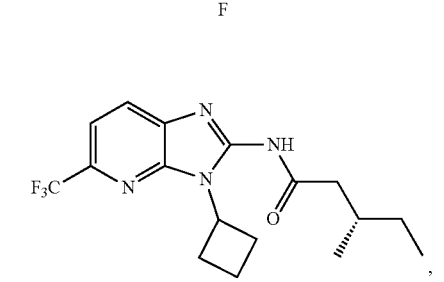
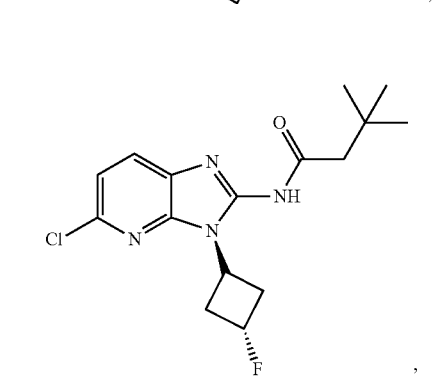

241
-continued
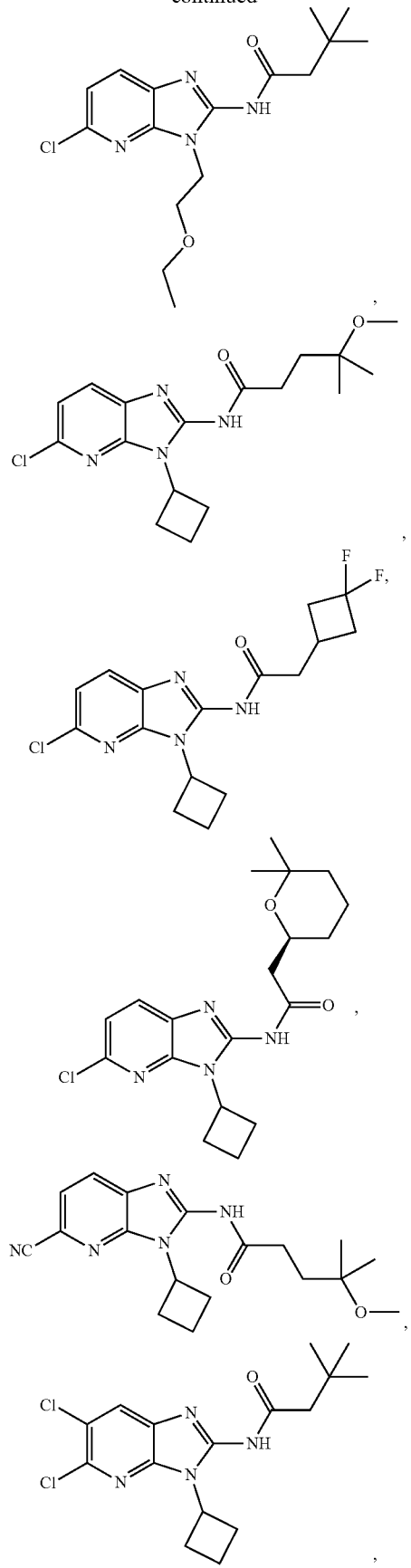
242
-continued
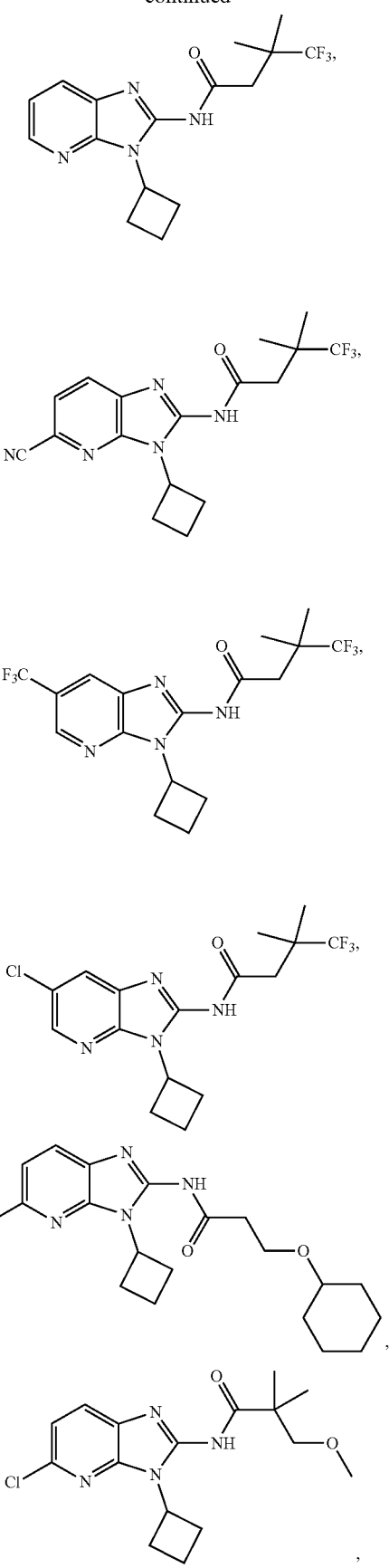

243
-continued
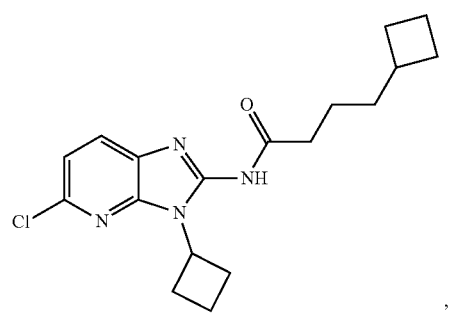
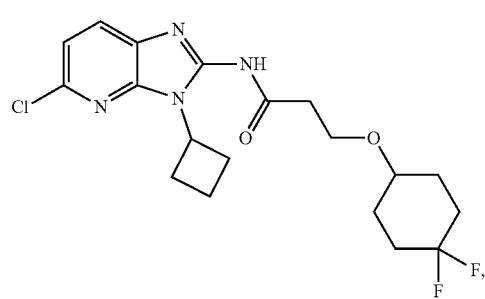
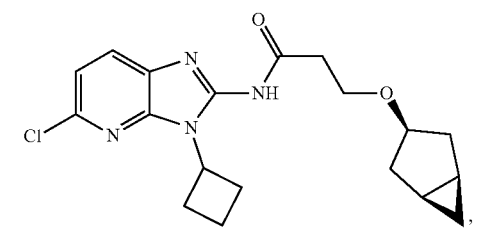
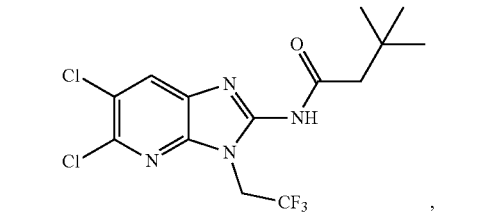
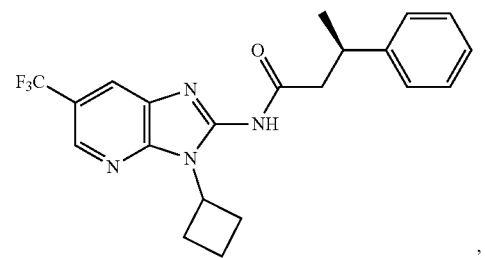
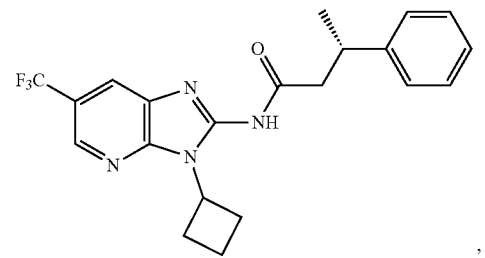
244
-continued
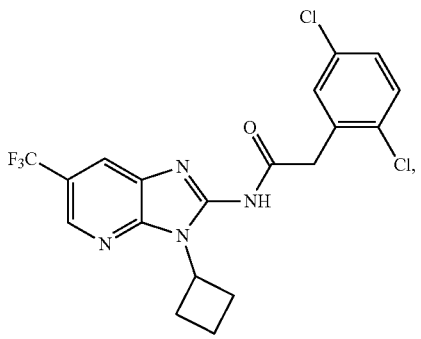
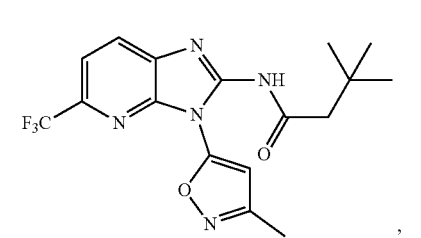
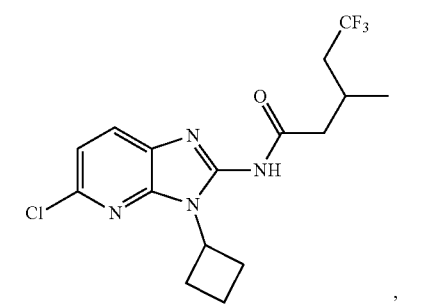
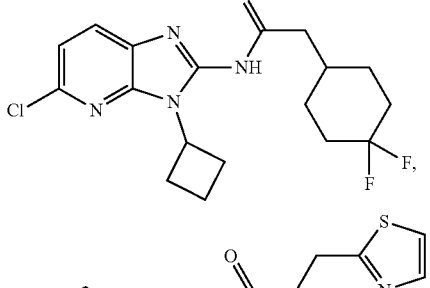
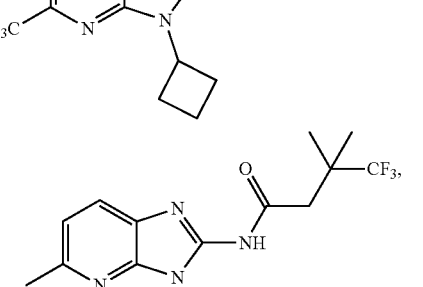
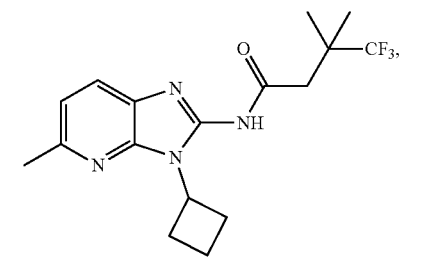

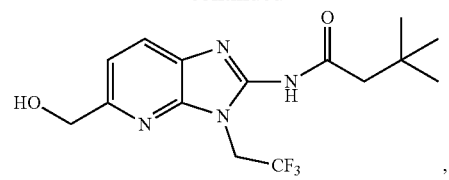,
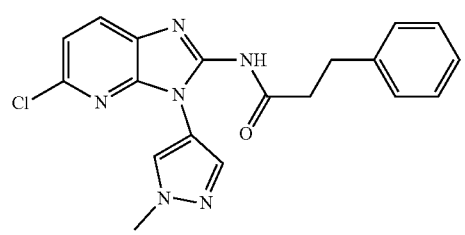,
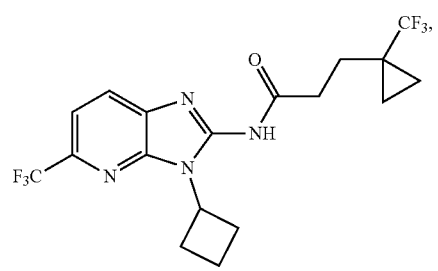,
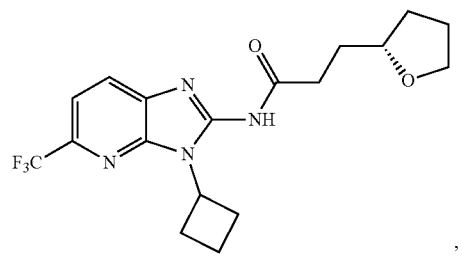,
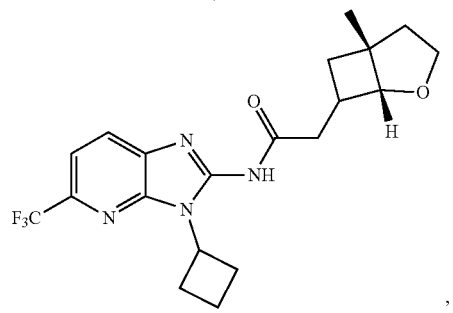,
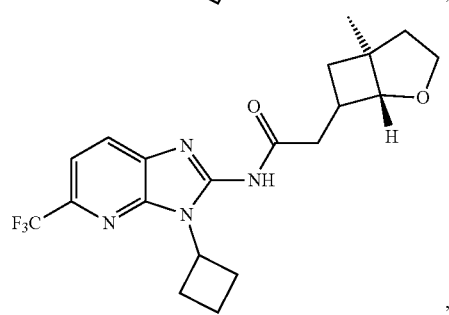,
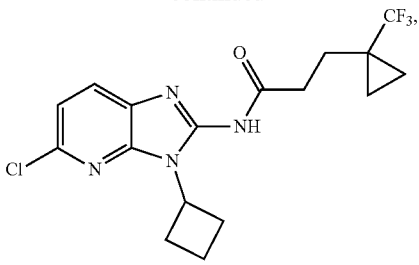,
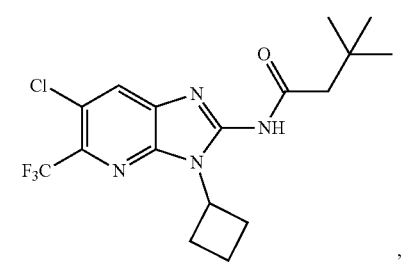,
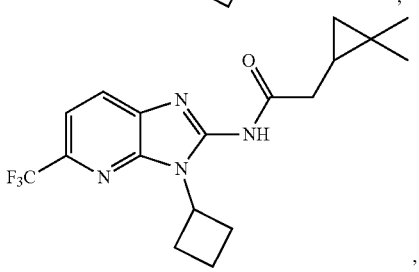,
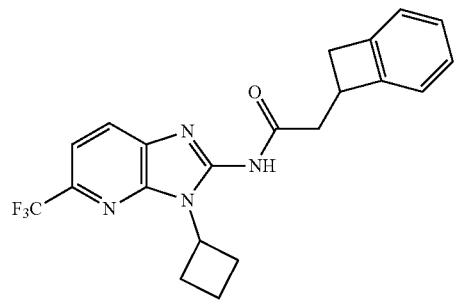,
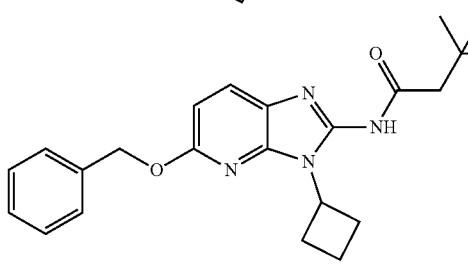,
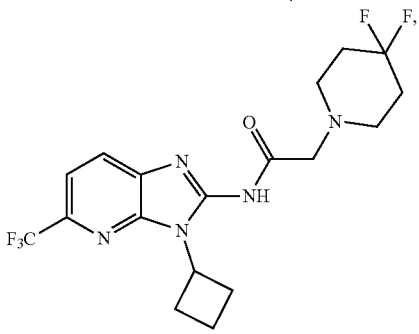, 247
-continued
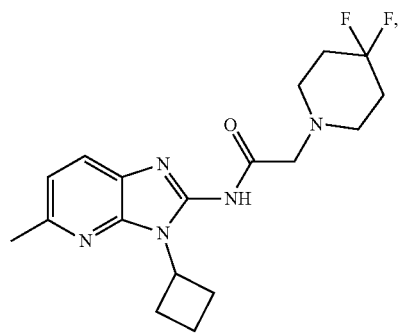
,
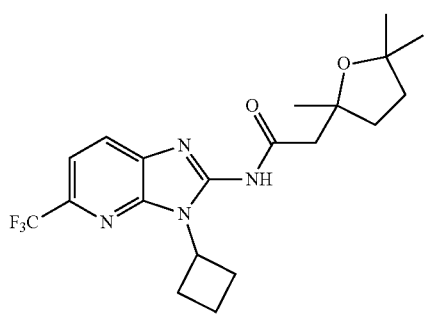
,
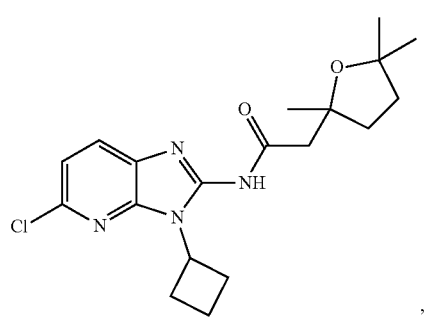
,
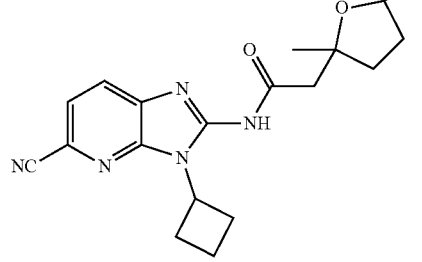
,
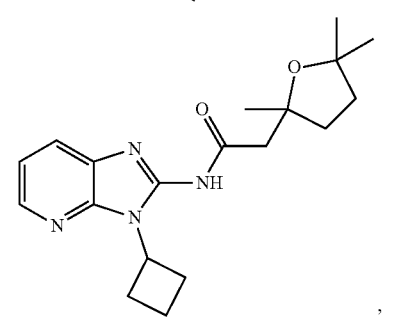
,
248
-continued
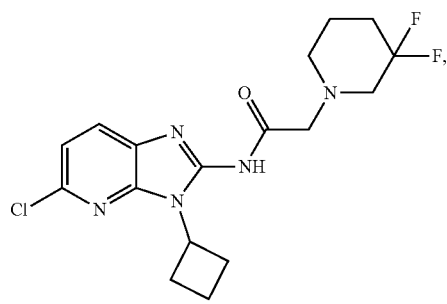
,
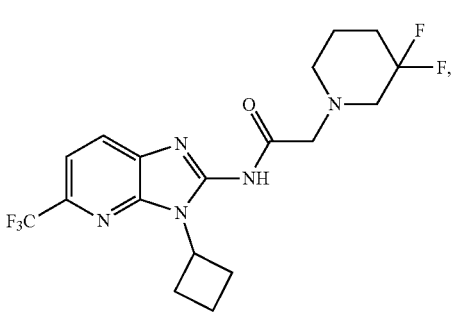
,
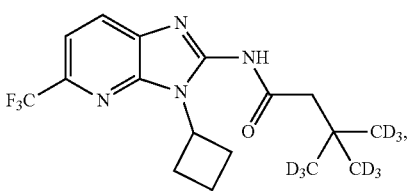
,
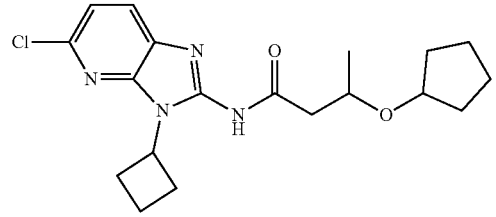
,
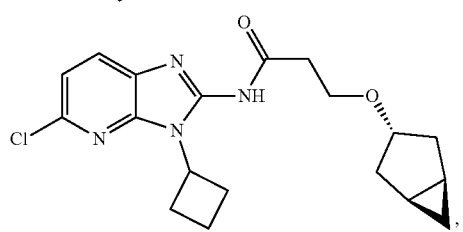
,
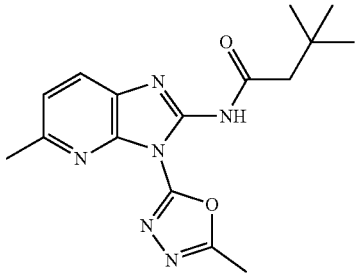
, 249
-continued
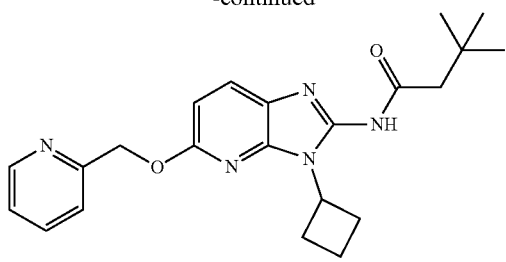
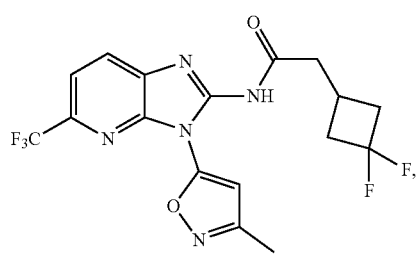
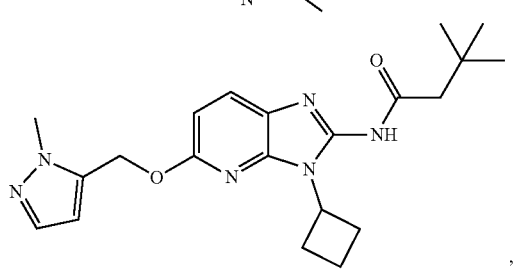
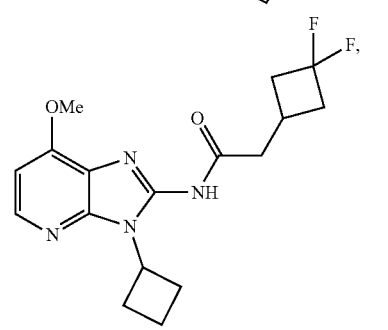
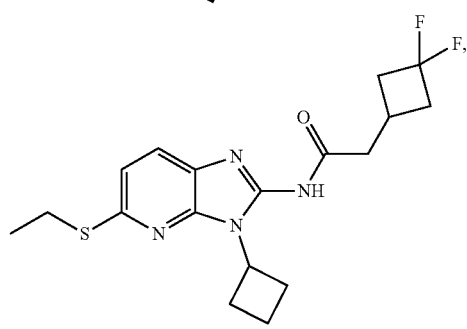
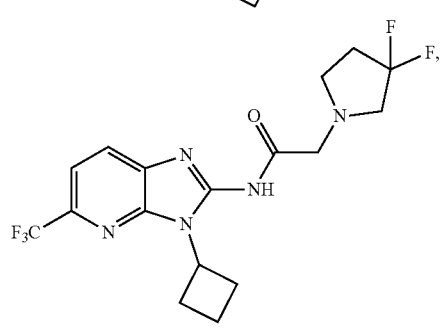
250
-continued
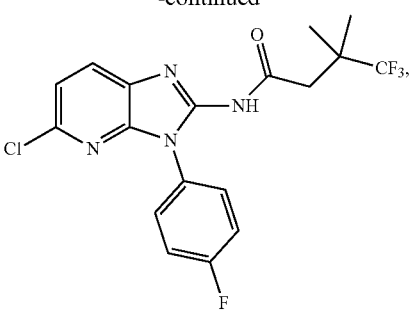
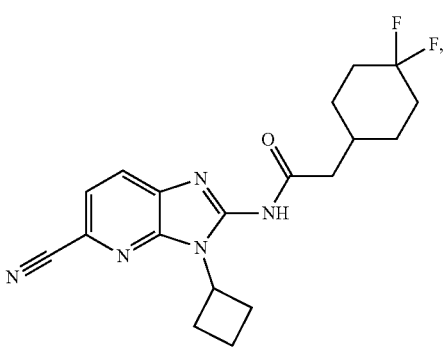
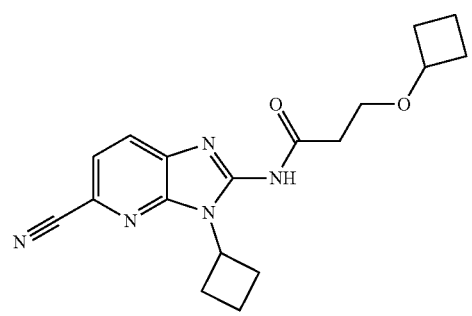
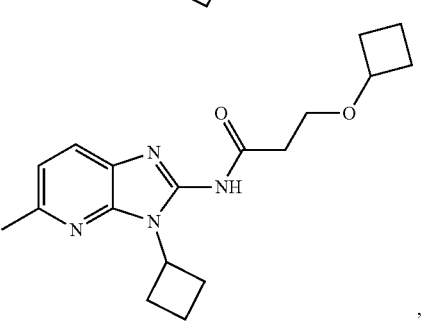
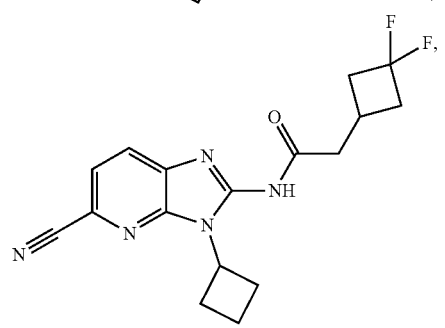

251
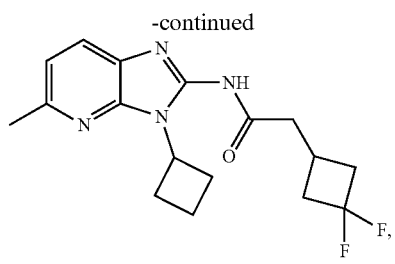
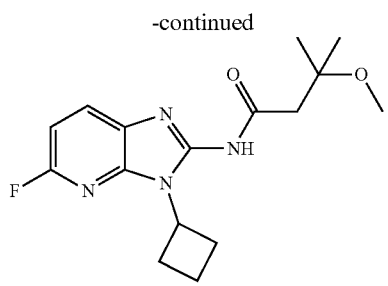
252

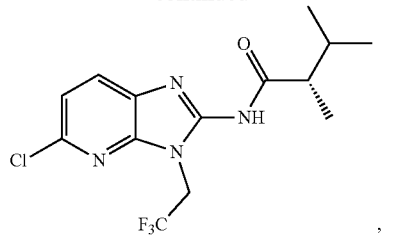

,

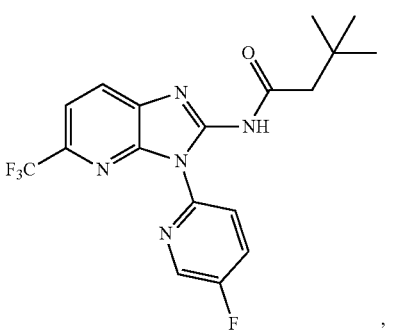

,

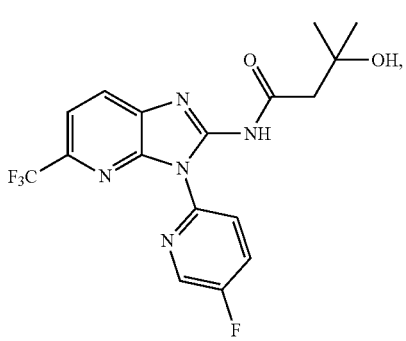

,

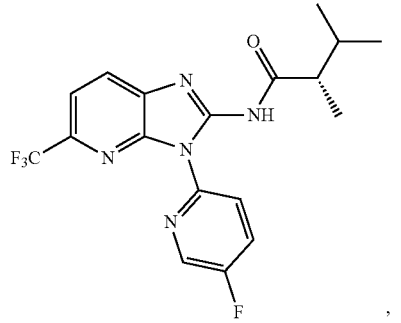

,

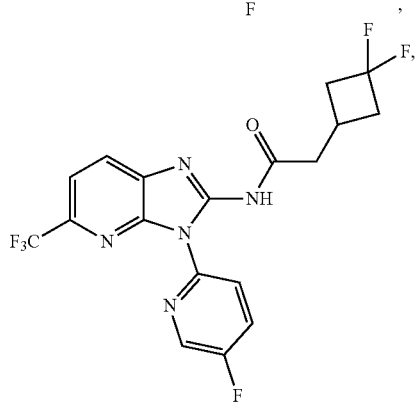

,

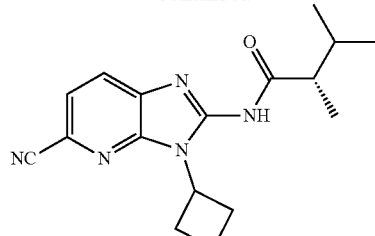

,

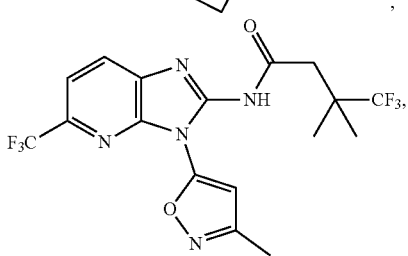

,

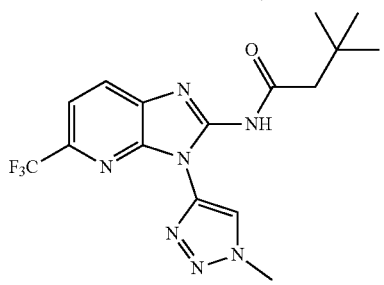

,

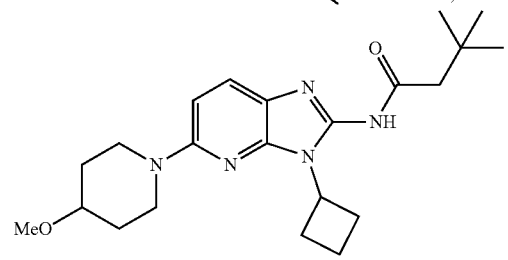

.

Embodiment 40

A composition comprising a compound of any of embodiments 1-39, wherein the composition is pharmaceutically acceptable.

Embodiment 41

A pharmaceutical dosage form comprising a compound of any of embodiments 1-39.

Embodiment 42

A method of treating a disorder associated with a Kv7 potassium channel activator comprising administering an effective amount of a compound of any of embodiments 1-39 to a mammal in need thereof.

Embodiment 43

The method of embodiment 42, wherein the disorder is epilepsy, pain, migraine, a disorder of neurotransmitter release, a smooth muscle contractility disorder, a dyskinesia, dystonia, mania, or a hearing disorder.

Embodiment 44

The method embodiment 42, wherein the disorder is epilepsy, neuropathic pain, inflammatory pain, persistent pain, cancer pain, postoperative pain, migraine, anxiety, substance abuse, schizophrenia, a bladder disorder, a vasculature disorder, a dyskinesia, dystonia, mania, a hearing disorder, or tinnitus.

A compound represented by a formula:

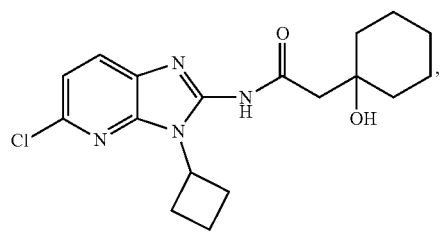

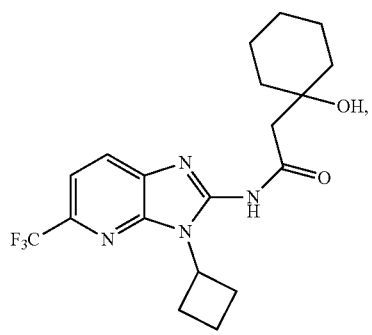

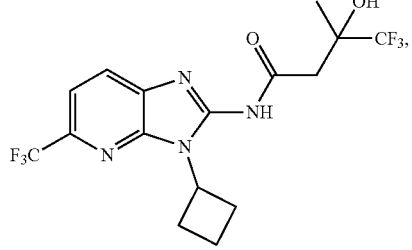

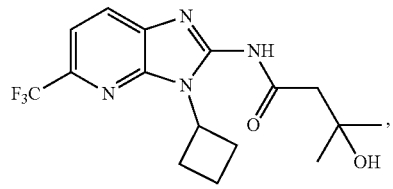

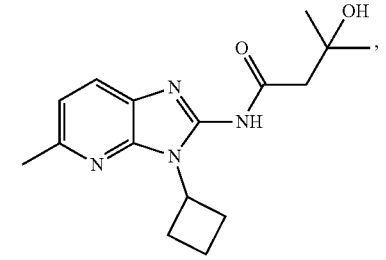

-continued

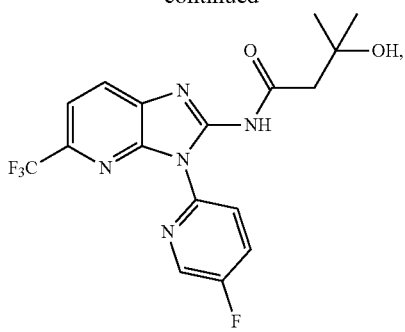

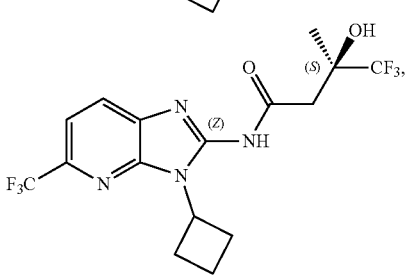

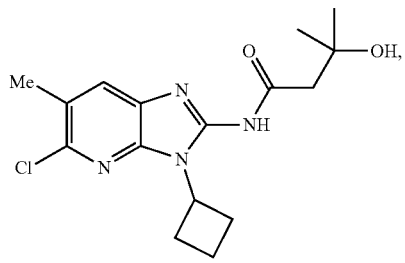

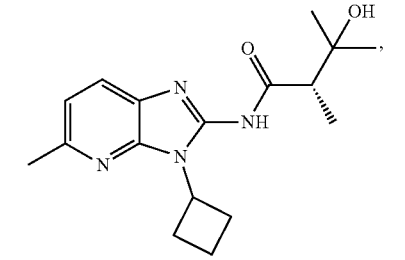

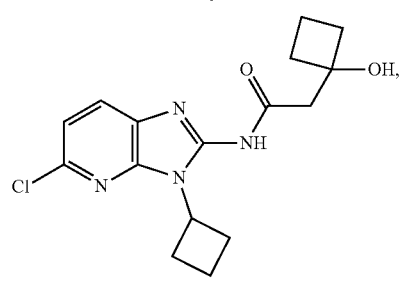

257
-continued
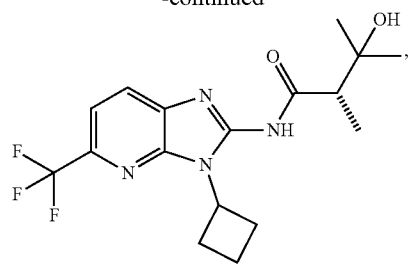
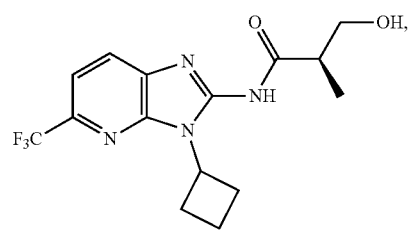
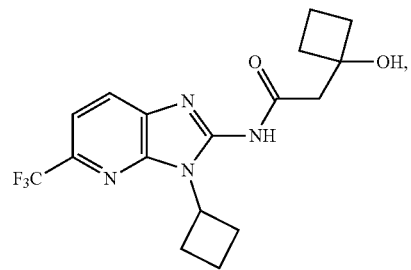
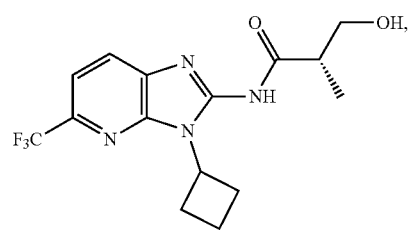
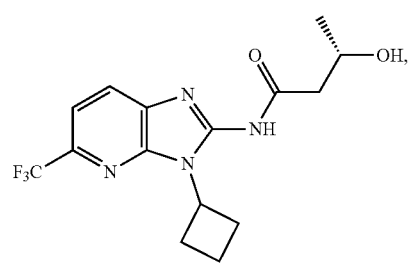
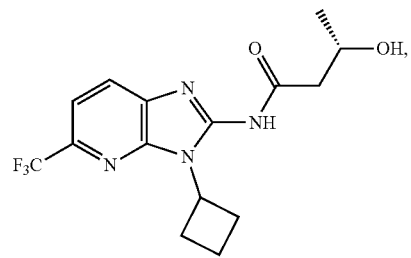
258
-continued
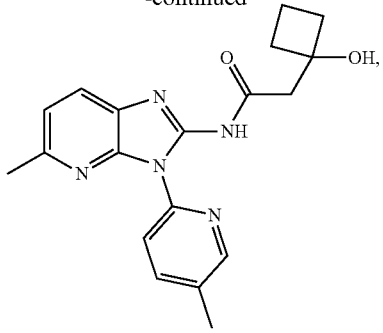
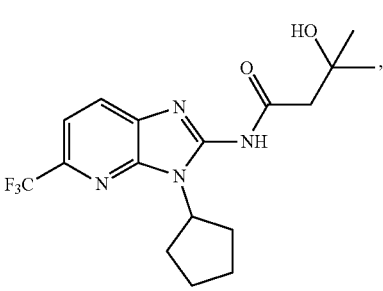
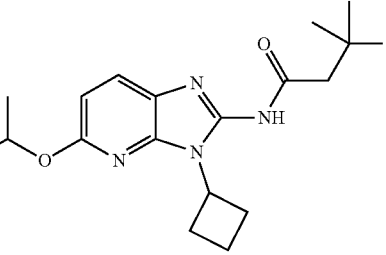
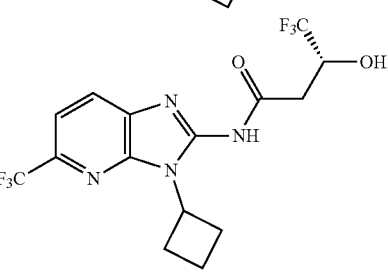
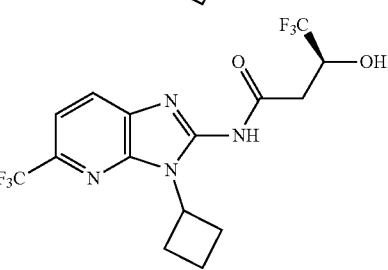
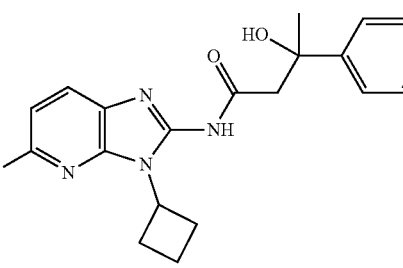

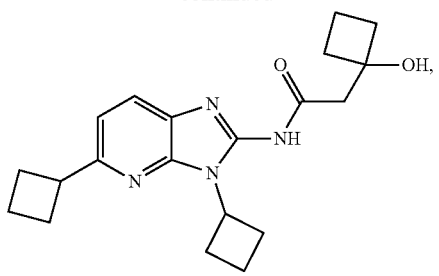
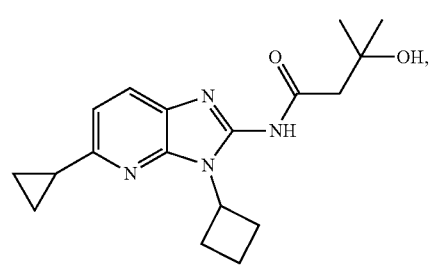
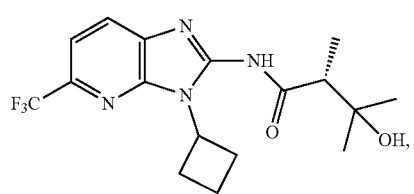
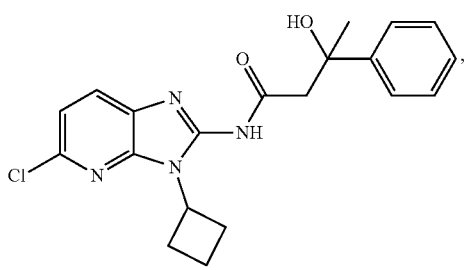
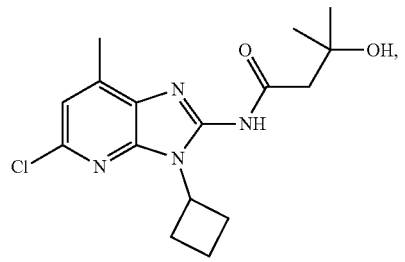
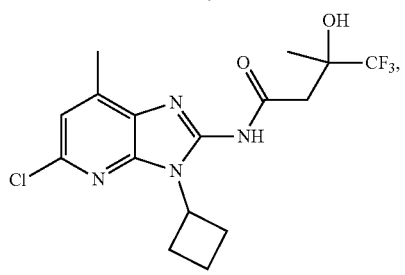
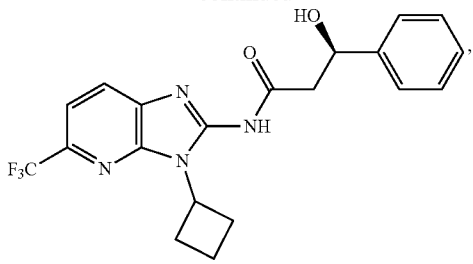
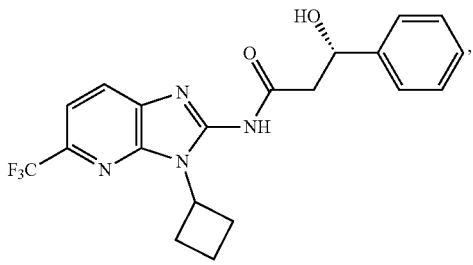
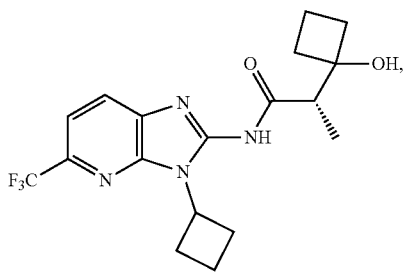
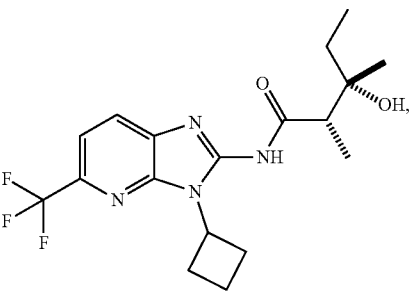
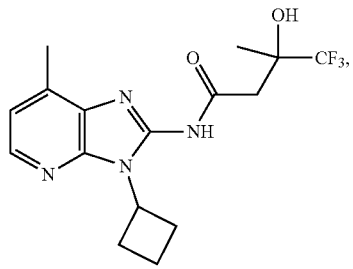
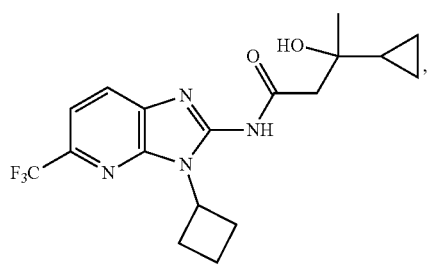

261
-continued
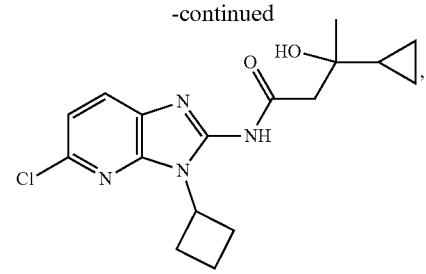
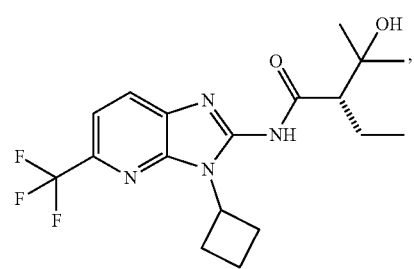
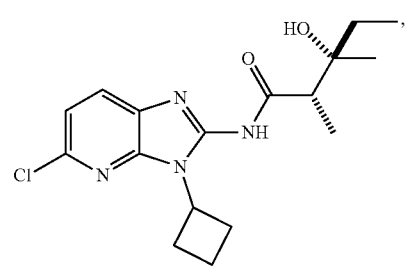
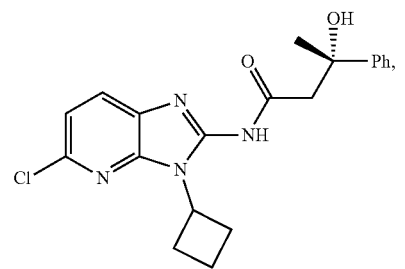
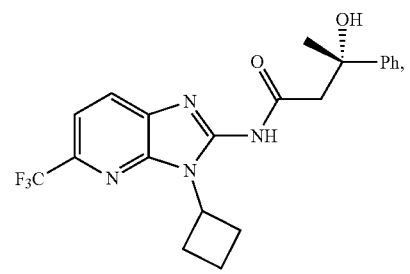
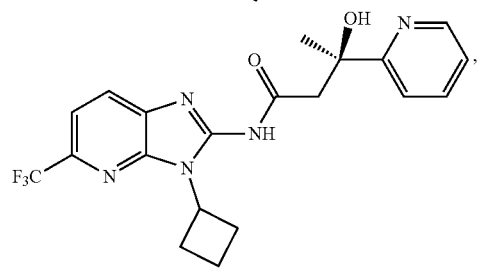
262
-continued
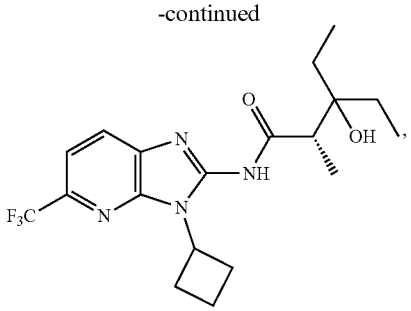
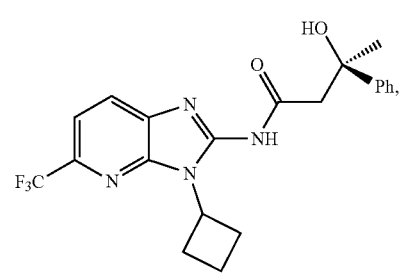
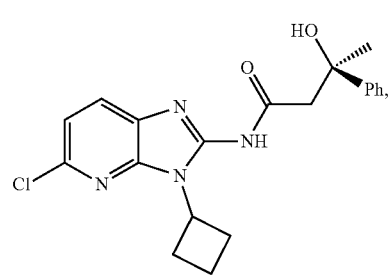
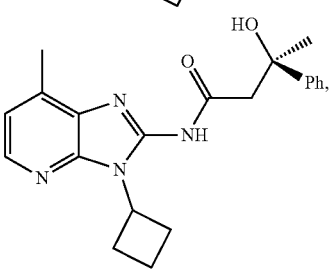
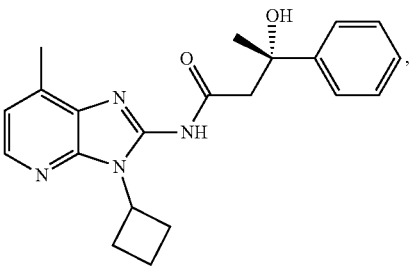
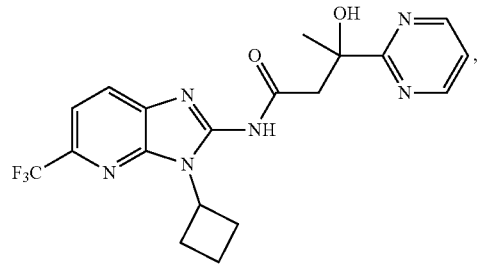

263
-continued
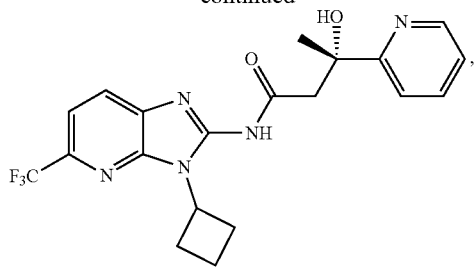
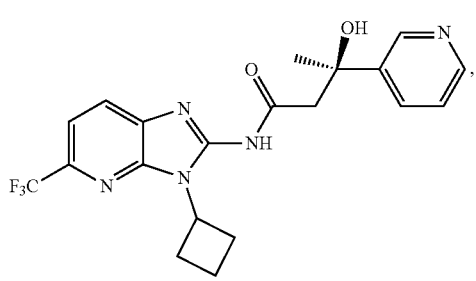
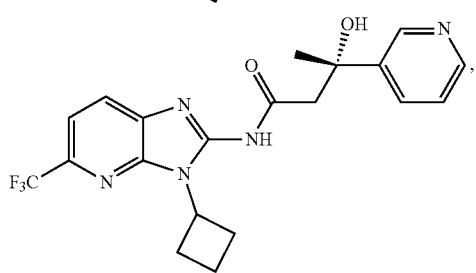
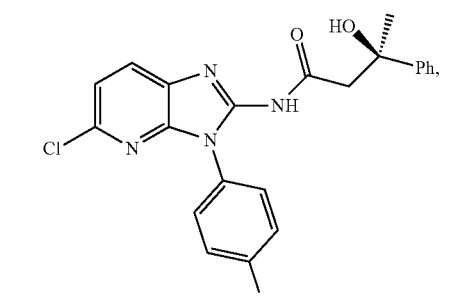
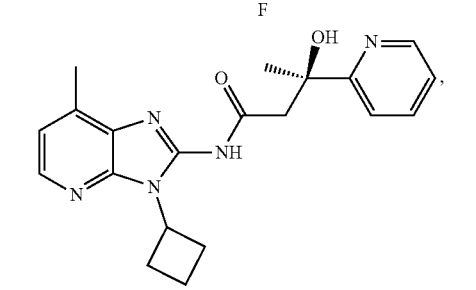
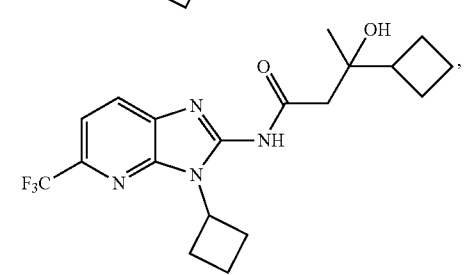
264
-continued
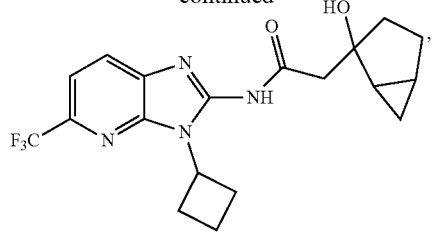
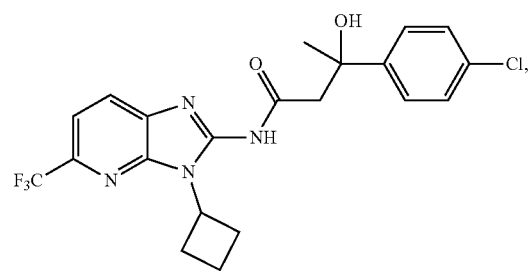
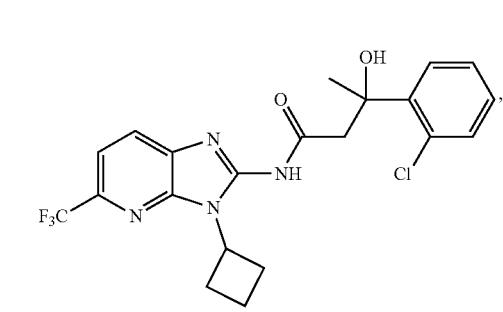
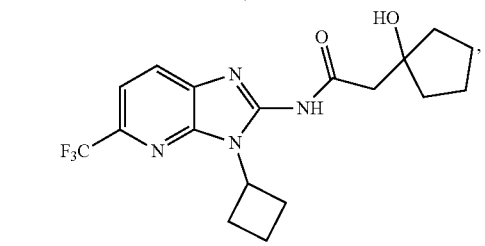
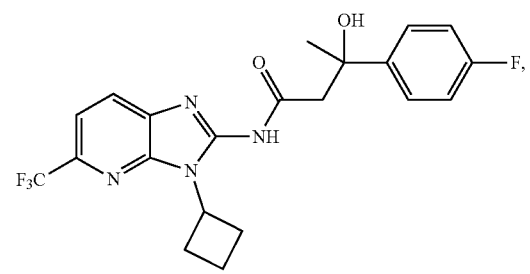
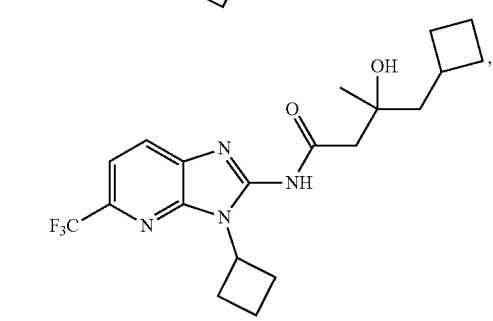

-continued
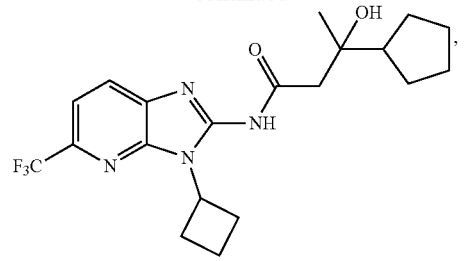
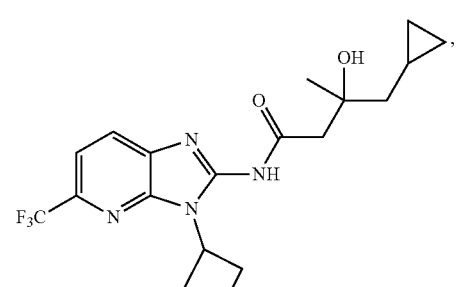
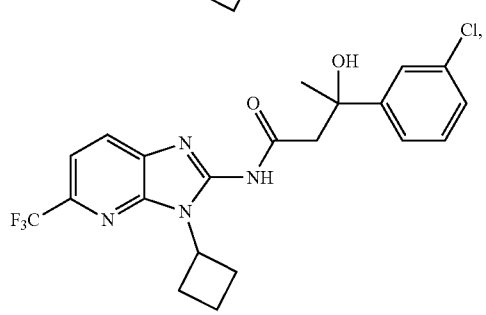
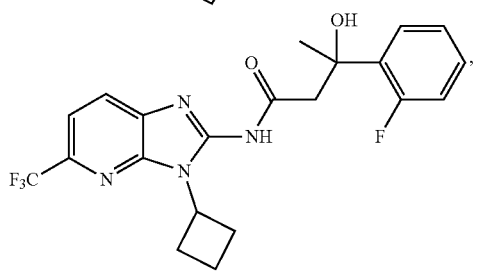
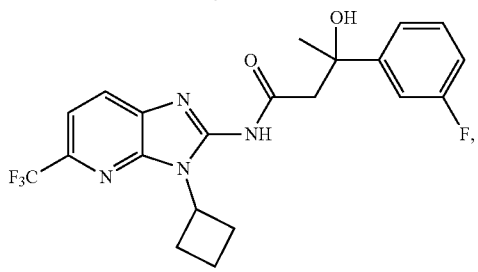
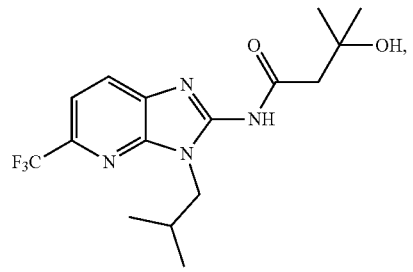
-continued
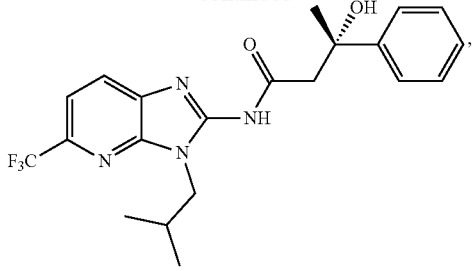
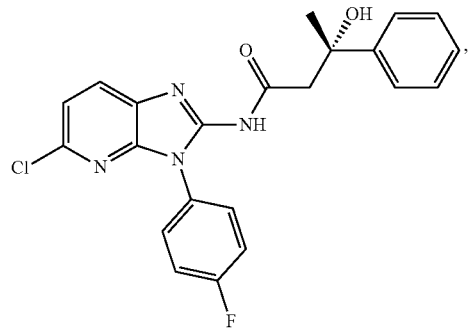
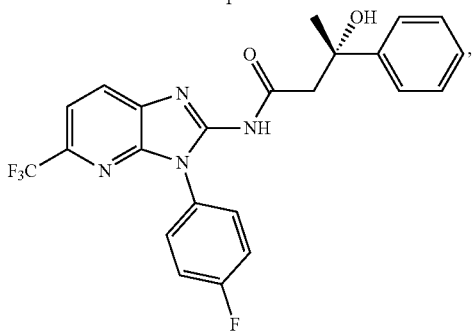
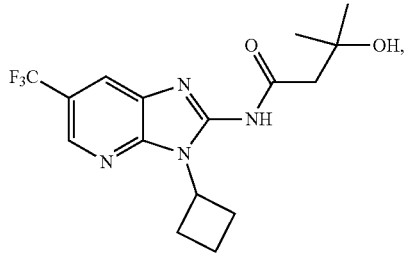
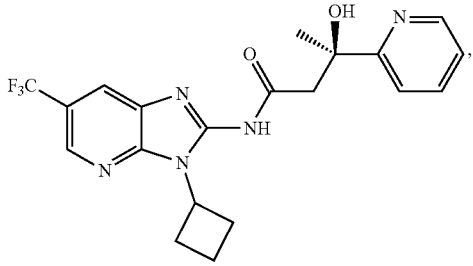
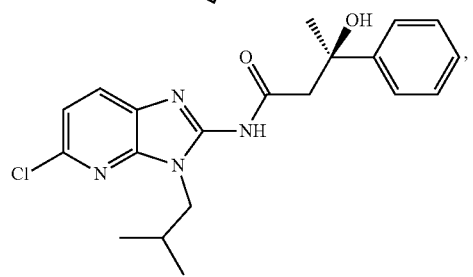

267
-continued
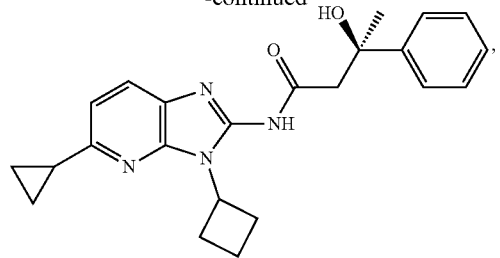
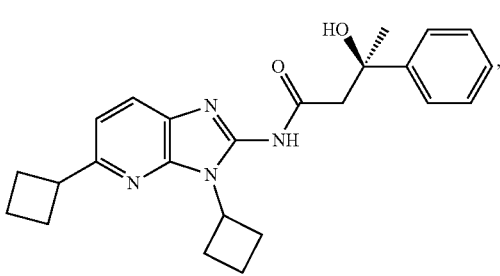
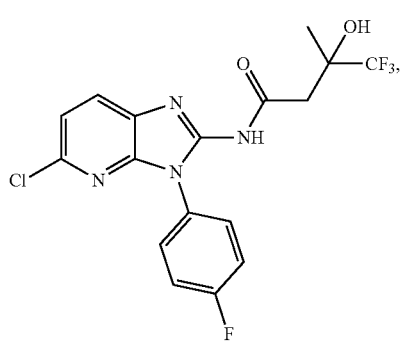
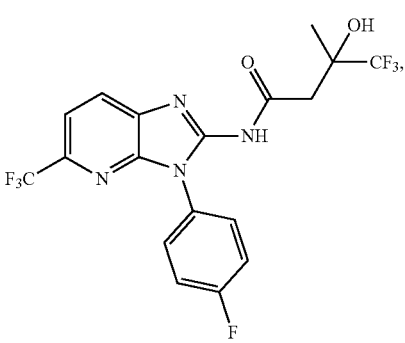
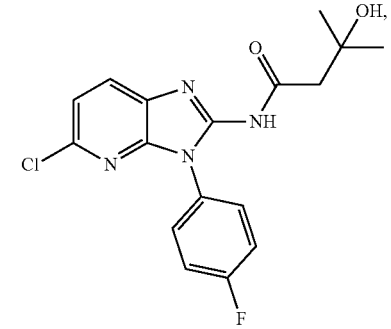
268
-continued
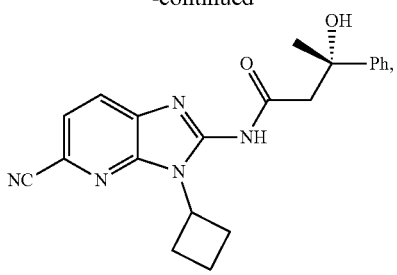
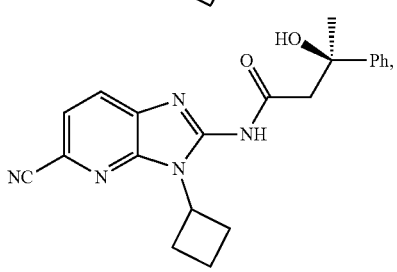
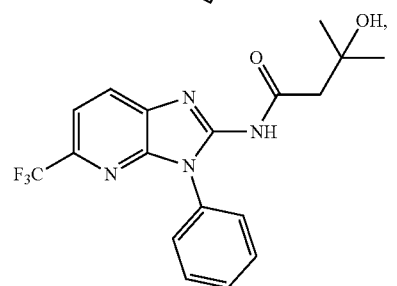
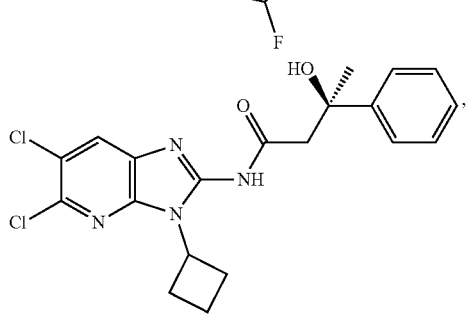
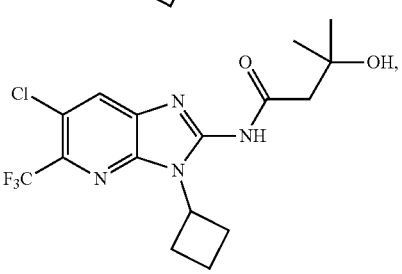
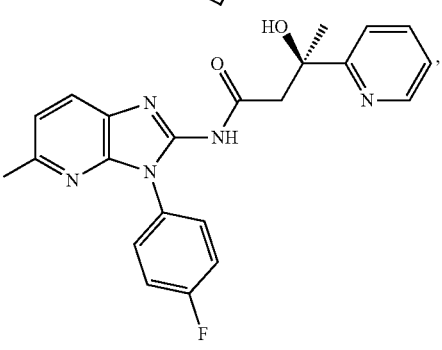

-continued
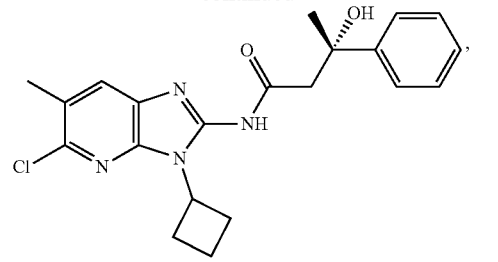
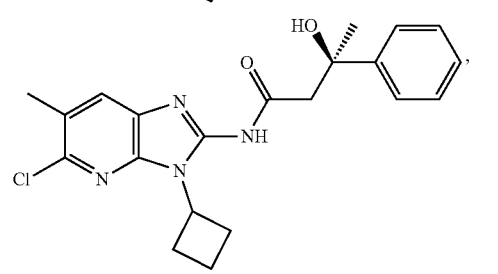
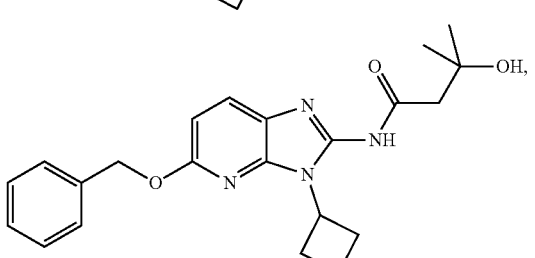
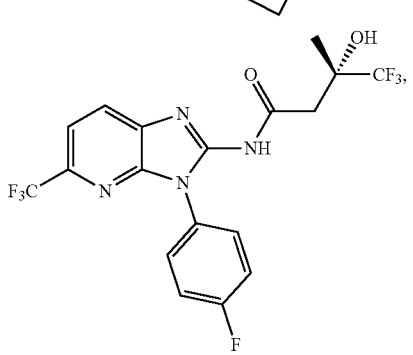
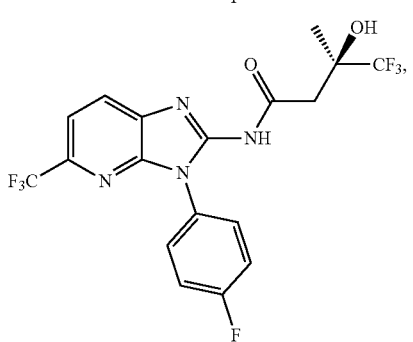
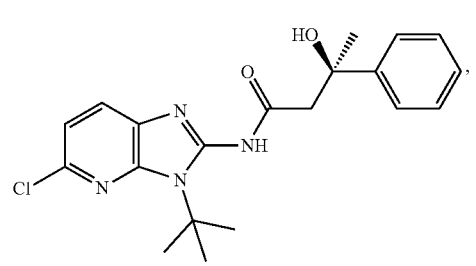
-continued
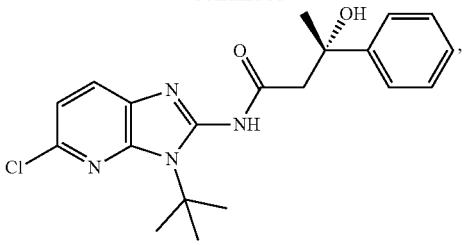
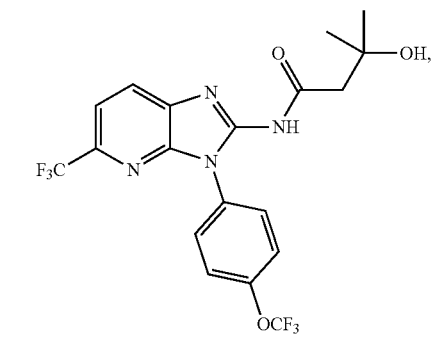
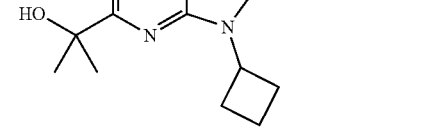
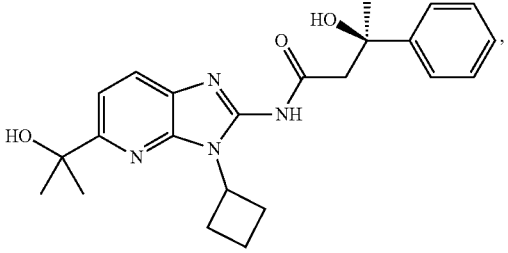
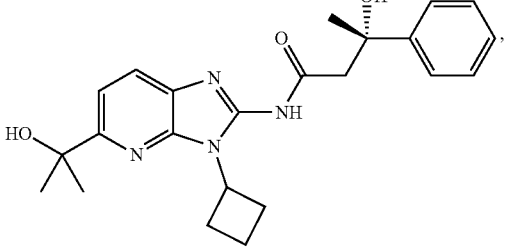
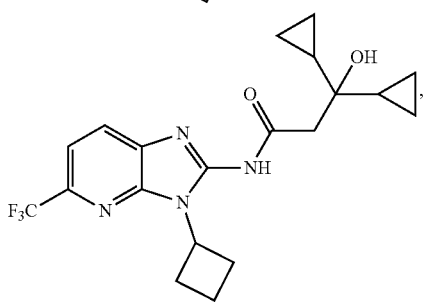

271
-continued
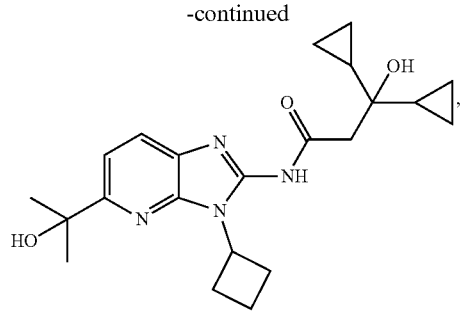
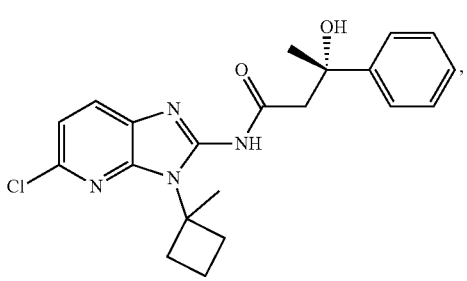
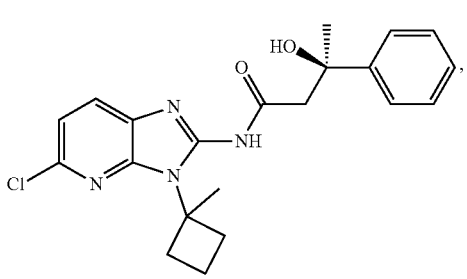
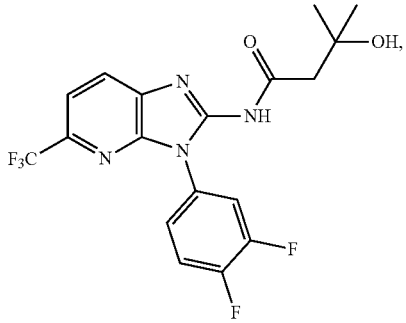
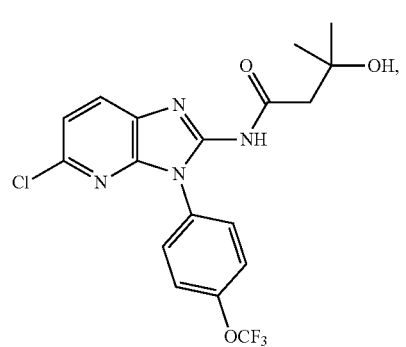
272
-continued
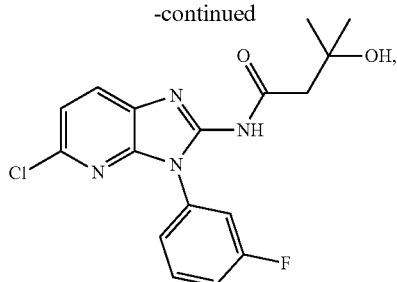
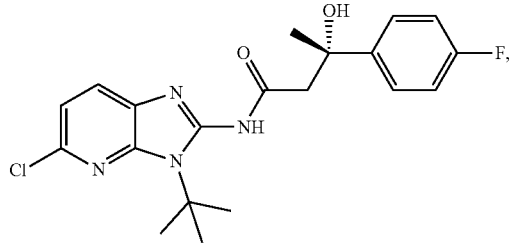
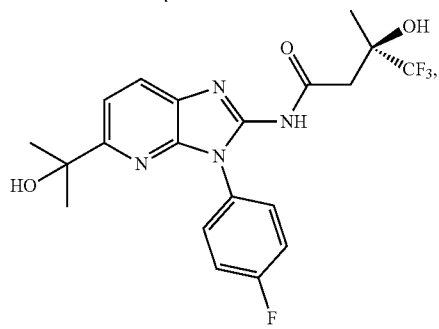
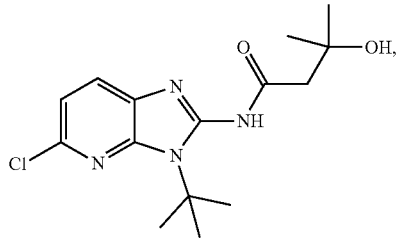
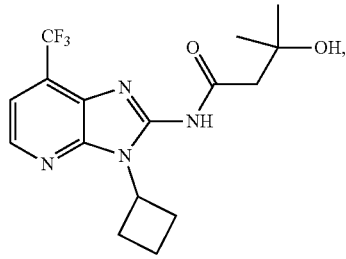
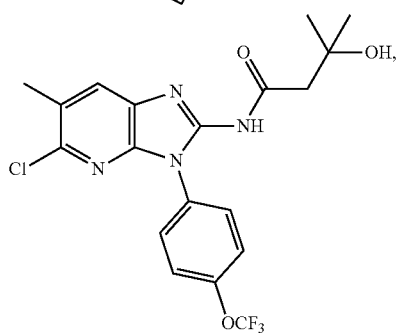

-continued
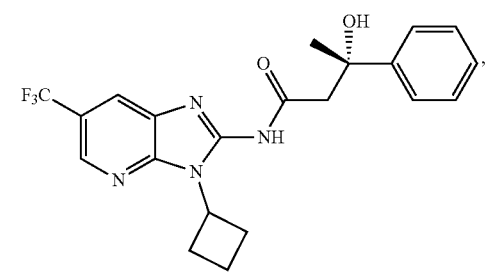
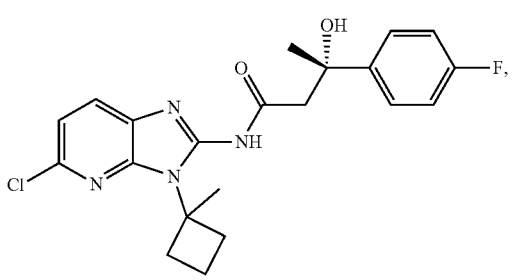
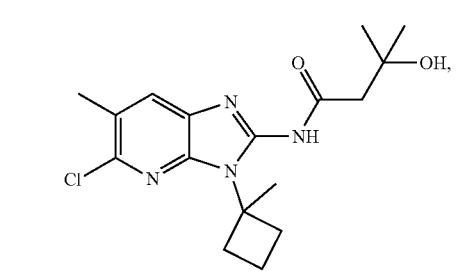
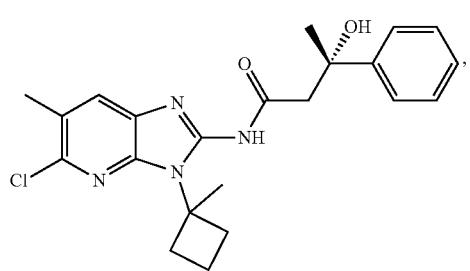
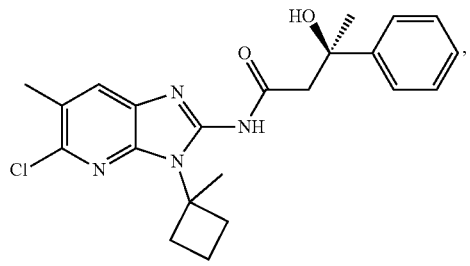
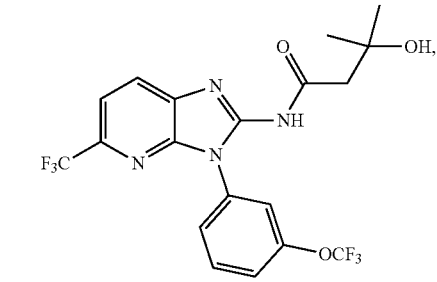
-continued
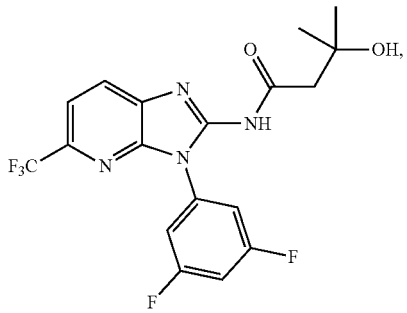
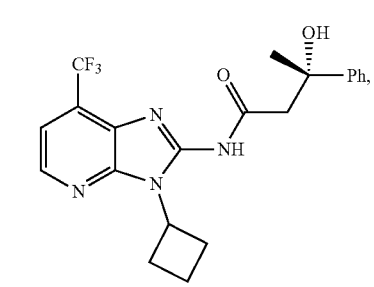
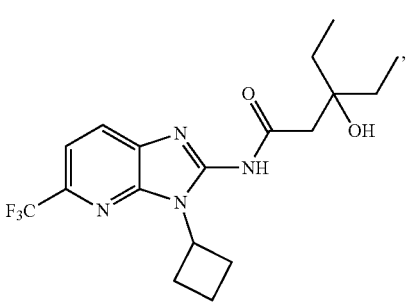
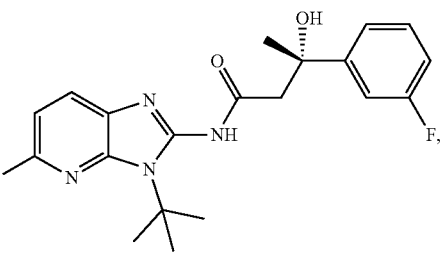
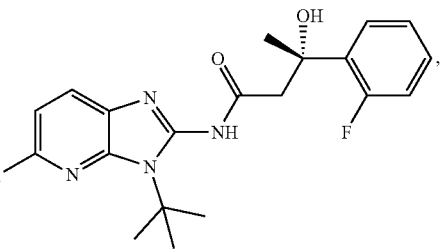
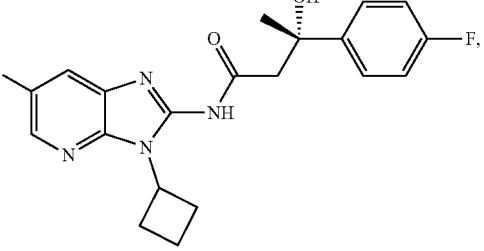

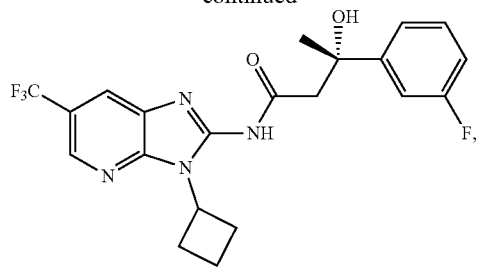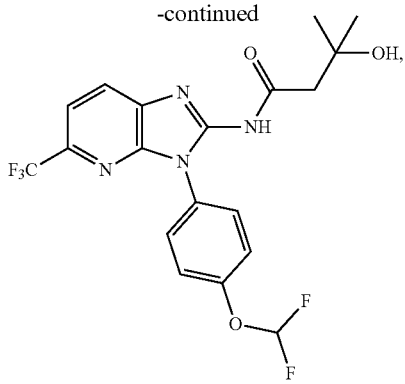

277
-continued
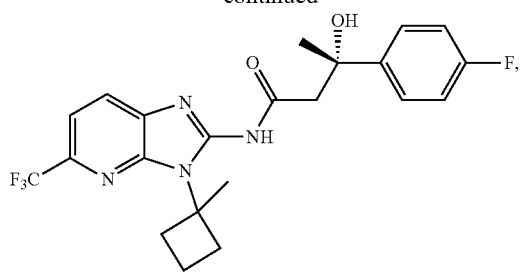
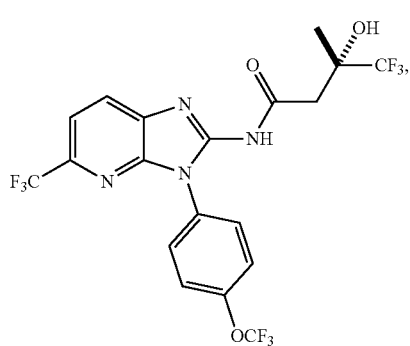
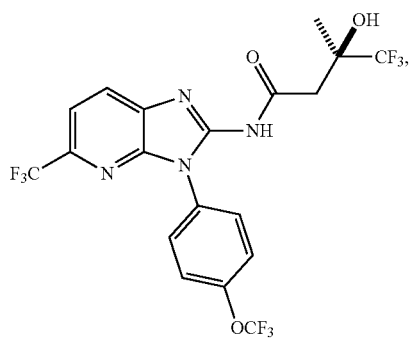
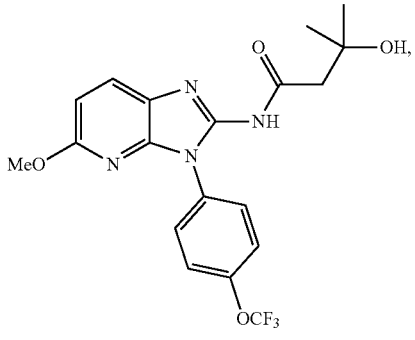
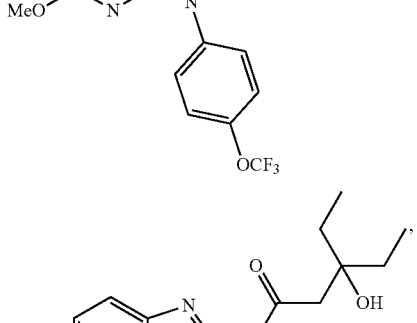
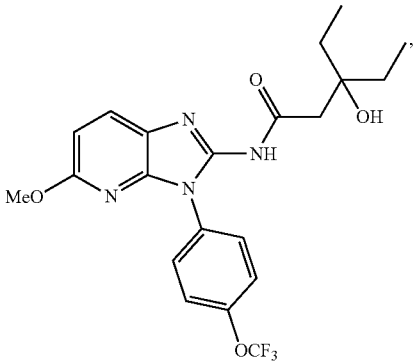
278
-continued
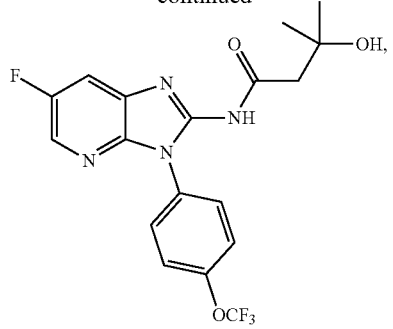
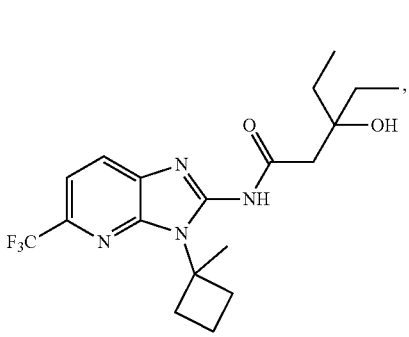
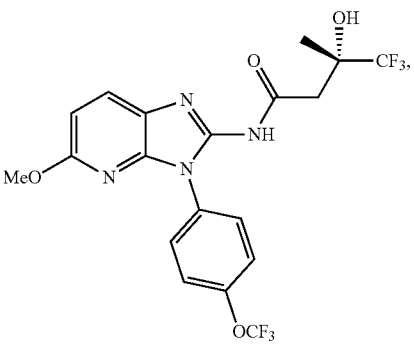
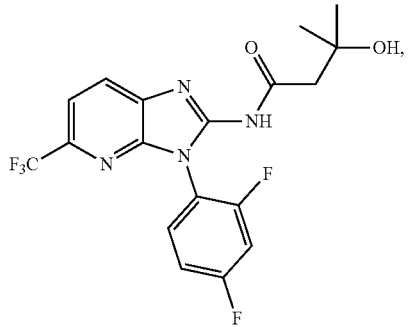
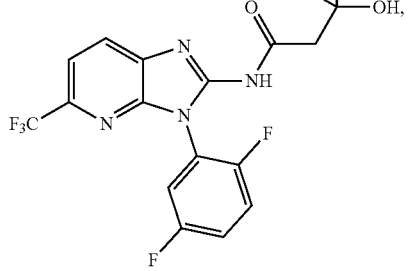

279
-continued
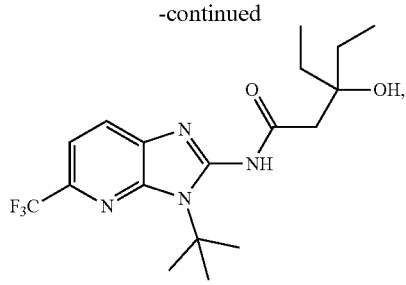
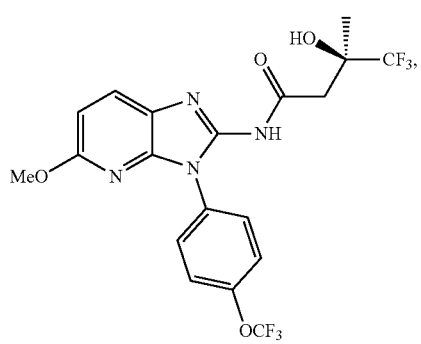
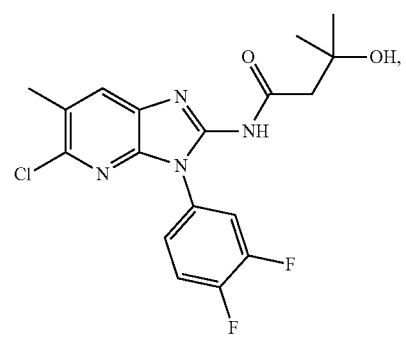
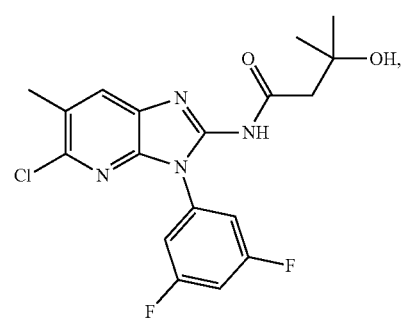
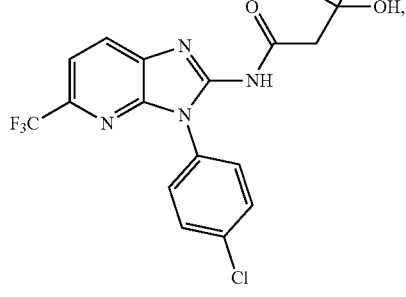
280
-continued
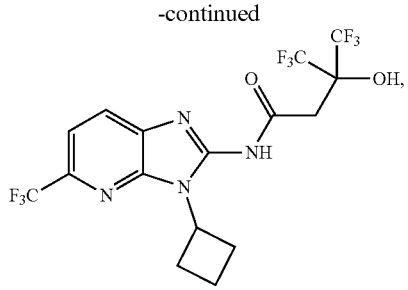
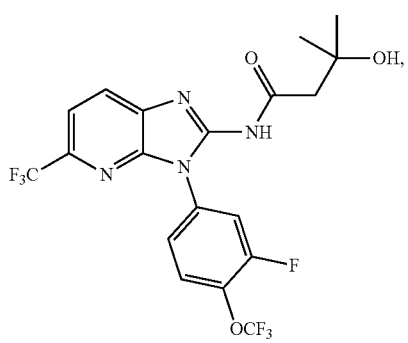
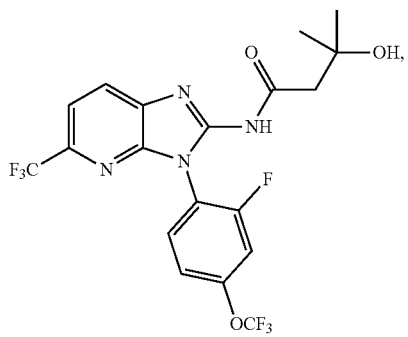
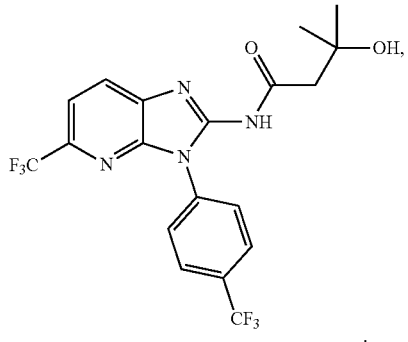
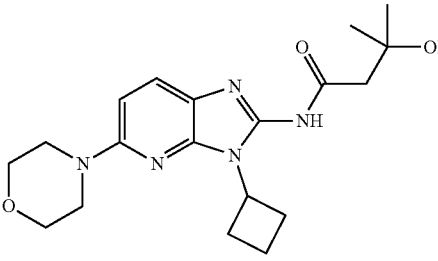

-continued
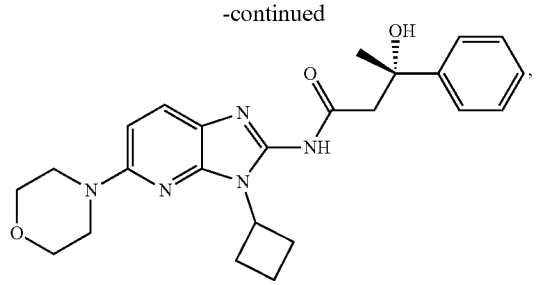
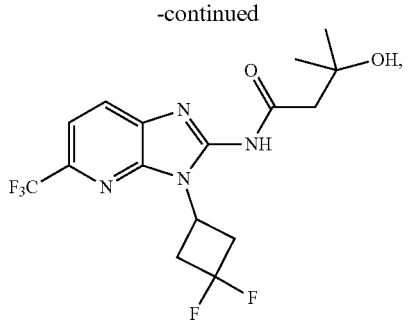
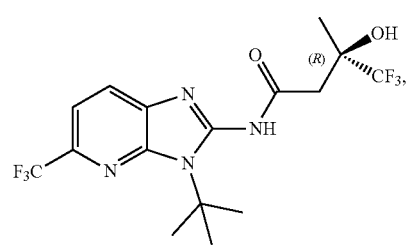
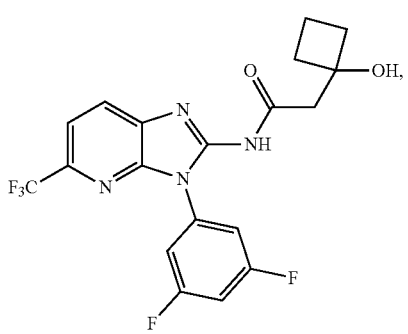
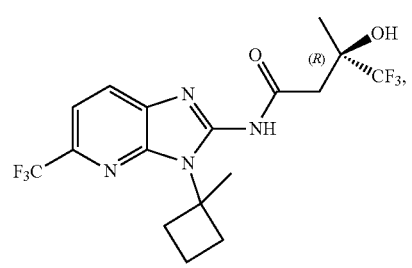
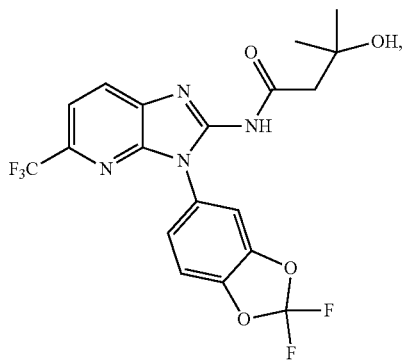
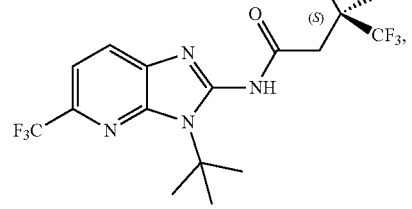
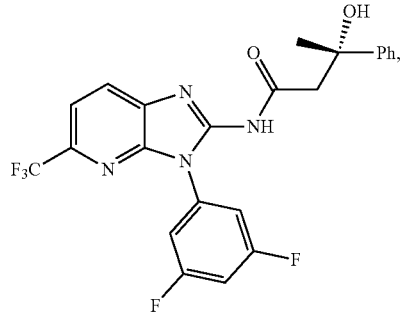
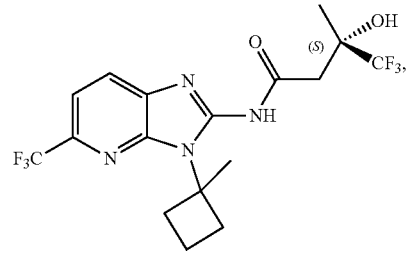
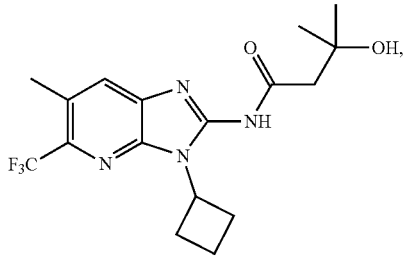
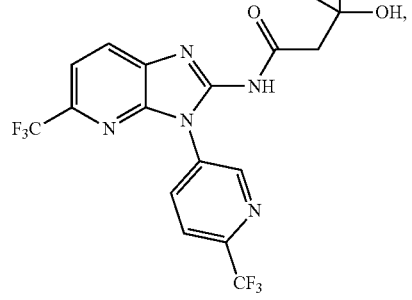

283
-continued
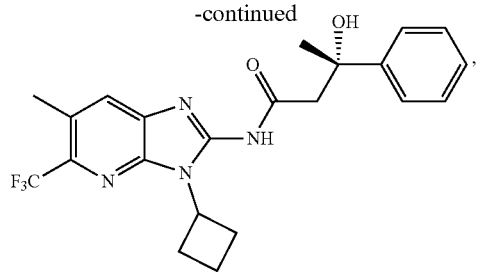
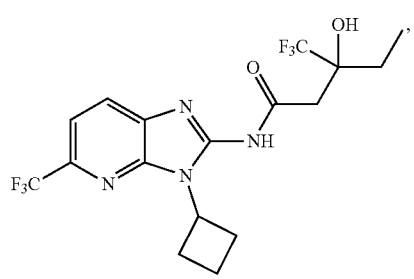
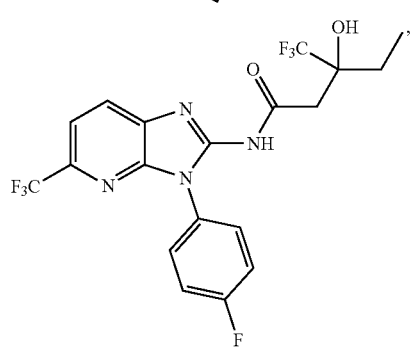
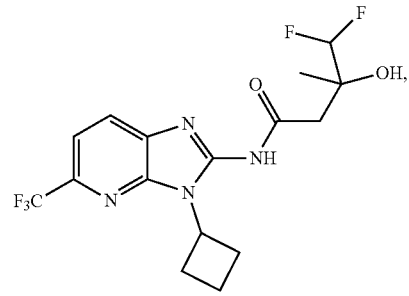
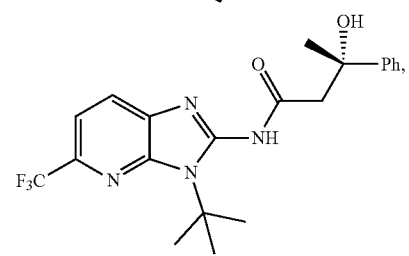
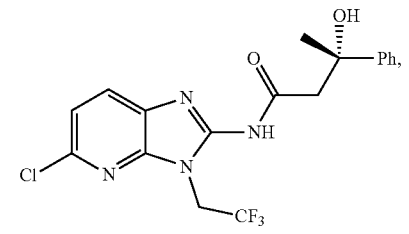
284
-continued
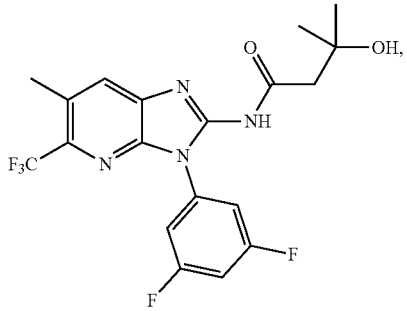
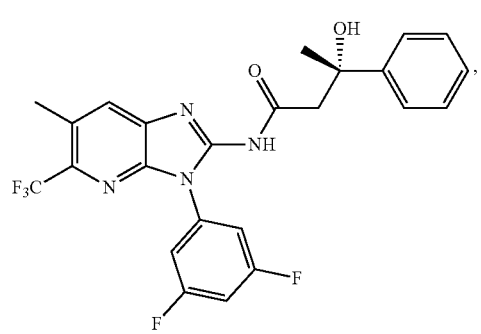
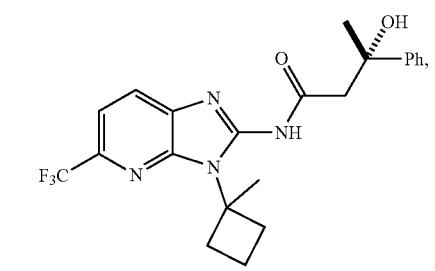
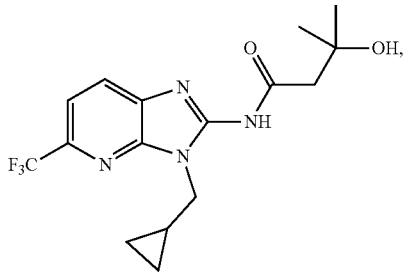
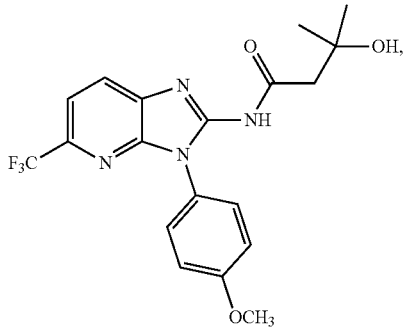

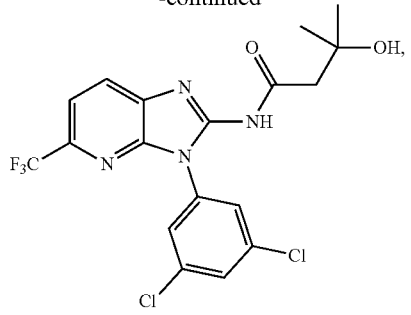
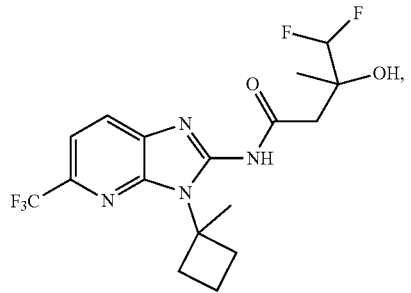
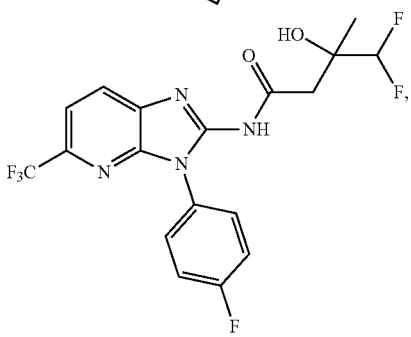
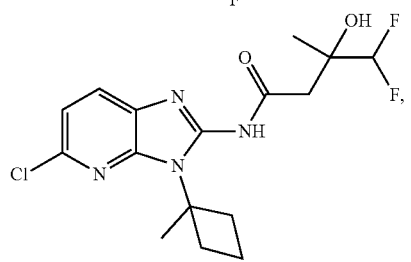
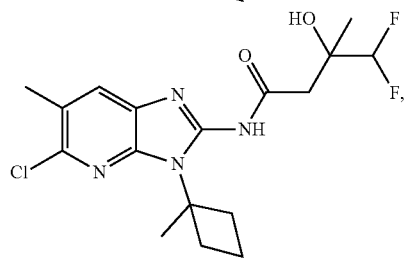
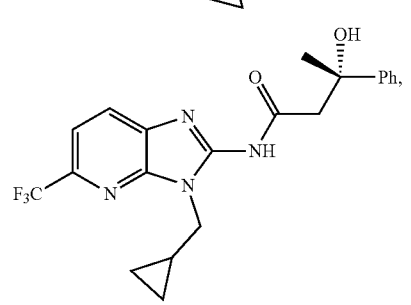
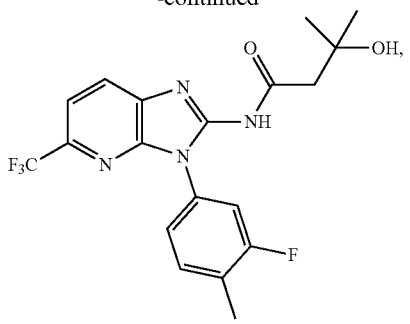
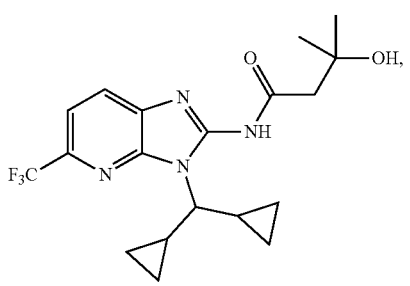
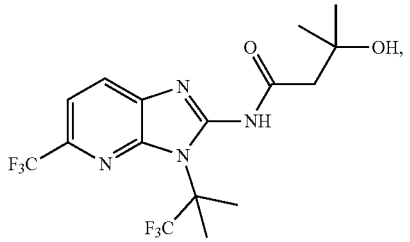
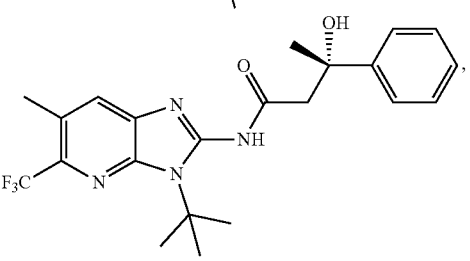
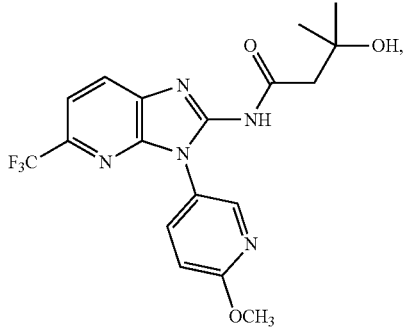

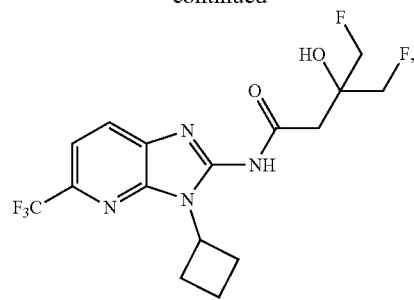
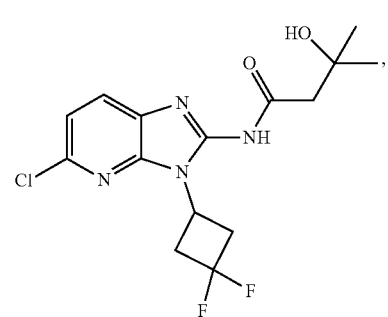
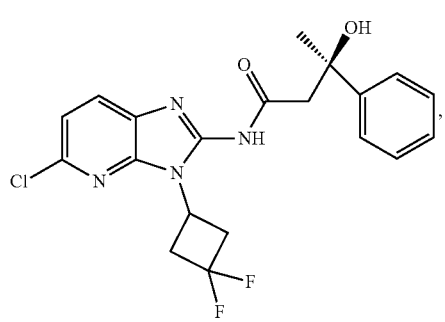
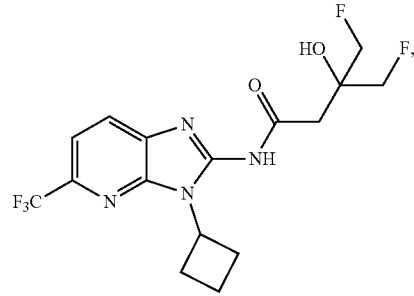
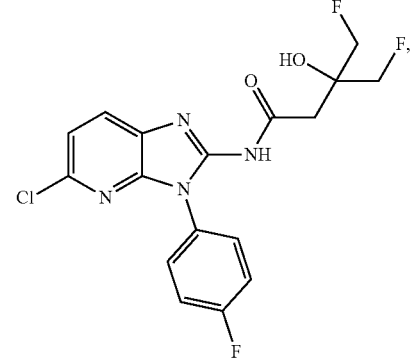
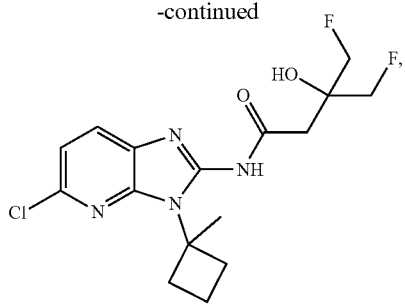
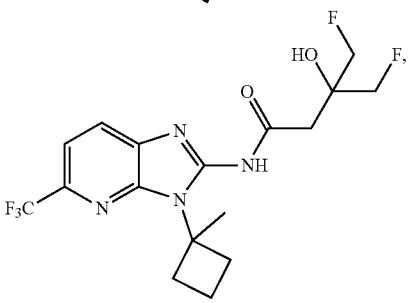
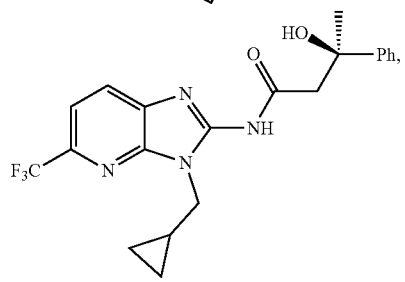
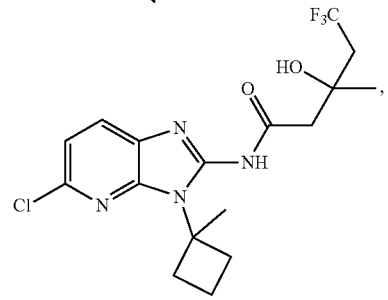
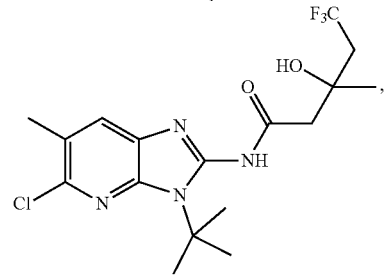
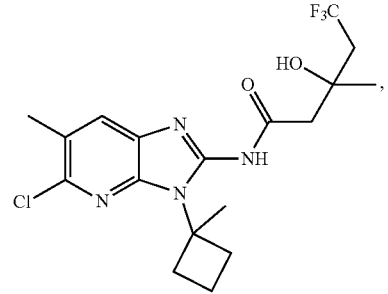

289
-continued
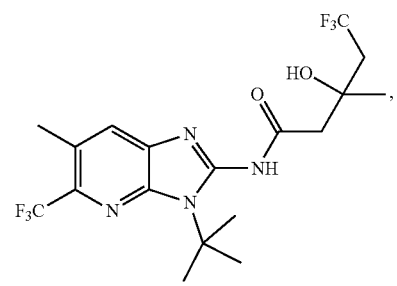
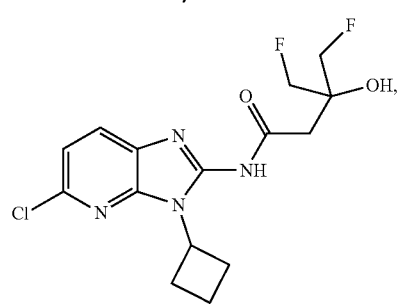
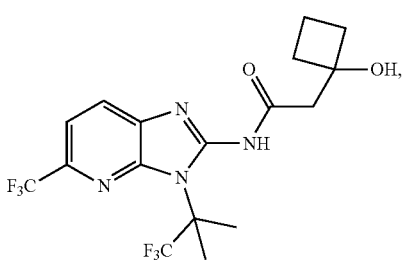
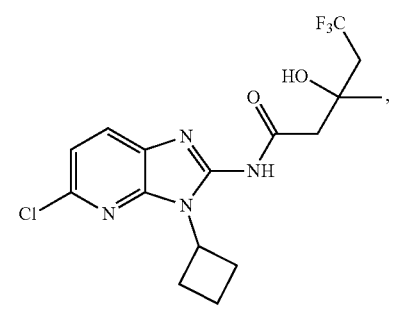
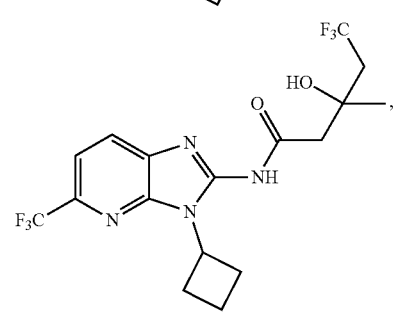
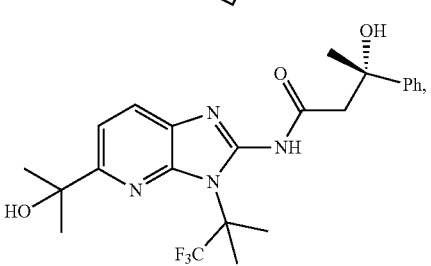
290
-continued
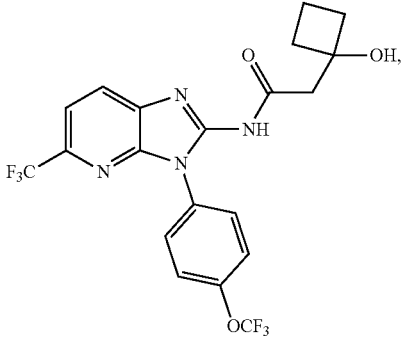
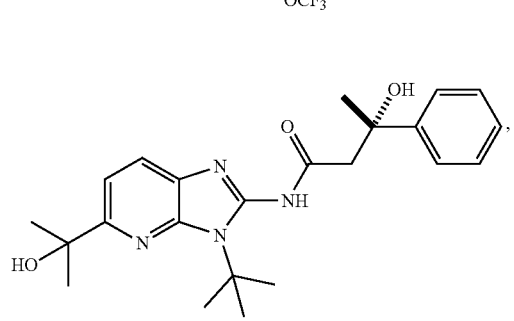
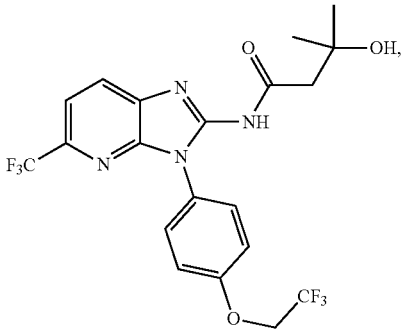
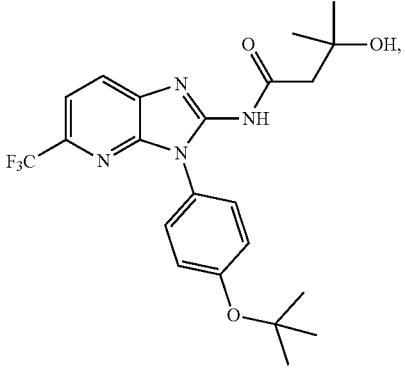
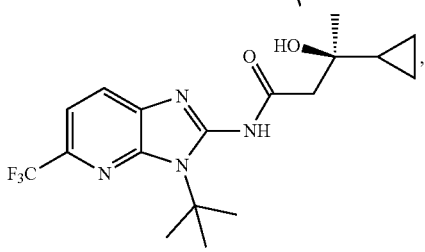

291
-continued
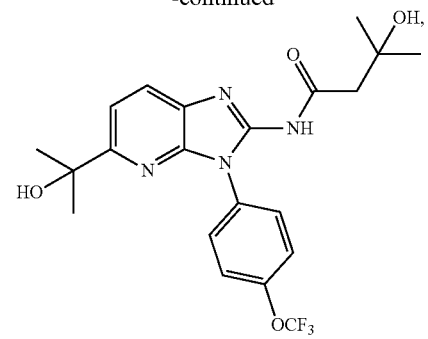
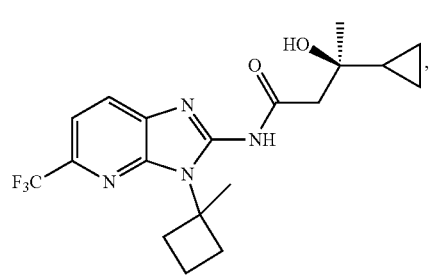
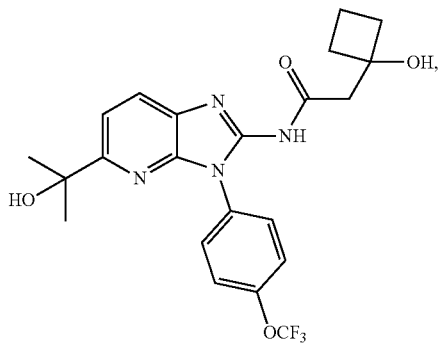
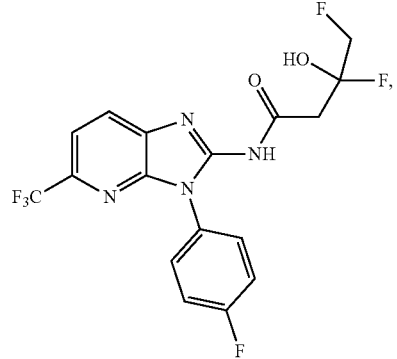
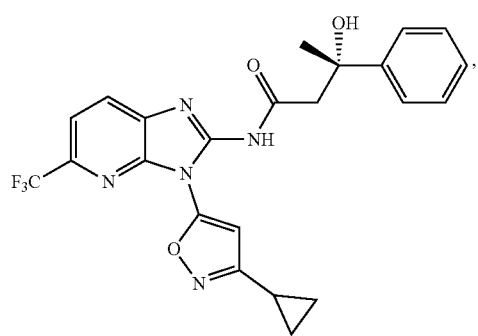
292
-continued
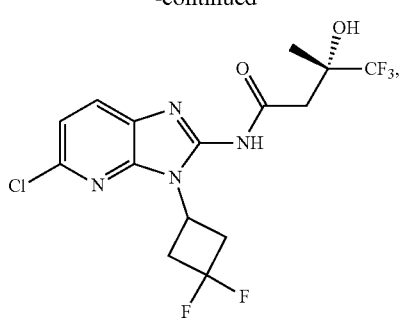
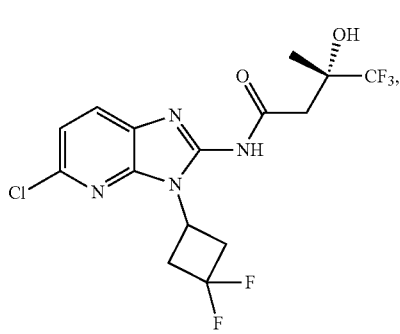
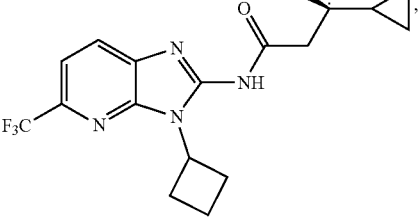
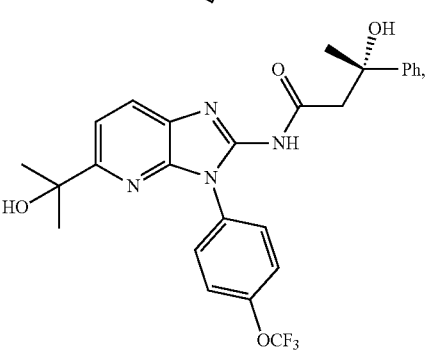
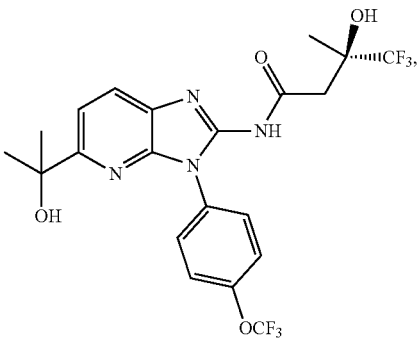

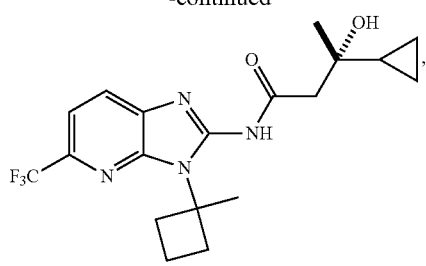
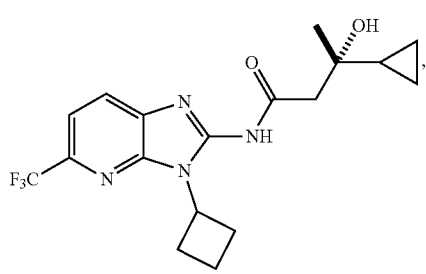
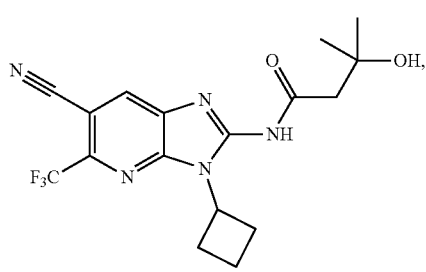
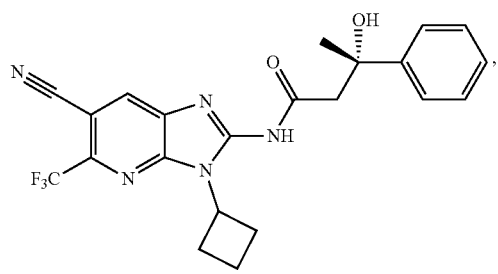
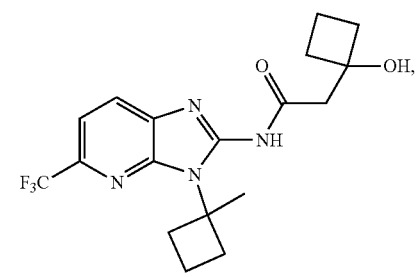
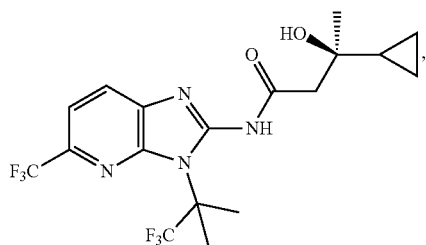
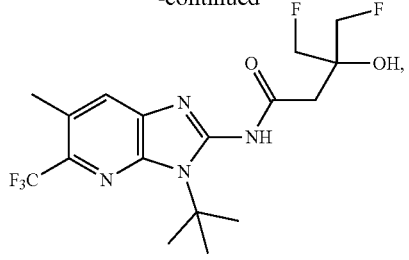
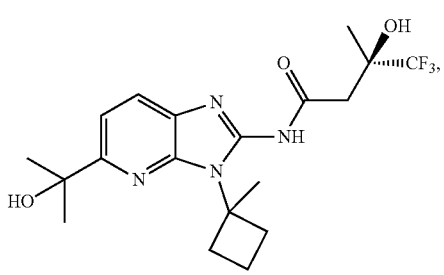
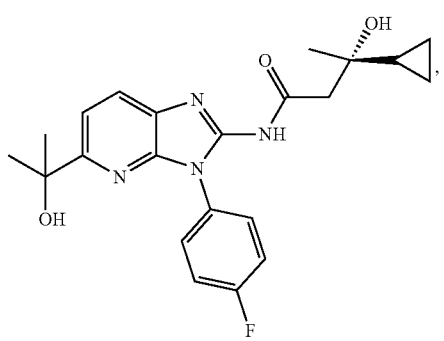
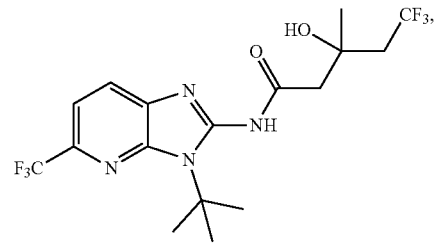
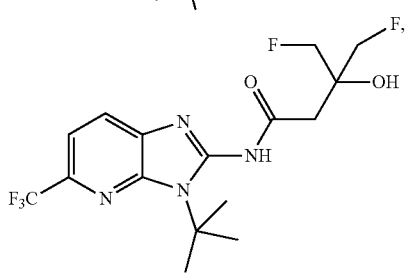
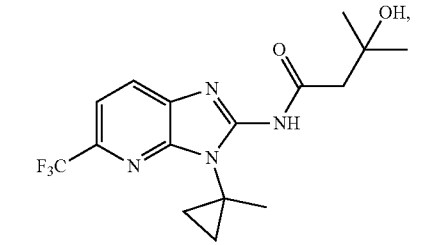

295
-continued
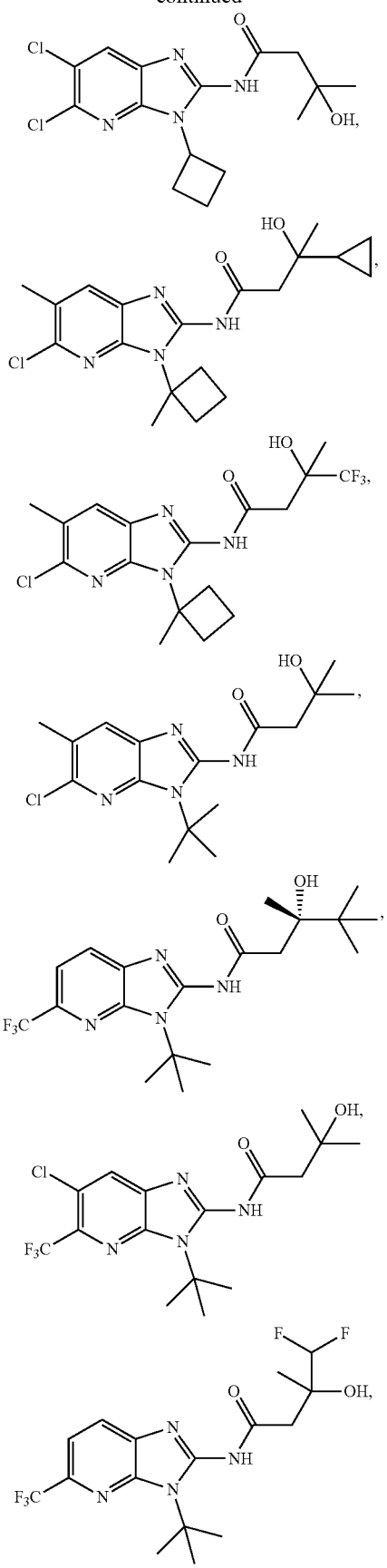
296
-continued
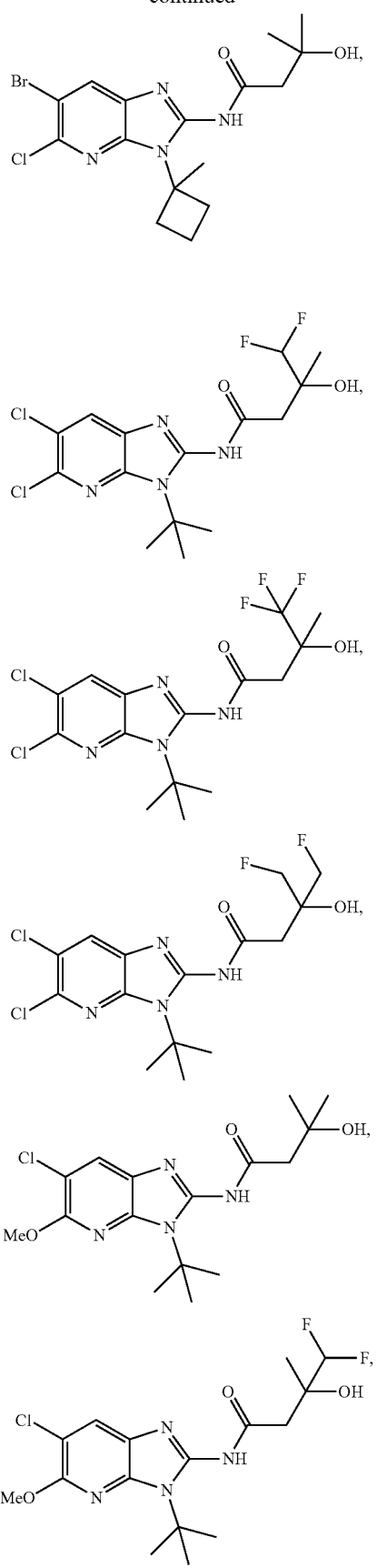

-continued
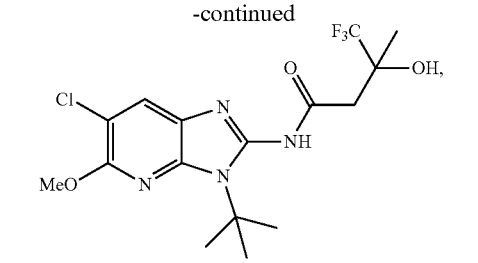
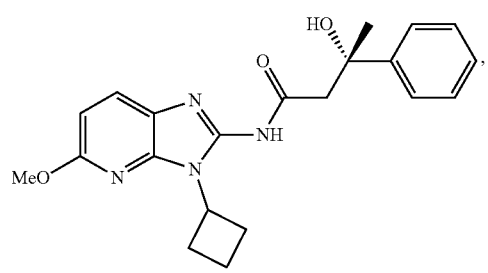
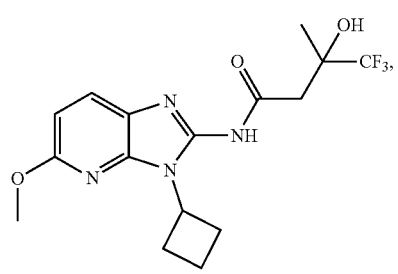
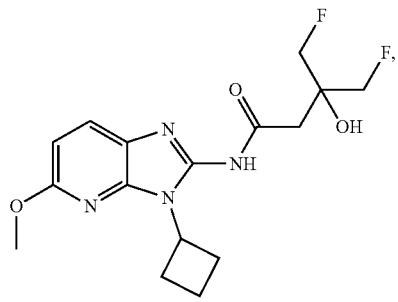
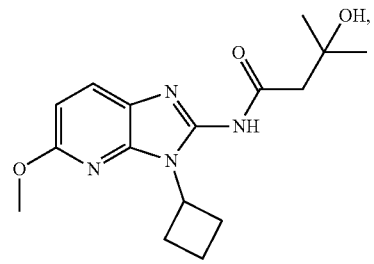
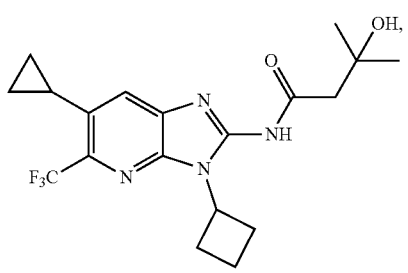
-continued
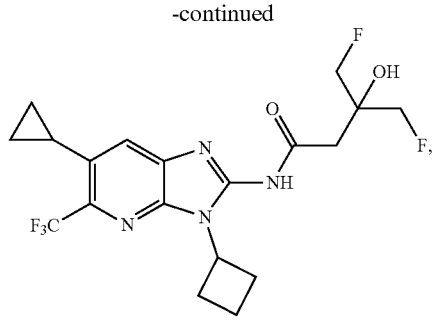
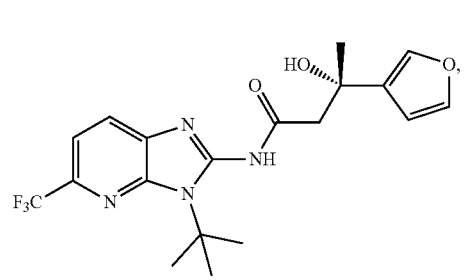
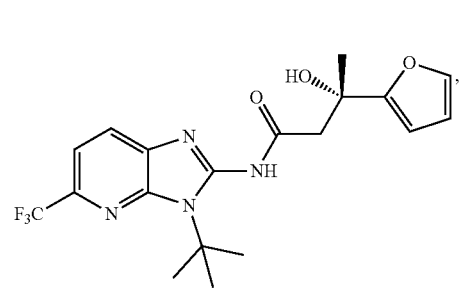
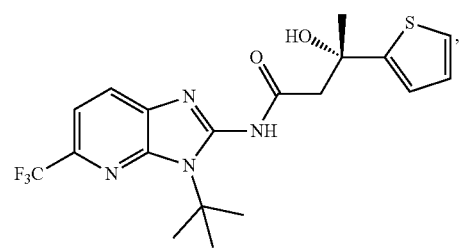
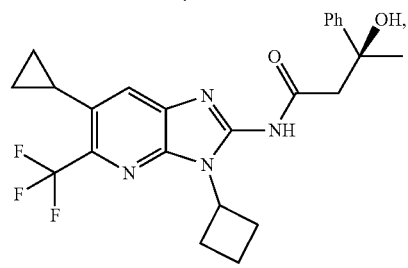
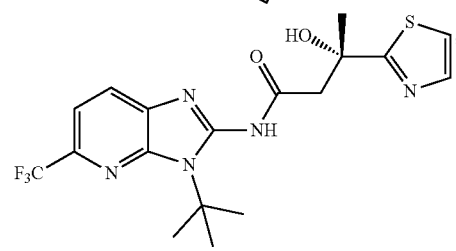

299
-continued
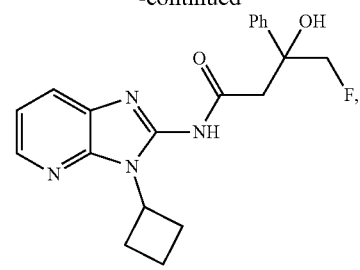
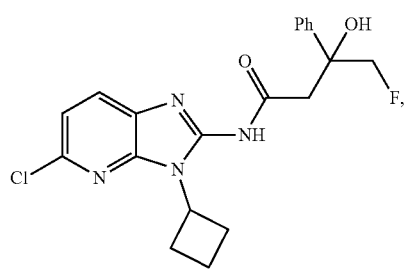
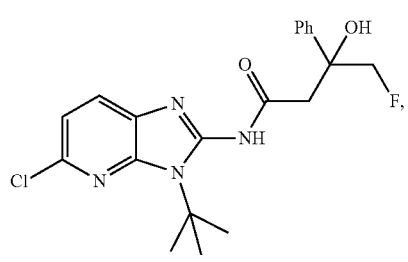
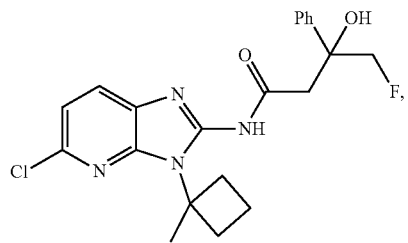
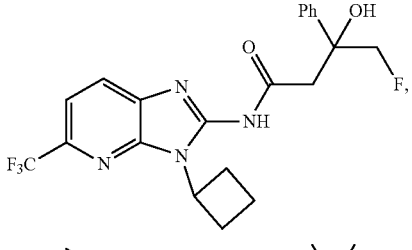
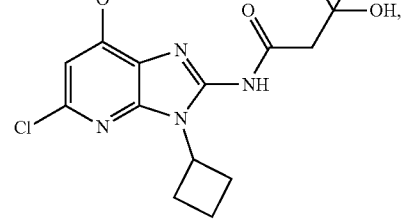
300
-continued
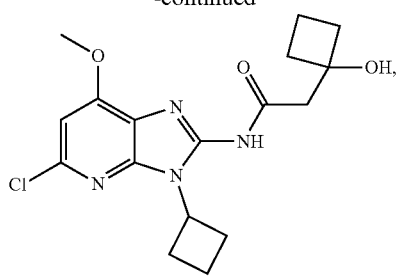
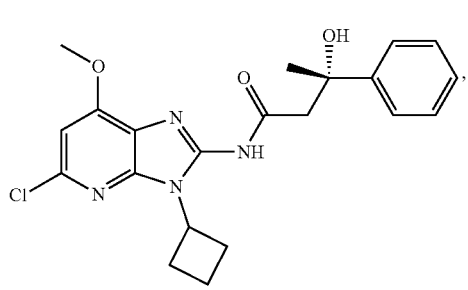
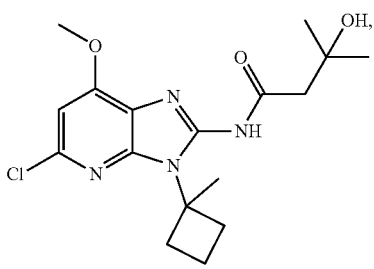
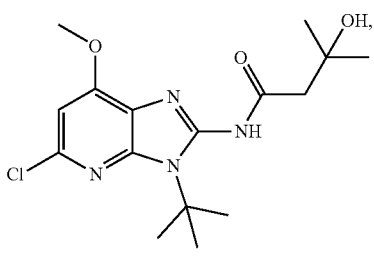
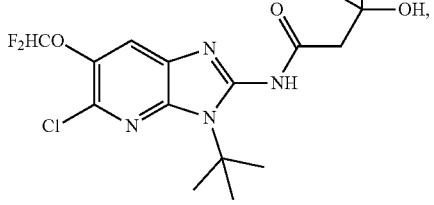
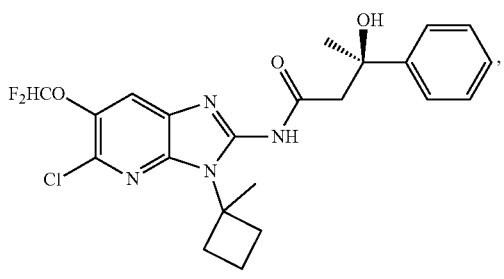

301
-continued
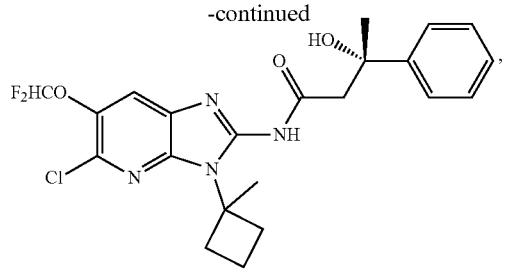
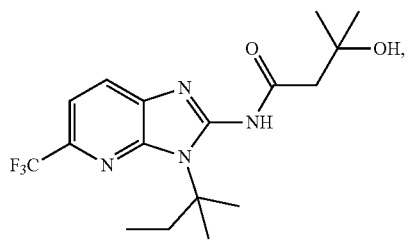
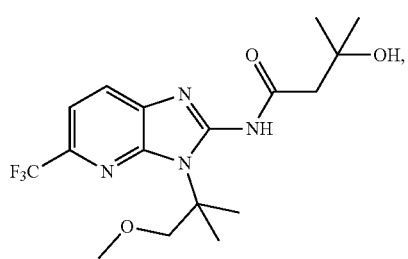
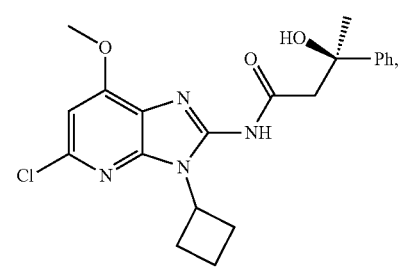
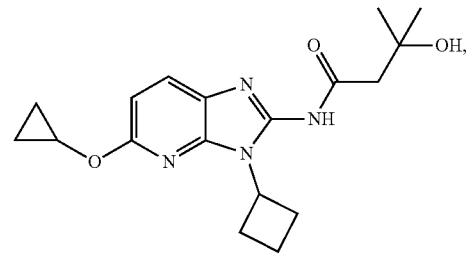
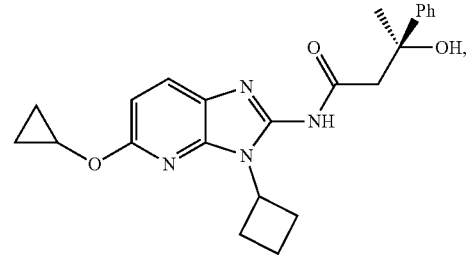
302
-continued
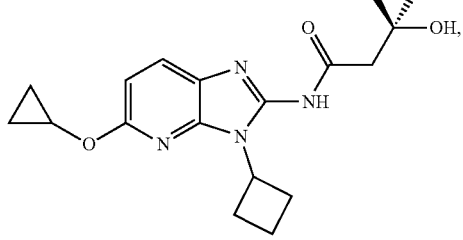
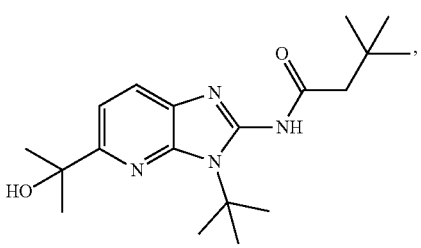
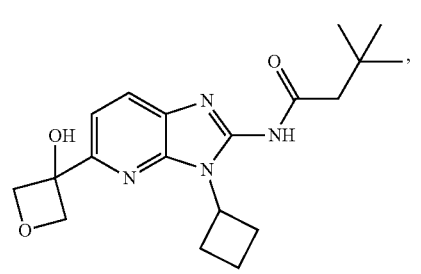
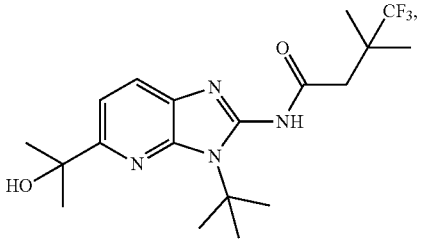
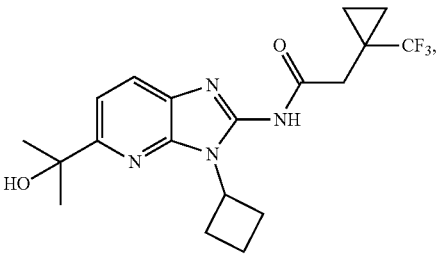
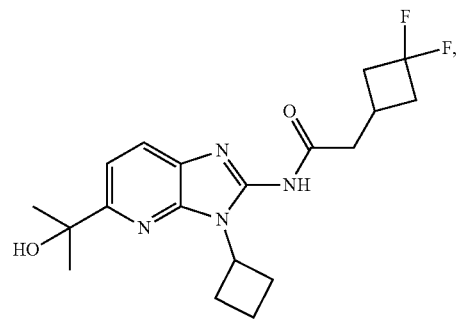

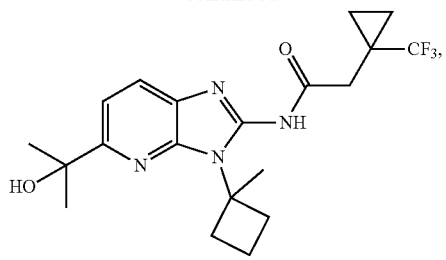
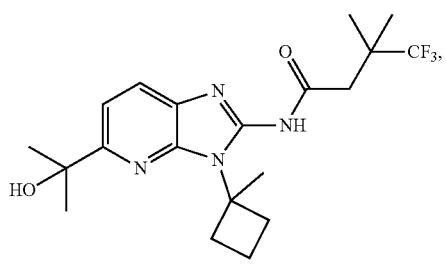
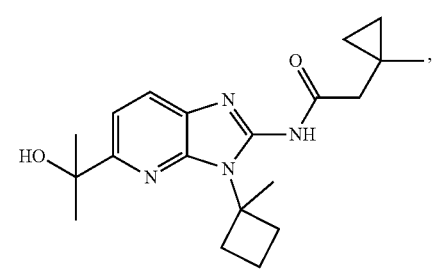
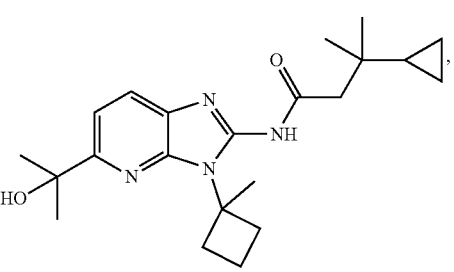
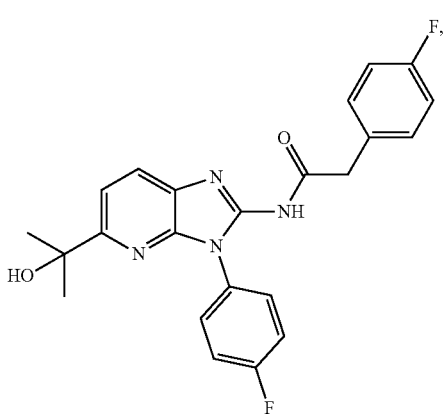
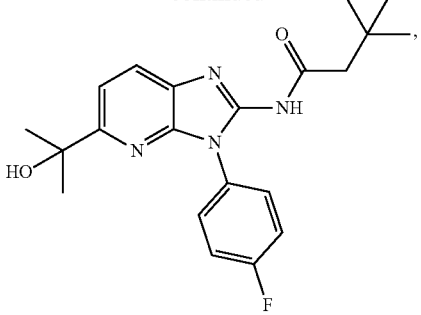
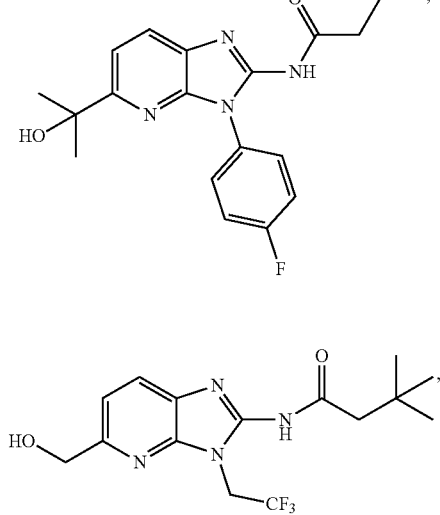
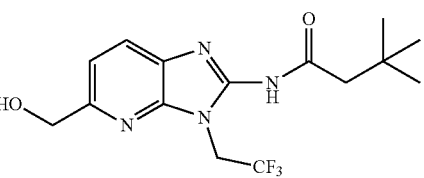
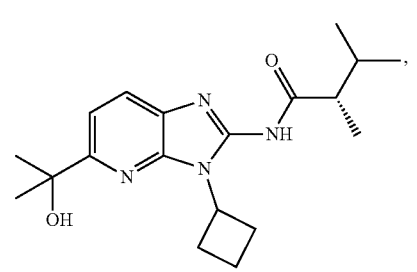
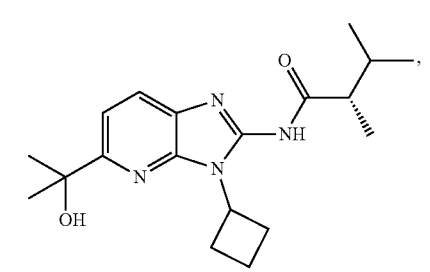
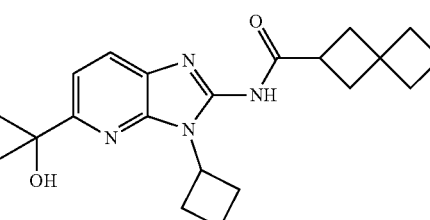
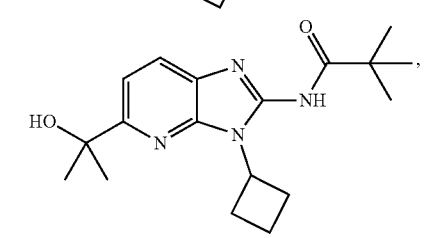
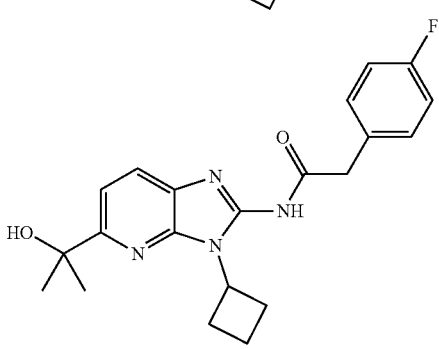

-continued

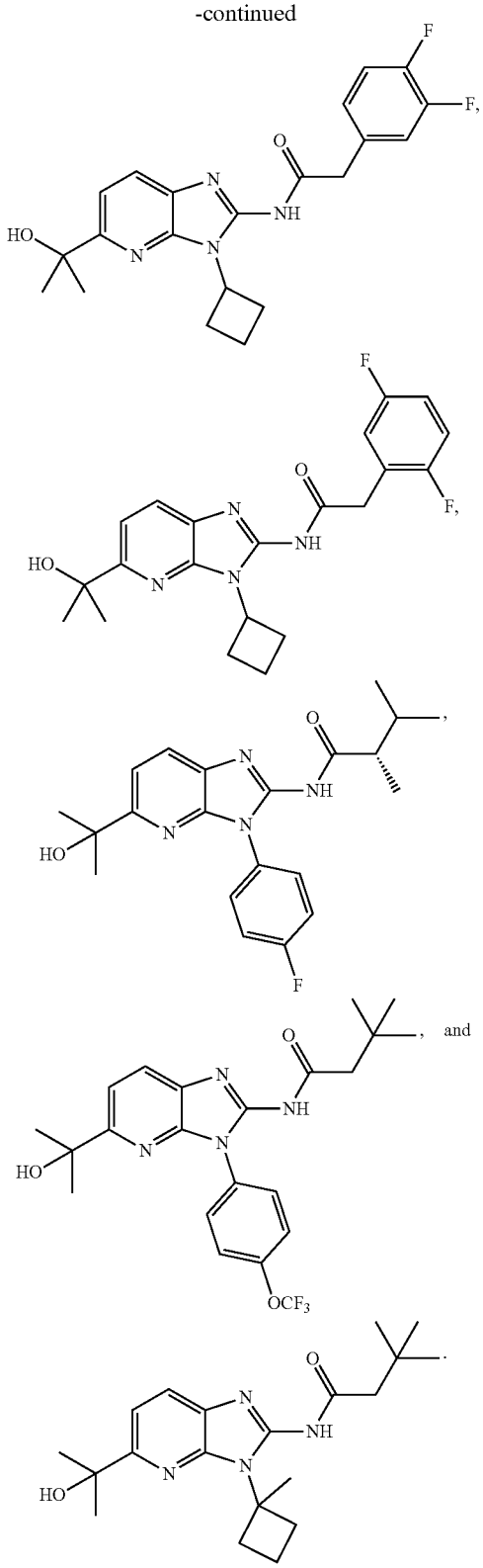

Biological Assay Methods
$K_v7.2/7.3$ Activation Assay

The ability of compounds to potentiate K-currents in Kv7.2/7.3 containing HEK cells was assessed using planar patch-clamp on the QPatch automated screening platform.

Cell Line:

The hKv7.2/7.3 cell line was obtained from Chantest (Cleveland, Ohio 44128) cat.# CT6147. These HEK cells will express the $K_v7.2/7.3$ ion channels when induced.

Cell Culture:

Cells were maintained in a media containing DMEM/F12; 50/50 (GIBCO cat.#11330), 10% Fetal Bovine Serum (FBS) (GIBCO cat.#26140), 100 units/mL Penicillin-Streptomycin (GIBCO cat.#15140), 0.005 mg/mL Blasticidin (INVIVOGEN cat.# ant-bl-1), 0.5 mg/mL Geneticin (GIBCO cat.#10131), 0.1 mg/mL Zeocin (GIBCO cat.# R25001). Cells used in the electrophysiology assay were maintained in a media without Blasticidin, Geneticin and Zeocin for 2 days and channel expression was induced by adding tetracycline (BIOLINE cat.# BIO-87030) at a final concentration of 1 mg/mL. Cells were grown in T-175 flask to ~75% confluency. Currents were recorded 24 hours after channel induction.

Compound Plates:

Test compounds were prepared by performing serial dilutions on a Biomek $NX^P$ (BECKMAN COULTER). Final dilutions were made in external recording solution with a final DMSO concentration of 0.1% DMSO. For single concentration screens each plate had 10 μM retigabine as a positive control and 0.1% DMSO as a negative control.

Electrophysiology:

On the day of the experiment cells were washed with Hank's Balanced Salt Solution (HBBS) (GIBCO cat.#14175) and harvested with Tryple (GIBCO cat.#12604). Cells were then centrifuged at 2000 rpm for 5 minutes and resuspended in CHO—S-SFM (GIBCO cat.#12052) at ~3×10⁶ cells/mL. Cells were stirred for 30 minutes before experiments were started. External recording solution contained (in mM): NaCl (145), KCl (4), CaCl₂ (2), MgCl₂ (1), HEPES (10) and Glucose (10); pH was adjusted to 7.4 with NaOH and the osmolarity was adjusted to 300-305 mOsM with sucrose if necessary. Internal solution contained (in mM): KCl (125), KF (10), EGTA (5), Na₂ATP (5), MgCl₂ (3.2), HEPES (5); pH was adjusted to 7.2 with KOH and the osmolarity was adjusted to 298-302 mOsM with sucrose.

Potassium channel activity was measured on the QPatch HTX (Sophion Bioscience) using QPlates with 48-wells/plate. Each cell was taken as an independent experiment and only one compound was tested per well. Potassium channel activity was elicited by holding at −80 mV and stepping to −30 mV for 1 s followed by a 100 ms pulse to −120 mV.

Single Concentration Screen:

Baseline conditions were obtained by recording 5 sweeps in the external solution only, this was repeated for three applications of the external solution. The effect of test compounds on elicited current was then assessed by recording 5 sweeps in the presence of a 3 μM or 10 μM compound solution. The steady-state current at the end of the 1 s pulse to −30 mV was measured to determine the fold increase from baseline.

TABLE 2

$K_v7.2/7.3$ Single Concentration Screen Results

| Example Number | $K_v7.2/7.3$ Activity at 3 μM* | $K_v7.2/7.3$ Activity at 10 μM* |
|---|---|---|
| 1 | | +/− |
| 2 | | + |
| 3 | | +++ |
| 4 | | +/− |

TABLE 2-continued $K_v7.2/7.3$ Single Concentration Screen Results

| Example Number | $K_v7.2/7.3$ Activity at 3 μM* | $K_v7.2/7.3$ Activity at 10 μM* |
|---|---|---|
| 5 | + | + |
| 6 | − | +/− |
| 7 | | +/− |
| 8 | | + |
| 9 | | +++ |
| 10 | | + |
| 11 | | ++ |
| 12 | | + |
| 13 | | +/− |
| 14 | | ++ |
| 15 | | + |
| 16 | | +/− |
| 17 | | +/− |
| 18 | + | + |
| 19 | | +/− |
| 20 | | ++ |
| 21 | | +/− |
| 22 | + | ++ |
| 23 | | + |
| 24 | +++ | +++ |
| 25 | + | ++ |
| 26 | | +/− |
| 27 | | +++ |
| 28 | + | +++ |
| 29 | | +++ |
| 30 | | + |
| 31 | | +/− |
| 32 | | +/− |
| 33 | | +++ |
| 34 | | − |
| 35 | ++ | +++ |
| 36 | | +++ |
| 37 | | +/− |
| 38 | | +/− |
| 39 | ++ | +++ |
| 40 | | ++ |
| 41 | | + |
| 42 | + | +++ |
| 43 | + | +++ |
| 44 | | + |
| 45 | | +/− |
| 46 | | + |
| 47 | | +++ |
| 48 | | + |
| 49 | | + |
| 50 | | +/− |
| 51 | +/− | + |
| 52 | + | +/− |
| 53 | +/− | + |
| 54 | | ++ |
| 55 | + | ++ |
| 56 | | ++ |
| 57 | +/− | + |
| 58 | − | + |
| 59 | | +/− |
| 60 | | + |
| 61 | + | + |
| 62 | | +/− |
| 63 | | ++ |
| 64 | | + |
| 65 | + | + |
| 66 | + | |
| 67 | | ++ |
| 68 | ++ | |
| 69 | + | |
| 70 | + | |
| 71 | | + |
| 72 | ++ | |
| 73 | | + |
| 74 | +/− | |
| 75 | | + |
| 76 | | + |
| 77 | | + |
| 78 | | + |
| 79 | | +/− |
| 80 | +/− | ++ |
| 81 | | + |
| 82 | | +/− |
| 83 | | + |
| 84 | | +/− |
| 85 | + | |
| 86 | + | |
| 87 | | ++ |
| 88 | + | + |
| 89 | | + |
| 90 | + | + |
| 91 | | +++ |
| 92 | | ++ |
| 93 | + | + |
| 94 | +/− | |
| 95 | | ++ |
| 96 | | +++ |
| 97 | | + |
| 98 | | + |
| 99 | | +/− |
| 100 | | + |
| 101 | | +/− |
| 102 | + | + |
| 103 | +/− | + |
| 104 | + | + |
| 105 | + | +++ |
| 106 | | +/− |
| 107 | + | |
| 108 | +++ | ++ |
| 109 | + | ++ |
| 110 | + | |
| 111 | +/− | + |
| 112 | + | ++ |
| 113 | +/− | + |
| 114 | + | + |
| 115 | + | + |
| 116 | + | + |
| 117 | +/− | +/− |
| 118 | + | ++ |
| 119 | | +/− |
| 120 | ++ | +++ |
| 121 | + | + |
| 122 | | +/− |
| 123 | + | ++ |
| 124 | + | +++ |
| 125 | + | + |
| 126 | ++ | ++ |
| 127 | + | + |
| 128 | + | ++ |
| 129 | | + |
| 130 | + | + |
| 131 | + | ++ |
| 132 | + | +++ |
| 133 | ++ | ++ |
| 134 | ++ | ++ |
| 135 | + | + |
| 136 | | +/− |
| 137 | | + |
| 138 | + | + |
| 139 | + | + |
| 140 | + | + |
| 141 | | +/− |
| 142 | +/− | |
| 143 | +/− | |
| 144 | + | |
| 145 | +/− | |
| 146 | ++ | |
| 147 | +/− | |
| 148 | +/− | |
| 149 | + | |
| 150 | +/− | |
| 151 | − | |
| 152 | +/− | |
| 153 | + | |
| 154 | + | + |

TABLE 2-continued $K_v7.2/7.3$ Single Concentration Screen Results

| Example Number | $K_v7.2/7.3$ Activity at 3 μM* | $K_v7.2/7.3$ Activity at 10 μM* |
|---|---|---|
| 155 | ++ | |
| 156 | ++ | |
| 157 | +/− | |
| 158 | +/− | |
| 159 | + | |
| 160 | + | |
| 161 | +/− | |
| 162 | + | |
| 163 | + | |
| 164 | + | |
| 165 | + | ++ |
| 166 | + | |
| 167 | + | |
| 168 | + | |
| 169 | + | |
| 170 | + | |
| 171 | ++ | |
| 172 | +/− | |
| 173 | +/− | |
| 174 | + | |
| 175 | +/− | |
| 176 | +/− | |
| 177 | + | |
| 178 | +/− | |
| 179 | +/− | |
| 180 | +/− | |
| 181 | +/− | |
| 182 | + | |
| 183 | +/− | |
| 184 | +/− | |
| 185 | +/− | |
| 186 | + | |
| 187 | +/− | |
| 188 | +/− | |
| 189 | +/− | |
| 190 | + | |
| 191 | + | |
| 192 | +/− | |
| 193 | +/− | |
| 194 | +/− | |
| 195 | + | + |
| 196 | ++ | ++ |
| 197 | +/− | |
| 198 | + | |
| 199 | +/− | |
| 200 | +/− | |
| 201 | +/− | |
| 202 | +/− | |
| 203 | + | |
| 204 | +/− | |
| 205 | + | |
| 206 | +/− | |
| 207 | +/− | |
| 208 | +/− | +/− |
| 209 | +/− | |
| 210 | +/− | |
| 211 | +/− | |
| 212 | + | + |
| 213 | +/− | |
| 214 | + | |
| 215 | +/− | |
| 216 | + | |
| 217 | +/− | |
| 218 | +/− | |
| 219 | +/− | |
| 220 | + | |
| 221 | + | |
| 222 | +/− | |
| 223 | − | |
| 224 | +/− | +/− |
| 225 | + | |
| 226 | +/− | |
| 227 | + | |
| 228 | +/− | |
| 229 | +/− | |
| 230 | + | |
| 231 | + | |
| 232 | +/− | |
| 233 | +/− | |
| 234 | +/− | |
| 235 | + | |
| 236 | ++ | |
| 237 | ++ | |
| 238 | + | |
| 239 | +/− | |
| 240 | + | |
| 241 | + | |
| 242 | +/− | |
| 243 | +/− | |
| 244 | + | |
| 245 | +/− | |
| 246 | +/− | + |
| 247 | +/− | |
| 248 | + | |
| 249 | + | |
| 250 | +/− | |
| 251 | + | |
| 252 | +/− | |
| 253 | +/− | |
| 254 | + | |
| 255 | +/− | |
| 256 | +/− | |
| 257 | + | |
| 258 | ++ | |
| 259 | +/− | |
| 260 | +/− | |
| 261 | + | |
| 262 | ++ | |
| 263 | + | |
| 264 | ++ | |
| 265 | +/− | |
| 266 | + | |
| 267 | +/− | |
| 268 | + | |
| 269 | +/− | |
| 270 | + | |
| 271 | + | |

*Increase in current from $K_v7.2/K_v7.3$ co-expressing HEK cells, measured at compound concentration of 3 or 10 μM, as a range from <1.2-fold increase over baseline (−) up to >6-fold increase over baseline (+++).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:
1. A compound represented by a formula:

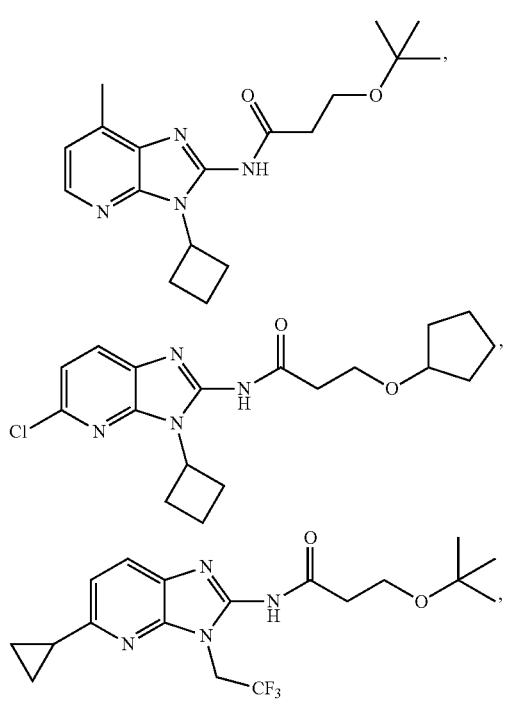

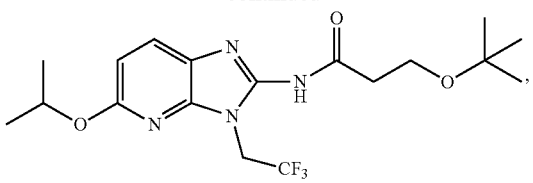

-continued

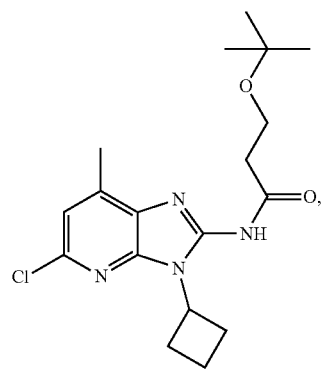

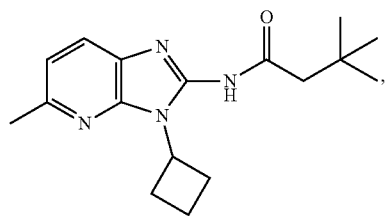

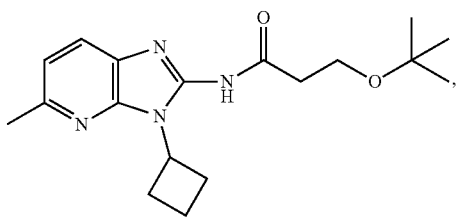

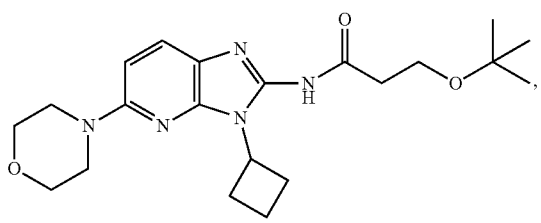

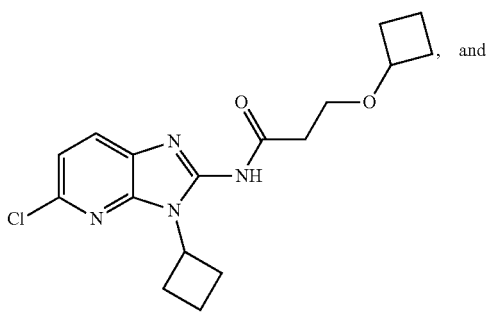

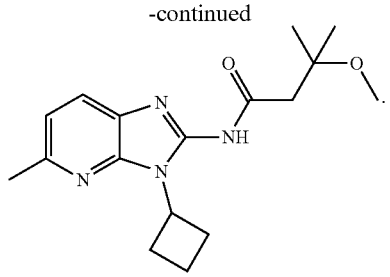
* * * * *